(12) United States Patent
Kuribayashi et al.

(10) Patent No.: US 8,785,462 B2
(45) Date of Patent: Jul. 22, 2014

(54) 5-HYDROXYPYRIMIDINE-4-CARBOXAMIDE DERIVATIVE

(75) Inventors: Takeshi Kuribayashi, Tokyo (JP); Hideki Kubota, Tokyo (JP); Naoki Tanaka, Tokyo (JP); Takeshi Fukuda, Tokyo (JP); Takashi Tsuji, Tokyo (JP); Riki Goto, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 13/503,340

(22) PCT Filed: Oct. 20, 2010

(86) PCT No.: PCT/JP2010/068476
§ 371 (c)(1),
(2), (4) Date: Apr. 20, 2012

(87) PCT Pub. No.: WO2011/049126
PCT Pub. Date: Apr. 28, 2011

(65) Prior Publication Data
US 2012/0220609 A1 Aug. 30, 2012

(30) Foreign Application Priority Data
Oct. 21, 2009 (JP) .................................. 2009-242884

(51) Int. Cl.
A61K 31/505 (2006.01)
A61K 31/40 (2006.01)
C07D 239/02 (2006.01)

(52) U.S. Cl.
USPC ............................ 514/269; 514/429; 544/298

(58) Field of Classification Search
USPC .................................. 514/269, 429; 544/298
See application file for complete search history.

(56) References Cited

U.S. PATENT DOCUMENTS 7,323,475 B2   1/2008   Arend et al.

FOREIGN PATENT DOCUMENTS

| CN | 1816527 A | 8/2006 |
|---|---|---|
| CN | 101394843 A | 3/2009 |
| WO | WO 03/049686 | 6/2003 |
| WO | WO 03/053997 | 7/2003 |
| WO | WO 2004/108681 | 12/2004 |
| WO | WO 2005/014532 | 2/2005 |
| WO | WO 2006/133391 | 12/2006 |
| WO | WO 2007/038571 | 4/2007 |
| WO | WO 2007/136990 | 11/2007 |
| WO | WO 2007/150011 | 12/2007 |
| WO | WO 2008/002576 | 1/2008 |
| WO | 2008/089051 A1 | 7/2008 |
| WO | 2008/089052 A2 | 7/2008 |
| WO | WO 2009/117269 | 9/2009 |
| WO | WO 2009/131127 | 10/2009 |
| WO | WO 2009/131129 | 10/2009 |
| WO | WO 2011/049127 | 4/2011 |
| WO | WO 2011/132633 | 10/2011 |

OTHER PUBLICATIONS

Miyaura, N., Suzuki, A., "Palladium-Catalyzed Cross-Coupling Reactions of Organoboron Compounds," Chem. Rev., 1995, 95, 2457-2483.
Miyaura, N., Yamada, K., Suzuki, A., "A new stereospecific cross-coupling by the palladium-catalyzed reaction of 1-alkenylboranes with 1-alkenyl or 1-alkynylhalides," Tetrahedron Lett., 1979, 36, 3437-40.
U.S. Appl. No. 12/988,947, filed Nov. 20, 2010 Takeshi Kuribayashi.
English translation of Search Report issued Jun. 25, 2013 in the corresponding Chinese Application No. 2010800582110.
International Search Report for related International Application No. PCT/JP2009/057937, mailed on May 26, 2009 (in English & Japanese).

(Continued)

Primary Examiner — Kamal Saeed
Assistant Examiner — Ebenezer O Sackey
(74) Attorney, Agent, or Firm — Locke Lord, LLP

(57) ABSTRACT

The present invention provides a compound which enhances the production of erythropoietin. The present invention provides a compound represented by formula (1):

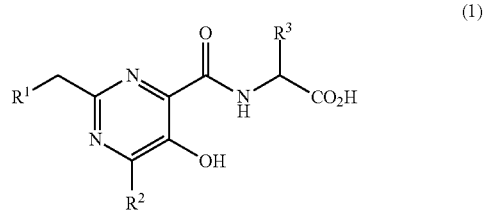

[wherein, $R^1$: formula (1A):

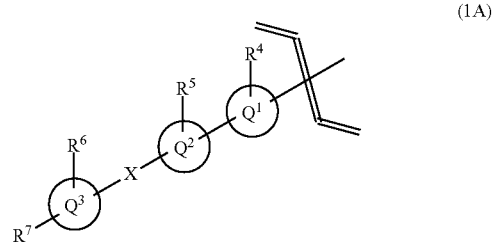

[wherein, $R^4$ and $R^5$: H, halogen, or alkyl; $R^6$: H, halogen, alkyl, or the like; $R^7$: substitutable hydroxyalkyl, substitutable hydroxyhalo alkyl, substitutable alkoxyalkyl, or the like; substituent group α: oxo, hydroxy, amino, or the like; ring $Q^1$: a monocyclic heterocyclic group; ring $Q^2$: a monocyclic hydrocarbon ring group, or a monocyclic heterocyclic group; ring $Q^3$: a monocyclic hydrocarbon ring group, or a monocyclic heterocyclic group; X: a single bond, methylene, ethylene, or the like]; $R^2$: alkyl, or methylsulfanyl; and $R^3$: H, or methyl], or the like.

55 Claims, No Drawings

(56) References Cited

OTHER PUBLICATIONS

International Preliminary Report on Patentability and Written Opinion of the International Searching Authority, for related International Application No. PCT/JP2009/057937, issued on Dec. 18, 2010 (in English & Japanese).

Baudoux, J. et al., "Electrophilic Fluorination With N-F Reagents," *Organic Reactions*, vol. 69, 2007 (Chapter 2, in particular).

Culbertson, T.P., "Synthesis of 5,6-Dihydroxy-2-phenyl-4-pyrimidinecarboxylic Acid, Methyl Ester, a Corrected Structure," *Journal Heterocyclic Chemistry*, 16:1423-1424, 1979.

Dreher, S.D. et al., "Highly Selective Synethesis of 2-substituted-5-hydroxy-6-oxo-1,6-dihydropyrimidine-4-carboxylic Acid Derivatives Using a Novel Protected Dihydroxyfumarate," *Tetrahedron Letters*, 45: pp. 6023-6025, 2004.

Ishikawa, N., "Synthesis and Function of Fluorine Compounds," *CMC Inc.*, Tokyo, 1987, original Japanese text with an English translation of the relevant part of this reference. (pp. 155-166, in particular).

Izumiya, N. et al., "Basics and Experiments of Peptide Synthesis," *Maruzen Publishing*, 1985, original Japanese text with an English translation of the relevant part of this reference. (pp. 89-134, in particular).

Jiang, L. et al., "Palladium-Catalyzed Aromatic Carbon-Nitrogen Bond Formation" *Metal-Catalyzed Cross-Coupling Reactions, 2nd Edition*, Edited by A de Meijere et al, chapter 13, pp. 699-760.

Molander, G.A. et al., "Cross-Coupling Reactions of Primary Alkylboronic Acids with Aryl Triflates and Aryl Halides," *Tetrahedron*, 58:1465-1470, 2002.

Saburo, A., "Organic Synthesis IV—Acid•Amino Acid•Peptide," *The Chemical Society of Japan, Maruzen Company, Limited*, Experimental Chemistry Lecture 22, 4th Edition, edited by Kusumoto, S., 1990, original Japanese text with an English translation of the relevant part of this reference. (pp. 259-271, in particular).

Tsuji, J., "Palladium Reagents and Catalysts," *New Perspectives for the 21st Century*, 2004, (Chapter 3, in particular).

Zou, G. et al., "Ag(I)-promoted Suzuki-Miyaura cross-couplings of n-alkylboronic acids,"*Tetrahedron Letters*, 42:7213-7215, 2001.

Ishiyama, T., Takagi, J., Ishida, K., Miyaura, N., Anastasi, N. R., Hartwig, J. F., "Mild Iridium-catalyzed Borylation of Arenes. High Turnover Numbers, Room Temperature Reactions, and Isolation of a Potential intermediate" J. Am. Chem. Soc., 2002, 124, 390.

Ishiyama, T., Takagi, J., Hartwig, J. F., Miyaura, N., Angew. "A Stoichiometric Aromatic C-H Borylation Catalyzed by Iridium(1)/2,2'-Bipyridine Complexes at Room Temperature" Chem. Int. Ed., 2002, 41, 3056.

Ishiyama, T., Murata, M., Miyaura, N., "Palladium(0)-Catalyzed Cross-Coupling Reaction of Alkoxydiboron with Haloarenes: A Direct Procedure for Arylboronic Esters" J. Org. Chem., 1995, 60, 7508.

International Search Report for International Application No. PCT/JP2010/068476, mailed on Jan. 25, 2011.

Green, Theodora W.; Peter G. M. Wuts. Protective Groups in Organic Synthesis. John Wiley & Sons, Inc, 1991.

European Search Report, issued in corresponding EP Application No. 10 82 4975, dated Feb. 1, 2013.

5-HYDROXYPYRIMIDINE-4-CARBOXAMIDE DERIVATIVE

This application is a national phase entry under 35 U.S.C. §371 of International Application Number PCT/JP2010/068476, filed on Oct. 20, 2010, entitled "5-HYDROXYPYRIMIDINE-4-CARBOXAMIDE DERIVATIVE", which claims the benefit of Japanese Patent Application Number JP 2009-242884, filed on Oct. 21, 2009, all of which are hereby incorporated by reference.

FIELD OF THE INVENTION

The present invention relates to low-molecular-weight compounds having an erythropoietin production-enhancing activity.

BACKGROUND

Erythropoietin (hereinafter abbreviated as EPO) is a glycoprotein hormone that is essential for erythrocyte hematopoiesis. It is normally secreted from the kidneys and promotes production of erythrocytes by acting on erythrocyte stem cells present in bone marrow. In diseases presenting with a decrease in intrinsic EPO production (such as chronic renal failure), since erythrocyte production decreases and symptoms of anemia are exhibited, treatment is provided in the form of replacement therapy using gene-recombinant human EPO. However, this gene-recombinant human EPO has been indicated as having shortcomings such as being a biological preparation and associated with expensive health care costs, having poor convenience due to being an injection and having antigenicity.

On the other hand, compounds such as pyridine derivatives, cinnoline derivatives, quinoline derivatives, isoquinoline derivatives (see Patent Documents 1 to 6 and 8), 6-hydroxy-2,4-dioxo-tetrahydropyrimidine derivatives (see Patent Document 7) or 4-hydroxypyrimidine-5-carboxamide derivatives (see Patent Document 9) are known to be low molecular weight EPO inducers. Further, 5-hydroxypyrimidine-4-carboxamide derivatives (International Publication No. WO 2009/131127 or International Publication No. WO 2009/131129) are known.

PRIOR ART DOCUMENTS

Patent Documents

[Patent Document 1] International Publication No. WO 2003/049686
[Patent Document 2] International Publication No. WO 2003/053997
[Patent Document 3] International Publication No. WO 2004/108681
[Patent Document 4] International Publication No. WO 2006/133391
[Patent Document 5] International Publication No. WO 2007/038571
[Patent Document 6] International Publication No. WO 2007/136990
[Patent Document 7] International Publication No. WO 2007/150011
[Patent Document 8] International Publication No. WO 2008/002576
[Patent Document 9] International Publication No. WO 2009/117269

SUMMARY OF THE INVENTION

Object of the Invention

The inventors of the present invention conducted studies for the purpose of providing novel low molecular weight compounds that have a superior EPO production-enhancing activity and that are useful for the treatment of diseases caused by decreased EPO, and for the purpose of providing a medicament containing such compounds.

Means for Achieving the Object

In order to solve the aforementioned problems, the inventors of the present invention found that novel compounds having a 5-hydroxypyrimidine-4-carboxamide structure have superior EPO production-enhancing activity and that they are effective for treating diseases caused by decreased EPO, thereby leading to completion of the present invention.

According to the present invention, novel 5-hydroxypyrimidine-4-carboxamide compounds represented by the following general formula (1), pharmacologically acceptable esters thereof or pharmacologically acceptable salts thereof (hereinafter collectively referred to as compounds of the present invention), are provided.

Namely, the present invention relates to the following:
(1) a compound represented by the following general formula (1):

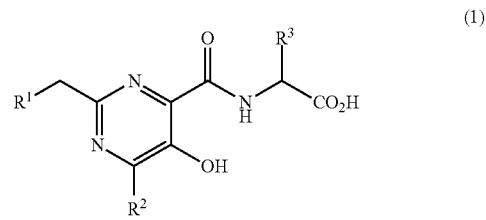

(1)

[wherein,
$R^1$ represents a group represented by the following general formula (1A):

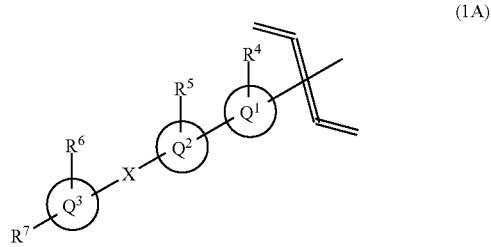

(1A)

[wherein,
$R^4$ and $R^5$ each independently represents a hydrogen atom, a halogen atom or a $C_1$-$C_6$ alkyl group,
$R^6$ represents a hydrogen atom, a halogen atom, a $C_1$-$C_6$ alkyl group, a carbamoyl group, a $C_1$-$C_6$ alkylcarbamoyl group, or a ($C_1$-$C_6$ alkyl) ($C_1$-$C_6$ alkyl)carbamoyl group,
$R^7$ represents a hydroxy $C_1$-$C_6$ alkyl group which may have 1 or 2 substituents independently selected from substituent group α, a hydroxyhalo $C_1$-$C_6$ alkyl group which may have 1 or 2 substituents independently selected from substituent group α, a $C_1$-$C_6$ alkoxy $C_1$-$C_6$ alkyl group which may have 1 or 2 substituents independently selected from substituent group α, a ($C_1$-$C_6$ alkoxy)carbonyl group which may have 1 or 2 substituents independently selected from substituent group α, a $C_1$-$C_6$ alkoxy $C_1$-$C_6$ alkoxy $C_1$-$C_6$ alkyl group which may have 1 or 2 substituents independently selected from substituent group α, a hydroxy $C_1$-$C_6$ alkoxy group which may have 1 or 2 substituents independently selected from substituent group α, a $C_1$-$C_6$ alkylcarbamoyl group which may have 1 or 2 substituents independently selected from substituent group α, a ($C_1$-$C_6$ alkyl) ($C_1$-$C_6$ alkyl)carbamoyl group which may have 1 or 2 substituents independently selected from substituent group α, a $C_1$-$C_6$ alkoxycarbamoyl group which may have 1 or 2 substituents independently selected from substituent group α, a $C_1$-$C_6$ alkylcarbamoyl $C_1$-$C_6$ alkyl group which may have 1 or 2 substituents independently selected from substituent group α, a ($C_1$-$C_6$ alkyl) ($C_1$-$C_6$ alkyl)carbamoyl $C_1$-$C_6$ alkyl group which may have 1 or 2 substituents independently selected from substituent group α, a $C_2$-$C_7$ alkanoylamino group which may have 1 or 2 substituents independently selected from substituent group α, a $C_2$-$C_7$ alkanoylamino $C_1$-$C_6$ alkyl group which may have 1 or 2 substituents independently selected from substituent group α, or a $C_2$-$C_7$ alkanoyloxy $C_1$-$C_6$ alkyl group which may have 1 or 2 substituents independently selected from substituent group α, substituent group α represents a group consisting of an oxo group, a hydroxy group, an amino group, a carboxy group, a carbamoyl group, a $C_1$-$C_6$ alkoxy group, a halo $C_1$-$C_6$ alkoxy group, a $C_2$-$C_7$ alkanoylamino group, a hydroxyimino group, and a $C_1$-$C_6$ alkoxyimino group, ring $Q^1$ represents a monocyclic heterocyclic group (wherein the heterocyclic group includes a 5- to 7-membered aromatic heterocycle and non-aromatic heterocycle, and contains 1 or 2 atoms selected from the group consisting of a nitrogen atom, a sulfur atom and an oxygen atom), ring $Q^2$ represents a monocyclic hydrocarbon ring group (wherein the hydrocarbon ring group includes a 5- to 7-membered aromatic hydrocarbon ring and a non-aromatic hydrocarbon ring), or a monocyclic heterocyclic group (wherein the heterocyclic group includes a 5- to 7-membered aromatic heterocycle and non-aromatic heterocycle, and contains 1 or 2 atoms selected from the group consisting of a nitrogen atom, a sulfur atom and an oxygen atom), ring $Q^3$ represents a monocyclic hydrocarbon ring group (wherein the hydrocarbon ring group includes a 5- to 7-membered aromatic hydrocarbon ring and a non-aromatic hydrocarbon ring), or a monocyclic heterocyclic group (wherein the heterocyclic group includes a 5- to 7-membered aromatic heterocycle and non-aromatic heterocycle, and contains 1 or 2 atoms selected from the group consisting of a nitrogen atom, a sulfur atom and an oxygen atom), and X represents a single bond, methylene, or ethylene], $R^2$ represents a $C_1$-$C_3$ alkyl group or a methylsulfanyl group, and $R^3$ denotes a hydrogen atom or a methyl group], a pharmacologically acceptable ester thereof, or a pharmacologically acceptable salt thereof, (2) a compound, pharmacologically acceptable ester thereof, or pharmacologically acceptable salt thereof according to (1) above, wherein $R^2$ is a methyl group or a methylsulfanyl group, (3) a compound, pharmacologically acceptable ester thereof, or pharmacologically acceptable salt thereof according to (1) above, wherein $R^2$ is a methyl group, (4) a compound, pharmacologically acceptable ester thereof, or pharmacologically acceptable salt thereof according to any one of (1) to (3) above, wherein $R^3$ is a hydrogen atom, (5) a compound, pharmacologically acceptable ester thereof, or pharmacologically acceptable salt thereof according to any one of (1) to (4) above, wherein $R^4$ is a hydrogen atom, (6) a compound, pharmacologically acceptable ester thereof, or pharmacologically acceptable salt thereof according to any one of (1) to (5) above, wherein $R^5$ is a hydrogen atom, a halogen atom or a methyl group, (7) a compound, pharmacologically acceptable ester thereof, or pharmacologically acceptable salt thereof according to any one of (1) to (5) above, wherein $R^5$ is a hydrogen atom, (8) a compound, pharmacologically acceptable ester thereof, or pharmacologically acceptable salt thereof according to any one of (1) to (7) above, wherein $R^6$ is a hydrogen atom, a halogen atom, or a methyl group, (9) a compound, pharmacologically acceptable ester thereof, or pharmacologically acceptable salt thereof according to any one of (1) to (7) above, wherein $R^6$ is a hydrogen atom,

(10) a compound, pharmacologically acceptable ester thereof, or pharmacologically acceptable salt thereof according to any one of (1) to (9) above, wherein $R^7$ is a hydroxy $C_1$-$C_6$ alkyl group, a hydroxyhalo $C_1$-$C_6$ alkyl group, a $C_1$-$C_6$ alkoxy $C_1$-$C_6$ alkyl group, a hydroxy $C_1$-$C_6$ alkoxy $C_1$-$C_6$ alkyl group, a ($C_1$-$C_6$ alkoxy)carbonyl group, a $C_1$-$C_6$ alkoxy $C_1$-$C_6$ alkoxy $C_1$-$C_6$ alkyl group, a hydroxy $C_1$-$C_6$ alkoxy group, a $C_1$-$C_6$ alkylcarbamoyl group, a ($C_1$-$C_6$ alkyl) ($C_1$-$C_6$ alkyl)carbamoyl group, a hydroxy $C_1$-$C_6$ alkylcarbamoyl group, a $C_1$-$C_6$ alkoxycarbamoyl group, a $C_1$-$C_6$ alkylcarbamoyl $C_1$-$C_6$ alkyl group, a ($C_1$-$C_6$ alkyl) ($C_1$-$C_6$ alkyl)carbamoyl $C_1$-$C_6$ alkyl group, or a hydroxy $C_1$-$C_6$ alkylcarbamoyl $C_1$-$C_6$ alkyl group,

(11) a compound, pharmacologically acceptable ester thereof, or pharmacologically acceptable salt thereof according to any one of (1) to (9) above, wherein $R^7$ is a hydroxymethyl group, a 1-hydroxyethyl group, a 2-hydroxyethyl group, a 1,1-difluoro-2-hydroxyethyl group, a 2-hydroxypropyl group, a 3-hydroxypropyl group, a 1,1-difluoro-2-hydroxypropyl group, a 2-hydroxybutyl group, a 2-hydroxy-1,1-dimethylethyl group, a 1,1-difluoro-2-hydroxy-2-methylpropyl group, a methoxymethyl group, a 2-hydroxy-3-methoxypropyl group, a methoxycarbonyl group, an ethoxycarbonyl group, a methoxymethoxymethyl group, a 1-methoxymethoxyethyl group, a 2-hydroxyethoxy group, a methylcarbamoyl group, a dimethylcarbamoyl group, a methylcarbamoylmethyl group, a dimethylcarbamoylmethyl group, a hydroxyethylcarbamoyl group, or a hydroxyethylcarbamoylmethyl group,

(12) a compound, pharmacologically acceptable ester thereof, or pharmacologically acceptable salt thereof according to any one of (1) to (9) above, wherein $R^7$ is a hydroxymethyl group, a 1-hydroxyethyl group, a 2-hydroxyethyl group, a 2-hydroxypropyl group, a 3-hydroxypropyl group, a 2-hydroxybutyl group, a 2-hydroxy-1,1-dimethylethyl group, a methoxymethyl group, a 2-hydroxy-3-methoxypropyl group, an ethoxycarbonyl group, a 1-methoxymethoxyethyl group, a 2-hydroxyethoxy group, a methylcarbamoyl group, a dimethylcarbamoyl group, or a dimethylcarbamoylmethyl group,

(13) a compound, pharmacologically acceptable ester thereof, or pharmacologically acceptable salt thereof according to any one of (1) to (12) above, wherein the ring $Q^1$ is a monocyclic heterocyclic group (wherein the heterocyclic group includes a 6-membered aromatic heterocycle and non-aromatic heterocycle, and contains 1 or 2 nitrogen atoms),

(14) a compound, pharmacologically acceptable ester thereof, or pharmacologically acceptable salt thereof according to any one of (1) to (12) above, wherein the ring $Q^1$ is a piperidyl group,

(15) a compound, pharmacologically acceptable ester thereof, or pharmacologically acceptable salt thereof according to any one of (1) to (14) above, wherein the ring $Q^2$ is a monocyclic hydrocarbon ring group (wherein the hydrocarbon ring group includes a 6-membered aromatic hydrocarbon ring and a non-aromatic hydrocarbon ring), or a monocyclic heterocyclic group (wherein the heterocyclic group includes a 6-membered aromatic heterocycle and non-aromatic heterocycle, and contains 1 or 2 nitrogen atoms),

(16) a compound, pharmacologically acceptable ester thereof, or pharmacologically acceptable salt thereof according to any one of (1) to (14) above, wherein the ring $Q^2$ is a phenyl group or a pyridyl group,

(17) a compound, pharmacologically acceptable ester thereof, or pharmacologically acceptable salt thereof according to any one of (1) to (16) above, wherein the ring $Q^3$ is a monocyclic hydrocarbon ring group (wherein the hydrocarbon ring group includes a 6-membered aromatic hydrocarbon ring and a non-aromatic hydrocarbon ring), or a monocyclic heterocyclic group (wherein the heterocyclic group includes a 6-membered aromatic heterocycle and non-aromatic heterocycle, and contains 1 or 2 nitrogen atoms),

(18) a compound, pharmacologically acceptable ester thereof, or pharmacologically acceptable salt thereof according to any one of (1) to (16) above, wherein the ring $Q^3$ is a phenyl group or a pyridyl group,

(19) a compound, pharmacologically acceptable ester thereof, or pharmacologically acceptable salt thereof according to any one of (1) to (18) above, wherein X is a single bond or methylene,

(20) a compound, pharmacologically acceptable ester thereof, or pharmacologically acceptable salt thereof according to any one of (1) to (4) above, wherein:

$R^1$ is a group represented by the following general formula (1B)

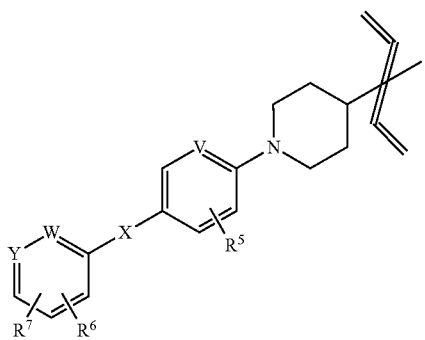

[wherein, $R^5$ represents a hydrogen atom, a halogen atom or a $C_1$-$C_6$ alkyl group, $R^6$ represents a hydrogen atom, a halogen atom, a $C_1$-$C_6$ alkyl group, a carbamoyl group, a $C_1$-$C_6$ alkylcarbamoyl group, or a ($C_1$-$C_6$ alkyl)($C_1$-$C_6$ alkyl)carbamoyl group, $R^7$ represents a hydroxymethyl group, a 1-hydroxyethyl group, a 2-hydroxyethyl group, a 1,1-difluoro-2-hydroxyethyl group, a 2-hydroxypropyl group, a 3-hydroxypropyl group, a 1,1-difluoro-2-hydroxypropyl group, a 2-hydroxybutyl group, a 2-hydroxy-1,1-dimethylethyl group, a 1,1-difluoro-2-hydroxy-2-methylpropyl group, a methoxymethyl group, a 2-hydroxy-3-methoxypropyl group, a methoxycarbonyl group, an ethoxycarbonyl group, a methoxymethoxymethyl group, a 1-methoxymethoxyethyl group, a 2-hydroxyethoxy group, a methylcarbamoyl group, a dimethylcarbamoyl group, a methylcarbamoylmethyl group, a dimethylcarbamoylmethyl group, a hydroxyethylcarbamoyl group, or a hydroxyethylcarbamoylmethyl group, V, W and Y, each independently, represent a carbon atom (having 1 hydrogen atom) or a nitrogen atom, and X represents a single bond or methylene],

(21) a compound, pharmacologically acceptable ester thereof, or pharmacologically acceptable salt thereof according to any one of (1) to (4) above, wherein:

$R^1$ represents a group represented by any one of the following general formula (1B-1) to general formula (1B-8)

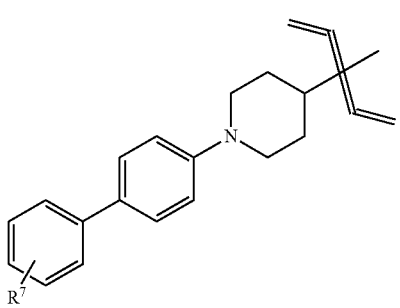

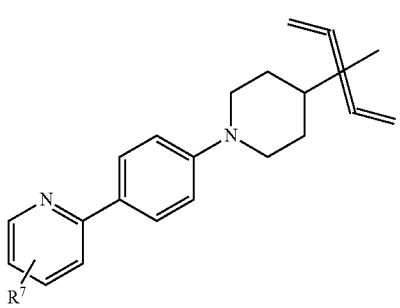

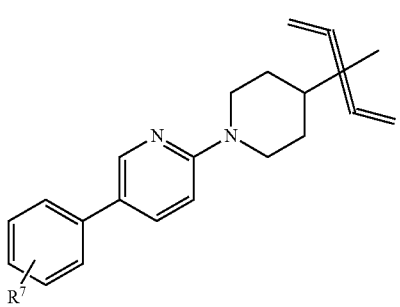

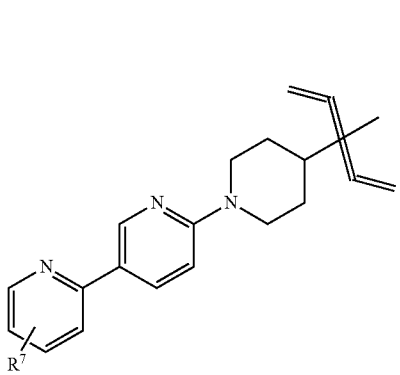

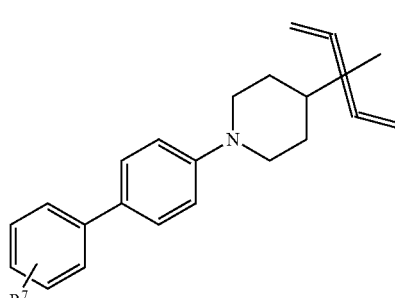
(1B-1)

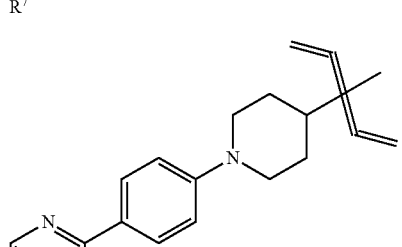
(1B-2)

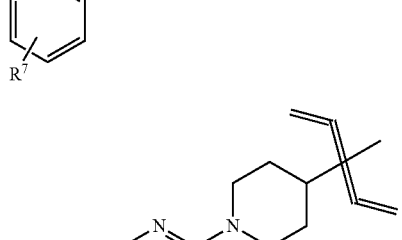
(1B-3)

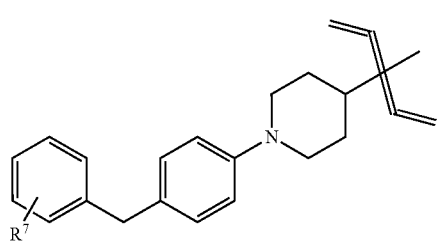
(1B-5)

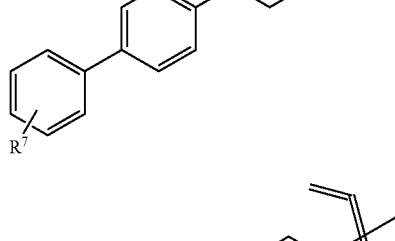
(1B-5)

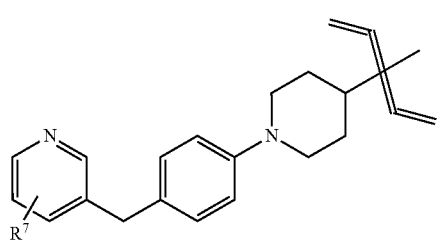
(1B-6)

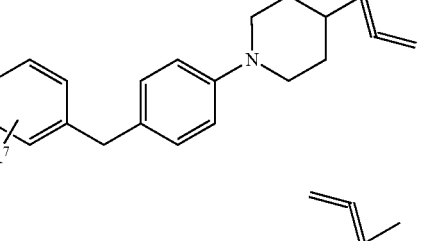
(1B-6)

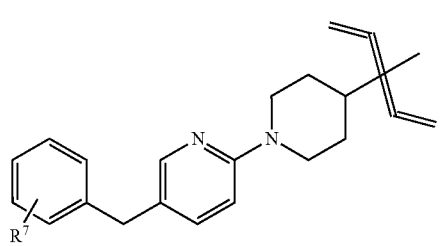
(1B-7)

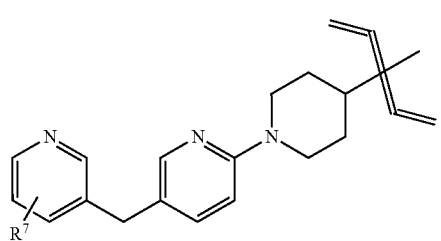
(1B-8)

[wherein,

R⁷ represents a hydroxymethyl group, a 1-hydroxyethyl group, a 2-hydroxyethyl group, a 1,1-difluoro-2-hydroxyethyl group, a 2-hydroxypropyl group, a 3-hydroxypropyl group, a 1,1-difluoro-2-hydroxypropyl group, a 2-hydroxybutyl group, a 2-hydroxy-1,1-dimethylethyl group, a 1,1-difluoro-2-hydroxy-2-methylpropyl group, a methoxymethyl group, a 2-hydroxy-3-methoxypropyl group, a methoxycarbonyl group, an ethoxycarbonyl group, a methoxymethoxymethyl group, a 1-methoxymethoxyethyl group, a 2-hydroxyethoxy group, a methylcarbamoyl group, a dimethylcarbamoyl group, a methylcarbamoylmethyl group, a dimethylcarbamoylmethyl group, a hydroxyethylcarbamoyl group, or a hydroxyethylcarbamoylmethyl group],

(22) a compound, pharmacologically acceptable ester thereof, or pharmacologically acceptable salt thereof according to any one of (1) to (4) above, wherein:

R¹ represents a group represented by any one of the following general formula (1B-1), general formula (1B-2), general formula (1B-3), general formula (1B-5), or general formula (1B-6)

[wherein,

R⁷ represents a hydroxymethyl group, a 1-hydroxyethyl group, a 2-hydroxyethyl group, a 1,1-difluoro-2-hydroxyethyl group, a 2-hydroxypropyl group, a 3-hydroxypropyl group, a 1,1-difluoro-2-hydroxypropyl group, a 2-hydroxybutyl group, a 2-hydroxy-1,1-dimethylethyl group, a 1,1-difluoro-2-hydroxy-2-methylpropyl group, a methoxymethyl group, a 2-hydroxy-3-methoxypropyl group, a methoxycarbonyl group, an ethoxycarbonyl group, a methoxymethoxymethyl group, a 1-methoxymethoxyethyl group, a 2-hydroxyethoxy group, a methylcarbamoyl group, a dimethylcarbamoyl group, a methylcarbamoylmethyl group, a dimethylcarbamoylmethyl group, a hydroxyethylcarbamoyl group, or a hydroxyethylcarbamoylmethyl group],

(23) a compound, pharmacologically acceptable ester thereof, or pharmacologically acceptable salt thereof according to any one of (20) to (22) above, wherein $R^7$ represents a hydroxymethyl group, a 1-hydroxyethyl group, a 2-hydroxyethyl group, a 2-hydroxypropyl group, a 3-hydroxypropyl group, a 2-hydroxybutyl group, a 2-hydroxy-1,1-dimethylethyl group, a methoxymethyl group, a 2-hydroxy-3-methoxypropyl group, an ethoxycarbonyl group, a 1-methoxymethoxyethyl group, a 2-hydroxyethoxy group, a methylcarbamoyl group, a dimethylcarbamoyl group, or a dimethylcarbamoylmethyl group,

(24) a compound, pharmacologically acceptable ester thereof, or pharmacologically acceptable salt thereof according to any one of (20) to (22) above, wherein, in the case where $R^7$ represents a group having a hydroxy group (a hydroxy $C_1$-$C_6$ alkyl group, a hydroxyhalo $C_1$-$C_6$ alkyl group, a hydroxy $C_1$-$C_6$ alkoxy group, a hydroxy $C_1$-$C_6$ alkylcarbamoyl group, or a hydroxy $C_1$-$C_6$ alkylcarbamoyl $C_1$-$C_6$ alkyl group), the hydroxy group forms an ester bond with a $C_1$-$C_6$ alkanoyl group,

(25) a compound or pharmaceutically acceptable salt thereof according to (1) above, selected from the following:

({[5-hydroxy-2-{(1-[4'-(hydroxymethyl)biphenyl-4-yl]piperidin-4-yl}methyl)-6-methylpyrimidin-4-yl]carbonyl}amino)acetic acid, ({[2-{(1-[4'-(acetoxymethyl)biphenyl-4-yl]piperidin-4-yl}methyl)-5-hydroxy-6-methylpyrimidin-4-yl]carbonyl}amino)acetic acid, ({[5-hydroxy-2-{(1-[4'-(1-hydroxyethyl)biphenyl-4-yl]piperidin-4-yl}methyl)-6-methylpyrimidin-4-yl]carbonyl}amino)acetic acid, ({[5-hydroxy-2-{(1-[4'-(2-hydroxyethyl)biphenyl-4-yl]piperidin-4-yl}methyl)-6-methylpyrimidin-4-yl]carbonyl}amino)acetic acid, ({[5-hydroxy-2-{(1-[4'-(2-hydroxypropyl)biphenyl-4-yl]piperidin-4-yl}methyl)-6-methylpyrimidin-4-yl]carbonyl}amino)acetic acid, ({[5-hydroxy-2-{(1-[4'-(2-hydroxy-1,1-dimethylethyl)biphenyl-4-yl]piperidin-4-yl}methyl)-6-methylpyrimidin-4-yl]carbonyl}amino)acetic acid, ({[2-{(1-[4'-(dimethylcarbamoyl)biphenyl-4-yl]piperidin-4-yl}methyl)-5-hydroxy-6-methylpyrimidin-4-yl]carbonyl}amino)acetic acid, ({[5-hydroxy-6-methyl-2-{(1-[4'-(methylcarbamoyl)biphenyl-4-yl]piperidin-4-yl}methyl)pyrimidin-4-yl]carbonyl}amino)acetic acid,

[({2-[(1-{4'-[2-(dimethylamino)-2-oxoethyl]biphenyl-4-yl}piperidin-4-yl)methyl]-5-hydroxy-6-methylpyrimidin-4-yl}carbonyl)amino]acetic acid,

[({5-hydroxy-2-[(1-{4-[4-(hydroxymethyl)benzyl]phenyl}piperidin-4-yl)methyl]-6-methylpyrimidin-4-yl}carbonyl)amino]acetic acid,

[({5-hydroxy-2-[(1-{4-[3-(hydroxymethyl)benzyl]phenyl}piperidin-4-yl)methyl]-6-methylpyrimidin-4-yl}carbonyl)amino]acetic acid,

[({5-hydroxy-2-[(1-{4-[5-(1-hydroxyethyl)pyridin-2-yl]phenyl}piperidin-4-yl)methyl]-6-methylpyrimidin-4-yl}carbonyl)amino]acetic acid, {[(5-hydroxy-2-{[1-(4-{5-[1-(methoxymethoxy)ethyl]pyridin-2-yl}phenyl)piperidin-4-yl]methyl}-6-methylpyrimidin-4-yl)carbonyl]amino}acetic acid,

[({2-[(1-{4-[5-(1-acetoxyethyl)pyridin-2-yl]phenyl}piperidin-4-yl)methyl]-5-hydroxy-6-methylpyrimidin-4-yl}carbonyl)amino]acetic acid,

[({5-hydroxy-2-[(1-{4-[5-(hydroxymethyl)pyridin-2-yl]phenyl}piperidin-4-yl)methyl]-6-methylpyrimidin-4-yl}carbonyl)amino]acetic acid,

[({2-[(1-{4-[5-(ethoxycarbonyl)pyridin-2-yl]phenyl}piperidin-4-yl)methyl]-5-hydroxy-6-methylpyrimidin-4-yl}carbonyl)amino]acetic acid,

[({2-[(1-{4-[2-(ethoxycarbonyl)benzyl]phenyl}piperidin-4-yl)methyl]-5-hydroxy-6-methylpyrimidin-4-yl}carbonyl)amino]acetic acid, {[(5-hydroxy-2-{[1-(4-{[6-(2-hydroxyethoxy)pyridin-3-yl]methyl}phenyl)piperidin-4-yl]methyl}-6-methylpyrimidin-4-yl)carbonyl]amino}acetic acid,

[({5-hydroxy-2-[(1-{5-[4-(hydroxymethyl)phenyl]pyridin-2-yl}piperidin-4-yl)methyl]-6-methylpyrimidin-4-yl}carbonyl)amino]acetic acid,

[({5-hydroxy-2-[(1-{5-[4-(2-hydroxypropyl)phenyl]pyridin-2-yl}piperidin-4-yl)methyl]-6-methylpyrimidin-4-yl}carbonyl)amino]acetic acid,

[({5-hydroxy-2-[(1-{5-[4-(2-hydroxy-1,1-dimethylethyl)phenyl]pyridin-2-yl}piperidin-4-yl)methyl]-6-methylpyrimidin-4-yl}carbonyl)amino]acetic acid, ({[2-{(1-[2-chloro-4'-(hydroxymethyl)biphenyl-4-yl]piperidin-4-yl}methyl)-5-hydroxy-6-methylpyrimidin-4-yl]carbonyl}amino)acetic acid, ({[5-hydroxy-2-{(1-[4'-(hydroxymethyl)-2-methylbiphenyl-4-yl]piperidin-4-yl}methyl)-6-methylpyrimidin-4-yl]carbonyl}amino)acetic acid, ({[2-{(1-[3'-chloro-4'-(hydroxymethyl)biphenyl-4-yl]piperidin-4-yl}methyl)-5-hydroxy-6-methylpyrimidin-4-yl]carbonyl}amino)acetic acid, ({[5-hydroxy-2-{(1-[4'-(hydroxymethyl)-2'-methylbiphenyl-4-yl]piperidin-4-yl}methyl)-6-methylpyrimidin-4-yl]carbonyl}amino)acetic acid, ({[5-hydroxy-2-{(1-[4'-(hydroxymethyl)-2,3'-dimethylbiphenyl-4-yl]piperidin-4-yl}methyl)-6-methylpyrimidin-4-yl]carbonyl}amino)acetic acid, ({[5-hydroxy-2-{(1-[4'-(2-hydroxybutyl)biphenyl-4-yl]piperidin-4-yl}methyl)-6-methylpyrimidin-4-yl]carbonyl}amino)acetic acid,

[({5-hydroxy-2-[(1-{4-[4-(2-hydroxypropyl)benzyl]phenyl}piperidin-4-yl)methyl]-6-methylpyrimidin-4-yl}carbonyl)amino]acetic acid,

[({5-hydroxy-2-[(1-{4-[4-(2-hydroxy-1,1-dimethylethyl)benzyl]phenyl}piperidin-4-yl)methyl]-6-methylpyrimidin-4-yl}carbonyl)amino]acetic acid, ({[2-{(1-[4'-(1,1-difluoro-2-hydroxyethyl)biphenyl-4-yl]piperidin-4-yl}methyl)-5-hydroxy-6-methylpyrimidin-4-yl]carbonyl}amino)acetic acid, ({[2-{(1-[4'-(1,1-difluoro-2-hydroxypropyl)biphenyl-4-yl]piperidin-4-yl}methyl)-5-hydroxy-6-methylpyrimidin-4-yl]carbonyl}amino)acetic acid, ({[2-{(1-[4'-(1,1-difluoro-2-hydroxy-2-methylpropyl)biphenyl-4-yl]piperidin-4-yl}methyl)-5-hydroxy-6-methylpyrimidin-4-yl]carbonyl}amino)acetic acid, {[(5-[(2,2-dimethylpropanoyl)oxy]-2-{[1-(4'-{[(2,2-dimethylpropanoyl)oxy]methyl}biphenyl-4-yl)piperidin-4-yl]methyl}-6-methylpyrimidin-4-yl)carbonyl]amino}acetic acid, {[(2-{[1-(4'-{[(2,2-dimethylpropanoyl)oxy]methyl}biphenyl-4-yl)piperidin-4-yl]methyl}-5-hydroxy-6-methylpyrimidin-4-yl)carbonyl]amino}acetic acid, ({[5-hydroxy-2-{(1-[4'-(methoxymethyl)biphenyl-4-yl]piperidin-4-yl}methyl)-6-methylpyrimidin-4-yl]carbonyl}amino)acetic acid, ({[2-{(1-[2'-fluoro-4'-(hydroxymethyl)biphenyl-4-yl]piperidin-4-yl}methyl)-5-hydroxy-6-methylpyrimidin-4-yl]carbonyl}amino)acetic acid, ({[2-{(1-[3'-fluoro-4'-(hydroxymethyl)biphenyl-4-yl]piperidin-4-yl}methyl)-5-hydroxy-6-methylpyrimidin-4-yl]carbonyl}amino)acetic acid, ({[2-{(1-[2-fluoro-4'-(hydroxymethyl)biphenyl-4-yl]piperidin-4-yl}methyl)-5-hydroxy-6-methylpyrimidin-4-yl]carbonyl}amino)acetic acid, ({[2-{(1-[3-fluoro-4'-(hydroxymethyl)biphenyl-4-yl]piperidin-4-yl}methyl)-5-hydroxy-6-methylpyrimidin-4-yl]carbonyl}amino)acetic acid, ({[5-hydroxy-2-{(1-[4'-(hydroxymethyl)-3'-methylbiphenyl-4-yl]piperidin-4-yl}methyl)-6-methylpyrimidin-4-yl]carbonyl}amino)acetic acid, ({[2-{(1-[3',5'-difluoro-4'-(hydroxymethyl)biphenyl-4-yl]piperidin-4-yl}methyl)-5-hydroxy-6-methylpyrimidin-4-yl]carbonyl}amino)acetic acid, ({[2-{(1-[3',5'-dichloro-4'-(hydroxymethyl)biphenyl-4-yl]piperidin-4-yl}methyl)-5-hydroxy-6-methylpyrimidin-4-yl]carbonyl}amino)acetic acid, ({[2-{(1-[3',5'-dimethyl-4'-(hydroxymethyl)biphenyl-4-yl]piperidin-4-yl}methyl)-5-hydroxy-6-methylpyrimidin-4-yl]carbonyl}amino)acetic acid,

[({5-hydroxy-2-[(1-{4'-[2-hydroxy-3-methoxypropyl]biphenyl-4-yl}piperidin-4-yl)methyl]-6-methylpyrimidin-4-yl}carbonyl)amino]acetic acid, ({[5-hydroxy-2-{(1-[4'-(3-hydroxypropyl)biphenyl-4-yl]piperidin-4-yl}methyl)-6-methylpyrimidin-4-yl]carbonyl}amino)acetic acid, ({[5-hydroxy-2-{(1-[4'-(hydroxymethyl)-3'-isopropylbiphenyl-4-yl]piperidin-4-yl}methyl)-6-methylpyrimidin-4-yl]carbonyl}amino)acetic acid,

[({2-[(1-{5-[3-fluoro-4-(hydroxymethyl)phenyl]pyridin-2-yl}piperidin-4-yl)methyl]-5-hydroxy-6-methylpyrimidin-4-yl}carbonyl)amino]acetic acid,

[({2-[(1-{5-[3-chloro-4-(hydroxymethyl)phenyl]pyridin-2-yl}piperidin-4-yl)methyl]-5-hydroxy-6-methylpyrimidin-4-yl}carbonyl)amino]acetic acid, or

[({5-hydroxy-2-[(1-{5-[4-(hydroxymethyl)-3-methylphenyl]pyridin-2-yl}piperidin-4-yl)methyl]-6-methylpyrimidin-4-yl}carbonyl)amino]acetic acid,

(26) a pharmaceutical composition containing as an active ingredient a compound, pharmacologically acceptable ester thereof, or pharmacologically acceptable salt thereof according to any one of (1) to (25) above,

(27) a pharmaceutical composition according to (26) above, for the prophylaxis and/or treatment of anemia,

(28) a pharmaceutical composition according to (27) above, wherein the anemia is nephrogenic anemia, anemia of prematurity, anemia incidental to chronic diseases, anemia incidental to cancer chemotherapy, cancerous anemia, inflammation-associated anemia, or anemia incidental to congestive heart failure,

(29) a pharmaceutical composition according to (27) above, wherein the anemia is anemia incidental to chronic kidney disease,

(30) a pharmaceutical composition according to (26) above, for producing erythropoietin,

(31) use of a compound, pharmacologically acceptable ester thereof, or pharmacologically acceptable salt thereof according to any one of (1) to (25) above, for producing a medicament,

(32) use according to (31) above, wherein the medicament is a medicament for the prophylaxis and/or treatment of anemia,

(33) use according to (32) above, wherein the anemia is nephrogenic anemia, anemia of prematurity, anemia incidental to chronic diseases, anemia incidental to cancer chemotherapy, cancerous anemia, inflammation-associated anemia, or anemia incidental to congestive heart failure,

(34) use according to (32) above, wherein the anemia is anemia incidental to chronic kidney disease,

(35) a method for producing erythropoietin, comprising: administering a pharmacologically effective amount of a compound, pharmacologically acceptable ester thereof, or pharmacologically acceptable salt thereof according to any one of (1) to (25) above to a mammal or bird,

(36) a method for the treatment or prophylaxis of a disease, comprising: administering a pharmacologically effective amount of a compound, pharmacologically acceptable ester thereof, or pharmacologically acceptable salt thereof according to any one of (1) to (25) above to a mammal,

(37) a method according to (36) above, wherein the disease is anemia,

(38) a method according to (36) above, wherein the disease is nephrogenic anemia, anemia of prematurity, anemia incidental to chronic diseases, anemia incidental to cancer chemotherapy, cancerous anemia, inflammation-associated anemia, or anemia incidental to congestive heart failure,

(39) a method according to (36) above, wherein the disease is anemia incidental to chronic kidney disease,

(40) a method according to any one of (36) to (39) above, wherein the mammal is a human,

(41) a compound, pharmacologically acceptable ester thereof, or pharmacologically acceptable salt thereof according to any one of (1) to (25) above, for use in a method for the treatment or prophylaxis of a disease,

(42) a compound, pharmacologically acceptable ester thereof, or pharmacologically acceptable salt thereof according to (41) above, wherein the disease is anemia,

(43) a compound, pharmacologically acceptable ester thereof, or pharmacologically acceptable salt thereof according to (41) above, wherein the disease is nephrogenic anemia, anemia of prematurity, anemia incidental to chronic diseases, anemia incidental to cancer chemotherapy, cancerous anemia, inflammation-associated anemia, or anemia incidental to congestive heart failure, or

(44) a compound, pharmacologically acceptable ester thereof, or pharmacologically acceptable salt thereof according to (41) above, wherein the disease is anemia incidental to chronic kidney disease.

In one aspect, the present invention provides:

(45) a compound, pharmacologically acceptable ester thereof, or pharmacologically acceptable salt thereof according to (1) above, wherein:

$R^6$ represents a hydrogen atom, a halogen atom, or a $C_1$-$C_6$ alkyl group, and $R^7$ represents a hydroxy $C_1$-$C_6$ alkyl group which may have 1 or 2 substituents independently selected from substituent group α, a hydroxyhalo $C_1$-$C_6$ alkyl group which may have 1 or 2 substituents independently selected from substituent group α, a ($C_1$-$C_6$ alkoxy)carbonyl group which may have 1 or 2 substituents independently selected from substituent group α, a $C_1$-$C_6$ alkoxy $C_1$-$C_6$ alkoxy $C_1$-$C_6$ alkyl group which may have 1 or 2 substituents independently selected from substituent group α, a hydroxy $C_1$-$C_6$ alkoxy group which may have 1 or 2 substituents independently selected from substituent group α, a $C_1$-$C_6$ alkylcarbamoyl group which may have 1 or 2 substituents independently selected from substituent group α, a ($C_1$-$C_6$ alkyl) ($C_1$-$C_6$ alkyl)carbamoyl group which may have 1 or 2 substituents independently selected from substituent group α, a $C_1$-$C_6$ alkoxycarbamoyl group which may have 1 or 2 substituents independently selected from substituent group α, a $C_1$-$C_6$ alkylcarbamoyl $C_1$-$C_6$ alkyl group which may have 1 or 2 substituents independently selected from substituent group α, a ($C_1$-$C_6$ alkyl) ($C_1$-$C_6$ alkyl)carbamoyl $C_1$-$C_6$ alkyl group which may have 1 or 2 substituents independently selected from substituent group α, a $C_2$-$C_7$ alkanoylamino group which may have 1 or 2 substituents independently selected from substituent group α, or a $C_2$-$C_7$ alkanoylamino $C_1$-$C_6$ alkyl group which may have 1 or 2 substituents independently selected from substituent group α.

The compound of the present invention represented by the aforementioned general formula (1) has a 5-hydroxypyrimidine-4-carboxamide skeleton. A substituent at position 2 of said pyrimidine ring has 3 cyclic groups, and said cyclic groups have a specific substituent. The compound of the present invention, pharmacologically acceptable ester thereof, or pharmacologically acceptable salt thereof has a superior EPO production-enhancing activity.

The following provides an explanation of substituents in the compound of the present invention.

A "halogen atom" in the definitions of $R^4$, $R^5$, and $R^6$ refers to a fluorine atom, a chlorine atom, a bromine atom or an iodine atom, preferably, a fluorine atom.

A "$C_1$-$C_3$ alkyl group" in the definition of $R^2$ refers to a straight or branched chain alkyl group having 1 to 3 carbon atoms. Examples include a methyl group, an ethyl group, a propyl group, and an isopropyl group.

A "$C_1$-$C_6$ alkyl group" in the definitions of $R^4$, $R^5$, and $R^6$ refers to a straight or branched chain alkyl group having 1 to 6 carbon atoms. Examples include a methyl group, an ethyl group, a propyl group, an isopropyl group, a butyl group, a sec-butyl group, a tert-butyl group, a pentyl group, an isopentyl group, a 2-methylbutyl group, a neopentyl group, a 1-ethylpropyl group, a hexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, a 2-ethylbutyl group, and the like. The $C_1$-$C_6$ alkyl group is preferably a $C_1$-$C_4$ alkyl group, more preferably a $C_1$-$C_3$ alkyl group.

A "hydroxy $C_1$-$C_6$ alkyl group" in the definition of $R^7$ refers to a group in which one or more hydrogen atoms (preferably, 1 or 2 hydrogen atoms) of the aforementioned "$C_1$-$C_6$ alkyl group" are substituted with a hydroxy group. Examples include a hydroxymethyl group, a 1-hydroxyethyl group, a 2-hydroxyethyl group, a 1-hydroxypropyl group, a 2-hydroxypropyl group, a 3-hydroxypropyl group, a 2-hydroxy-1,1-dimethylethyl group, a 2-hydroxybutyl group, a 2-hydroxypentyl group, and the like. The hydroxy $C_1$-$C_6$ alkyl group is preferably a hydroxy $C_1$-$C_4$ alkyl group, more preferably a hydroxy $C_1$-$C_3$ alkyl group.

A "hydroxyhalo $C_1$-$C_6$ alkyl group" in the definition of $R^7$ refers to a group in which 1 or 2 hydrogen atoms on a carbon atom of the aforementioned "hydroxy $C_1$-$C_6$ alkyl group" are substituted with an aforementioned "halogen atom". Examples include a 1-fluoro-2-hydroxyethyl group, a 1,1-difluoro-2-hydroxyethyl group, a 1-fluoro-2-hydroxypropyl group, a 1,1-difluoro-2-hydroxypropyl group, a 1,1-difluoro-3-hydroxypropyl group, a 1,1-difluoro-2-hydroxy-2-methylpropyl group, and the like. The hydroxyhalo $C_1$-$C_6$ alkyl group is preferably a hydroxyhalo $C_1$-$C_4$ alkyl group, more preferably a hydroxyhalo $C_1$-$C_3$ alkyl group.

A "$C_1$-$C_6$ alkoxy $C_1$-$C_6$ alkyl group" in the definition of $R^7$ refers to a group in which 1 hydrogen atom of the aforementioned "$C_1$-$C_6$ alkyl group" is substituted with the following "$C_1$-$C_6$ alkoxy group". Examples include a methoxymethyl group, a methoxyethyl group, a methoxypropyl group, a methoxybutyl group, an ethoxymethyl group, an ethoxyethyl group, an ethoxypropyl group, an ethoxybutyl group, a methoxypentyl group, and the like. The $C_1$-$C_6$ alkoxy $C_1$-$C_6$ alkyl group is preferably a $C_1$-$C_4$ alkoxy $C_1$-$C_4$ alkyl group, more preferably a $C_1$-$C_2$ alkoxy $C_1$-$C_2$ alkyl group.

A "$C_1$-$C_6$ alkoxy group" in the definition of the substituent group α refers to a group in which an aforementioned "$C_1$-$C_6$ alkyl group" is bonded to an oxygen atom. Examples include a methoxy group, an ethoxy group, an n-propoxy group, an n-butoxy group, an s-butoxy group, a tert-butoxy group, an n-pentoxy group, and the like. The $C_1$-$C_6$ alkoxy group is preferably a $C_1$-$C_4$ alkoxy group, more preferably a $C_1$-$C_2$ alkoxy group.

A "halo $C_1$-$C_6$ alkoxy group" in the definition of the substituent group α refers to a group in which 1 or 2 hydrogen atoms of the aforementioned "$C_1$-$C_6$ alkoxy group" are substituted with an aforementioned "halogen atom". Examples include a fluoromethoxy group, a chloromethoxy group, a 1-fluoroethoxy group, a 1-chloroethoxy group, a 2-fluoroethoxy group, a 1,2-difluoropropoxy group, and the like. The halo $C_1$-$C_6$ alkoxy group is preferably a halo $C_1$-$C_4$ alkoxy group, more preferably a halo $C_1$-$C_3$ alkoxy group.

A "$C_1$-$C_6$ alkoxyimino group" in the definition of the substituent group α refers to a group in which an aforementioned "$C_1$-$C_6$ alkoxy group" is bonded to an imino group. Examples include methoxyimino, ethoxyimino, n-propoxyimino, isopropoxyimino, n-butoxyimino, isobutoxyimino, s-butoxyimino, tert-butoxyimino, n-pentoxyimino, isopentoxyimino, 2-methylbutoxyimino, and the like. The $C_1$-$C_6$ alkoxyimino group is preferably a $C_1$-$C_4$ alkoxyimino group, more preferably a $C_1$-$C_3$ alkoxyimino group.

A "($C_1$-$C_6$ alkoxy)carbonyl group" in the definition of $R^7$ refers to a group in which an aforementioned "$C_1$-$C_6$ alkoxy group" is bonded to a carbonyl group. Examples include a methoxycarbonyl group, an ethoxycarbonyl group, an n-propoxycarbonyl group, an n-butoxycarbonyl group, and the like. The ($C_1$-$C_6$ alkoxy)carbonyl group is preferably a ($C_1$-$C_4$ alkoxy)carbonyl group, more preferably a ($C_1$-$C_3$ alkoxy)carbonyl group.

A "$C_1$-$C_6$ alkoxy $C_1$-$C_6$ alkoxy $C_1$-$C_6$ alkyl group" in the definition of $R^7$ refers to a group in which 1 hydrogen atom on the $C_1$-$C_6$ alkoxy of an aforementioned "$C_1$-$C_6$ alkoxy $C_1$-$C_6$ alkyl group" is substituted with an aforementioned "$C_1$-$C_6$ alkoxy group". Examples include a methoxymethoxymethyl group, an ethoxymethoxymethyl group, a methoxymethoxyethyl group (e.g., a 1-methoxymethoxyethyl group), a 2-ethoxymethoxyethyl group, a 3-methoxymethoxypropyl group, and the like. The $C_1$-$C_6$ alkoxy $C_1$-$C_6$ alkoxy $C_1$-$C_6$ alkyl group is preferably a $C_1$-$C_4$ alkoxy $C_1$-$C_4$ alkoxy $C_1$-$C_4$ alkyl group, more preferably a $C_1$-$C_2$ alkoxy $C_1$-$C_2$ alkoxy $C_1$-$C_2$ alkyl group.

A "hydroxy $C_1$-$C_6$ alkoxy group" in the definition of $R^7$ refers to a group in which 1 hydrogen atom of the aforementioned "$C_1$-$C_6$ alkoxy group" is substituted with a hydroxy group. Examples include a hydroxymethoxy group, a hydroxyethoxy group (e.g., a 2-hydroxyethoxy group), a 2-hydroxypropoxy group, and the like. The hydroxy $C_1$-$C_6$ alkoxy group is preferably a hydroxy $C_1$-$C_4$ alkoxy group, more preferably a hydroxy $C_1$-$C_3$ alkoxy group.

A "$C_1$-$C_6$ alkylcarbamoyl group" in the definitions of $R^6$ and $R^7$ refers to a group in which 1 hydrogen atom of a carbamoyl group is substituted with an aforementioned "$C_1$-$C_6$ alkyl group". Examples include a methylcarbamoyl group, an ethylcarbamoyl group, a propylcarbamoyl group, and the like. The $C_1$-$C_6$ alkylcarbamoyl group is preferably a $C_1$-$C_4$ alkylcarbamoyl group, more preferably a $C_1$-$C_3$ alkylcarbamoyl group.

A "($C_1$-$C_6$ alkyl) ($C_1$-$C_6$ alkyl)carbamoyl group" in the definitions of $R^6$ and $R^7$ refers to a group in which 2 hydrogen atoms of a carbamoyl group are each substituted with an aforementioned "$C_1$-$C_6$ alkyl group". Examples include a dimethylcarbamoyl group, a methylethylcarbamoyl group, a methylpropylcarbamoyl group, a diethylcarbamoyl group, and the like. The ($C_1$-$C_6$ alkyl) ($C_1$-$C_6$ alkyl)carbamoyl group is preferably a ($C_1$-$C_4$ alkyl) ($C_1$-$C_4$ alkyl)carbamoyl group, more preferably a ($C_1$-$C_2$ alkyl) ($C_1$-$C_2$ alkyl)carbamoyl group.

A "$C_1$-$C_6$ alkoxycarbamoyl group" in the definition of $R^7$ refers to a group in which 1 hydrogen atom of a carbamoyl group is substituted with an aforementioned "$C_1$-$C_6$ alkoxy group". Examples include a methoxycarbamoyl group, an ethoxycarbamoyl group, an n-propoxycarbamoyl group, and the like. The $C_1$-$C_6$ alkoxycarbamoyl group is preferably a $C_1$-$C_4$ alkoxycarbamoyl group, more preferably a $C_1$-$C_3$ alkoxycarbamoyl group.

A "$C_1$-$C_6$ alkylcarbamoyl $C_1$-$C_6$ alkyl group" in the definition of $R^7$ refers to a group in which 1 hydrogen atom of an aforementioned "$C_1$-$C_6$ alkyl group" is substituted with an aforementioned "$C_1$-$C_6$ alkylcarbamoyl group". Examples include a methylcarbamoylmethyl group, an ethylcarbamoylmethyl group, a propylcarbamoylmethyl group, a methylcarbamoylethyl group, an ethylcarbamoylethyl group, and the like. The $C_1$-$C_6$ alkylcarbamoyl $C_1$-$C_6$ alkyl group is preferably a $C_1$-$C_4$ alkylcarbamoyl $C_1$-$C_4$ alkyl group, more preferably a $C_1$-$C_2$ alkylcarbamoyl $C_1$-$C_2$ alkyl group.

A "($C_1$-$C_6$ alkyl) ($C_1$-$C_6$ alkyl)carbamoyl $C_1$-$C_6$ alkyl group" in the definition of $R^7$ refers to a group in which 1 hydrogen atom of an aforementioned "$C_1$-$C_6$ alkyl group" is substituted with an aforementioned "($C_1$-$C_6$ alkyl) ($C_1$-$C_6$ alkyl)carbamoyl group". Examples include a dimethylcarbamoylmethyl group, an ethylmethylcarbamoylmethyl group, and the like. The ($C_1$-$C_6$ alkyl) ($C_1$-$C_6$ alkyl)carbamoyl $C_1$-$C_6$ alkyl group is preferably a ($C_1$-$C_4$ alkyl) ($C_1$-$C_4$ alkyl)carbamoyl $C_1$-$C_4$ alkyl group, more preferably a ($C_1$-$C_2$ alkyl) ($C_1$-$C_2$ alkyl)carbamoyl $C_1$-$C_2$ alkyl group.

A "$C_2$-$C_7$ alkanoylamino group" in the definitions of $R^7$ and substituent group α refers to, for example, a group in which a straight or branched chain alkanoyl group having 2 to 7 carbons (e.g., an acetyl group, a propionyl group, a butyryl group, an isobutyryl group, a pentanoyl group, a pivaloyl group, a valeryl group, an isovaleryl group, a hexanoyl group, a heptanoyl group, and the like) is bonded to an amino group. Examples include an acetylamino group, a propionylamino group, a butyrylamino group, an isobutyrylamino group, a pentanoylamino group, and the like. The $C_2$-$C_7$ alkanoylamino group is preferably a $C_2$-$C_5$ alkanoylamino group, more preferably a $C_2$-$C_4$ alkanoylamino group.

A "$C_2$-$C_7$ alkanoylamino $C_1$-$C_6$ alkyl group" in the definition of $R^7$ refers to a group in which 1 hydrogen atom of an aforementioned "$C_1$-$C_6$ alkyl group" is substituted with an aforementioned "$C_2$-$C_7$ alkanoylamino group". Examples include an acetylaminomethyl group, a propionylaminomethyl group, a butyrylaminomethyl group, an isobutyrylaminomethyl group, a pentanoylaminomethyl group, and the like. The $C_2$-$C_7$ alkanoylamino $C_1$-$C_6$ alkyl group is preferably a $C_2$-$C_5$ alkanoylamino $C_1$-$C_4$ alkyl group, more preferably a $C_2$-$C_3$ alkanoylamino $C_1$-$C_2$ alkyl group.

A "$C_2$-$C_7$ alkanoyloxy $C_1$-$C_6$ alkyl group" in the definition of $R^7$ refers to a group in which a hydrogen atom on an oxygen atom of an aforementioned "hydroxy $C_1$-$C_6$ alkyl group" is substituted with an aforementioned "$C_2$-$C_7$ alkanoyl group". Examples include an acetyloxymethyl group, a propionyloxymethyl group, a butyryloxymethyl group, an isobutyryloxymethyl group, a pentanoyloxymethyl group, and the like.

The $C_2$-$C_7$ alkanoyloxy $C_1$-$C_6$ alkyl group is preferably a $C_2$-$C_5$ alkanoyloxy $C_1$-$C_4$ alkyl group, more preferably a $C_2$-$C_3$ alkanoyloxy $C_1$-$C_2$ alkyl group.

A "monocyclic hydrocarbon ring group" in the definitions of ring $Q^2$ and ring $Q^3$ refers to a saturated, partially unsaturated or unsaturated 5- to 7-membered monocyclic hydrocarbon group. Examples include monocyclic aromatic hydrocarbon ring groups such as a phenyl group; and monocyclic non-aromatic hydrocarbon ring groups such as a cyclopentyl group, a cyclohexyl group, a cycloheptyl group, a cyclopentenyl group, a cyclohexenyl group, and a cycloheptenyl group. In the present invention, a 6-membered aromatic hydrocarbon ring group or non-aromatic hydrocarbon ring group is preferred, and a 6-membered aromatic hydrocarbon ring group is more preferred.

A "monocyclic heterocyclic group" in the definitions of ring $Q^1$, ring $Q^2$ and ring $Q^3$ refers to a saturated, partially unsaturated or unsaturated 5- to 7-membered monocyclic heterocyclic group containing 1 or 2 atoms selected from the group consisting of a nitrogen atom, a sulfur atom and an oxygen atom. Examples include monocyclic non-aromatic heterocyclic groups such as a tetrahydrofuranyl group, a tetrahydropyranyl group, a dioxolanyl group, a dioxanyl group, a dioxepanyl group, a pyrrolidinyl group, a piperidyl group, an azepanyl group, a dihydropyrrolyl group, a dihydropyridyl group, a tetrahydropyridyl group, a piperadinyl group, a morpholinyl group, a dihydrooxazolyl group, and a dihydrothiazolyl group; monocyclic aromatic heterocyclic groups such as a pyrrolyl group, a pyridyl group, a thienyl group, a furyl group, a pyrimidinyl group, a pyranyl group, a pyridazinyl group, a pyrazinyl group, a pyrazolyl group, an imidazolyl group, a thiazolyl group, an isothiazolyl group, an oxazolyl group, and an isoxazolyl group; and the like. As the "monocyclic heterocyclic group" in the present invention, a 6-membered aromatic heterocyclic group or non-aromatic heterocyclic group containing 1 or 2 nitrogen atoms is preferred, and a 6-membered aromatic heterocyclic group or non-aromatic heterocyclic group containing 1 nitrogen atom is more preferred. As the monocyclic heterocyclic group in the ring $Q^1$, a 6-membered non-aromatic heterocyclic group containing 1 nitrogen atom is even more preferred.

$R^1$ in the compound of the present invention is explained hereinafter.

In the compound of the present invention, $R^1$ refers to a group represented by the following general formula (1A).

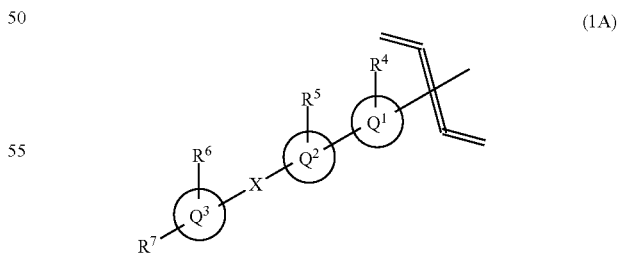

(1A)

In the above general formula (1A), $R^4$ and $R^5$ each independently refers to a hydrogen atom, a halogen atom or a $C_1$-$C_6$ alkyl group, and $R^6$ refers to a hydrogen atom, a halogen atom, a $C_1$-$C_6$ alkyl group, a carbamoyl group, a $C_1$-$C_6$ alkylcarbamoyl group, or a ($C_1$-$C_6$ alkyl) ($C_1$-$C_6$ alkyl)carbamoyl group.

In the present invention, $R^4$ is preferably a hydrogen atom.

In the present invention, $R^5$ is preferably a hydrogen atom, a halogen atom or a methyl group, and more preferably a hydrogen atom.

In the present invention, $R^6$ is preferably a hydrogen atom, a halogen atom, or a methyl group, more preferably a hydrogen atom, a chlorine atom, or a methyl group, and even more preferably a hydrogen atom.

In the present invention, $R^7$ is a hydroxy $C_1$-$C_6$ alkyl group which may have 1 or 2 substituents independently selected from substituent group α, a hydroxyhalo $C_1$-$C_6$ alkyl group which may have 1 or 2 substituents independently selected from substituent group α, a $C_1$-$C_6$ alkoxy $C_1$-$C_6$ alkyl group which may have 1 or 2 substituents independently selected from substituent group α, a ($C_1$-$C_6$ alkoxy)carbonyl group which may have 1 or 2 substituents independently selected from substituent group α, a $C_1$-$C_6$ alkoxy $C_1$-$C_6$ alkoxy $C_1$-$C_6$ alkyl group which may have 1 or 2 substituents independently selected from substituent group α, a hydroxy $C_1$-$C_6$ alkoxy group which may have 1 or 2 substituents independently selected from substituent group α, a $C_1$-$C_6$ alkylcarbamoyl group which may have 1 or 2 substituents independently selected from substituent group α, a ($C_1$-$C_6$ alkyl) ($C_1$-$C_6$ alkyl)carbamoyl group which may have 1 or 2 substituents independently selected from substituent group α, a $C_1$-$C_6$ alkoxycarbamoyl group which may have 1 or 2 substituents independently selected from substituent group α, a $C_1$-$C_6$ alkylcarbamoyl $C_1$-$C_6$ alkyl group which may have 1 or 2 substituents independently selected from substituent group α, a ($C_1$-$C_6$ alkyl) ($C_1$-$C_6$ alkyl)carbamoyl $C_1$-$C_6$ alkyl group which may have 1 or 2 substituents independently selected from substituent group α, a $C_2$-$C_7$ alkanoylamino group which may have 1 or 2 substituents independently selected from substituent group α, a $C_2$-$C_7$ alkanoylamino $C_1$-$C_6$ alkyl group which may have 1 or 2 substituents independently selected from substituent group α, or a $C_2$-$C_7$ alkanoyloxy $C_1$-$C_6$ alkyl group which may have 1 or 2 substituents independently selected from substituent group α, and the substituent group α refers to a group consisting of an oxo group, a hydroxy group, an amino group, a carboxy group, a carbamoyl group, a $C_1$-$C_6$ alkoxy group, a halo $C_1$-$C_6$ alkoxy group, a $C_2$-$C_7$ alkanoylamino group, a hydroxyimino group, and a $C_1$-$C_6$ alkoxyimino group.

The substituent group α in the present invention is preferably a group consisting of a hydroxy group, a $C_1$-$C_6$ alkoxy group, a halo $C_1$-$C_6$ alkoxy group, and a $C_2$-$C_7$ alkanoylamino group, more preferably a group consisting of a hydroxy group and a $C_1$-$C_2$ alkoxy group.

In the present invention, $R^7$ is preferably a hydroxy $C_1$-$C_6$ alkyl group, a dihydroxy $C_1$-$C_6$ alkyl group, a ($C_1$-$C_6$ alkoxy)hydroxy $C_1$-$C_6$ alkyl group, a (halo $C_1$-$C_6$ alkoxy)hydroxy $C_1$-$C_6$ alkyl group, a ($C_2$-$C_7$ alkanoylamino)hydroxy $C_1$-$C_6$ alkyl group, a hydroxyhalo $C_1$-$C_6$ alkyl group, a dihydroxyhalo $C_1$-$C_6$ alkyl group, a ($C_1$-$C_6$ alkoxy)hydroxyhalo $C_1$-$C_6$ alkyl group, a (halo $C_1$-$C_6$ alkoxy)hydroxyhalo $C_1$-$C_6$ alkyl group, a ($C_2$-$C_7$ alkanoylamino)hydroxyhalo $C_1$-$C_6$ alkyl group, a $C_1$-$C_6$ alkoxy $C_1$-$C_6$ alkyl group, a hydroxy $C_1$-$C_6$ alkoxy $C_1$-$C_6$ alkyl group, a dihydroxy $C_1$-$C_6$ alkoxy $C_1$-$C_6$ alkyl group, a (halo $C_1$-$C_6$ alkoxy)$C_1$-$C_6$ alkoxy $C_1$-$C_6$ alkyl group, a ($C_2$-$C_7$ alkanoylamino)$C_1$-$C_6$ alkoxy $C_1$-$C_6$ alkyl group, a ($C_1$-$C_6$ alkoxy)carbonyl group, a (hydroxy $C_1$-$C_6$ alkoxy)carbonyl group, a ($C_1$-$C_6$ alkoxy $C_1$-$C_6$ alkoxy)carbonyl group, a (halo $C_1$-$C_6$ alkoxy $C_1$-$C_6$ alkoxy)carbonyl group, a ($C_2$-$C_7$ alkanoylamino $C_1$-$C_6$ alkoxy)carbonyl group, a $C_1$-$C_6$ alkoxy $C_1$-$C_6$ alkoxy $C_1$-$C_6$ alkyl group, a hydroxy $C_1$-$C_6$ alkoxy $C_1$-$C_6$ alkoxy $C_1$-$C_6$ alkyl group, a $C_1$-$C_6$ alkoxy $C_1$-$C_6$ alkoxy $C_1$-$C_6$ alkoxy $C_1$-$C_6$ alkyl group, a halo $C_1$-$C_6$ alkoxy $C_1$-$C_6$ alkoxy $C_1$-$C_6$ alkoxy $C_1$-$C_6$ alkyl group, a $C_2$-$C_7$ alkanoylamino $C_1$-$C_6$ alkoxy $C_1$-$C_6$ alkoxy $C_1$-$C_6$ alkyl group, a hydroxy $C_1$-$C_6$ alkoxy group, a dihydroxy $C_1$-$C_6$ alkoxy group, a ($C_1$-$C_6$ alkoxy)hydroxy $C_1$-$C_6$ alkoxy group, a (halo $C_1$-$C_6$ alkoxy)hydroxy $C_1$-$C_6$ alkoxy group, a ($C_2$-$C_7$ alkanoylaminohydroxy $C_1$-$C_6$ alkoxy group, a $C_1$-$C_6$ alkylcarbamoyl group, a hydroxy $C_1$-$C_6$ alkylcarbamoyl group, a $C_1$-$C_6$ alkoxy $C_1$-$C_6$ alkylcarbamoyl group, a halo $C_1$-$C_6$ alkoxy $C_1$-$C_6$ alkylcarbamoyl group, a ($C_2$-$C_7$ alkanoylamino)$C_1$-$C_6$ alkylcarbamoyl group, a ($C_1$-$C_6$ alkyl)($C_1$-$C_6$ alkyl)carbamoyl group, a (hydroxy $C_1$-$C_6$ alkyl) ($C_1$-$C_6$ alkyl)carbamoyl group, a ($C_1$-$C_6$ alkoxy $C_1$-$C_6$ alkyl) ($C_1$-$C_6$ alkyl)carbamoyl group, a (halo $C_1$-$C_6$ alkoxy $C_1$-$C_6$ alkyl) ($C_1$-$C_6$ alkyl)carbamoyl group, a ($C_2$-$C_7$ alkanoylamino $C_1$-$C_6$ alkyl) ($C_1$-$C_6$ alkyl)carbamoyl group, a dihydroxy $C_1$-$C_6$ alkylcarbamoyl group, a ($C_1$-$C_6$ alkoxy)hydroxy $C_1$-$C_6$ alkylcarbamoyl group, a (halo $C_1$-$C_6$ alkoxy)hydroxy $C_1$-$C_6$ alkylcarbamoyl group, a ($C_2$-$C_7$ alkanoylamino)hydroxy $C_1$-$C_6$ alkylcarbamoyl group, a $C_1$-$C_6$ alkoxycarbamoyl group, a hydroxy $C_1$-$C_6$ alkoxycarbamoyl group, a ($C_1$-$C_6$ alkoxy $C_1$-$C_6$ alkoxy)carbamoyl group, a (halo $C_1$-$C_6$ alkoxy $C_1$-$C_6$ alkoxy)carbamoyl group, a ($C_2$-$C_7$ alkanoylamino $C_1$-$C_6$ alkoxy)carbamoyl group, a $C_1$-$C_6$ alkylcarbamoyl $C_1$-$C_6$ alkyl group, a hydroxy $C_1$-$C_6$ alkylcarbamoyl $C_1$-$C_6$ alkyl group, a ($C_1$-$C_6$ alkoxy $C_1$-$C_6$ alkyl)carbamoyl $C_1$-$C_6$ alkyl group, a (halo $C_1$-$C_6$ alkoxy $C_1$-$C_6$ alkyl)carbamoyl $C_1$-$C_6$ alkyl group, a ($C_2$-$C_7$ alkanoylamino $C_1$-$C_6$ alkyl)carbamoyl $C_1$-$C_6$ alkyl group, a ($C_1$-$C_6$ alkyl) ($C_1$-$C_6$ alkyl)carbamoyl $C_1$-$C_6$ alkyl group, a (hydroxy $C_1$-$C_6$ alkyl) ($C_1$-$C_6$ alkyl)carbamoyl $C_1$-$C_6$ alkyl group, a ($C_1$-$C_6$ alkoxy $C_1$-$C_6$ alkyl) ($C_1$-$C_6$ alkyl)carbamoyl $C_1$-$C_6$ alkyl group, a (halo $C_1$-$C_6$ alkoxy $C_1$-$C_6$ alkyl) ($C_1$-$C_6$ alkyl)carbamoyl $C_1$-$C_6$ alkyl group, a ($C_2$-$C_7$ alkanoylamino $C_1$-$C_6$ alkyl) ($C_1$-$C_6$ alkyl)carbamoyl $C_1$-$C_6$ alkyl group, a ($C_1$-$C_6$ alkoxy)hydroxy $C_1$-$C_6$ alkylcarbamoyl $C_1$-$C_6$ alkyl group, a (halo $C_1$-$C_6$ alkoxy)hydroxy $C_1$-$C_6$ alkylcarbamoyl $C_1$-$C_6$ alkyl group, or a ($C_2$-$C_7$ alkanoylamino)hydroxy $C_1$-$C_6$ alkylcarbamoyl $C_1$-$C_6$ alkyl group, more preferably a hydroxy $C_1$-$C_6$ alkyl group, a hydroxyhalo $C_1$-$C_6$ alkyl group, a $C_1$-$C_6$ alkoxy $C_1$-$C_6$ alkyl group, a hydroxy $C_1$-$C_6$ alkoxy $C_1$-$C_6$ alkyl group, a ($C_1$-$C_6$ alkoxy)carbonyl group, a $C_1$-$C_6$ alkoxy $C_1$-$C_6$ alkoxy $C_1$-$C_6$ alkyl group, a hydroxy $C_1$-$C_6$ alkoxy group, a $C_1$-$C_6$ alkylcarbamoyl group, a ($C_1$-$C_6$ alkyl) ($C_1$-$C_6$ alkyl)carbamoyl group, a hydroxy $C_1$-$C_6$ alkylcarbamoyl group, a $C_1$-$C_6$ alkoxycarbamoyl group, a $C_1$-$C_6$ alkylcarbamoyl $C_1$-$C_6$ alkyl group, a ($C_1$-$C_6$ alkyl) ($C_1$-$C_6$ alkyl)carbamoyl $C_1$-$C_6$ alkyl group, or a hydroxy $C_1$-$C_6$ alkylcarbamoyl $C_1$-$C_6$ alkyl group, even more preferably a hydroxymethyl group, a 1-hydroxyethyl group, a 2-hydroxyethyl group, a 1,1-difluoro-2-hydroxyethyl group, a 2-hydroxypropyl group, a 3-hydroxypropyl group, a 1,1-difluoro-2-hydroxypropyl group, a 2-hydroxybutyl group, a 2-hydroxy-1,1-dimethylethyl group, a 1,1-difluoro-2-hydroxy-2-methylpropyl group, a methoxymethyl group, a 2-hydroxy-3-methoxypropyl group, a methoxycarbonyl group, an ethoxycarbonyl group, a methoxymethoxymethyl group, a 1-methoxymethoxyethyl group, a 2-hydroxyethoxy group, a methylcarbamoyl group, a dimethylcarbamoyl group, a methylcarbamoylmethyl group, a dimethylcarbamoylmethyl group, a hydroxyethylcarbamoyl group, or a hydroxyethylcarbamoylmethyl group, and particularly preferably a hydroxymethyl group, a 1-hydroxyethyl group, a 2-hydroxyethyl group, a 2-hydroxypropyl group, a 3-hydroxypropyl group, a 2-hydroxybutyl group, a 2-hydroxy-1,1-dimethylethyl group, a methoxymethyl group, a 2-hydroxy-3-methoxypropyl group, an ethoxycarbonyl group, a 1-methoxymethoxyethyl group, a 2-hydroxyethoxy group, a methylcarbamoyl group, a dimethylcarbamoyl group, or a dimethylcarbamoylmethyl group.

In the present invention, X is preferably a single bond or methylene, and more preferably a single bond.

In the present invention, $R^1$ is preferably a group represented by the following general formula (1B).

[Chemical 7]

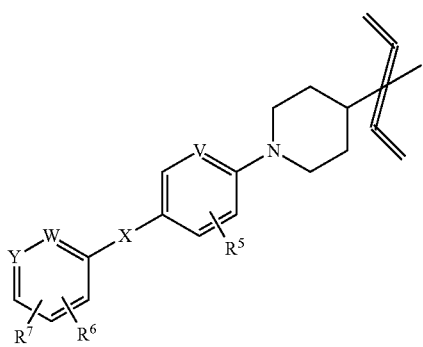

(1B)

In the above general formula (1B), V, W, and Y each independently refers to a carbon atom (having 1 hydrogen atom) or a nitrogen atom, X refers to a single bond or methylene, $R^5$ refers to a hydrogen atom, a halogen atom or a $C_1$-$C_6$ alkyl group, $R^6$ refers to a hydrogen atom, a halogen atom, a $C_1$-$C_6$ alkyl group, a carbamoyl group, a $C_1$-$C_6$ alkylcarbamoyl group, or a ($C_1$-$C_6$ alkyl)($C_1$-$C_6$ alkyl)carbamoyl group, and $R^7$ refers to a hydroxymethyl group, a 1-hydroxyethyl group, a 2-hydroxyethyl group, a 1,1-difluoro-2-hydroxyethyl group, a 2-hydroxypropyl group, a 3-hydroxypropyl group, a 1,1-difluoro-2-hydroxypropyl group, a 2-hydroxybutyl group, a 2-hydroxy-1,1-dimethylethyl group, a 1,1-difluoro-2-hydroxy-2-methylpropyl group, a methoxymethyl group, a 2-hydroxy-3-methoxypropyl group, a methoxycarbonyl group, an ethoxycarbonyl group, a methoxymethoxymethyl group, a 1-methoxymethoxyethyl group, a 2-hydroxyethoxy group, a methylcarbamoyl group, a dimethylcarbamoyl group, a methylcarbamoylmethyl group, a dimethylcarbamoylmethyl group, a hydroxyethylcarbamoyl group, or a hydroxyethylcarbamoylmethyl group. The aforementioned $R^7$ is preferably a hydroxymethyl group, a 1-hydroxyethyl group, a 2-hydroxyethyl group, a 2-hydroxypropyl group, a 3-hydroxypropyl group, a 2-hydroxybutyl group, a 2-hydroxy-1,1-dimethylethyl group, a methoxymethyl group, a 2-hydroxy-3-methoxypropyl group, an ethoxycarbonyl group, a 1-methoxymethoxyethyl group, a 2-hydroxyethoxy group, a methylcarbamoyl group, a dimethylcarbamoyl group, or a dimethylcarbamoylmethyl group.

In the compounds of the present invention, $R^1$ is more preferably a group represented by the following general formula (1B-1) to general formula (1B-8).

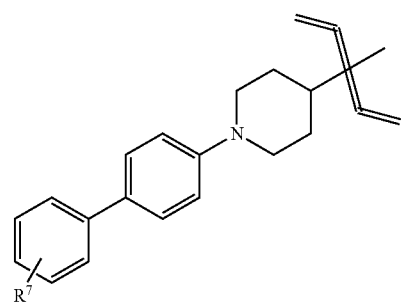

(1B-1)

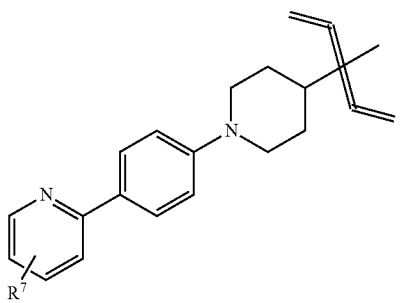

(1B-2)

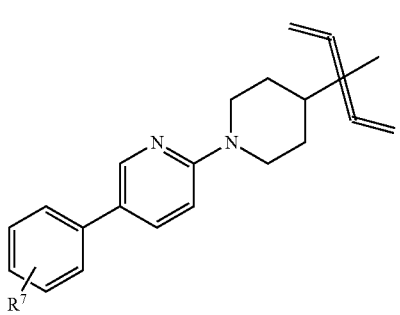

(1B-3)

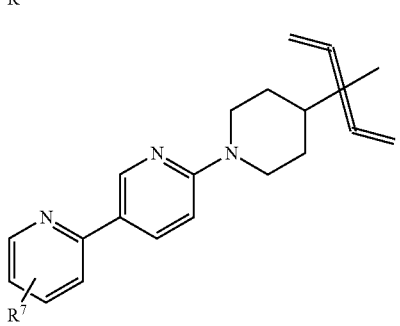

(1B-4)

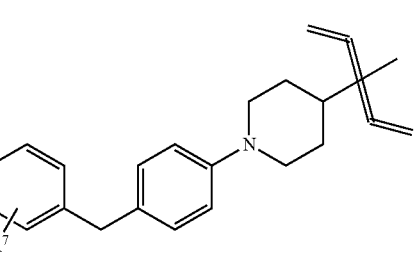

(1B-5)

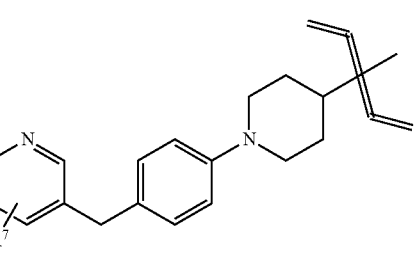

(1B-6)

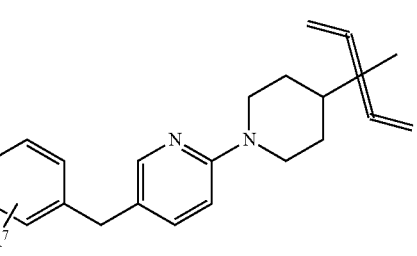

(1B-7)

(1B-8)

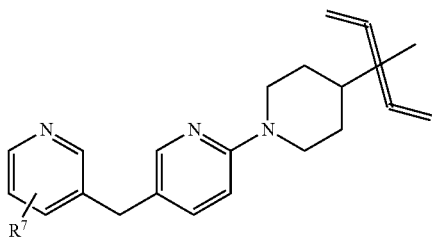

R¹ is even more preferably a group represented by the following general formula (1B-1), general formula (1B-2), general formula (1B-3), general formula (1B-5), or general formula (1B-6).

(!B-1)

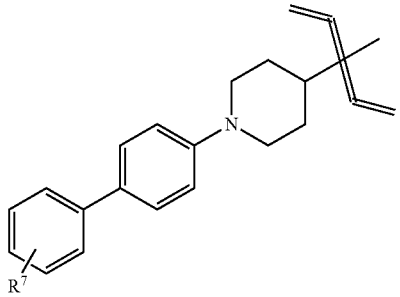

(1B-2)

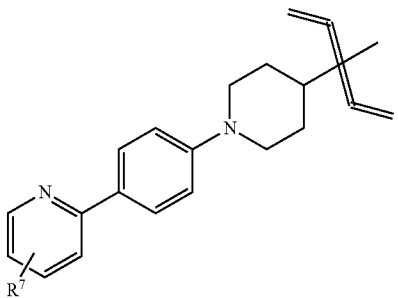

(1B-3)

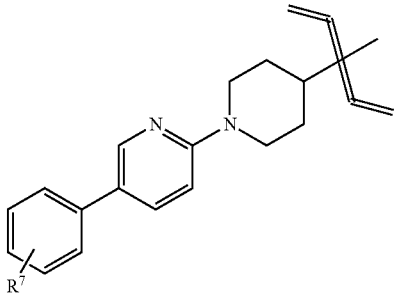

(1B-5)

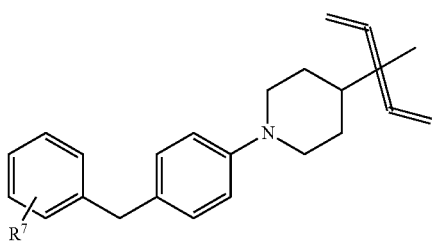

(1B-6)

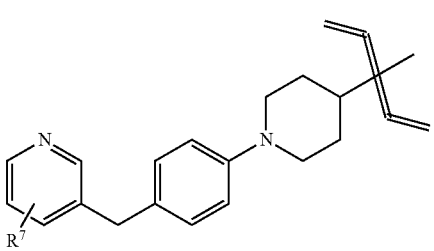

In the above general formula (1B-1) to general formula (1B-8), $R^7$ refers to a hydroxymethyl group, a 1-hydroxyethyl group, a 2-hydroxyethyl group, a 1,1-difluoro-2-hydroxyethyl group, a 2-hydroxypropyl group, a 3-hydroxypropyl group, a 1,1-difluoro-2-hydroxypropyl group, a 2-hydroxybutyl group, a 2-hydroxy-1,1-dimethylethyl group, a 1,1-difluoro-2-hydroxy-2-methylpropyl group, a methoxymethyl group, a 2-hydroxy-3-methoxypropyl group, a methoxycarbonyl group, an ethoxycarbonyl group, a methoxymethoxymethyl group, a 1-methoxymethoxyethyl group, a 2-hydroxyethoxy group, a methylcarbamoyl group, a dimethylcarbamoyl group, a methylcarbamoylmethyl group, a dimethylcarbamoylmethyl group, a hydroxyethylcarbamoyl group, or a hydroxyethylcarbamoylmethyl group. The aforementioned $R^7$ is preferably a hydroxymethyl group, a 1-hydroxyethyl group, a 2-hydroxyethyl group, a 2-hydroxypropyl group, a 3-hydroxypropyl group, a 2-hydroxybutyl group, a 2-hydroxy-1,1-dimethylethyl group, a methoxymethyl group, a 2-hydroxy-3-methoxypropyl group, an ethoxycarbonyl group, a 1-methoxymethoxyethyl group, a 2-hydroxyethoxy group, a methylcarbamoyl group, a dimethylcarbamoyl group, or a dimethylcarbamoylmethyl group.

In the compounds of the present invention, $R^2$ refers to a $C_1$-$C_2$ alkyl group or a methylsulfanyl group, preferably a methyl group or a methylsulfanyl group, and more preferably a methyl group.

In the compounds of the present invention, $R^3$ refers to a hydrogen atom or a methyl group, preferably a hydrogen atom.

The "pharmacologically acceptable ester" in the present invention refers to, in the case where the compound of the present invention has a hydroxyl group and/or a carboxy group, an ester compound obtainable from formation of an ester bond between these groups and a pharmacologically acceptable group.

Examples of a group that forms an ester bond with a hydroxy group of the compounds of the present invention include "$C_2$-$C_7$ alkanoyl groups" having 2 to 7 carbons such as an acetyl group, a propionyl group, a butyryl group, an isobutyryl group, a pentanoyl group, a pivaloyl group, a valeryl group, and an isovaleryl group; "aryl $C_2$-$C_7$ alkanoyl groups" such as a phenylacetyl group; or aryl carbonyl groups such as a benzoyl group, and an acetyl group is preferable. Here, the "aryl $C_2$-$C_7$ alkanoyl group" refers to a group in which 1 hydrogen atom of an aforementioned "$C_2$-$C_7$ alkanoyl group" is substituted with an aromatic hydrocarbon ring group such as a phenyl group.

In the compounds of the present invention, in the case where $R^7$ refers to a substituent having a hydroxy group (a hydroxy $C_1$-$C_6$ alkyl group, a hydroxyhalo $C_1$-$C_6$ alkyl group, a hydroxy $C_1$-$C_6$ alkoxy group, a hydroxy $C_1$-$C_6$ alkylcarbamoyl group, or a hydroxy $C_1$-$C_6$ alkylcarbamoyl $C_1$-$C_6$ alkyl group), said hydroxy group may form an ester bond with an aforementioned "$C_2$-$C_7$ alkanoyl group" (preferably an acetyl group).

Examples of a group that forms an ester bond with a carboxy group of the compounds of the present invention include the aforementioned "$C_1$-$C_6$ alkyl group", and a methyl group or an ethyl group is preferable.

A pharmacologically acceptable ester of the compounds of the present invention can have a pharmacological activity, per se, or can be used as a prodrug. In the case where the above pharmacologically acceptable ester is used as a prodrug, an ester per se need not have a pharmacological activity, but a compound produced by hydrolysis of an ester bond in vivo can have a pharmacological activity.

The compound of the present invention is preferably one selected from the following compounds, or pharmacologically acceptable salts thereof:

({[5-hydroxy-2-{(1-[4'-(hydroxymethyl)biphenyl-4-yl]piperidin-4-yl}methyl)-6-methylpyrimidin-4-yl]carbonyl}amino)acetic acid, ({[2-{(1-[4'-(acetoxymethyl)biphenyl-4-yl]piperidin-4-yl}methyl)-5-hydroxy-6-methylpyrimidin-4-yl]carbonyl}amino)acetic acid, ({[5-hydroxy-2-{(1-[4'-(1-hydroxyethyl)biphenyl-4-yl]piperidin-4-yl}methyl)-6-methylpyrimidin-4-yl]carbonyl}amino)acetic acid, ({[5-hydroxy-2-{(1-[4'-(2-hydroxyethyl)biphenyl-4-yl]piperidin-4-yl}methyl)-6-methylpyrimidin-4-yl]carbonyl}amino)acetic acid, ({[5-hydroxy-2-{(1-[4'-(2-hydroxypropyl)biphenyl-4-yl]piperidin-4-yl}methyl)-6-methylpyrimidin-4-yl]carbonyl}amino)acetic acid, ({[5-hydroxy-2-{(1-[4'-(2-hydroxy-1,1-dimethylethyl)biphenyl-4-yl]piperidin-4-yl}methyl)-6-methylpyrimidin-4-yl]carbonyl}amino)acetic acid, ({[2-{(1-[4'-(dimethylcarbamoyl)biphenyl-4-yl]piperidin-4-yl}methyl)-5-hydroxy-6-methylpyrimidin-4-yl]carbonyl}amino)acetic acid, ({[5-hydroxy-6-methyl-2-{(1-[4'-(methylcarbamoyl)biphenyl-4-yl]piperidin-4-yl}methyl)pyrimidin-4-yl]carbonyl}amino)acetic acid,

[({2-[(1-{4'-[2-(dimethylamino)-2-oxoethyl]biphenyl-4-yl}piperidin-4-yl)methyl]-5-hydroxy-6-methylpyrimidin-4-yl}carbonyl)amino]acetic acid,

[({5-hydroxy-2-[(1-{4-[4-(hydroxymethyl)benzyl]phenyl}piperidin-4-yl)methyl]-6-methylpyrimidin-4-yl}carbonyl)amino]acetic acid,

[({5-hydroxy-2-[(1-{4-[3-(hydroxymethyl)benzyl]phenyl}piperidin-4-yl)methyl]-6-methylpyrimidin-4-yl}carbonyl)amino]acetic acid,

[({5-hydroxy-2-[(1-{4-[5-(1-hydroxyethyl)pyridin-2-yl]phenyl}piperidin-4-yl)methyl]-6-methylpyrimidin-4-yl}carbonyl)amino]acetic acid, {[(5-hydroxy-2-{[1-(4-{5-[1-(methoxymethoxy)ethyl]pyridin-2-yl}phenyl)piperidin-4-yl]methyl}-6-methylpyrimidin-4-yl)carbonyl]amino}acetic acid,

[({2-[(1-{4-[5-(1-acetoxyethyl)pyridin-2-yl]phenyl}piperidin-4-yl)methyl]-5-hydroxy-6-methylpyrimidin-4-yl}carbonyl)amino]acetic acid,

[({5-hydroxy-2-[(1-{4-[5-(hydroxymethyl)pyridin-2-yl]phenyl}piperidin-4-yl)methyl]-6-methylpyrimidin-4-yl}carbonyl)amino]acetic acid,

[({2-[(1-{4-[5-(ethoxycarbonyl)pyridin-2-yl]phenyl}piperidin-4-yl)methyl]-5-hydroxy-6-methylpyrimidin-4-yl}carbonyl)amino]acetic acid,

[({2-[(1-{4-[2-(ethoxycarbonyl)benzyl]phenyl}piperidin-4-yl)methyl]-5-hydroxy-6-methylpyrimidin-4-yl}carbonyl)amino]acetic acid, {[(5-hydroxy-2-{[1-(4-{[6-(2-hydroxyethoxy)pyridin-3-yl]methyl}phenyl)piperidin-4-yl]methyl}-6-methylpyrimidin-4-yl)carbonyl]amino}acetic acid,

[({5-hydroxy-2-[(1-{5-[4-(hydroxymethyl)phenyl]pyridin-2-yl}piperidin-4-yl)methyl]-6-methylpyrimidin-4-yl}carbonyl)amino]acetic acid,

[({5-hydroxy-2-[(1-{5-[4-(2-hydroxypropyl)phenyl]pyridin-2-yl}piperidin-4-yl)methyl]-6-methylpyrimidin-4-yl}carbonyl)amino]acetic acid,

[({5-hydroxy-2-[(1-{5-[4-(2-hydroxy-1,1-dimethylethyl)phenyl]pyridin-2-yl}piperidin-4-yl)methyl]-6-methylpyrimidin-4-yl}carbonyl)amino]acetic acid, ({[2-{(1-[2-chloro-4'-(hydroxymethyl)biphenyl-4-yl]piperidin-4-yl}methyl)-5-hydroxy-6-methylpyrimidin-4-yl]carbonyl}amino)acetic acid, ({[5-hydroxy-2-{(1-[4'-(hydroxymethyl)-2-methylbiphenyl-4-yl]piperidin-4-yl}methyl)-6-methylpyrimidin-4-yl]carbonyl}amino)acetic acid, ({[2-{(1-[3'-chloro-4'-(hydroxymethyl)biphenyl-4-yl]piperidin-4-yl}methyl)-5-hydroxy-6-methylpyrimidin-4-yl]carbonyl}amino)acetic acid, ({[5-hydroxy-2-{(1-[4'-(hydroxymethyl)-2'-methylbiphenyl-4-yl]piperidin-4-yl}methyl)-6-methylpyrimidin-4-yl]carbonyl}amino)acetic acid, ({[5-hydroxy-2-{(1-[4'-(hydroxymethyl)-2,3'-dimethylbiphenyl-4-yl]piperidin-4-yl}methyl)-6-methylpyrimidin-4-yl]carbonyl}amino)acetic acid, ({[5-hydroxy-2-{(1-[4'-(2-hydroxybutyl)biphenyl-4-yl]piperidin-4-yl}methyl)-6-methylpyrimidin-4-yl]carbonyl}amino)acetic acid,

[({5-hydroxy-2-[(1-{4-[4-(2-hydroxypropyl)benzyl]phenyl}piperidin-4-yl)methyl]-6-methylpyrimidin-4-yl}carbonyl)amino]acetic acid,

[({5-hydroxy-2-[(1-{4-[4-(2-hydroxy-1,1-dimethylethyl)benzyl]phenyl}piperidin-4-yl)methyl]-6-methylpyrimidin-4-yl}carbonyl)amino]acetic acid, ({[2-{(1-[4'-(1,1-difluoro-2-hydroxyethyl)biphenyl-4-yl]piperidin-4-yl}methyl)-5-hydroxy-6-methylpyrimidin-4-yl]carbonyl}amino)acetic acid, ({[2-{(1-[4'-(1,1-difluoro-2-hydroxypropyl)biphenyl-4-yl]piperidin-4-yl}methyl)-5-hydroxy-6-methylpyrimidin-4-yl]carbonyl}amino)acetic acid, ({[2-{(1-[4'-(1,1-difluoro-2-hydroxy-2-methylpropyl)biphenyl-4-yl]piperidin-4-yl}methyl)-5-hydroxy-6-methylpyrimidin-4-yl]carbonyl}amino)acetic acid, {[(5-[(2,2-dimethylpropanoyl)oxy]-2-{[1-(4'-{[(2,2-dimethylpropanoyl)oxy]methyl}biphenyl-4-yl)piperidin-4-yl]methyl}-6-methylpyrimidin-4-yl)carbonyl]amino}acetic acid, {[(2-{[1-(4'-{[(2,2-dimethylpropanoyl)oxy]methyl}biphenyl-4-yl)piperidin-4-yl]methyl}-5-hydroxy-6-methylpyrimidin-4-yl)carbonyl]amino}acetic acid, ({[5-hydroxy-2-{(1-[4'-(methoxymethyl)biphenyl-4-yl]piperidin-4-yl}methyl)-6-methylpyrimidin-4-yl]carbonyl}amino)acetic acid, ({[2-{(1-[2'-fluoro-4'-(hydroxymethyl)biphenyl-4-yl]piperidin-4-yl}methyl)-5-hydroxy-6-methylpyrimidin-4-yl]carbonyl}amino)acetic acid, ({[2-{(1-[3'-fluoro-4'-(hydroxymethyl)biphenyl-4-yl]piperidin-4-yl}methyl)-5-hydroxy-6-methylpyrimidin-4-yl]carbonyl}amino)acetic acid, ({[2-{(1-[2-fluoro-4'-(hydroxymethyl)biphenyl-4-yl]piperidin-4-yl}methyl)-5-hydroxy-6-methylpyrimidin-4-yl]carbonyl}amino)acetic acid, ({[2-{(1-[3-fluoro-4'-(hydroxymethyl)biphenyl-4-yl]piperidin-4-yl}methyl)-5-hydroxy-6-methylpyrimidin-4-yl]carbonyl}amino)acetic acid, ({[5-hydroxy-2-{(1-[4'-(hydroxymethyl)-3'-methylbiphenyl-4-yl]piperidin-4-yl}methyl)-6-methylpyrimidin-4-yl]carbonyl}amino)acetic acid,
({[2-{(1-[3',5'-difluoro-4'-(hydroxymethyl)biphenyl-4-yl]piperidin-4-yl}methyl)-5-hydroxy-6-methylpyrimidin-4-yl]carbonyl}amino)acetic acid,
({[2-{(1-[3',5'-dichloro-4'-(hydroxymethyl)biphenyl-4-yl]piperidin-4-yl}methyl)-5-hydroxy-6-methylpyrimidin-4-yl]carbonyl}amino)acetic acid,
({[2-{(1-[3',5'-dimethyl-4'-(hydroxymethyl)biphenyl-4-yl]piperidin-4-yl}methyl)-5-hydroxy-6-methylpyrimidin-4-yl]carbonyl}amino)acetic acid,
[({5-hydroxy-2-[(1-{4'-[2-hydroxy-3-methoxypropyl]biphenyl-4-yl}piperidin-4-yl)methyl]-6-methylpyrimidin-4-yl}carbonyl)amino]acetic acid,
({[5-hydroxy-2-{(1-[4'-(3-hydroxypropyl)biphenyl-4-yl]piperidin-4-yl}methyl)-6-methylpyrimidin-4-yl]carbonyl}amino)acetic acid,
({[5-hydroxy-2-{(1-[4'-(hydroxymethyl)-3'-isopropylbiphenyl-4-yl]piperidin-4-yl}methyl)-6-methylpyrimidin-4-yl]carbonyl}amino)acetic acid,
[({2-[(1-{5-[3-fluoro-4-(hydroxymethyl)phenyl]pyridin-2-yl}piperidin-4-yl)methyl]-5-hydroxy-6-methylpyrimidin-4-yl}carbonyl)amino]acetic acid,
[({2-[(1-{5-[3-chloro-4-(hydroxymethyl)phenyl]pyridin-2-yl}piperidin-4-yl)methyl]-5-hydroxy-6-methylpyrimidin-4-yl}carbonyl)amino]acetic acid, or
[({5-hydroxy-2-[(1-{5-[4-(hydroxymethyl)-3-methylphenyl]pyridin-2-yl}piperidin-4-yl)methyl]-6-methylpyrimidin-4-yl}carbonyl)amino]acetic acid.

In the compounds of the present invention, geometrical isomers or tautomers may be present depending on the types of substituents. Further, in the case where the compounds of the present invention have an asymmetric carbon atom, optical isomers may be present. These separated isomers (e.g., enantiomers or diastereomers) and mixtures thereof (e.g., racemates or diastereomeric mixtures) are included in the present invention. Further, labeled compounds, namely compounds in which one or more atoms of compounds of the present invention have been substituted with a corresponding radioactive isotope or non-radioactive isotope in an arbitrary ratio, are also included in the present invention.

In the case where the compound of the present invention has a basic group such as an amino group, a pharmacologically acceptable acid addition salt can be formed, if desired. Examples of such acid addition salts include hydrohalic acid salts such as hydrofluorides, hydrochlorides, hydrobromides or hydroiodides; inorganic acid salts such as nitrates, perchlorates, sulfates or phosphates; lower alkanesulfonates such as methanesulfonates, trifluoromethanesulfonates or ethanesulfonates; aryl sulfonates such as benzenesulfonates or p-toluenesulfonates; organic acid salts such as acetates, malates, fumarates, succinates, citrates, tartrates, oxalates or maleates; and amino acid salts such as ornithinates, glutamates or aspartates, and hydrohalic acid salts and organic acid salts are preferable.

In the case where the compound of the present invention has an acidic group such as a carboxy group, generally a pharmacologically acceptable base addition salt can be formed. Examples of such base addition salts include alkali metal salts such as sodium salts, potassium salts or lithium salts; alkaline earth metal salts such as calcium salts or magnesium salts; inorganic salts such as ammonium salts; and organic amine salts such as dibenzylamine salts, morpholine salts, phenylglycine alkyl ester salts, ethylenediamine salts, N-methylglucamine salts, diethylamine salts, triethylamine salts, cyclohexylamine salts, dicyclohexylamine salts, N,N'-dibenzylethylenediamine salts, diethanolamine salts, N-benzyl-N-(2-phenylethoxy)amine salts, piperazine salts, tetramethylammonium salts or tris(hydroxymethyl)aminomethane salts.

The compounds of the present invention may also be present as a free form or a solvate. Although there are no particular limitations on the solvate provided it is pharmacologically acceptable, preferred specific examples include hydrates and ethanolates, or the like. Further, in the case where a nitrogen atom is present in a compound represented by the general formula (1), it may be in the form of an N-oxide, and these solvates and N-oxide forms are also included within the scope of the present invention.

Although the compounds of the present invention can be present in the form of various isomers including geometrical isomers such as a cis form or trans form, tautomers, or optical isomers such as a d form or l form depending on the types of substituents and combinations thereof, the compounds of the present invention also include all the isomers and mixtures of the isomers in any ratio thereof, unless otherwise specifically limited.

Further, the compounds of the present invention can contain a non-natural ratio of isotopes in one or more atoms constituting such compounds. Examples of the isotopes include deuterium ($^2$H;D), tritium ($^3$H;T), iodine-125 ($^{125}$I), carbon-14 ($^{14}$C), or the like. Further, the compounds of the present invention can be radiolabeled with radioisotopes such as, for example, tritium ($^3$H), iodine-125 ($^{125}$I), carbon-14 ($^{14}$C), or the like. A radiolabeled compound is useful as a therapeutic or prophylactic agent, a research reagent (e.g., an assay reagent), and a diagnostic agent (e.g., an in vivo diagnostic imaging agent). The compounds of the present invention containing all ratios of radioactive or non-radioactive isotopes are included within the scope of the present invention.

The compounds of the present invention can also be produced by applying various known synthesis methods depending on the basic skeleton thereof or types of substituents. In so doing, depending on the types of functional groups, it is possible to protect this functional group with a suitable protecting group at stages from a raw material to an intermediate, or substitute it with a group that can be easily converted to this functional group. Examples of such functional groups include an amino group, a hydroxy group, a carboxy group, and the like, and examples of their protecting groups include those described in, for example, Protective Groups in Organic Synthesis, 3$^{rd}$ ed., Greene, T. W. and Wuts, P. G. M., John Wiley & Sons, Inc., New York, 1999, and these protecting groups can be appropriately selected and used depending on the reaction conditions thereof. According to such methods, a desired compound can be obtained by introducing this protecting group and carrying out the reaction followed by removing the protecting group as necessary, or converting it to a desired group. The resulting compounds of the present invention can be identified, and their composition or purity can be analyzed, by standard analytical technologies such as elementary analysis, NMR, mass spectroscopy or IR analysis.

Raw materials and reagents used to produce the compounds of the present invention can be purchased from commercial suppliers, or can be synthesized according to methods described in the literature.

In the present invention, examples of anemia include nephrogenic anemia, anemia of prematurity, anemia incidental to chronic diseases, anemia incidental to cancer chemotherapy, cancerous anemia, inflammation-associated anemia, and anemia incidental to congestive heart failure. Examples of the anemia incidental to chronic diseases include anemia incidental to chronic renal diseases, and examples of the anemia incidental to chronic renal diseases include chronic renal failure. Further, the patient to whom the compound of the present invention is administered can be a patient who receives or does not receive dialysis.

Effects of the Invention

The compounds of the present invention, pharmacologically acceptable esters thereof or pharmacologically acceptable salts thereof demonstrate a superior EPO production-enhancing activity in an assay system using Hep3B cells, and have superior safety. Namely, EPO production can be enhanced by administering a pharmaceutical composition containing a compound of the present invention, a pharmacologically acceptable ester thereof or a pharmacologically acceptable salt thereof to a mammal (such as a human, cow, horse, or pig) or bird (such as a chicken). Thus, a pharmaceutical composition containing a compound of the present invention, pharmacologically acceptable ester thereof or pharmacologically acceptable salt thereof can be used for the prophylaxis and/or treatment of diseases caused by decreased EPO, or diseases or pathological conditions in which EPO is decreased such as ischemic cerebrovascular disease, or for auto-transfusion in patients scheduled to undergo surgery. Examples of diseases caused by decreased EPO include anemia, and particularly nephrogenic anemia (dialysis stage, conservation stage), anemia of prematurity, anemia incidental to chronic diseases, anemia incidental to cancer chemotherapy, cancerous anemia, inflammation-associated anemia, and anemia incidental to congestive heart failure.

MODE FOR CARRYING OUT THE INVENTION

The following provides examples of representative methods for producing the compounds of the present invention. Furthermore, the production methods of the present invention are not limited to the examples shown below.

Compounds having the general formula (1) of the present invention can be obtained according to methods described below.

(Step 1)

Step 1 is a step for producing a compound having the general formula (1) from a compound having the general formula (2) to be subsequently described.

Step 1

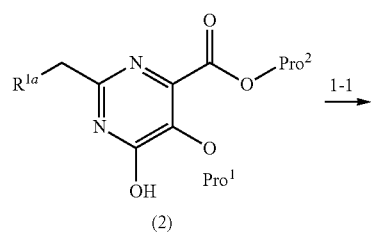

(2)

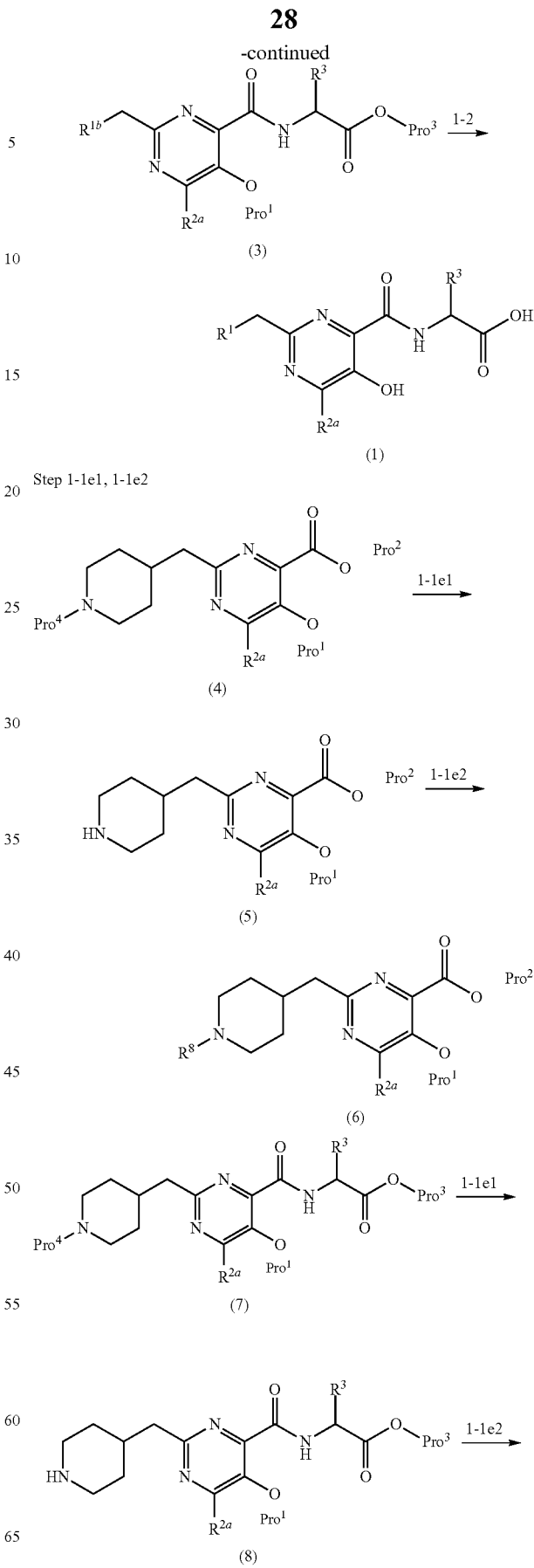

-continued

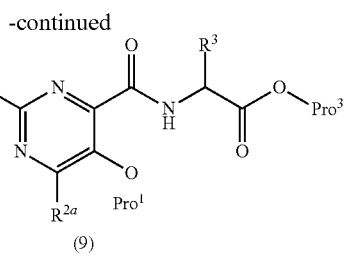

(9)

In the above formulae, $R^1$ to $R^3$ have the same meaning as previously defined, $R^8$ refers to a substituted or unsubstituted aryl group or heteroaryl group, $R^{1a}$ and $R^{1b}$ refers to a group that can be the aforementioned $R^1$ or a precursor thereof, $R^{2a}$ refers to a group that can be the aforementioned $R^2$ or a precursor thereof, and $Pro^1$ through $Pro^4$ refer to protecting groups of the respective functional groups selected from known protecting groups (e.g., Protective Groups in Organic Synthesis, $3^{rd}$ ed., Greene, T. W., Wuts, P. G. M., John Wiley & Sons, Inc., New York, 1999, etc.). Although there are no particular limitations on $Pro^1$ through $Pro^4$ provided they are stable during the reaction and do not inhibit the reaction, preferably $Pro^1$ is a benzyl group, $Pro^2$ is a tert-butyl group, $Pro^3$ is a methyl group, an ethyl group, a tert-butyl group, or a benzyl group, and $Pro^4$ is a tert-butoxycarbonyl group. Although there are no particular limitations on $X^1$ in Step 1-1c, Step 1-1d, or Step 1-1e provided it is a substituent that forms a leaving group together with oxygen to which it is attached, it is preferably a trifluoromethanesulfonyl group.

The following provides a detailed description of each step.
(Step 1-1)

Step 1-1 is a step for producing a compound having the general formula (3) from a compound having the general formula (2) to be subsequently described. Examples of essential reactions include:

Step 1-1a: deprotection reaction of protecting group $Pro^2$;
Step 1-1b: condensation reaction with amino acid or amino acid salt having the general formula $H_2NCH(R^3)CO_2Pro^3$;
Step 1-1c: reaction for introducing a leaving group (—$OX^1$) into a hydroxyl group at position 6; and
Step 1-1d: reaction for converting the leaving group (—$OX^1$) to the substituent $R^{2a}$. Further,
Step 1-1e: reaction for converting $R^{1a}$ to $R^{1b}$ can be added, as necessary. Steps 1-1a to 1-1e may be carried out in any order.
(Step 1-1a)

This step is a step for deprotecting the protecting group $Pro^2$. A known method described in, for example, Protective Groups in Organic Synthesis, $3^{rd}$ ed., Greene, T. W., Wuts, P. G. M., John Wiley & Sons, Inc., New York, 1999, and the like can be suitably selected corresponding to the $Pro^2$ used, and this step is carried out in accordance therewith. Here, a tert-butyl group is selected as a preferred $Pro^2$, and a method in which $Pro^2$ is converted to a hydrogen atom using a base in an inert solvent (Step 1-1a1), and a method in which $Pro^2$ is converted to a hydrogen atom using an acid in an inert solvent (Step 1-1a2) is described, but this step is not limited thereto.
(Step 1-1a1)

This step is a step for converting $Pro^2$ to a hydrogen atom using a suitable base in an inert solvent.

Although there are no particular limitations on the solvent used provided it does not inhibit the reaction and dissolves the starting material to a certain degree, preferred examples include aromatic hydrocarbons such as benzene, toluene or xylene; halogenated hydrocarbons such as dichloromethane or chloroform; ethers such as diethyl ether, tetrahydrofuran, 1,4-dioxane or 1,2-dimethoxyethane; alcohols such as methanol, ethanol or tert-butanol; esters such as ethyl acetate or propyl acetate; nitriles such as acetonitrile; amides such as formamide or N,N-dimethylformamide; sulfoxides such as dimethyl sulfoxide; a mixture of a plurality of organic solvents in an arbitrary ratio, and a mixture thereof with water in an arbitrary ratio.

Although there are no particular limitations on the base used provided it is used as a base in conventional reactions, examples include organic bases such as triethylamine, N,N-diisopropylethylamine, N-methylmorpholine, lutidine or pyridine; alkali metal carbonates such as sodium carbonate or potassium carbonate; alkaline earth metal carbonates such as calcium carbonate; alkali metal hydrogencarbonates such as potassium hydrogencarbonate; alkaline earth metal hydrogencarbonates such as calcium hydrogencarbonate; alkali metal hydroxides such as sodium hydroxide or potassium hydroxide; alkaline earth metal hydroxides such as calcium hydroxide; and alkali metal phosphates such as tripotassium phosphate.

Varying according to the raw material compounds, reagents and the like, the reaction temperature is normally −10 to 150° C. and preferably 10 to 90° C.

Varying according to the raw material compounds, reagents and the like, the reaction time is normally 1 minute to 24 hours and preferably 10 minutes to 6 hours.

Following completion of the reaction, the desired compound can be obtained as a solid by distilling off the organic solvent and adding an acid. On the other hand, in the case where a solid is unable to be obtained by adding an acid, the desired compound can be obtained by extracting an organic substance with an organic solvent such as ethyl acetate, drying the organic layer with a commonly used procedure, and subsequently concentrating it under reduced pressure.

The resulting compound can be further purified if necessary using an ordinary method, for example, recrystallization, reprecipitation, silica gel column chromatography, or the like.
(Step 1-1a2)

This step is a step for converting $Pro^2$ to a hydrogen atom using a suitable acid in an inert solvent.

Although there are no particular limitations on the solvent used provided it does not inhibit the reaction and dissolves the starting material to a certain degree, preferred examples include aromatic hydrocarbons such as benzene, toluene or xylene; halogenated hydrocarbons such as dichloromethane or chloroform; esters such as ethyl acetate or propyl acetate; ethers such as diethyl ether, tetrahydrofuran, 1,4-dioxane or 1,2-dimethoxyethane; alcohols such as methanol or ethanol; nitriles such as acetonitrile; amides such as formamide or N,N-dimethylformamide; sulfoxides such as dimethyl sulfoxide; a mixture of a plurality of organic solvents in an arbitrary ratio, and a mixture thereof with water in an arbitrary ratio.

Although there are no particular limitations on the acid used provided it is used as an acid in conventional reactions, examples include inorganic acids such as hydrochloric acid or sulfuric acid; Lewis acids such as boron trifluoride, boron trichloride, boron tribromide or iodo trimethylsilane; and organic acids such as trifluoroacetic acid.

Varying according to the raw material compounds, reagents and the like, the reaction temperature is normally −100 to 150° C. and preferably −78 to 100° C.

Varying according to the raw material compounds, reagents and the like, the reaction time is normally 5 minutes to 24 hours and preferably 10 minutes to 6 hours.

Following completion of the reaction, the desired compound can be obtained as a solid by distilling off the organic solvent and adding a base. On the other hand, in the case where a solid is unable to be obtained by adding a base, the desired compound can be obtained by extracting an organic substance with an organic solvent such as ethyl acetate, drying the organic layer with a commonly used procedure, and subsequently concentrating it under reduced pressure.

The resulting compound can be further purified if necessary using a conventional method, for example, recrystallization, reprecipitation, silica gel column chromatography, or the like.

(Step 1-1b)

This step is a step for condensing a carboxylic acid obtained in Step 1-1a and an amino acid or amino acid salt having the general formula $H_2NCH(R^3)CO_2Pro^3$, and is carried out using a condensation agent in an inert solvent and in the presence or absence of base.

Although there are no particular limitations on the solvent used provided it does not inhibit the reaction and dissolves the starting material to a certain degree, preferred examples include aromatic hydrocarbons such as benzene, toluene or xylene; halogenated hydrocarbons such as dichloromethane or chloroform; esters such as ethyl acetate or propyl acetate; ethers such as diethyl ether, tetrahydrofuran, 1,4-dioxane or 1,2-dimethoxyethane; alcohols such as methanol, ethanol or tert-butanol; nitriles such as acetonitrile; amides such as formamide or N,N-dimethylformamide; sulfoxides such as dimethyl sulfoxide; a mixture of a plurality of organic solvents in an arbitrary ratio, and a mixture thereof with water in an arbitrary ratio.

Although there are no particular limitations on the base used provided it is used as a base in conventional reactions, preferred examples include organic bases such as triethylamine, N,N-diisopropylethylamine, N-methylmorpholine, lutidine or pyridine; alkali metal carbonates such as sodium carbonate or potassium carbonate; alkaline earth metal carbonates such as calcium carbonate; alkali metal hydrogencarbonates such as potassium hydrogencarbonate; alkaline earth metal hydrogencarbonates such as calcium hydrogencarbonate; alkali metal hydroxides such as sodium hydroxide; alkaline earth metal hydroxides such as calcium hydroxide; and alkali metal phosphates such as tripotassium phosphate.

Although there are no particular limitations on the condensation agent used provided it is used as a condensation agent that forms an amide bond (e.g., Shoichi Kusumoto et al., Experimental Science Course IV, Chemical Society of Japan, Maruzen Publishing, 1990; Nobuo Izumiya et al., Peptide Synthesis Basics and Experimentation, Maruzen Publishing, 1985), preferred examples include O-benzotriazole-N,N,N',N'-tetramethyluronium hexafluorophosphate (HBTU), 2-(1H-benzotriazol-1-yl)-1,1,3,3-tetramethyluronium tetrafluoroborate (TBTU), 1-(3-dimethylaminopropyl)-3-ethylcarbodiimide hydrochloride (EDCI), 4-(2-{[(cyclohexylimino)methylene]amino}ethyl-4-methylmorpholin-4-ium para-toluenesulfonate (CMC), dicyclohexylcarbodiimide (DCC), 1,1'-carbonylbis(1H-imidazole) (CDI), (1H-benzotriazol-1-yloxy)(tripyrrolidin-1-yl)phosphonium hexafluorophosphate (PyBOP), bromo(tripyrrolidin-1-yl)phosphonium hexafluorophosphate (PyBrOP), 4-(4,6-dimethoxy-1,3,5-triazin-2-yl)-4-methylmorpholinium chloride (DMT-MM) 2-chloro-4,6-dimethoxy-1,3,5-triazine (DMT) and the like. An additive such as 1-hydroxybenzotriazole (HOBT) or N,N-dimethylaminopyridine may also be added.

Varying according to the raw material compounds, reagents and the like, the reaction temperature is normally −10° C. to 150° C. and preferably 0° C. to 100° C.

Varying according to the raw material compounds, reagents and the like, the reaction time is normally 5 minutes to 48 hours and preferably 10 minutes to 24 hours.

Following completion of the reaction, the desired compound of the present reaction can be obtained by, for example, concentrating the reaction mixture, adding an organic solvent such as ethyl acetate and washing with water followed by separating the organic layer containing the desired compound, drying with anhydrous sodium sulfate and the like, and distilling off the solvent.

The resulting compound can be further purified if necessary using a conventional method, for example, recrystallization, reprecipitation, silica gel column chromatography, or the like.

(Step 1-1c)

This step is a step for converting a hydroxyl group at position 6 to a leaving group ($-OX^1$), and is carried out by reacting the hydroxyl group with an acid chloride or acid anhydride in an inert solvent and in the presence or absence of a base.

Although there are no particular limitations on the solvent used provided it does not inhibit the reaction and dissolves the starting material to a certain degree, preferred examples include aromatic hydrocarbons such as benzene, toluene or xylene; halogenated hydrocarbons such as dichloromethane or chloroform; esters such as ethyl acetate or propyl acetate; ethers such as diethyl ether, tetrahydrofuran, 1,4-dioxane or 1,2-dimethoxyethane; nitriles such as acetonitrile; amides such as formamide or N,N-dimethylformamide; sulfoxides such as dimethyl sulfoxide; and a mixture of a plurality of organic solvents in an arbitrary ratio.

Although there are no particular limitations on the acid chloride or acid anhydride used provided it is an acid chloride or acid anhydride that has $X^1$ such that an $-OX^1$ group becomes a known leaving group, preferred examples include substituted or unsubstituted alkylsulfonic acid anhydrides or arylsulfonic acid anhydrides such as trifluoromethanesulfonic acid anhydride, substituted or unsubstituted alkylsulfonyl chlorides or arylsulfonyl chlorides such as methanesulfonyl chloride or p-toluenesulfonyl chloride, and substituted or unsubstituted alkyl phosphoric acid chlorides or aryl phosphoric acid chlorides.

Although there are no particular limitations on the base used provided it is used as a base in conventional reactions, preferred examples include organic bases such as triethylamine, N,N-diisopropylethylamine, N-methylmorpholine, lutidine or pyridine; alkali metal carbonates such as sodium carbonate or potassium carbonate; alkaline earth metal carbonates such as calcium carbonate; alkali metal hydrogencarbonates such as potassium hydrogencarbonate; alkaline earth metal hydrogencarbonates such as calcium hydrogencarbonate; alkali metal hydroxides such as sodium hydroxide; alkaline earth metal hydroxides such as calcium hydroxide; and alkali metal phosphates such as tripotassium phosphate.

Varying according to the raw material compounds, reagents and the like, the reaction temperature is normally −100° C. to 150° C. and preferably −80° C. to 40° C.

Varying according to the raw material compounds, reagents and the like, the reaction time is normally 5 minutes to 24 hours and preferably 10 minutes to 6 hours.

Following completion of the reaction, the desired compound of the present reaction can be obtained by, for example, concentrating the reaction mixture, adding an organic solvent such as ethyl acetate and washing with water followed by separating the organic layer containing the desired compound, drying with anhydrous sodium sulfate and the like, and distilling off the solvent.

The resulting compound can be further purified if necessary using a conventional method, for example, recrystallization, reprecipitation, silica gel column chromatography, or the like.

(Step 1-1d)

This step is a step for converting a leaving group (—$OX^1$) to substituent $R^{2a}$. In the case where $R^{2a}$ is an alkyl group or alkenyl group, this step is carried out by reacting the leaving group with an alkyl boron compound or alkenyl boron compound in an inert solvent, in the presence or absence of a base, in the presence or absence of an additive, and in the presence of a metal catalyst (1-1d1). Further, in the case where $R^{2a}$ is a methylsulfanyl group, this step is carried out by reacting the leaving group with methanethiol or a metal salt of methanethiol in an inert solvent and in the presence or absence of a base (1-1d2).

(Step 1-1d1)

This step is a step for converting a leaving group (—$OX^1$) to an alkyl group or alkenyl group, and is carried out by reacting the leaving group with an alkyl boron compound or alkenyl boron compound in an inert solvent, in the presence or absence of a base, in the presence or absence of an additive, and in the presence of a metal catalyst. This reaction condition is suitably selected from known methods described in, for example, Zou, G., Reddy, Y. K., Falck, J. R., Tetrahedron Lett., 2001, 42, 7213; Molander, G. A., Yun, C.-S., Tetrahedron, 2002, 58, 1465; Tsuji, J., Palladium Reagents and Catalysts, John Wiley & Sons, Inc., England, 2004; Metal-Catalyzed Cross-Coupling Reactions, de Meijere, A., Diederich, F., Wiley-VCH, Weinheim, 2004, and the like, and this step is carried out in accordance therewith. Although the reaction conditions of this step are preferably as follows, they are not limited thereto.

Although there are no particular limitations on the solvent used provided it does not inhibit the reaction and dissolves the starting material to a certain degree, preferred examples include aromatic hydrocarbons such as benzene, toluene or xylene; halogenated hydrocarbons such as dichloromethane or chloroform; esters such as ethyl acetate or propyl acetate; ethers such as diethyl ether, tetrahydrofuran, 1,4-dioxane or 1,2-dimethoxyethane; alcohols such as methanol, ethanol or tert-butanol; nitriles such as acetonitrile; amides such as formamide or N,N-dimethylformamide; sulfoxides such as dimethyl sulfoxide; a mixture of a plurality of organic solvents in an arbitrary ratio, and a mixture thereof with water in an arbitrary ratio.

Although there are no particular limitations on the base used provided it is used as a base in conventional reactions, preferred examples include organic bases such as triethylamine, N,N-diisopropylethylamine, N-methylmorpholine, lutidine or pyridine; alkali metal carbonates such as sodium carbonate or potassium carbonate; alkaline earth metal carbonates such as calcium carbonate; alkali metal hydrogencarbonates such as potassium hydrogencarbonate; alkaline earth metal hydrogencarbonates such as calcium hydrogencarbonate; alkali metal hydroxides such as sodium hydroxide; alkaline earth metal hydroxides such as calcium hydroxide; alkali metal phosphates such as tripotassium phosphate; and metal alkoxides such as sodium tert-butoxide or potassium tert-butoxide.

Although there are no particular limitations on the additive used provided it is used in known methods, preferred examples include metal oxides such as silver oxide or alumina; phosphines such as triphenylphosphine, tri-tert-butylphosphine, tricyclohexylphosphine, tri(o-tolyl)phosphine, diphenylphosphinoferrocene, 2-dicyclohexylphosphino-2',6'-dimethoxy-1,1'-biphenyl (S-PHOS), 2-dicyclohexylphosphino-2',4',6'-triisopropyl-1,1'-biphenyl (X-PHOS) or 2,2'-bis(diphenylphosphino)-1,1'-binaphthyl (BINAP); phosphine oxides such as triphenylphosphine oxide; metal salts such as lithium chloride, potassium fluoride or cesium fluoride; and ammonium salts such as tetrabutylammonium bromide. These may also be used in combination in an arbitrary ratio.

Although there are no particular limitations on the metal catalyst used provided it is used in known methods, preferred examples include palladium catalysts such as tetrakis(triphenylphosphine)palladium, bis(tri-tert-butylphosphine)palladium, palladium diacetate, palladium dichloride-diphenylphosphinoferrocene complex, palladium dichloride-benzonitrile complex, palladium dichloride-acetonitrile complex, bis(dibenzylideneacetone)palladium, tris(dibenzylideneacetone)dipalladium, bis[1,2-bis(diphenylphosphino)ethane]palladium, 3-chloropyridine[1,3-bis(2,6-diisopropylphenyl)imidazol-2-ylidene]palladium or palladium-activated carbon.

Although there are no particular limitations on the alkyl boron compound or alkenyl boron compound used provided it is used as a known reaction reagent, examples include methyl borate, methyl borate ester, trifluoro(methyl)boranuide metal salt, ethyl borate, ethyl borate ester or ethyltrifluoroboranuide metal salt in the case where $R^{2a}$ is an alkyl group, and vinyl borate, 4,4,5,5-tetramethyl-2-vinyl-1,3,2-dioxaborolane, vinyl borate ester, vinyltrifluoroboranuide metal salt, allyl borate, allyl borate ester or allyl(trifluoro)boranuide metal salt in the case where $R^{2a}$ is an alkenyl group.

There are no particular limitations on the ester moiety of the alkyl borate ester, metal of the trifluoro(alkyl)boranuide metal salt, ester moiety of the alkenyl borate ester and metal of the trifluoro(alkenyl)boranuide metal salt provided they are known compounds or are synthesized in accordance with known methods.

Varying according to the raw material compounds, reagents and the like, the reaction temperature is normally −10° C. to 200° C. and preferably 0° C. to 150° C.

Varying according to the raw material compounds, reagents and the like, the reaction time is normally 5 minutes to 48 hours and preferably 10 minutes to 12 hours.

Following completion of the reaction, the desired compound of this reaction can be obtained by, for example, concentrating the reaction mixture, adding an organic solvent such as ethyl acetate and washing with water followed by separating the organic layer containing the desired compound, drying with anhydrous sodium sulfate and the like, and distilling off the solvent.

The resulting compound can be further purified if necessary using a conventional method, for example, recrystallization, reprecipitation, silica gel column chromatography, or the like.

Furthermore, in the case where $R^{2a}$ is an alkenyl group, this alkenyl group can be converted to a corresponding alkyl group by carrying out the hydrogenation reaction according to the reaction conditions similar to those in step 1-2a1 to be described later.

(Step 1-1d2)

This step is a step for converting a leaving group (—$OX^1$) to a methylsulfanyl group, and is carried out by reacting methanethiol or a metal salt of methanethiol in an inert solvent and in the presence or absence of a base.

Although there are no particular limitations on the solvent used provided it does not inhibit the reaction and dissolves the starting material to a certain degree, preferred examples include aromatic hydrocarbons such as benzene, toluene or xylene; halogenated hydrocarbons such as dichloromethane or chloroform; esters such as ethyl acetate or propyl acetate; ethers such as diethyl ether, tetrahydrofuran, 1,4-dioxane or 1,2-dimethoxyethane; nitriles such as acetonitrile; amides such as formamide or N,N-dimethylformamide; alcohols such as methanol or ethanol; sulfoxides such as dimethyl sulfoxide; a mixture of a plurality of organic solvents in an arbitrary ratio, and a mixture thereof with water in an arbitrary ratio.

Although there are no particular limitations on the metal in a metal salt of the methanethiol used, preferred examples include alkali metals such as sodium and alkaline earth metals such as magnesium.

Although there are no particular limitations on the base used provided it is used as a base in conventional reactions, preferred examples include organic bases such as triethylamine, N,N-diisopropylethylamine, N-methylmorpholine, lutidine or pyridine; alkali metal carbonates such as sodium carbonate or potassium carbonate; alkaline earth metal carbonates such as calcium carbonate; alkali metal hydrogencarbonates such as potassium hydrogencarbonate; alkaline earth metal hydrogencarbonates such as calcium hydrogencarbonate; alkali metal hydroxides such as sodium hydroxide; alkaline earth metal hydroxides such as calcium hydroxide; alkali metal phosphates such as tripotassium phosphate; and metal alkoxides such as sodium tert-butoxide or potassium tert-butoxide.

Varying according to the raw material compounds, reagents and the like, the reaction temperature is normally −10° C. to 150° C. and preferably 0° C. to 100° C.

Varying according to the raw material compounds, reagents and the like, the reaction time is normally 5 minutes to 48 hours and preferably 10 minutes to 12 hours.

Following completion of the reaction, the desired compound of the present reaction can be obtained by, for example, concentrating the reaction mixture, adding an organic solvent such as ethyl acetate and washing with water followed by separating the organic layer containing the desired compound, drying with anhydrous sodium sulfate and the like, and distilling off the solvent.

The resulting compound can be further purified if necessary using a conventional method, for example, recrystallization, reprecipitation, silica gel column chromatography, or the like.

(Step 1-1e)

This step is a step for converting $R^{1a}$ to $R^{1b}$, and the synthesis method varies according to the types of heterocycles of ring $Q^4$. The following provides a description of the case where $R^{1a}$ has the ring $Q^1$, the ring $Q^1$ is a heterocycle containing a nitrogen atom, and the heterocycle has a protecting group $Pro^4$ on this nitrogen atom.

Examples of essential reactions of (Step 1-1e) include the following:

Step 1-1e1: deprotecting reaction of protecting group $Pro^4$; and

Step 1-1e2: reaction for introducing substituent $R^8$.

The aforementioned reaction formulae of Step 1-1e1 and Step 1-1e2 indicate the case where $R^{1a}$ is a piperidin-4-yl group having protecting group $Pro^4$ at position 1, and the following explanation of Step 1-1e1 indicates the case where $Pro^4$ is a tert-butoxycarbonyl group, but Step 1-1e1 is not limited thereto.

(Step 1-1e1)

This step is a step for producing a compound having the general formula (5) or (8). Depending on $Pro^4$ used as a protecting group, a known method described, for example, in Protective Groups in Organic Synthesis, $3^{rd}$ ed., Greene, T. W., Wuts, P. G. M., John Wiley & Sons, Inc., New York, 1999, and the like is suitably selected, and this step is carried out in accordance therewith. In the case where $Pro^4$ is a tert-butoxycarbonyl group, this step is carried out by adding a suitable reagent to a compound having the general formula (4) or (7) in an inert solvent.

Although there are no particular limitations on the solvent used provided it does not inhibit the reaction and dissolves the starting material to a certain degree, preferred examples include aromatic hydrocarbons such as benzene, toluene or xylene; halogenated hydrocarbons such as dichloromethane or chloroform; ethers such as diethyl ether, tetrahydrofuran, 1,4-dioxane or 1,2-dimethoxyethane; esters such as ethyl acetate or propyl acetate; nitriles such as acetonitrile; amides such as formamide or N,N-dimethylformamide; sulfoxides such as dimethyl sulfoxide; and a mixture of a plurality of organic solvents in an arbitrary ratio.

Although there are no particular limitations on the reagent used provided it is used as a reagent that deprotects a tert-butoxycarbonyl group in conventional reactions, preferred examples include inorganic acids such as hydrochloric acid or sulfuric acid; organic acids such as acetic acid or trifluoroacetic acid; Lewis acids such as trimethylsilyl iodide or boron trifluoride; acid chlorides such as acetyl chloride; and alkali metal hydroxides such as sodium hydroxide.

Varying according to the raw material compounds, reagents and the like, the reaction temperature is normally −10° C. to 100° C. and preferably 10° C. to 50° C.

Varying according to the raw material compounds, reagents and the like, the reaction time is normally 5 minutes to 24 hours and preferably 10 minutes to 6 hours.

Following completion of the reaction, a solid substance can be obtained by distilling off the solvent and adding n-hexane or the like to the resulting residue. This substance is obtained by filtration, and subsequently dried to obtain a salt of the compound having the general formula (5) or (8). On the other hand, in the case where a solid substance is unable to be obtained by adding n-hexane, the desired compound can be obtained by extracting an organic substance with an organic solvent such as ethyl acetate followed by concentrating the organic layer after having dried it with a commonly used procedure, or concentrating it as it is under reduced pressure.

(Step 1-1e2)

This step can be carried out in accordance with (i) Step 1-1e2-1; (ii) a combination of Steps 1-1e2-2 and 1-1e2-3; or (iii) a combination of Steps 1-1e2-2, 1-1e2-4 and 1-1e2-5.

(Step 1-1e2-1)

This step is a step for producing a compound having the general formula (6) or (9), and is carried out by reacting a substituted or unsubstituted aryl halide or heteroaryl halide, or aryl pseudohalide or heteroaryl pseudohalide containing ring $Q^2$ and ring $Q^3$ with a compound having the general formula (5) or (8) in an inert solvent, in the presence or absence of a base, in the presence or absence of an additive, and in the presence of a metal catalyst. This reaction condition is suitably selected from known methods described in, for example, Tsuji, J., Palladium Reagents and Catalysts, John Wiley & Sons, Inc., England, 2004; Jiang, L., Buchwald, S. L., Palladium-Catalyzed Aromatic Carbon-Nitrogen Bond Formation; Metal-Catalyzed Cross-Coupling Reactions, de Meijere, A., Diederich, F., Wiley-VCH, Weinheim, 2004, Chapter 13, and the like, and this step is carried out in accordance therewith. Although the reaction conditions of this step are preferably as follows, they are not limited thereto.

Although there are no particular limitations on the solvent used provided it does not inhibit the reaction and dissolves the starting material to a certain degree, preferred examples include aromatic hydrocarbons such as benzene, toluene or xylene; halogenated hydrocarbons such as dichloromethane or chloroform; esters such as ethyl acetate or propyl acetate; ethers such as diethyl ether, tetrahydrofuran, 1,4-dioxane or 1,2-dimethoxyethane; alcohols such as methanol, ethanol or tert-butanol; nitriles such as acetonitrile, amides such as formamide or N,N-dimethylformamide; sulfoxides such as dimethyl sulfoxide; a mixture of a plurality of organic solvents in an arbitrary ratio, and a mixture thereof with water in an arbitrary ratio.

Although there are no particular limitations on the base used provided it is used as a base in conventional reactions, preferred examples include organic bases such as triethylamine, N,N-diisopropylethylamine, N-methylmorpholine, lutidine or pyridine; alkali metal carbonates such as sodium carbonate or potassium carbonate; alkaline earth metal carbonates such as calcium carbonate; alkali metal hydrogencarbonates such as potassium hydrogencarbonate; alkaline earth metal hydrogencarbonates such as calcium hydrogencarbonate; alkali metal hydroxides such as sodium hydroxide; alkaline earth metal hydroxides such as calcium hydroxide; alkali metal acetates such as sodium acetate or potassium acetate, alkali metal phosphates such as tripotassium phosphate; metal alkoxides such as sodium tert-butoxide or potassium tert-butoxide; organometallic amides such as lithium diisopropylamide or sodium hexamethyldisilazide; organometallic compounds such as tert-butyl lithium; and metal hydrides such as potassium hydride.

Although there are no particular limitations on the additive used provided it is used in known methods, preferred examples include metal oxides such as silver oxide or alumina; phosphines such as triphenylphosphine, tri-tert-butylphosphine, tricyclohexylphosphine, tri(o-tolyl)phosphine, diphenylphosphinoferrocene, 2-dicyclohexylphosphino-2',6'-dimethoxy-1,1'-biphenyl (S-PHOS), 2-dicyclohexylphosphino-2',4',6'-triisopropyl-1,1'-biphenyl (X-PHOS) or 2,2'-bis(diphenylphosphino)-1,1'-binaphthyl (BINAP); phosphine oxides such as triphenylphosphine oxide; metal salts such as lithium chloride, potassium fluoride or cesium fluoride; and ammonium salts such as tetrabutylammonium bromide. These may be used in combination in an arbitrary ratio.

Although there are no particular limitations on the metal catalyst used provided it is used in known methods, preferred examples include palladium catalysts such as tetrakis(triphenylphosphine) palladium, bis(tri-tert-butylphosphine) palladium, palladium diacetate, a palladium dichloride-diphenylphosphinoferrocene complex, a palladium dichloride-benzonitrile complex, a palladium dichloride-acetonitrile complex, bis(dibenzylideneacetone) palladium, tris(dibenzylideneacetone)dipalladium, bis[1,2-bis(diphenylphosphino)ethane]palladium, 3-chloropyridine[1,3-bis(2,6-diisopropylphenyl)imidazo-2-ylidene]palladium or palladium-activated carbon.

A pseudohalide refers to a compound having a pseudohalogen group, and the pseudohalogen group refers to a group that is known to undergo oxidative addition to a low-valent transition metal catalyst in the same manner as halogen atoms in a coupling reaction using a transition metal catalyst. Although there are no particular limitations on the pseudohalogen group provided it is a group in which the aforementioned oxidative addition reaction is known to occur, examples include sulfonyloxy groups such as a trifluoromethanesulfonyloxy group, a methanesulfonyloxy group or a p-toluenesulfonyloxy group; acyloxy groups such as an acetyloxy group; diazonium groups and phosphonyloxy groups.

There are no particular limitations on the substituted or unsubstituted aryl halide or heteroaryl halide, or aryl pseudohalide or heteroaryl pseudohalide used provided it is a known compound or is synthesized in accordance with known methods.

Varying according to the raw material compounds, reagents and the like, the reaction temperature is normally −10° C. to 200° C. and preferably 0° C. to 150° C.

Varying according to the raw material compounds, reagents and the like, the reaction time is normally 5 minutes to 48 hours and preferably 10 minutes to 12 hours.

Following completion of the reaction, the desired compound of this reaction can be obtained by, for example, concentrating the reaction mixture, adding an organic solvent such as ethyl acetate and washing with water followed by separating the organic layer containing the desired compound, drying with anhydrous sodium sulfate and the like, and distilling off the solvent.

The resulting compound can be further purified if necessary using a conventional method, for example, recrystallization, reprecipitation, silica gel column chromatography, or the like.

(Step 1-1e2-2)

This step is a step for reacting a substituted or unsubstituted aryl halide or heteroaryl halide, or aryl pseudohalide or heteroaryl pseudohalide containing ring $Q^2$ and not containing ring $Q^3$ with a compound having the general formula (5) or (8) in an inert solvent, in the presence or absence of a base, in the presence or absence of an additive, and in the presence of a metal catalyst.

This step can be carried out in accordance with Step 1-1e2-1.

(Step 1-1e2-3)

This step is a step for reacting a compound having a leaving group such as a halogen atom or —$OX^1$ group on ring $Q^2$ obtained in Step 1-1e2-2 with a substituted or unsubstituted arylboronic acid or heteroarylboronic acid in an inert solvent, in the presence or absence of a base, in the presence or absence of an additive, and in the presence of a metal catalyst, thereby producing a compound having the general formula (6) or (9). This reaction condition is suitably selected from known methods described in, for example, Miyaura, N., Yamada, K., Suzuki, A., Tetrahedron Lett., 1979, 36, 3437; Miyaura, N., Suzuki, A., Chem. Rev., 1995, 95, 2457, and the like, and this step is carried out in accordance therewith. Although the reaction conditions of this step are preferably as follows, they are not limited thereto.

Although there are no particular limitations on the solvent used provided it does not inhibit the reaction and dissolves the starting material to a certain degree, preferred examples include aromatic hydrocarbons such as benzene, toluene or xylene; halogenated hydrocarbons such as dichloromethane or chloroform; esters such as ethyl acetate or propyl acetate; ethers such as diethyl ether, tetrahydrofuran, 1,4-dioxane or 1,2-dimethoxyethane; alcohols such as methanol, ethanol or tert-butanol; nitriles such as acetonitrile, amides such as formamide or N,N-dimethylformamide; sulfoxides such as dimethyl sulfoxide; a mixture of a plurality of organic solvents in an arbitrary ratio, and a mixture thereof with water in an arbitrary ratio.

Although there are no particular limitations on the base used provided it is used as a base in conventional reactions, preferred examples include organic bases such as triethylamine, N,N-diisopropylethylamine, N-methylmorpholine, lutidine or pyridine; alkali metal carbonates such as sodium carbonate or potassium carbonate; alkaline earth metal carbonates such as calcium carbonate; alkali metal hydrogencarbonates such as potassium hydrogencarbonate; alkaline earth metal hydrogencarbonates such as calcium hydrogencarbonate; alkali metal hydroxides such as sodium hydroxide; alkaline earth metal hydroxides such as calcium hydroxide; alkali metal acetates such as sodium acetate or potassium acetate, alkali metal phosphates such as tripotassium phosphate; metal alkoxides such as sodium tert-butoxide or potassium tert-butoxide; organometallic amides such as lithium diisopropylamide or sodium hexamethyldisilazide; organometallic compounds such as tert-butyl lithium; and metal hydrides such as potassium hydride.

Although there are no particular limitations on the additive used provided it is used in known methods, preferred examples include metal oxides such as silver oxide or alumina; phosphines such as triphenylphosphine, tri-tert-butylphosphine, tricyclohexylphosphine, tri(o-tolyl)phosphine, diphenylphosphinoferrocene, 2-dicyclohexylphosphino-2',6'-dimethoxy-1,1'-biphenyl (S-PHOS), 2-dicyclohexylphosphino-2',4',6'-triisopropyl-1,1'-biphenyl (X-PHOS) or 2,2'-bis(diphenylphosphino)-1,1'-binaphthyl (BINAP); phosphine oxides such as triphenylphosphine oxide; metal salts such as lithium chloride, potassium fluoride or cesium fluoride; and ammonium salts such as tetrabutylammonium bromide. These may be used in combination in an arbitrary ratio.

Although there are no particular limitations on the metal catalyst used provided it is used in known methods, preferred examples include palladium catalysts such as tetrakis(triphenylphosphine) palladium, bis(tri-tert-butylphosphine) palladium, palladium diacetate, palladium dichloride-diphenylphosphinoferrocene complex, palladium dichloride-benzonitrile complex, palladium dichloride-acetonitrile complex, bis(dibenzylideneacetone) palladium, tris(dibenzylideneacetone)dipalladium, bis[1,2-bis(diphenylphosphino)ethane]palladium, 3-chloropyridine[1,3-bis(2,6-diisopropylphenyl)imidazo-2-ylidene]palladium or palladium-activated carbon.

Varying according to the raw material compounds, reagents and the like, the reaction temperature is normally −10° C. to 200° C. and preferably 0° C. to 150° C.

Varying according to the raw material compounds, reagents and the like, the reaction time is normally 5 minutes to 48 hours and preferably 10 minutes to 12 hours.

Following completion of the reaction, the desired compound of this reaction can be obtained by, for example, concentrating the reaction mixture, adding an organic solvent such as ethyl acetate and washing with water followed by separating the organic layer containing the desired compound, drying with anhydrous sodium sulfate and the like, and distilling off the solvent.

The resulting compound can be further purified if necessary using a conventional method, for example, recrystallization, reprecipitation, silica gel column chromatography, or the like.

(Step 1-1e2-4)

This step is a step for reacting a compound having a leaving group such as a halogen atom or —$OX^1$ group on ring $Q^2$ obtained in Step 1-1e2-2 with a boron reagent in an inert solvent, in the presence or absence of a base, in the presence or absence of an additive, and in the presence of a metal catalyst, thereby converting it to a corresponding boron compound. This reaction condition is suitably selected from known methods described in, for example, Ishiyama, T., Murata, M., Miyaura, N., J. Org. Chem., 1995, 60, 7508; Ishiyama, T., Takagi, J., Ishida, K., Miyaura, N., Anastasi, N. R., Hartwig, J. F., J. Am. Chem. Soc., 2002, 124, 390; Ishiyama, T., Takagi, J., Hartwig, J. F., Miyaura, N., Angew. Chem. Int. Ed., 2002, 41, 3056, and the like, and this step is carried out in accordance therewith. Although the reaction conditions of this step are preferably as follows, they are not limited thereto.

Although there are no particular limitations on the solvent used provided it does not inhibit the reaction and dissolves the starting material to a certain degree, preferred examples include aromatic hydrocarbons such as benzene, toluene or xylene; halogenated hydrocarbons such as dichloromethane or chloroform; esters such as ethyl acetate or propyl acetate; ethers such as diethyl ether, tetrahydrofuran, 1,4-dioxane or 1,2-dimethoxyethane; alcohols such as methanol, ethanol or tert-butanol; nitriles such as acetonitrile, amides such as formamide or N,N-dimethylformamide; sulfoxides such as dimethyl sulfoxide; a mixture of a plurality of organic solvents in an arbitrary ratio, and a mixture thereof with water in an arbitrary ratio.

Although there are no particular limitations on the boron reagent used provided it is used in known methods, preferred examples include 4,4,4',4',5,5,5',5'-octamethyl-2,2'-bi-1,3,2-dioxaborolane.

Although there are no particular limitations on the base used provided it is used as a base in conventional reactions, preferred examples include organic bases such as triethylamine, N,N-diisopropylethylamine, N-methylmorpholine, lutidine or pyridine; alkali metal carbonates such as sodium carbonate or potassium carbonate; alkaline earth metal carbonates such as calcium carbonate; alkali metal hydrogencarbonates such as potassium hydrogencarbonate; alkaline earth metal hydrogencarbonates such as calcium hydrogencarbonate; alkali metal hydroxides such as sodium hydroxide; alkaline earth metal hydroxides such as calcium hydroxide; alkali metal acetates such as sodium acetate or potassium acetate, alkali metal phosphates such as tripotassium phosphate; metal alkoxides such as sodium tert-butoxide or potassium tert-butoxide; organometallic amides such as lithium diisopropylamide or sodium hexamethyldisilazide; organometallic compounds such as tert-butyl lithium; and metal hydrides such as potassium hydride.

Although there are no particular limitations on the additive used provided it is used in known methods, preferred examples include metal oxides such as silver oxide or alumina; phosphines such as triphenylphosphine, tri-tert-butylphosphine, tricyclohexylphosphine, tri(o-tolyl)phosphine, diphenylphosphinoferrocene, 2-dicyclohexylphosphino-2',6'-dimethoxy-1,1'-biphenyl (S-PHOS), 2-dicyclohexylphosphino-2',4',6'-triisopropyl-1,1'-biphenyl (X-PHOS) or 2,2'-bis(diphenylphosphino)-1,1'-binaphthyl (BINAP); phosphine oxides such as triphenylphosphine oxide; metal salts such as lithium chloride, potassium fluoride or cesium fluoride; and ammonium salts such as tetrabutylammonium bromide. These may be used in combination in an arbitrary ratio.

Although there are no particular limitations on the metal catalyst used provided it is used in known methods, preferred examples include palladium catalysts such as tetrakis(triphenylphosphine) palladium, bis(tri-tert-butylphosphine) palladium, palladium diacetate, palladium dichloride-diphenylphosphinoferrocene complex, palladium dichloride-benzonitrile complex, palladium dichloride-acetonitrile complex, bis(dibenzylideneacetone) palladium, tris(dibenzylideneacetone)dipalladium, bis[1,2-bis(diphenylphosphino)ethane]palladium, 3-chloropyridine[1,3-bis(2,6-diisopropylphenyl)imidazo-2-ylidene]palladium or palladium-activated carbon.

Varying according to the raw material compounds, reagents and the like, the reaction temperature is normally −10° C. to 200° C. and preferably 0° C. to 150° C.

Varying according to the raw material compounds, reagents and the like, the reaction time is normally 5 minutes to 48 hours and preferably 10 minutes to 12 hours.

Following completion of the reaction, the desired compound of the present reaction can be obtained by, for example, concentrating the reaction mixture, adding an organic solvent such as ethyl acetate and washing with water followed by separating the organic layer containing the desired compound, drying with anhydrous sodium sulfate and the like, and distilling off the solvent.

The resulting compound can be further purified if necessary using a conventional method, for example, recrystallization, reprecipitation, silica gel column chromatography, or the like.

(Step 1-1e2-5)

This step is a step for reacting a boron compound obtained in Step 1-1e2-4 with a substituted or unsubstituted aryl halide or heteroaryl halide, or aryl pseudohalide or heteroaryl pseudohalide containing ring $Q^3$ in an inert solvent, in the presence or absence of a base, in the presence or absence of an additive, and in the presence of a metal catalyst, thereby producing a compound having the general formula (6) or (9). This step can be carried out in accordance with Step 1-1e2-3.

(Step 1-2)

Step 1-2 is a step for producing a compound having the general formula (1) from a compound having the general formula (3).

Examples of Essential Reactions Include:

Step 1-2a: deprotection reaction of protecting group $Pro^1$;
Step 1-2b: deprotection reaction of protecting group $Pro^3$.
Further,
Step 1-2c: reaction for converting $R^{1b}$ to $R^1$; and
Step 1-2d: reaction for converting $R^{2a}$ to $R^2$ can be added, as necessary. Steps 1-2a to 1-2d may be carried out in any order.

(Step 1-2a)

This step is a step for deprotecting the protecting group $Pro^1$. A known method described in, for example, Protective Groups in Organic Synthesis, $3^{rd}$ ed., Greene, T. W., Wuts, P. G. M., John Wiley & Sons, Inc., New York, 1999, and the like can be suitably selected depending to the $Pro^1$ used, and this reaction is carried out in accordance therewith. Here, a benzyl group is selected as a preferable $Pro^1$, and a method in which $Pro^1$ is converted to a hydrogen atom using a catalyst under hydrogen atmosphere, in an inert solvent, in the presence or absence of an additive (Step 1-2a1), a method in which $Pro^1$ is converted to a hydrogen atom using a catalyst in the presence of an organic compound that can serve as a hydrogen source, in a nitrogen or argon atmosphere, in an inert solvent and in the presence or absence of an additive (Step 1-2a2), or a method in which $Pro^1$ is converted to a hydrogen atom using a suitable acid in an inert solvent (Step 1-2a3) is described, but this method is not limited thereto.

(Step 1-2a1)

This step is a step for converting $Pro^1$ to a hydrogen atom using a catalyst in a hydrogen atmosphere, in an inert solvent and in the presence or absence of an additive.

Although there are no particular limitations on the solvent used provided it does not inhibit the reaction and dissolves the starting material to a certain degree, preferred examples include aromatic hydrocarbons such as benzene, toluene or xylene; halogenated hydrocarbons such as dichloromethane or chloroform; esters such as ethyl acetate or propyl acetate; ethers such as diethyl ether, tetrahydrofuran, 1,4-dioxane or 1,2-dimethoxyethane; alcohols such as methanol or ethanol; nitriles such as acetonitrile; amides such as formamide or N,N-dimethylformamide; sulfoxides such as dimethyl sulfoxide; a mixture of a plurality of organic solvents in an arbitrary ratio, and a mixture thereof with water in an arbitrary ratio.

Although there are no particular limitations on the additive used provided it is used in known methods, examples include hydrochloric acid.

Although there are no particular limitations on the metal catalyst used provided it is used in known methods, preferred examples include palladium-activated carbon, tris(triphenylphosphine) rhodium chloride or palladium hydroxide.

Varying according to the raw material compounds, reagents and the like, the reaction temperature is normally −100° C. to 150° C. and preferably 0° C. to 100° C.

Varying according to the raw material compounds, reagents and the like, the reaction time is normally 1 minute to 24 hours and preferably 5 minutes to 10 hours.

Following completion of the reaction, the desired compound of this reaction can be obtained by, for example, filtering out an insoluble matter and concentrating the filtrate under reduced pressure. The resulting compound can be further purified if necessary by using a conventional method such as recrystallization, reprecipitation, silica gel column chromatography, or the like.

In the case where $R^{2a}$ is an alkenyl group, this alkenyl group can be converted to the corresponding alkyl group in this step.

(Step 1-2a2)

This step is a step for converting $Pro^1$ to a hydrogen atom using a catalyst in the presence of an organic compound that can serve as a hydrogen source, in a nitrogen or argon atmosphere, in an inert solvent and in the presence or absence of an additive.

Although there are no particular limitations on the solvent used provided it does not inhibit the reaction and dissolves the starting material to a certain degree, preferred examples include aromatic hydrocarbons such as benzene, toluene or xylene; halogenated hydrocarbons such as dichloromethane or chloroform; esters such as ethyl acetate or propyl acetate; ethers such as diethyl ether, tetrahydrofuran, 1,4-dioxane or 1,2-dimethoxyethane; alcohols such as methanol or ethanol; nitriles such as acetonitrile; amides such as formamide or N,N-dimethylformamide; sulfoxides such as dimethyl sulfoxide; a mixture of a plurality of organic solvents in an arbitrary ratio, and a mixture thereof with water in an arbitrary ratio.

Although there are no particular limitations on the organic compound used provided it is used in known methods, examples include formic acid.

Although there are no particular limitations on the additive used provided it is used in known methods, examples include hydrochloric acid.

Although there are no particular limitations on the metal catalyst used provided it is used in known methods, preferred examples include palladium-activated carbon, tris(triphenylphosphine) rhodium chloride, palladium hydroxide, or the like.

Varying according to the raw material compounds, reagents and the like, the reaction temperature is normally −100° C. to 150° C. and preferably −78° C. to 100° C.

Varying according to the raw material compounds, reagents and the like, the reaction time is normally 5 minutes to 24 hours and preferably 10 minutes to 6 hours.

Following completion of the reaction, the desired compound of this reaction can be obtained by, for example, concentrating the reaction mixture, adding an organic solvent such as ethyl acetate and washing with water followed by separating the organic layer containing the desired compound, drying with anhydrous sodium sulfate and the like, and distilling off the solvent.

The resulting compound can be further purified if necessary using a conventional method such as recrystallization, reprecipitation, silica gel column chromatography, or the like.
(Step 1-2a3)

This step is a step for converting $Pro^1$ to a hydrogen atom using a suitable acid in an inert solvent. This step can be carried out in accordance with Step 1-1a2.
(Step 1-2b)

This step is a step for deprotecting the protecting group $Pro^3$. This step can be carried out in accordance with step 1-1a. In the case where $Pro^3$ is a benzyl group, this step can also be carried out in accordance with Step 1-2a1.
(Step 1-2c)

This step is a step for converting $R^{1b}$ to $R^1$. This step can be carried out in accordance with step 1-1e2. In the case where $R^{1b}$ has a protecting group, this step further includes a step for deprotecting the same. Depending on the protecting group used, a known method described, for example, in Protective Groups in Organic Synthesis, $3^{rd}$ ed., Greene, T. W., Wuts, P. G. M., John Wiley & Sons, Inc., New York, 1999, and the like is suitably selected, and this step is carried out in accordance therewith. Here, a methoxymethyl group or a tert-butyl(dimethyl)silyl group is selected as a preferable protecting group, and a method in which a methoxymethyl group is deprotected using an acid in an inert solvent (Step 1-2c1), a method in which a tert-butyl(dimethyl)silyl group is deprotected using an acid in an inert solvent (Step 1-2c2), or a method in which a tert-butyl(dimethyl)silyl group is deprotected using a fluorine compound in an inert solvent (Step 1-2c3) is described, but this method is not limited thereto.
(Step 1-2c1)

This step is a step for deprotecting a methoxymethyl group, and can be carried out in accordance with Step 1-1a2.
(Step 1-2c2)

This step is a step for deprotecting a tert-butyl(dimethyl) silyl group, and can be carried out in accordance with Step 1-1a2.
(Step 1-2c3)

This step is a step for deprotecting a tert-butyl(dimethyl) silyl group, and is carried out using a fluorine compound in an inert solvent.

Although there are no particular limitations on the solvent used provided it does not inhibit the reaction and dissolves the starting material to a certain degree, preferred examples include aromatic hydrocarbons such as benzene, toluene or xylene; halogenated hydrocarbons such as dichloromethane or chloroform; esters such as ethyl acetate or propyl acetate; ethers such as diethyl ether, tetrahydrofuran, 1,4-dioxane or 1,2-dimethoxyethane; alcohols such as methanol, ethanol or tert-butanol; nitriles such as acetonitrile; amides such as formamide or N,N-dimethylformamide; sulfoxides such as dimethyl sulfoxide; a mixture of a plurality of organic solvents in an arbitrary ratio, and a mixture thereof with water in an arbitrary ratio.

Although there are no particular limitations on the fluorine compound used provided it is used in the deprotection of a silyl group, preferred examples include tetrabutylammonium fluoride, tris(dimethylamino)sulfonium difluorotrimethylsilicate, or the like.

Varying according to the raw material compounds, reagents and the like, the reaction temperature is normally $-100°$ C. to $150°$ C. and preferably $-20°$ C. to $100°$ C.

Varying according to the raw material compounds, reagents and the like, the reaction time is normally 5 minutes to 24 hours and preferably 10 minutes to 6 hours.

Following completion of the reaction, the desired compound of this reaction can be obtained by, for example, concentrating the reaction mixture, adding an organic solvent such as ethyl acetate and washing with water followed by separating the organic layer containing the desired compound, drying with anhydrous sodium sulfate and the like, and distilling off the solvent.

The resulting compound can be further purified if necessary using a conventional method such as recrystallization, reprecipitation, silica gel column chromatography, or the like.
(Step 1-2d)

This step is a step for converting $R^{2a}$ to $R^2$, and, in the case where $R^{2a}$ is an alkenyl group, this alkenyl group can be converted to the corresponding alkyl group in accordance with Step 1-2a1.
(Step 2)

Step 2 is a step for producing compound (2) used in Step 1.

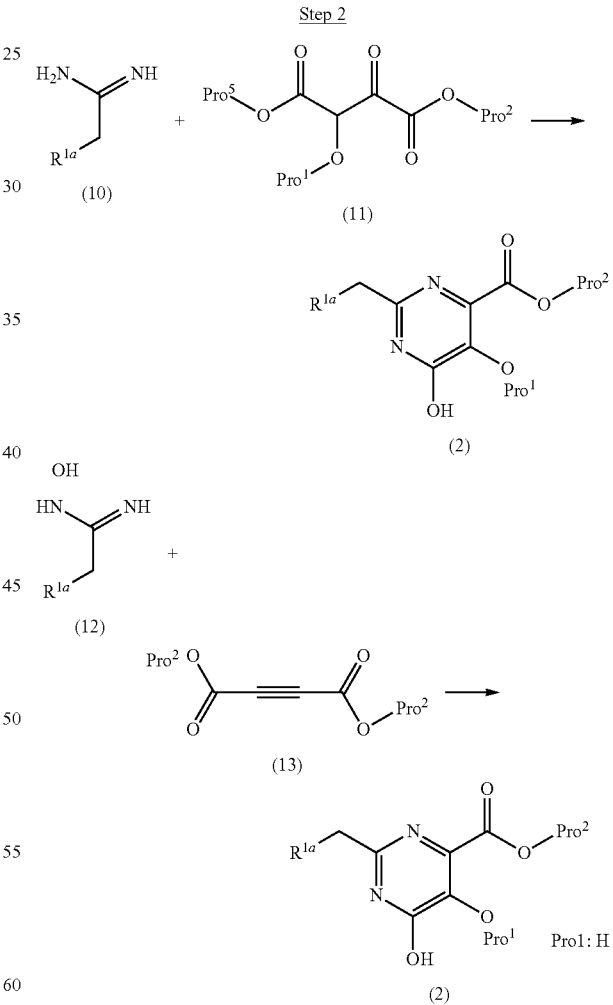

In the above formulae, $R^{1a}$ refers to the same meaning as previously defined, and $Pro^5$ refers to a protecting group of each functional group selected from known protecting groups (e.g., *Protective Groups in Organic Synthesis*, $3^{rd}$ ed., Greene, T. W., Wuts, P. G. M., John Wiley & Sons, Inc., New York, 1999, etc.). Although there are no particular limitations on Pro$^5$ provided it is present stably during the reaction and does not inhibit the reaction, a methyl group is preferred.

A compound having the general formula (2) can be synthesized using a known method (e.g., (i) a method in which substituted ethanimidamide (10) and a 2-alkyloxy-3-oxosuccinic acid diester (11), synthesized in accordance with known methods, are condensed in the presence of a base: Dreher, S. D., Ikemoto, N., Gresham, V., Liu, J., Dormer, P. G., Balsells, J., Mathre, D., Novak, T., Armstrong III, J. D., Tetrahedron Lett., 2004, 45, 6023; or (ii) a method in which N-hydroxy-substituted ethanimidamides (12) and acetylene dicarboxylic acid diester (13) are condensed: Culbertson, T. P., J. Heterocycl. Chem., 1979, 16, 1423), or using a method in accordance with a known method.

The reaction products obtained according to each of the aforementioned steps are isolated and purified as non-solvates, salts thereof or various types of solvates such as hydrates. Salts thereof can be produced according to a conventional method. Isolation or purification is carried out by applying conventional methods such as extraction, concentration, distillation, crystallization, filtration, recrystallization, various types of chromatography, or the like.

Each type of isomer can be isolated in accordance with conventional methods by utilizing differences in physico-chemical properties between isomers. For example, optical isomers can be separated by common optical resolution methods (e.g., fractional crystallization, chromatography, etc.). In addition, optical isomers can also be produced from suitable optically active raw material compounds.

A formulation containing the compound of the present invention as an active ingredient is prepared using additives such as a carrier and an excipient used for conventional formulation. Administration of the compound of the present invention may be by oral administration in the form of tablets, pills, capsules, granules, powders, liquids, or the like, or parenteral administration in the form of injections (e.g., intravenous injection, intramuscular injection, etc.), suppositories, transcutaneous agents, nasal agents, inhalants, or the like. Dosage and frequency of administration of the compound of the present invention are suitably determined on an individual basis in consideration of such factors as symptoms and age or gender of the administered subject. The adult dosage is normally 0.001 to 100 mg/kg per administration for a human adult in the case of oral administration, and in the case of intravenous administration, the dosage is normally 0.0001 to 10 mg/kg per administration for a human adult. The frequency of administration is normally 1 to 6 times a day, or once a day to once for 7 days. It is also preferable that administration to a patient who receives dialysis is carried out once before or after each dialysis (preferably before dialysis) that the patient receives.

Solid formulations for oral administration according to the present invention may be tablets, powders, granules, or the like. Such formulations are produced in accordance with a conventional method by mixing one or more active substances with an inert excipient, lubricant, disintegrant, or dissolution aid. The excipient may be, for example, lactose, mannitol or glucose. The lubricant may be, for example, magnesium stearate. The disintegrant may be, for example, sodium carboxymethyl starch. The tablets or pills may be provided with a sugar coating, or a gastric or enteric coating as necessary.

Liquid formulations for oral administration may be pharmaceutically acceptable emulsions, liquids, suspensions, syrups, elixirs, or the like. Such formulations may contain commonly used inert solvents (e.g., purified water or ethanol), and may further contain solubilizers, wetting agents, suspending agents, sweeteners, corrigents, fragrances, or preservatives.

Injections for parenteral administration may be sterile aqueous or non-aqueous liquid formulations, suspensions or emulsions. Aqueous solvents for injection preparations may be, for example, distilled water or physiological saline. Non-aqueous solvents for injections may be, for example, propylene glycol, polyethylene glycol, vegetable oils such as olive oil, alcohols such as ethanol and Polysorbate 80 (Japanese Pharmacopoeia name). Such formulations may further contain isotonic agents, preservatives, wetting agents, emulsifiers, dispersants, stabilizers, or dissolution aids. These formulations may be sterilized, for example, by passing through a bacteria-retaining filter, incorporation of a bactericide, or irradiation. Further, it is also possible to use, as these formulations, compositions obtained by dissolving or suspending a sterile solid composition in sterile water or a solvent for injection prior to use.

EXAMPLES

Although the following provides examples and test examples to explain the present invention in more detail, the scope of the present invention is not limited thereto.

Example 1

({[5-Hydroxy-2-{(1-[4'-(hydroxymethyl)biphenyl-4-yl]piperidin-4-yl}methyl)-6-methylpyrimidin-4-yl]carbonyl}amino)acetic acid

[Chemical 12]

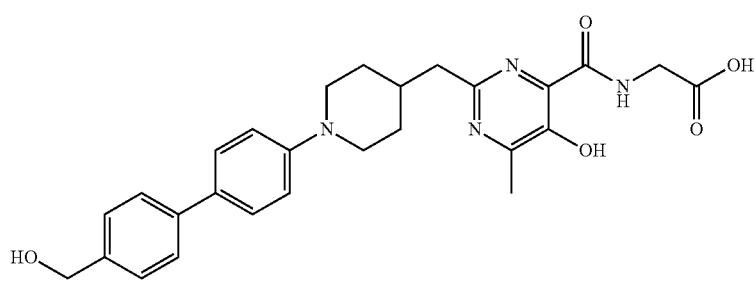

(1) tert-Butyl 4-(cyanomethylene)piperidine-1-carboxylate

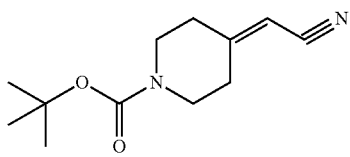

[Chemical 13]

Diethyl cyanomethylphosphonate (16 mL, 100 mmol) was dissolved in tetrahydrofuran (360 mL), and a solution of lithium hexamethyldisilazide in tetrahydrofuran (1 M, 100 mL, 100 mmol) and a solution of tert-butyl 4-oxopiperidine-1-carboxylate (18 g, 91 mmol) in tetrahydrofuran (36 mL) were added under a nitrogen atmosphere at −70° C., followed by stirring at the same temperature for 40 minutes. A saturated aqueous ammonium chloride solution was added to the reaction solution, followed by extraction with ethyl acetate, and the extract was washed with a saturated aqueous ammonium chloride solution. After the solvent was distilled off under reduced pressure, the resulting residue was purified by chromatography on a silica gel column (Moritex Corporation, elution solvent: hexane/ethyl acetate), and a fraction corresponding to the Rf value=0.41 (hexane/ethyl acetate=3/1) by thin layer chromatography was concentrated under reduced pressure to afford the title compound (22 g) as a white solid (quantitative yield).

$^1$H-NMR (500 MHz, CDCl$_3$) δ: 5.19 (1H, s), 3.56-3.46 (4H, m), 2.56 (2H, t, J=5 Hz), 2.33 (2H, t, J=5 Hz), 1.48 (9H, s).

(2) tert-Butyl 4-(cyanomethyl)piperidine-1-carboxylate

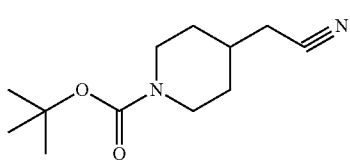

[Chemical 14]

tert-Butyl 4-(cyanomethylene)piperidine-1-carboxylate (20 g, 91 mmol) was dissolved in ethyl acetate (400 mL), and 10% palladium-activated carbon (3.0 g) was added, followed by stirring at room temperature for 3.5 hours under a hydrogen atmosphere. The reaction solution was filtered with celite, and the filtrate was concentrated under reduced pressure. The resulting residue was purified by chromatography on a silica gel column (Moritex Corporation, elution solvent: hexane/ethyl acetate), and a fraction corresponding to the Rf value=0.38 (hexane/ethyl acetate=3/1) by thin layer chromatography was concentrated under reduced pressure to afford the title compound (23 g) as a white solid (quantitative yield).

$^1$H-NMR (500 MHz, CDCl$_3$) δ: 4.24-4.07 (2H, m), 2.78-2.64 (2H, m), 2.32 (2H, d, J=6 Hz), 1.89-1.75 (3H, m), 1.46 (9H, s), 1.32-1.21 (2H, m).

(3) tert-Butyl 4-(2-amino-2-iminoethyl)piperidine-1-carboxylate acetate

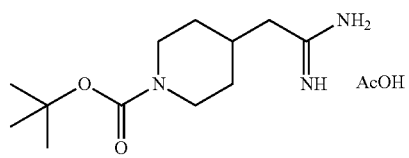

[Chemical 15]

tert-Butyl 4-(cyanomethyl)piperidine-1-carboxylate (91 mmol) was dissolved in ethanol (200 mL), and an aqueous hydroxylamine solution (50%, 17 mL, 170 mmol) was added, followed by heating to reflux for 3.5 hours. The reaction solution was cooled, and subsequently concentrated under reduced pressure to afford tert-butyl 4-[2-amino-2-(hydroxyimino)ethyl]piperidine-1-carboxylate as a colorless amorphous solid.

This was dissolved in 1,4-dioxane (100 mL), and acetic anhydride (17 mL, 180 mmol) and triethylamine (15 mL, 180 mmol) were added at room temperature, followed by stirring at the same temperature for 2 hours. After the reaction solution was diluted with ethyl acetate, it was washed sequentially with water, dilute hydrochloric acid and water, and the organic layer was dried over anhydrous sodium sulfate. After the solvent was distilled off under reduced pressure, the resulting solid was washed with hexane to afford tert-Butyl 4-[2-(acetoxyimino)-2-aminoethyl]piperidine-1-carboxylate as a white solid.

This was dissolved in ethanol (200 mL) and dichloromethane (40 mL), and 10% palladium-activated carbon (3.6 g) was added, followed by stirring under a hydrogen atmosphere at room temperature for 5 hours. The reaction solution was filtered with celite, and subsequently the filtrate was concentrated under reduced pressure to afford the title compound (24 g, 79 mmol) as a white solid (yield 85%).

$^1$H-NMR (500 MHz, DMSO-d$_6$) δ: 3.99-3.86 (2H, m), 2.81-2.58 (2H, m), 2.23 (2H, d, J=8 Hz), 1.85 (1H, m), 1.64 (3H, s), 1.64-1.56 (2H, m), 1.40 (9H, s), 0.99-1.08 (2H, m).

(4) tert-Butyl 5-(benzyloxy)-2-{[1-(tert-butoxycarbonyl)piperidin-4-yl]methyl}-6-hydroxypyrimidine-4-carboxylate

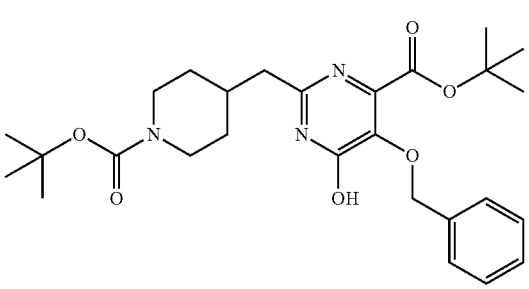

[Chemical 16]

Diisopropylamine (30 mL, 210 mmol) was dissolved in tetrahydrofuran (100 mL), and a solution of n-butyllithium in hexane (2.77 M, 77 mL, 210 mmol) was added dropwise at 3° C., followed by stirring at −78° C. for 30 minutes to prepare a solution of lithium diisopropylamide (LDA) in tetrahydrofuran.

tert-Butyl methyl oxalate (34 g, 210 mmol) and methyl (benzyloxy)acetate (35 g, 190 mmol) were dissolved in tetrahydrofuran (250 mL) and a solution of LDA in tetrahydrofuran prepared at −78° C. was added dropwise under a nitrogen atmosphere, followed by stirring at the same temperature for 3 hours. The temperature of the reaction solution was gradually raised to −40° C., and subsequently hydrochloric acid (2 M, 210 mL) was added, followed by extraction with ethyl acetate. The extract was washed with water and a saturated aqueous sodium chloride solution, followed by drying over anhydrous magnesium sulfate, and the solvent was distilled off under reduced pressure to afford 4-tert-butyl 1-methyl 2-(benzyloxy)-3-oxosuccinate (62 g) as a yellow oil.

A part of this oil (36 g, 120 mmol) and tert-butyl 4-(2-amino-2-iminoethyl)piperidine-1-carboxylate acetate (24 g, 79 mmol) were dissolved in methanol (240 mL), and at 3° C. a solution of sodium methoxide in methanol (28%, 48 mL, 240 mmol) was added, followed by stirring at room temperature for 14.5 hours. Hydrochloric acid (1 M, 130 mL) was added to the reaction solution, and subsequently a deposited solid was collected by filtration to afford the title compound (26 g, 52 mmol) as a white solid (yield 66%).

$^1$H-NMR (500 MHz, CDCl$_3$) δ: 7.47-7.44 (2H, m), 7.40-7.31 (3H, m), 5.23 (2H, s), 4.21-3.91 (2H, m), 2.74-2.58 (2H, m), 2.62 (2H, d, J=7 Hz), 2.06 (1H, m), 1.69-1.60 (2H, m), 1.53 (9H, s), 1.43 (9H, s), 1.28-1.16 (2H, m).

(5) tert-Butyl 5-(benzyloxy)-2-{[1-(tert-butoxycarbonyl)piperidin-4-yl]methyl}-6-{[(trifluoromethyl)sulfonyl]oxy}pyrimidine-4-carboxylate

[Chemical 17]

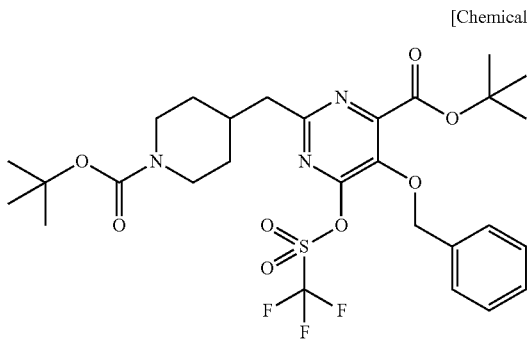

tert-Butyl 5-(benzyloxy)-2-{[1-(tert-butoxycarbonyl)piperidin-4-yl]methyl}-6-hydroxypyrimidine-4-carboxylate (5.0 g, 10 mmol) was dissolved in dichloromethane (100 mL), and trifluoromethanesulfonic anhydride (2.1 mL, 12 mmol) and triethylamine (2.1 mL, 15 mmol) were added at −78° C., followed by stirring at the same temperature for 30 minutes. After the reaction solution was concentrated under reduced pressure, the resulting residue was purified by chromatography on a silica gel column (Moritex Corporation, elution solvent: hexane/ethyl acetate), and a fraction corresponding to the Rf value=0.63 (hexane/ethyl acetate=2/1) by thin layer chromatography was concentrated under reduced pressure to afford the title compound (6.0 g, 9.5 mmol) as a yellow oil (yield 95%).

$^1$H-NMR (500 MHz, CDCl$_3$) δ: 7.44-7.36 (5H, m), 5.14 (2H, s), 4.21-3.95 (2H, m), 2.88 (2H, d, J=7 Hz), 2.80-2.62 (2H, m), 2.07 (1H, m), 1.67-1.60 (2H, m), 1.57 (9H, s), 1.46 (9H, s), 1.27-1.17 (2H, m).

(6) tert-Butyl 5-(benzyloxy)-2-{[1-(tert-butoxycarbonyl)piperidin-4-yl]methyl}-6-methylpyrimidine-4-carboxylate

[Chemical 18]

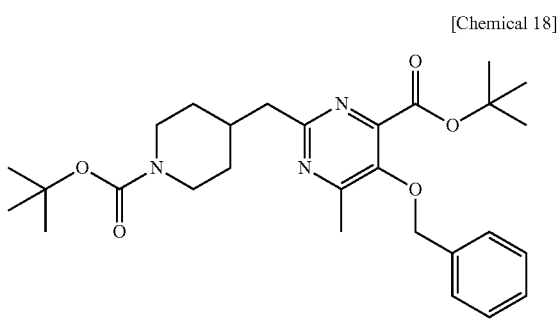 [SMILES: Cc1nc(CC2CCN(C(=O)OC(C)(C)C)CC2)nc(C(=O)OC(C)(C)C)c1OCc1ccccc1]

tert-Butyl 5-(benzyloxy)-2-{[1-(tert-butoxycarbonyl)piperidin-4-yl]methyl}-6-{[(trifluoromethyl)sulfonyl]oxy}pyrimidine-4-carboxylate (6.0 g, 9.5 mmol) was dissolved in tetrahydrofuran (90 mL) and, at room temperature, methylboronic acid (1.8 g, 30 mmol), silver oxide (6.7 g, 29 mmol), potassium carbonate (4.0 g, 29 mmol) and a [1,1'-bis(diphenylphosphino)ferrocene]palladium dichloride dichloromethane complex (0.78 g, 0.96 mmol) were added, followed by heating to reflux for 3 hours under a nitrogen atmosphere. The reaction solution was cooled to room temperature, and subsequently the insolubles were filtered off. After the filtrate was concentrated under reduced pressure, the resulting residue was purified by chromatography on a silica gel column (Moritex Corporation, elution solvent: hexane/ethyl acetate), and a fraction corresponding to the Rf value=0.34 (hexane/ethyl acetate=2/1) by thin layer chromatography was concentrated under reduced pressure to afford the title compound (4.4 g, 8.8 mmol) as a yellow oil (yield 93%).

$^1$H-NMR (500 MHz, CDCl$_3$) δ: 7.44-7.34 (5H, m), 5.00 (2H, s), 4.17-3.98 (2H, m), 2.85 (2H, d, J=7 Hz), 2.77-2.64 (2H, m), 2.44 (3H, s), 2.09 (1H, m), 1.66-1.59 (2H, m), 1.59 (9H, s), 1.45 (9H, s), 1.30-1.19 (2H, m).

(7) tert-Butyl 5-(benzyloxy)-6-methyl-2-(piperidin-4-ylmethyl)pyrimidine-4-carboxylate hydrochloride

[Chemical 19]

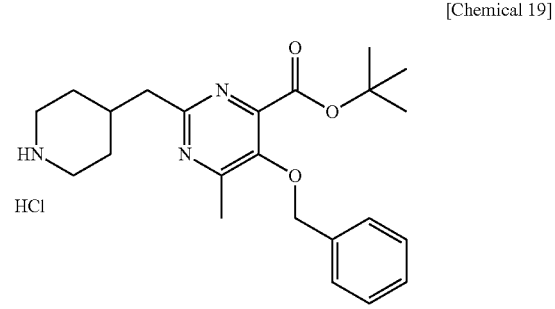 [SMILES: Cl ; Cc1nc(CC2CCNCC2)nc(C(=O)OC(C)(C)C)c1OCc1ccccc1]

tert-Butyl 5-(benzyloxy)-2-{[1-(tert-butoxycarbonyl)piperidin-4-yl]methyl}-6-methylpyrimidine-4-carboxylate (4.4 g, 8.8 mmol) was dissolved in ethyl acetate (44 mL), and a solution of hydrogen chloride in ethyl acetate (4 M, 68 mL, 270 mmol) was added, followed by stirring at room temperature for 3 hours. Hexane (100 mL) and ethyl acetate (100 mL) were added to the reaction solution, whereby a solid was deposited. The resulting solid was collected by filtration, and dried under reduced pressure to afford the title compound (3.7 g, 8.5 mmol) as a white solid (yield 95%).

$^1$H-NMR (500 MHz, DMSO-$d_6$) δ: 7.47-7.34 (5H, m), 4.99 (2H, s), 3.26-3.18 (2H, m), 2.90-2.78 (2H, m), 2.78 (2H, d, J=7 Hz), 2.46 (3H, s), 2.12 (1H, m), 1.78-1.70 (2H, m), 1.51 (9H, s), 1.51-1.39 (2H, m).

(8) [(4'-Bromobiphenyl-4-yl)methoxy](tert-butyl)dimethylsilane

[Chemical 20]

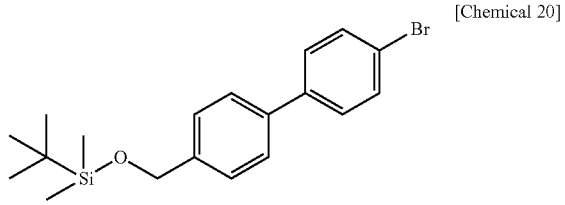 [SMILES: CC(C)(C)[Si](C)(C)OCc1ccc(-c2ccc(Br)cc2)cc1]

(4'-Bromobiphenyl-4-yl)methanol (0.70 g, 2.7 mmol) and imidazole (0.54 g, 8.0 mmol) were dissolved in tetrahydrofuran (20 mL), and tert-butyldimethylchlorosilane (1.2 g, 8.0 mmol) was added under a nitrogen atmosphere, followed by stirring at room temperature for 1 hour. Water was added to the reaction solution, which was extracted with ethyl acetate, and subsequently washed sequentially with a saturated sodium hydrogencarbonate solution, water and a saturated aqueous sodium chloride solution. After the organic layer was concentrated under reduced pressure, the resulting residue was purified by chromatography on a silica gel column (Moritex Corporation, elution solvent: hexane/ethyl acetate), and a fraction corresponding to the Rf value=0.90 (hexane/ethyl acetate=9/1) by thin layer chromatography was concentrated under reduced pressure to afford the title compound (0.92 g, 2.4 mmol) as a white solid (yield 91%).

$^1$H-NMR (500 MHz, CDCl$_3$) δ: 7.55 (2H, d, J=8 Hz), 7.52 (2H, d, J=8 Hz), 7.45 (2H, d, J=8 Hz), 7.40 (2H, d, J=8 Hz), 4.78 (2H, s), 0.96 (9H, s), 0.12 (6H, s).

(9) tert-Butyl 5-(benzyloxy)-2-{(1-[4'-({[tert-butyl(dimethyl)silyl]oxy}methyl)biphenyl-4-yl]piperidin-4-yl}methyl)-6-methylpyrimidine-4-carboxylate tert-Butyl 5-(benzyloxy)-6-methyl-2-(piperidin-4-ylmethyl)pyrimidine-4-carboxylate hydrochloride (1.0 g, 2.3 mmol), [(4'-bromobiphenyl-4-yl)methoxy](tert-butyl)dimethylsilane (0.92 g, 2.4 mmol), sodium tert-butoxide (0.67 g, 7.0 mmol), 2-dicyclohexylphosphino-2',4',6'-triisopropylbiphenyl (X-PHOS) (0.11 g, 0.23 mmol) and tris(dibenzylideneacetone)dipalladium (0.11 g, 0.12 mmol) were suspended in toluene (50 mL), followed by heating to reflux for 3 hours under a nitrogen atmosphere. The reaction solution was cooled to room temperature, and filtered with celite, and subsequently the filtrate was concentrated under reduced pressure. The resulting residue was purified by chromatography on a silica gel column (Moritex Corporation, elution solvent: hexane/ethyl acetate), and a fraction corresponding to the Rf value=0.50 (hexane/ethyl acetate=2/1) by thin layer chromatography was concentrated under reduced pressure to afford the title compound (0.98 g, 1.4 mmol) as a yellow oil (yield 61%).

$^1$H-NMR (500 MHz, CDCl$_3$) δ: 7.52 (2H, d, J=8 Hz), 7.49 (2H, d, J=8 Hz), 7.45-7.32 (7H, m), 6.99 (2H, d, J=8 Hz), 5.01 (2H, s), 4.76 (2H, s), 3.73 (2H, d, J=12 Hz), 2.91 (2H, d, J=7 Hz), 2.75 (2H, t, J=12 Hz), 2.46 (3H, s), 2.17-2.06 (1H, m), 1.80 (2H, d, J=12 Hz), 1.59 (9H, s), 1.54 (2H, q, J=12 Hz), 0.95 (9H, s), 0.11 (6H, s).

(10) tert-Butyl 5-(benzyloxy)-2-{(1-[4'-(hydroxymethyl)biphenyl-4-yl]piperidin-4-yl}methyl)-6-methylpyrimidine-4-carboxylate

[Chemical 22]

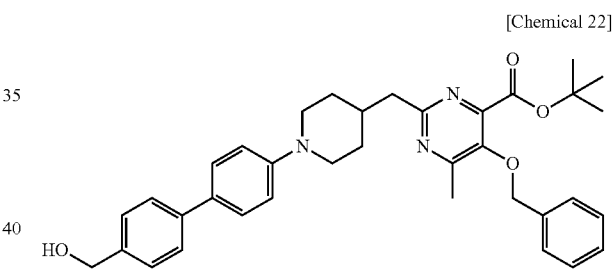

tert-Butyl 5-(benzyloxy)-2-{(1-[4'-({[tert-butyl(dimethyl)silyl]oxy}methyl)biphenyl-4-yl]piperidin-4-yl}methyl)-6-methylpyrimidine-4-carboxylate (0.98 g, 1.4 mmol) was dissolved in 1,4-dioxane (10 mL), and a solution of hydrogen chloride in dioxane (4 M, 1.0 mL, 4 mmol) was added, followed by stirring at room temperature for 1.5 hours. A saturated sodium hydrogencarbonate solution was added to the reaction solution for neutralization, followed by extraction

[Chemical 21]

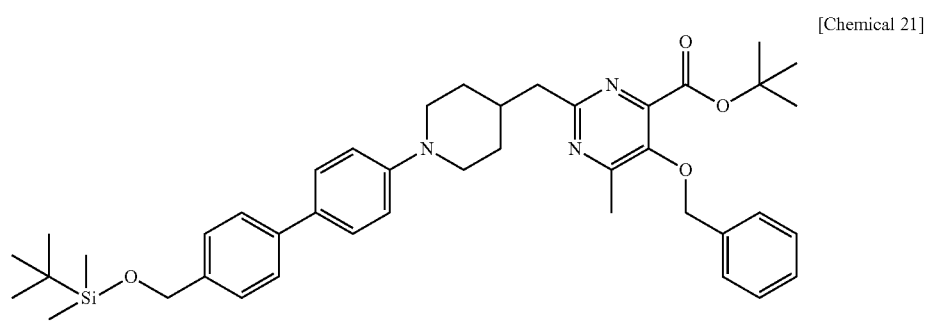 [SMILES: Cc1nc(CC2CCN(c3ccc(-c4ccc(CO[Si](C)(C)C(C)(C)C)cc4)cc3)CC2)nc(C(=O)OC(C)(C)C)c1OCc1ccccc1]

with ethyl acetate, and subsequently the organic layer was concentrated under reduced pressure to afford the title compound (0.81 g, 1.4 mmol) as a yellow oil (yield 99%).

$^1$H-NMR (500 MHz, CDCl$_3$) δ: 7.56 (2H, d, J=8 Hz), 7.50 (2H, d, J=8 Hz), 7.45-7.34 (7H, m), 7.00 (2H, d, J=8 Hz), 5.01 (2H, s), 4.72 (2H, s), 3.73 (2H, d, J=12 Hz), 2.91 (2H, d, J=7 Hz), 2.76 (2H, t, J=12 Hz), 2.46 (3H, s), 2.17-2.06 (1H, m), 1.80 (2H, d, J=12 Hz), 1.59 (9H, s), 1.54 (2H, q, J=12 Hz).

(11) Ethyl({[5-(benzyloxy)-2-({1-[4'-(hydroxymethyl)biphenyl-4-yl]piperidin-4-yl}methyl)-6-methylpyrimidin-4-yl]carbonyl}amino)acetate

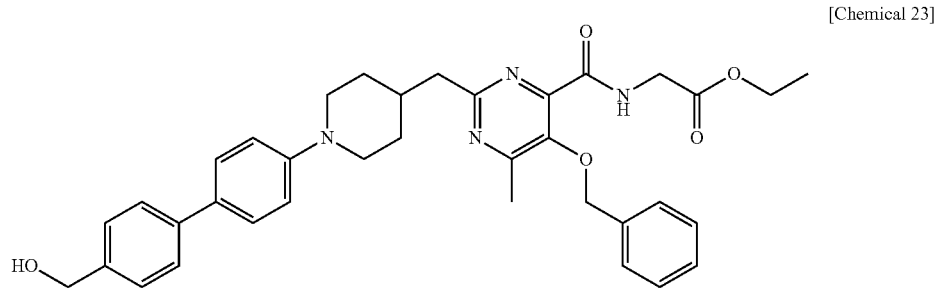 [SMILES: CCOC(=O)CNC(=O)c1nc(CC2CCN(c3ccc(-c4ccc(CO)cc4)cc3)CC2)nc(C)c1OCc1ccccc1]

[Chemical 23]

tert-Butyl 5-(benzyloxy)-2-{(1-[4'-(hydroxymethyl)biphenyl-4-yl]piperidin-4-yl}methyl)-6-methylpyrimidine-4-carboxylate (0.81 g, 1.4 mmol) was dissolved in a mixed solvent of tetrahydrofuran (10 mL) and methanol (10 mL), and an aqueous sodium hydroxide solution (5 M, 10 mL, 50 mmol) was added, followed by stirring at 50° C. for 15 minutes. The reaction solution was cooled to room temperature, and hydrochloric acid (5 M, 10 mL, 50 mmol) was added, followed by extraction with ethyl acetate. The organic layer was concentrated under reduced pressure to afford 5-(benzyloxy)-2-{(1-[4'-(hydroxymethyl)biphenyl-4-yl]piperidin-4-yl}methyl)-6-methylpyrimidine-4-carboxylic acid as a yellow solid.

This was dissolved in a mixed solvent of tetrahydrofuran (10 mL) and methanol (10 mL), and glycine ethyl ester hydrochloride (0.30 g, 2.1 mmol), 4-(4,6-dimethoxy-1,3,5-triazin-2-yl)-4-methylmorpholinium chloride (0.51 g, 1.8 mmol) and N-methylmorpholine (0.39 mL, 3.5 mmol) were added, followed by stirring at room temperature for 14 hours. The reaction solution was concentrated under reduced pressure, and the resulting residue was purified by chromatography on a silica gel column (Moritex Corporation, elution solvent: dichloromethane/ethyl acetate), and a fraction corresponding to the Rf value=0.60 (hexane/ethyl acetate=1/4) by thin layer chromatography was concentrated under reduced pressure to afford the title compound (0.32 g, 0.53 mmol) as a yellow solid (yield 38%).

$^1$H-NMR (500 MHz, CDCl$_3$) δ: 8.36 (1H, t, J=6 Hz), 7.56 (2H, d, J=8 Hz), 7.52-7.47 (4H, m), 7.43-7.34 (5H, m), 7.00 (2H, d, J=8 Hz), 5.12 (2H, s), 4.73 (2H, d, J=6 Hz), 4.30-4.19 (4H, m), 3.75 (2H, d, J=12 Hz), 2.90 (2H, d, J=7 Hz), 2.78 (2H, t, J=12 Hz), 2.47 (3H, s), 2.17-2.07 (1H, m), 1.79 (2H, d, J=12 Hz), 1.59-1.48 (2H, m), 1.32 (3H, t, J=7 Hz).

(12) Ethyl({[5-hydroxy-2-({1-[4'-(hydroxymethyl)biphenyl-4-yl]piperidin-4-yl}methyl)-6-methylpyrimidin-4-yl]carbonyl}amino)acetate

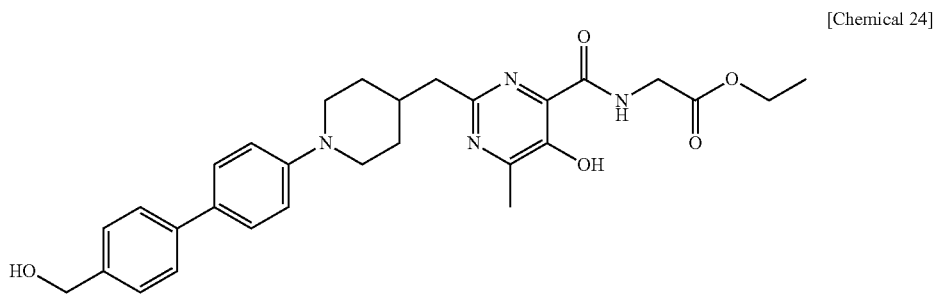 [SMILES: CCOC(=O)CNC(=O)c1nc(CC2CCN(c3ccc(-c4ccc(CO)cc4)cc3)CC2)nc(C)c1O]

[Chemical 24]

Ethyl({[5-(benzyloxy)-2-({1-[4'-(hydroxymethyl)biphenyl-4-yl]piperidin-4-yl}methyl)-6-methylpyrimidin-4-yl]carbonyl}amino)acetate (0.43 g, 0.71 mmol) was dissolved in a mixed solvent of ethyl acetate (20 mL) and dichloromethane (20 mL), and 10% palladium-activated carbon (0.080 g) was added, followed by stirring at room temperature for 2.5 hours under a hydrogen atmosphere. The reaction solution was filtered with celite, and the filtrate was concentrated under reduced pressure, whereby a solid was deposited. The resulting solid was collected by filtration, and dried under reduced pressure to afford the title compound (0.34 g, 0.66 mmol) as a white solid (yield 93%).

MS m/z: 519 (M+H)$^+$;

$^1$H-NMR (500 MHz, DMSO-d$_6$) δ: 11.83 (1H, s), 9.52 (1H, t, J=6 Hz), 7.54 (2H, d, J=8 Hz), 7.50 (2H, d, J=8 Hz), 7.34 (2H, d, J=8 Hz), 6.99 (2H, d, J=8 Hz), 5.17 (1H, brs), 4.50 (2H, s), 4.15 (2H, q, J=7 Hz), 4.09 (2H, d, J=6 Hz), 3.74

(2H, d, J=12 Hz), 2.79 (2H, d, J=7 Hz), 2.70 (2H, t, J=12 Hz), 2.45 (3H, s), 2.15-2.05 (1H, m), 1.68 (2H, d, J=12 Hz), 1.37 (2H, q, J=12 Hz), 1.21 (3H, t, J=7 Hz).

(13) ({[5-Hydroxy-2-({1-[4'-(hydroxymethyl)biphenyl-4-yl]piperidin-4-yl}methyl)-6-methylpyrimidin-4-yl]carbonyl}amino)acetic acid Ethyl({[5-hydroxy-2-({1-[4'-(hydroxymethyl)biphenyl-4-yl]piperidin-4-yl}methyl)-6-methylpyrimidin-4-yl]carbonyl}amino)acetate (0.22 g, 0.42 mmol) was dissolved in a mixed solvent of methanol (5 mL) and tetrahydrofuran (5 mL), and an aqueous sodium hydroxide solution (1 M, 5.0 mL) was added, followed by stirring at room temperature for 30 minutes. The reaction solution was concentrated under reduced pressure, and hydrochloric acid (1 M, 5.0 mL) was added to the resulting residue, whereby a solid was deposited. The resulting solid was collected by filtration, and dried under reduced pressure to afford the title compound (0.17 g, 0.35 mmol) as a pale yellowish white solid (yield 82%).

MS m/z: 491 (M+H)$^+$;
$^1$H-NMR (500 MHz, DMSO-d$_6$) δ: 12.87 (1H, brs), 11.92 (1H, s), 9.42 (1H, t, J=6 Hz), 7.54 (2H, d, J=8 Hz), 7.50 (2H, d, J=8 Hz), 7.34 (2H, d, J=8 Hz), 7.00 (2H, d, J=8 Hz), 5.17 (1H, t, J=6 Hz), 4.51 (2H, d, J=6 Hz), 4.01 (2H, d, J=6 Hz), 3.74 (2H, d, J=12 Hz), 2.78 (2H, d, J=7 Hz), 2.70 (2H, t, J=12 Hz), 2.45 (3H, s), 2.15-2.04 (1H, m), 1.68 (2H, d, J=12 Hz), 1.37 (2H, q, J=12 Hz).

Example 2

({[2-{(1-[4'-(Acetoxymethyl)biphenyl-4-yl]piperidin-4-yl}methyl)-5-hydroxy-6-methylpyrimidin-4-yl]carbonyl}amino)acetic acid ({[5-Hydroxy-2-{(1-[4'-(hydroxymethyl)biphenyl-4-yl}piperidin-4-yl}methyl)-6-methylpyrimidin-4-yl]carbonyl}amino)acetic acid (0.13 g, 0.27 mmol) was dissolved in acetonitrile (8 mL), and acetic anhydride (0.063 mL, 0.67 mmol), triethylamine (0.092 mL, 0.66 mmol) and 4-dimethylaminopyridine (0.081 g, 0.66 mmol) were added, followed by stirring at room temperature for 3 hours. After the reaction solution was concentrated under reduced pressure, the resulting residue was purified by chromatography on a silica gel column (Moritex Corporation, elution solvent: dichloromethane/methanol), and a fraction corresponding to the Rf value=0.20 (dichloromethane/methanol=9/1) by thin layer chromatography was concentrated under reduced pressure. A mixed solvent of ethanol and water was added to the residue, whereby a solid was deposited. The resulting solid was collected by filtration, and dried under reduced pressure to afford the title compound (0.070 g, 0.13 mmol) as a pale yellowish white solid (yield 50%).

MS m/z: 533 (M+H)$^+$;
$^1$H-NMR (500 MHz, DMSO-d$_6$) δ: 12.86 (1H, brs), 11.91 (1H, s), 9.42 (1H, brs), 7.59 (2H, d, J=8 Hz), 7.52 (2H, d, J=8 Hz), 7.39 (2H, d, J=8 Hz), 7.00 (2H, d, J=8 Hz), 5.08 (2H, s), 4.01 (2H, d, J=6 Hz), 3.75 (2H, d, J=12 Hz), 2.78 (2H, d, J=6 Hz), 2.71 (2H, t, J=12 Hz), 2.44 (3H, s), 2.16-2.03 (1H, m), 2.07 (3H, s), 1.68 (2H, d, J=12 Hz), 1.36 (2H, q, J=12 Hz).

Example 3

({[5-Hydroxy-2-{(1-[4'-(1-hydroxyethyl)biphenyl-4-yl]piperidin-4-yl}methyl)-6-methylpyrimidin-4-yl]carbonyl}amino)acetic acid

[Chemical 26]

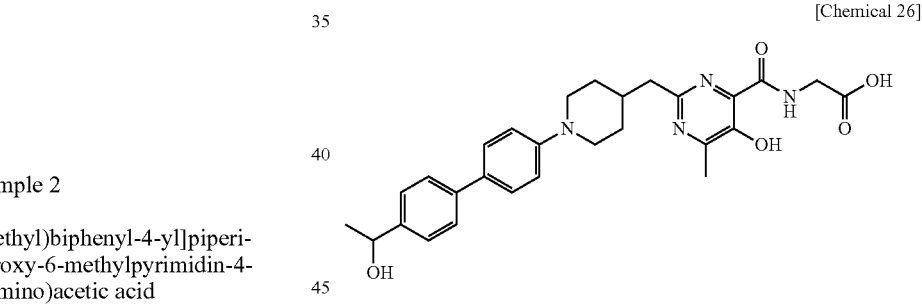

[Chemical 25]

(1) Ethyl({[2-{[1-(4'-acetylbiphenyl-4-yl)piperidin-4-yl]methyl}-5-(benzyloxy)-6-methylpyrimidin-4-yl]carbonyl}amino)acetate

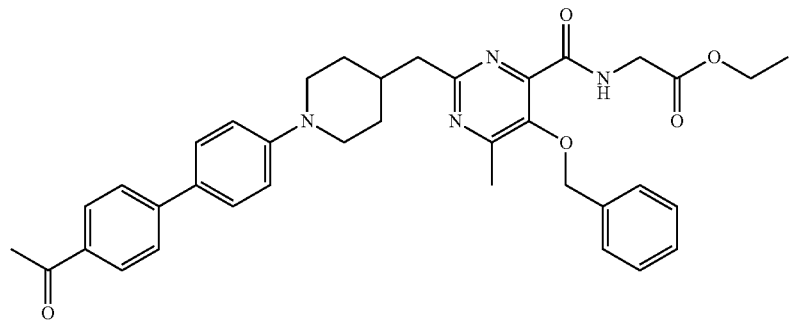

In accordance with Examples 1-(9) and 1-(11), but using 1-(4'-bromobiphenyl-4-yl)ethanone instead of [(4'-bromobiphenyl-4-yl)methoxy](tert-butyl)dimethylsilane, the title compound (yield 35%) was afforded as a yellow solid.

$^1$H-NMR (400 MHz, CDCl$_3$) δ: 8.35 (1H, t, J=5 Hz), 7.99 (2H, d, J=9 Hz), 7.65 (2H, d, J=9 Hz), 7.56 (2H, d, J=9 Hz), 7.51-7.47 (2H, m), 7.42-7.34 (3H, m), 7.01 (2H, d, J=9 Hz), 5.13 (2H, s), 4.27 (2H, q, J=7 Hz), 4.25 (2H, d, J=5 Hz), 3.79 (2H, d, J=13 Hz), 2.90 (2H, d, J=7 Hz), 2.81 (2H, t, J=13 Hz), 2.62 (3H, s), 2.47 (3H, s), 2.20-2.09 (1H, m), 1.80 (2H, d, J=13 Hz), 1.59-1.47 (2H, m), 1.32 (3H, t, J=7 Hz).

(2) Ethyl({[5-hydroxy-2-{(1-[4'-(1-hydroxyethyl)biphenyl-4-yl]piperidin-4-yl}methyl)-6-methylpyrimidin-4-yl]carbonyl}amino)acetate

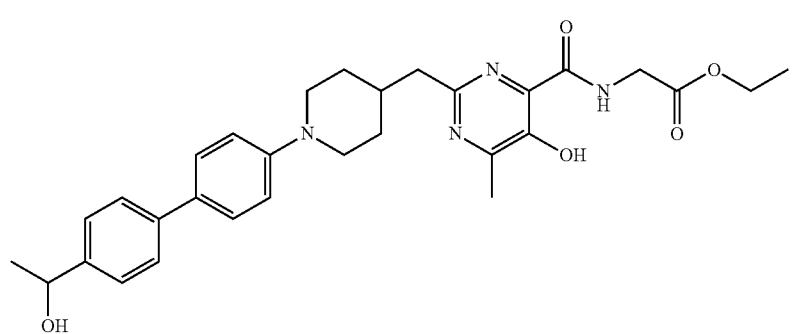

Ethyl({[2-{[1-(4'-acetylbiphenyl-4-yl)piperidin-4-yl]methyl}-5-(benzyloxy)-6-methylpyrimidin-4-yl]carbonyl}amino)acetate (0.67 g, 1.1 mmol) was dissolved in a mixed solvent of ethyl acetate (35 mL) and dichloromethane (35 mL), and 10% palladium-activated carbon (0.65 g) was added, followed by stirring at room temperature for 8 hours under a hydrogen atmosphere. After the reaction solution was filtered with celite, the filtrate was concentrated under reduced pressure. The resulting residue was purified by chromatography on a silica gel column (Moritex Corporation, elution solvent: dichloromethane/ethyl acetate), and a fraction corresponding to the Rf value=0.27 (dichloromethane/ethyl acetate=1/3) by thin layer chromatography was concentrated under reduced pressure to afford the title compound (0.44 g, 0.82 mmol) as a white solid (yield 77%).

MS m/z: 533 (M+H)$^+$;

$^1$H-NMR (400 MHz, CDCl$_3$) δ: 11.37 (1H, s), 8.50 (1H, t, J=6 Hz), 7.54 (2H, d, J=8 Hz), 7.49 (2H, d, J=9 Hz), 7.41 (2H, d, J=9 Hz), 6.99 (2H, d, J=8 Hz), 4.98-4.90 (1H, m), 4.29 (2H, q, J=7 Hz), 4.23 (2H, d, J=6 Hz), 3.74 (2H, d, J=12 Hz), 2.84 (2H, d, J=7 Hz), 2.76 (2H, t, J=12 Hz), 2.54 (3H, s), 2.13-2.01 (1H, m), 1.78 (2H, d, J=12 Hz), 1.59-1.45 (2H, m), 1.54 (3H, d, J=7 Hz), 1.33 (3H, t, J=7 Hz).

(3) ({[5-Hydroxy-2-({1-[4'-(1-hydroxyethyl)biphenyl-4-yl]piperidin-4-yl}methyl)-6-methylpyrimidin-4-yl]carbonyl}amino)acetic acid In accordance with Example 1-(13), but using ethyl({[5-hydroxy-2-({1-[4'-(1-hydroxyethyl)biphenyl-4-yl]piperidin-4-yl}methyl)-6-methylpyrimidin-4-yl]carbonyl}amino) acetate instead of ethyl({[5-hydroxy-2-({1-[4'-(hydroxymethyl)biphenyl-4-yl]piperidin-4-yl}methyl)-6-methylpyrimidin-4-yl]carbonyl}amino)acetate, the title compound (yield 96%) was afforded as a pale brown solid.

MS m/z: 505 (M+H)$^+$;

$^1$H-NMR (500 MHz, DMSO-d$_6$) δ: 9.31 (1H, t, J=6 Hz), 7.52 (2H, d, J=8 Hz), 7.48 (2H, d, J=9 Hz), 7.35 (2H, d, J=8 Hz), 6.98 (2H, d, J=9 Hz), 5.13 (1H, brs), 4.72 (1H, q, J=7 Hz), 3.92 (2H, d, J=6 Hz), 3.72 (2H, d, J=13 Hz), 2.78 (2H, d, J=7 Hz), 2.69 (2H, t, J=13 Hz), 2.43 (3H, s), 2.14-2.03 (1H, m), 1.68 (2H, d, J=13 Hz), 1.33 (3H, d, J=6 Hz), 1.42-1.30 (2H, m).

Example 4

({[5-Hydroxy-2-({1-[4'-(2-hydroxyethyl)biphenyl-4-yl]piperidin-4-yl}methyl)-6-methylpyrimidin-4-yl]carbonyl}amino)acetic acid

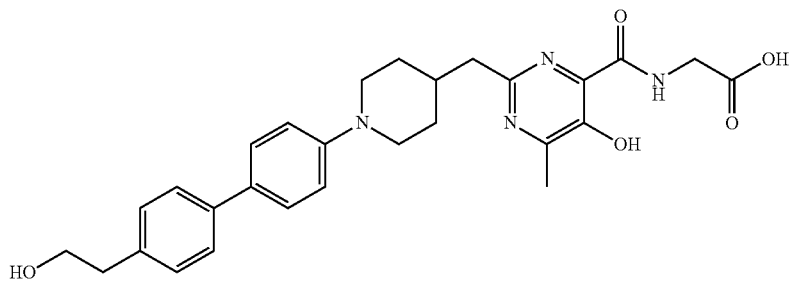

(1) tert-Butyl[2-(4-iodophenyl)ethoxy]dimethylsilane

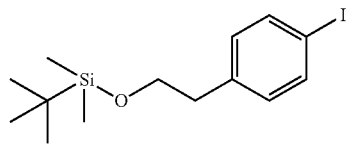

In accordance with Example 1-(8), but using 2-(4-iodophenyl)ethanol instead of (4'-Bromobiphenyl-4-yl)methanol, the title compound (yield 97%) was afforded as a colorless oil.

$^1$H-NMR (500 MHz, CDCl$_3$) δ: 7.59 (2H, d, J=8 Hz), 6.96 (2H, d, J=8 Hz), 3.77 (2H, t, J=7 Hz), 2.75 (2H, t, J=7 Hz), 0.86 (9H, s), −0.03 (6H, s).

(2) [2-(4'-Bromobiphenyl-4-yl)ethoxy](tert-butyl)dimethylsilane

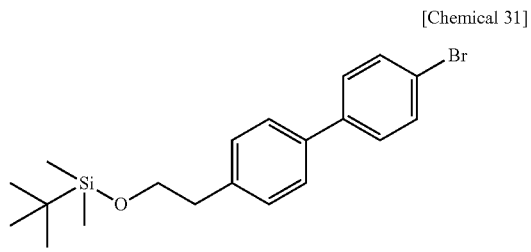 [SMILES: CC(C)(C)[Si](C)(C)OCCc1ccc(-c2ccc(Br)cc2)cc1]

tert-Butyl[2-(4-iodophenyl)ethoxy]dimethylsilane (7.1 g, 19.6 mmol), (4-bromophenyl)boronic acid (4.8 g, 23.9 mmol), tripotassium phosphate n-hydrate (10.4 g, 49.0 mmol) and a [1,1'-bis(diphenylphosphino)ferrocene]palladium dichloride dichloromethane complex (0.80 g, 0.98 mmol) were suspended in 1,2-dimethoxyethane (150 mL), followed by stirring at room temperature for 4 hours under a nitrogen atmosphere. After the reaction solution was filtered with celite, the filtrate was concentrated under reduced pressure. The resulting residue was purified by chromatography on a silica gel column (Moritex Corporation, elution solvent: hexane), and a fraction corresponding to the Rf value=0.90 (hexane/ethyl acetate=19/1) by thin layer chromatography was concentrated under reduced pressure to afford the title compound (2.0 g, 5.1 mmol) as a white solid (yield 26%).

$^1$H-NMR (500 MHz, CDCl$_3$) δ: 7.57 (2H, d, J=8 Hz), 7.50 (2H, d, J=8 Hz), 7.47 (2H, d, J=8 Hz), 7.31 (2H, d, J=8 Hz), 3.86 (2H, t, J=7 Hz), 2.89 (2H, t, J=7 Hz), 0.91 (9H, s), 0.03 (6H, s).

(3) ({[5-Hydroxy-2-{(1-[4'-(2-hydroxyethyl)biphenyl-4-yl]piperidin-4-yl}methyl)-6-methylpyrimidin-4-yl]carbonyl}amino)acetic acid In accordance with Examples 1-(9) to 1-(13), but using [2-(4'-bromobiphenyl-4-yl)ethoxy](tert-butyl)dimethylsilane instead of [(4'-bromobiphenyl-4-yl)methoxy](tert-butyl)dimethylsilane, the title compound (yield 15%) was afforded as a pale yellowish white solid.

MS m/z: 505 (M+H)$^+$;

$^1$H-NMR (500 MHz, DMSO-d$_6$) δ: 12.88 (1H, brs), 11.91 (1H, s), 9.41 (1H, t, J=6 Hz), 7.48 (4H, d, J=8 Hz), 7.24 (2H, d, J=8 Hz), 6.99 (2H, d, J=8 Hz), 4.65 (1H, t, J=6 Hz), 4.01 (2H, d, J=6 Hz), 3.73 (2H, d, J=12 Hz), 3.61 (2H, q, J=6 Hz), 2.78 (2H, d, J=7 Hz), 2.75-2.66 (4H, m), 2.44 (3H, s), 2.15-2.04 (1H, m), 1.68 (2H, d, J=12 Hz), 1.37 (2H, q, J=12 Hz).

Example 5

({[5-Hydroxy-2-{(1-[4'-(2-hydroxypropyl)biphenyl-4-yl]piperidin-4-yl}methyl)-6-methylpyrimidin-4-yl]carbonyl}amino)acetic acid

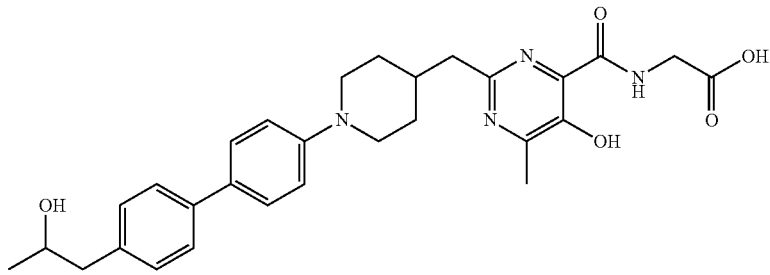

(1) 2-(4'-Bromobiphenyl-4-yl)-N-methoxy-N-methylacetamide

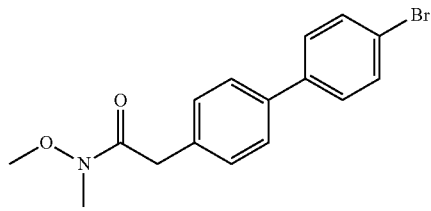

[Chemical 33]

(4'-Bromobiphenyl-4-yl)acetic acid (12 g, 37 mmol) was dissolved in a mixed solvent of tetrahydrofuran (200 mL) and methanol (200 mL), and N,O-dimethylhydroxylamine hydrochloride (5.4 g, 56 mmol), 4-(4,6-dimethoxy-1,3,5-triazin-2-yl)-4-methylmorpholinium chloride (15 g, 60 mmol) and N-methylmorpholine (6.1 mL, 56 mmol) were added, followed by stirring at room temperature for 1 hour. After the reaction solution was concentrated under reduced pressure, ethyl acetate was added to the resulting residue, and the organic layer was washed with water. After the solvent was distilled off under reduced pressure, the resulting residue was purified by chromatography on a silica gel column (Moritex Corporation, elution solvent: hexane/ethyl acetate), and a fraction corresponding to the Rf value=0.45 (hexane/ethyl acetate=1/1) by thin layer chromatography was concentrated under reduced pressure to afford the title compound (12 g, 37 mmol) as a white solid (yield 100%).

$^1$H-NMR (500 MHz, CDCl$_3$) δ: 7.55 (2H, d, J=8 Hz), 7.51 (2H, d, J=8 Hz), 7.45 (2H, d, J=8 Hz), 7.37 (2H, d, J=8 Hz), 3.82 (2H, s), 3.67 (3H, s), 3.22 (3H, s).

(2) (4'-Bromobiphenyl-4-yl)acetone

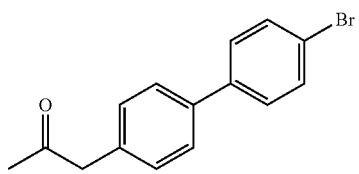

[Chemical 34]

A solution of methyllithium in diethyl ether (40 mL, 44 mmol) was diluted with tetrahydrofuran (120 mL), and a solution of 2-(4'-bromobiphenyl-4-yl)-N-methoxy-N-methylacetamide (12 g, 37 mmol) in tetrahydrofuran (50 mL) was added at −78° C., followed by stirring at the same temperature for 30 minutes. Water was added to the reaction solution, followed by extraction with ethyl acetate, and subsequently the solvent was distilled off under reduced pressure. The resulting residue was purified by chromatography on a silica gel column (Moritex Corporation, elution solvent: hexane/ethyl acetate), and a fraction corresponding to the Rf value=0.50 (hexane/ethyl acetate=4/1) by thin layer chromatography was concentrated under reduced pressure to afford the title compound (7.6 g, 26 mmol) as a white solid (yield 71%).

$^1$H-NMR (500 MHz, CDCl$_3$) δ: 7.56 (2H, d, J=8 Hz), 7.53 (2H, d, J=8 Hz), 7.45 (2H, d, J=8 Hz), 7.27 (2H, d, J=8 Hz), 3.76 (2H, s), 2.21 (3H, s).

(3) 1-(4'-Bromobiphenyl-4-yl)propan-2-ol

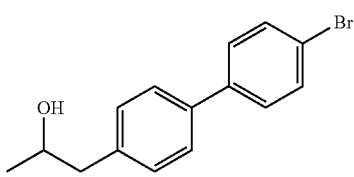

[Chemical 35]

(4'-Bromobiphenyl-4-yl)acetone (7.6 g, 26 mmol) was dissolved in ethanol (250 mL), and sodium borohydride (1.2 g, 32 mmol) was added at 0° C., followed by stirring at the same temperature for 30 minutes. After the reaction solution was concentrated under reduced pressure, ethyl acetate was added to the resulting residue, and the organic layer was washed with water. After the solvent was distilled off under reduced pressure, the resulting residue was purified by chromatography on a silica gel column (Moritex Corporation, elution solvent: hexane/ethyl acetate), and a fraction corresponding to the Rf value=0.45 (hexane/ethyl acetate=4/1) by thin layer chromatography was concentrated under reduced pressure to afford the title compound (7.6 g, 26 mmol) as a white solid (yield 99%).

$^1$H-NMR (500 MHz, CDCl$_3$) δ: 7.56 (2H, d, J=8 Hz), 7.51 (2H, d, J=8 Hz), 7.45 (2H, d, J=8 Hz), 7.30 (2H, d, J=8 Hz), 4.07 (1H, brs), 2.84 (1H, dd, J=13 Hz, 5 Hz), 2.73 (1H, dd, J=13 Hz, 3 Hz), 1.58-1.49 (1H, m), 1.28 (3H, d, J=6 Hz).

(4) [2-(4'-Bromobiphenyl-4-yl)-1-methylethoxy](tert-butyl)dimethylsilane

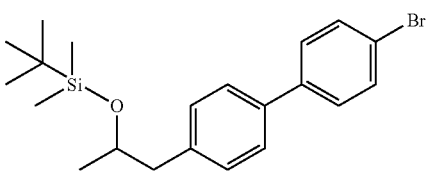

[Chemical 36]

In accordance with Example 1-(8), but using 1-(4'-bromobiphenyl-4-yl)propan-2-ol instead of (4'-bromobiphenyl-4-yl)methanol, the title compound (yield 96%) was afforded as a white solid.

$^1$H-NMR (500 MHz, CDCl$_3$) δ: 7.54 (2H, d, J=8 Hz), 7.45 (2H, d, J=8 Hz), 7.44 (2H, d, J=8 Hz), 7.24 (2H, d, J=8 Hz), 4.04-3.93 (1H, m), 2.80-2.67 (2H, m), 1.17 (3H, d, J=6 Hz), 0.83 (9H, s), −0.05 (3H, s), −0.17 (3H, s).

(5) ({[5-Hydroxy-2-{(1-[4'-(2-hydroxypropyl)biphenyl-4-yl]piperidin-4-yl}methyl)-6-methylpyrimidin-4-yl]carbonyl}amino)acetic acid In accordance with Examples 1-(9) to 1-(13), but using [2-(4'-bromobiphenyl-4-yl)-1-methylethoxy](tert-butyl)dimethylsilane instead of [(4'-bromobiphenyl-4-yl)methoxy](tert-butyl)dimethylsilane, the title compound (yield 35%) was afforded as a white solid.

MS m/z: 519 (M+H)$^+$;

$^1$H-NMR (400 MHz, DMSO-d$_6$) δ: 12.89 (1H, brs), 11.92 (1H, s), 9.41 (1H, t, J=6 Hz), 7.49 (2H, d, J=9 Hz), 7.48 (2H, d, J=9 Hz), 7.22 (2H, d, J=8 Hz), 6.98 (2H, d, J=8 Hz), 4.58 (1H, d, J=5 Hz), 4.01 (2H, d, J=6 Hz), 3.86-3.79 (1H, m), 3.73 (2H, d, J=12 Hz), 2.78 (2H, d, J=7 Hz), 2.74-2.65 (3H, m), 2.57 (1H, dd, J=13 Hz, 6 Hz), 2.44 (3H, s), 2.09-2.00 (1H, m), 1.69 (2H, d, J=12 Hz), 1.36 (2H, dq, J=12 Hz, 3 Hz), 1.05 (3H, d, J=6 Hz).

Example 6

({[5-Hydroxy-2-{(1-[4'-(2-hydroxy-1,1-dimethylethyl)biphenyl-4-yl]piperidin-4-yl}methyl)-6-methylpyrimidin-4-yl]carbonyl}amino)acetic acid

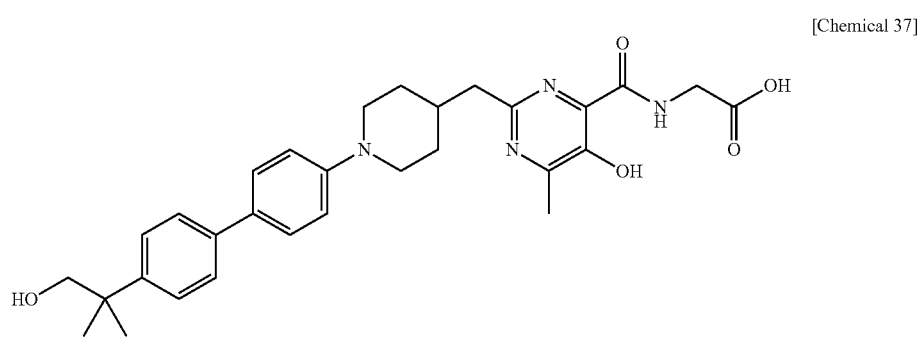 [SMILES: Cc1nc(CC2CCN(c3ccc(-c4ccc(C(C)(C)CO)cc4)cc3)CC2)nc(C(=O)NCC(=O)O)c1O]

[Chemical 37]

(1) Ethyl 2-(4'-bromobiphenyl-4-yl)-2-methylpropionate

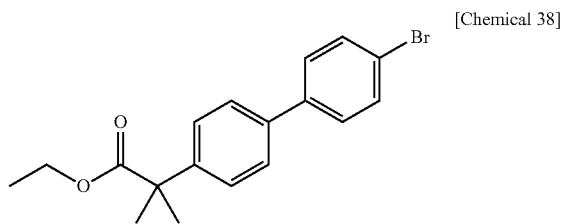 [SMILES: CCOC(=O)C(C)(C)c1ccc(-c2ccc(Br)cc2)cc1]

[Chemical 38]

Ethyl (4'-bromobiphenyl-4-yl)acetate (7.6 g, 24 mmol) was dissolved in tetrahydrofuran (130 mL), and sodium hydride (55%, 3.1 g, 71 mmol) was added at 0° C., followed by stirring at room temperature for 30 minutes. Methyl iodide (4.4 mL, 71 mmol) was added to the reaction solution, followed by stirring at room temperature for a further 20 hours. A saturated aqueous ammonium chloride solution was added to the reaction solution, followed by extraction with ethyl acetate, and subsequently the solvent was distilled off under reduced pressure. The resulting residue was purified by chromatography on a silica gel column (Moritex Corporation, elution solvent: hexane/ethyl acetate), and a fraction corresponding to the Rf value=0.50 (hexane/ethyl acetate=10/1) by thin layer chromatography was concentrated under reduced pressure to afford the title compound (6.2 g, 18 mmol) as a yellow oil (yield 76%).

$^1$H-NMR (500 MHz, CDCl$_3$) δ: 7.55 (2H, d, J=8 Hz), 7.52 (2H, d, J=8 Hz), 7.45 (2H, d, J=8 Hz), 7.40 (2H, d, J=8 Hz), 4.14 (2H, q, J=7 Hz), 1.61 (6H, s), 1.21 (3H, t, J=7 Hz).

(2) 2-(4'-Bromobiphenyl-4-yl)-2-methylpropan-1-ol

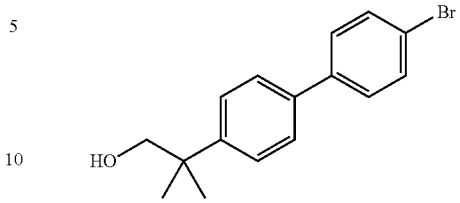

[Chemical 39]

Ethyl 2-(4'-bromobiphenyl-4-yl)-2-methylpropionate (6.2 g, 18 mmol) was dissolved in tetrahydrofuran (150 mL), and lithium aluminum hydride (0.68 g, 18 mmol) was added at 0° C., followed by stirring at the same temperature for 1.5 hours. Water was added to the reaction solution, and the insolubles were filtered with celite, followed by extraction with ethyl acetate. After the solvent was distilled off under reduced pressure, the resulting residue was purified by chromatography on a silica gel column (Moritex Corporation, elution solvent: hexane/ethyl acetate), and a fraction corresponding to the Rf value=0.40 (hexane/ethyl acetate=1/1) by thin layer chromatography was concentrated under reduced pressure to afford the title compound (5.0 g, 16 mmol) as a white solid (yield 92%).

$^1$H-NMR (500 MHz, CDCl$_3$) δ: 7.59-7.51 (4H, m), 7.49-7.43 (4H, m), 3.66 (2H, s), 1.38 (6H, s).

(3) 4-Bromo-4'-[2-(methoxymethoxy)-1,1-dimethylethyl]biphenyl

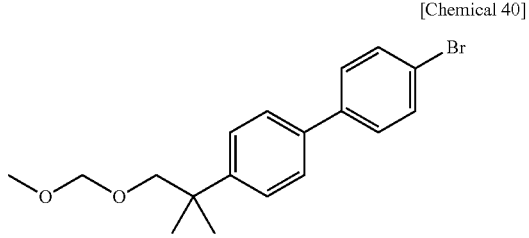 [SMILES: COCOCC(C)(C)c1ccc(-c2ccc(Br)cc2)cc1]

[Chemical 40]

2-(4'-Bromobiphenyl-4-yl)-2-methylpropan-1-ol (5.0 g, 16 mmol) was dissolved in toluene (40 mL), and chloromethyl methyl ether (2.5 mL, 33 mmol) and N,N-diisopropylethylamine (3.6 mL, 21 mmol) were added, followed by stirring at room temperature for 17 hours. After the reaction solution was diluted with ethyl acetate, the organic layer was washed with water. After the solvent was distilled off under reduced pressure, the resulting residue was purified by chromatography on a silica gel column (Moritex Corporation, elution solvent: hexane/ethyl acetate), and a fraction corresponding to the Rf value=0.45 (hexane/ethyl acetate=10/1) by thin layer chromatography was concentrated under reduced pressure to afford the title compound (5.8 g, 16 mmol) as a white solid (yield 100%).

$^1$H-NMR (500 MHz, CDCl$_3$) δ: 7.54 (2H, d, J=8 Hz), 7.51 (2H, d, J=8 Hz), 7.47 (2H, d, J=8 Hz), 7.45 (2H, d, J=8 Hz), 4.58 (2H, s), 3.60 (2H, s), 3.27 (3H, s), 1.39 (6H, s).

(4) ({[5-Hydroxy-2-{(1-[4'-(2-hydroxy-1,1-dimethylethyl)biphenyl-4-yl]piperidin-4-yl}methyl)-6-methylpyrimidin-4-yl]carbonyl}amino)acetic acid In accordance with Examples 1-(9) to 1-(13), but using 4-bromo-4'-[2-(methoxymethoxy)-1,1-dimethylethyl]biphenyl instead of [(4'-bromobiphenyl-4-yl)methoxy](tert-butyl)dimethylsilane, the title compound (yield 25%) was afforded as a white solid.

MS m/z: 533 (M+H)$^+$;

$^1$H-NMR (500 MHz, DMSO-d$_6$) δ: 12.86 (1H, brs), 11.91 (1H, s), 9.41 (1H, t, J=5 Hz), 7.50 (2H, d, J=9 Hz), 7.48 (2H, d, J=9 Hz), 7.39 (2H, d, J=8 Hz), 6.99 (2H, d, J=8 Hz), 4.67 (1H, brs), 4.00 (2H, d, J=5 Hz), 3.73 (2H, d, J=12 Hz), 3.42 (2H, s), 2.78 (2H, d, J=7 Hz), 2.70 (2H, t, J=12 Hz), 2.45 (3H, s), 2.15-2.05 (1H, m), 1.68 (2H, d, J=12 Hz), 1.36 (2H, dq, J=12 Hz, 3 Hz), 1.23 (6H, s).

Example 7

({[2-{(1-[4'-(Dimethylcarbamoyl)biphenyl-4-yl]piperidin-4-yl}methyl)-5-hydroxy-6-methylpyrimidin-4-yl]carbonyl}amino)acetic acid

[Chemical 41]

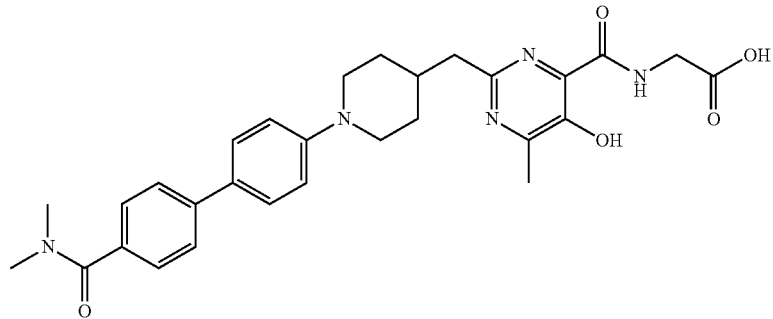

In accordance with Examples 1-(9) and 1-(11) to 1-(13), but using 4'-bromo-N,N-dimethylbiphenyl-4-carboxamide instead of [(4'-bromobiphenyl-4-yl)methoxy](tert-butyl)dimethylsilane, the title compound (yield 29%) was afforded as a pale yellowish white solid.

MS m/z: 532 (M+H)$^+$;

$^1$H-NMR (500 MHz, DMSO-d$_6$) δ: 12.88 (1H, brs), 11.91 (1H, s), 9.40 (1H, t, J=6 Hz), 7.65 (2H, d, J=8 Hz), 7.56 (2H, d, J=8 Hz), 7.43 (2H, d, J=8 Hz), 7.01 (2H, d, J=8 Hz), 4.01 (2H, d, J=6 Hz), 3.77 (2H, d, J=12 Hz), 2.97 (6H, brs), 2.78 (2H, d, J=7 Hz), 2.73 (2H, t, J=12 Hz), 2.44 (3H, s), 2.16-2.05 (1H, m), 1.69 (2H, d, J=12 Hz), 1.36 (2H, q, J=12 Hz).

Example 8

({[5-Hydroxy-6-methyl-2-{(1-[4'-(methylcarbamoyl)biphenyl-4-yl]piperidin-4-yl}methyl)pyrimidin-4-yl]carbonyl}amino)acetic acid

[Chemical 42]

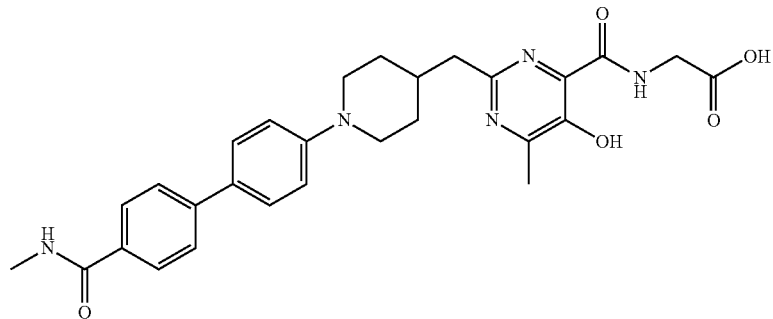

In accordance with Examples 1-(9) and 1-(11) to 1-(13), but using 4'-bromo-N-methylbiphenyl-4-carboxamide instead of [(4'-bromobiphenyl-4-yl)methoxy](tert-butyl)dimethylsilane, the title compound (yield 20%) was afforded as a yellow solid.

MS m/z: 518 (M+H)$^+$;

$^1$H-NMR (500 MHz, DMSO-d$_6$) δ: 9.28 (1H, brs), 8.42 (1H, d, J=4 Hz), 7.86 (2H, d, J=8 Hz), 7.68 (2H, d, J=8 Hz), 7.59 (2H, d, J=8 Hz), 7.01 (2H, d, J=8 Hz), 3.86 (2H, brs), 3.78 (2H, d, J=12 Hz), 2.81-2.69 (7H, m), 2.44 (3H, s), 2.15-2.05 (1H, m), 1.69 (2H, d, J=12 Hz), 1.36 (2H, q, J=12 Hz).

Example 9

[({2-[(1-{4'-[2-(Dimethylamino)-2-oxoethyl]biphenyl-4-yl}piperidin-4-yl)methyl]-5-hydroxy-6-methylpyrimidin-4-yl}carbonyl)amino]acetic acid

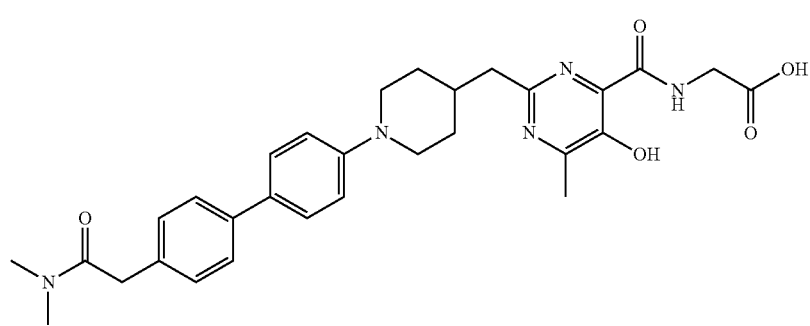

[Chemical 43]

(1) 2-(4'-Bromobiphenyl-4-yl)-N,N-dimethylacetamide

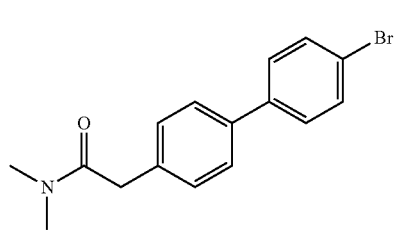

[Chemical 44]

(4'-Bromobiphenyl-4-yl)acetic acid (1.0 g, 3.4 mmol) was dissolved in a mixed solvent of tetrahydrofuran (20 mL) and methanol (20 mL), and dimethylamine hydrochloride (0.42 g, 5.2 mmol), 4-(4,6-dimethoxy-1,3,5-triazin-2-yl)-4-methylmorpholinium chloride (1.3 g, 4.7 mmol) and N-methylmorpholine (0.95 mL, 8.6 mmol) were added, followed by stirring at room temperature for 18 hours. After the reaction solution was concentrated under reduced pressure, the resulting residue was purified by chromatography on a silica gel column (Moritex Corporation, elution solvent: dichloromethane/ethyl acetate), and a fraction corresponding to the Rf value=0.55 (dichloromethane/ethyl acetate=1/1) by thin layer chromatography was concentrated under reduced pressure to afford the title compound (0.82 g, 2.6 mmol) as a white solid (yield 75%).

$^1$H-NMR (500 MHz, CDCl$_3$) δ: 7.55 (2H, d, J=8 Hz), 7.51 (2H, d, J=8 Hz), 7.44 (2H, d, J=8 Hz), 7.33 (2H, d, J=8 Hz), 3.75 (2H, s), 3.04 (3H, s), 2.99 (3H, s).

(2) [({2-[(1-{4'-[2-(Dimethylamino)-2-oxoethyl]biphenyl-4-yl}piperidin-4-yl)methyl]-5-hydroxy-6-methylpyrimidin-4-yl}carbonyl)amino]acetic acid In accordance with Examples 1-(9) and 1-(11) to 1-(13), but using 2-(4'-bromobiphenyl-4-yl)-N,N-dimethylacetamide instead of [(4'-bromobiphenyl-4-yl)methoxy](tert-butyl)dimethylsilane, the title compound (yield 11%) was afforded as a pale yellowish white solid.

MS m/z: 546 (M+H)$^+$;

$^1$H-NMR (500 MHz, DMSO-d$_6$) δ: 11.92 (1H, brs), 9.39 (1H, t, J=6 Hz), 7.52 (2H, d, J=8 Hz), 7.49 (2H, d, J=8 Hz), 7.24 (2H, d, J=8 Hz), 6.99 (2H, d, J=8 Hz), 4.00 (2H, d, J=6 Hz), 3.74 (2H, d, J=12 Hz), 3.69 (2H, s), 3.01 (3H, s), 2.84 (3H, s), 2.78 (2H, d, J=7 Hz), 2.70 (2H, t, J=12 Hz), 2.44 (3H, s), 2.15-2.04 (1H, m), 1.68 (2H, d, J=12 Hz), 1.37 (2H, q, J=12 Hz).

Example 10

[({5-Hydroxy-2-[(1-{4-[4-(hydroxymethyl)benzyl]phenyl}piperidin-4-yl)methyl]-6-methylpyrimidin-4-yl}carbonyl)amino]acetic acid

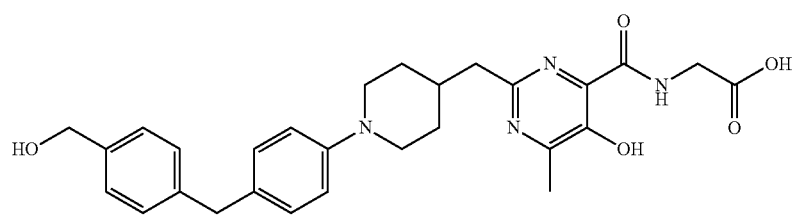

[Chemical 45]

(1) 1-Bromo-4-{4-[(methoxymethoxy)methyl]benzyl}benzene

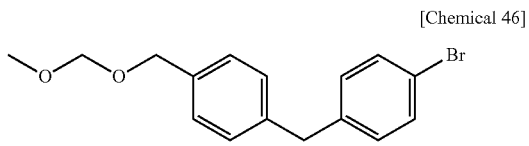 [SMILES: COCOCc1ccc(Cc2ccc(Br)cc2)cc1]

[Chemical 46]

[4-(4-Bromobenzyl)phenyl]methanol (2.7 g, 9.6 mmol) was dissolved in tetrahydrofuran (50 mL), and sodium hydride (55%, 0.50 g, 12 mmol) was added at 0° C., followed by stirring at the same temperature for 30 minutes under a nitrogen atmosphere. To the reaction solution at 0° C. was added dropwise a solution of chloromethyl methyl ether (1.0 g, 13 mmol) in tetrahydrofuran (10 mL), followed by stirring at room temperature for 4 hours. A saturated aqueous ammonium chloride solution was added to the reaction solution, followed by extraction with ethyl acetate, and the organic layer was dried over anhydrous sodium sulfate. After the solvent was distilled off under reduced pressure, the resulting residue was purified by chromatography on a silica gel column (Moritex Corporation, elution solvent: hexane/ethyl acetate), and a fraction corresponding to the Rf value=0.55 (hexane/ethyl acetate=4/1) by thin layer chromatography was concentrated under reduced pressure to afford the title compound (2.5 g, 7.8 mmol) as a colorless oil (yield 81%).

$^1$H-NMR (500 MHz, CDCl$_3$) δ: 7.39 (2H, d, J=8 Hz), 7.28 (2H, d, J=8 Hz), 7.15 (2H, d, J=8 Hz), 7.04 (2H, d, J=8 Hz), 4.70 (2H, s), 4.56 (2H, s), 3.92 (2H, s), 3.41 (3H, s).

(2) Ethyl {[(5-hydroxy-2-{[1-(4-{4-[(methoxymethoxy)methyl]benzyl}phenyl)piperidin-4-yl]methyl}-6-methylpyrimidin-4-yl)carbonyl]amino}acetate In accordance with Examples 1-(9), 1-(11) and 1-(12), but using 1-bromo-4-{4-[(methoxymethoxy)methyl]benzyl}benzene instead of [(4'-bromobiphenyl-4-yl)methoxy](tert-butyl)dimethylsilane, the title compound (yield 33%) was afforded as a yellow oil.

$^1$H-NMR (500 MHz, CDCl$_3$) δ: 11.36 (1H, s), 8.49 (1H, t, J=5 Hz), 7.28-7.23 (2H, m), 7.16 (2H, d, J=8 Hz), 7.04 (2H, d, J=7 Hz), 6.86 (2H, d, J=7 Hz), 4.69 (2H, s), 4.55 (2H, s), 4.28 (2H, q, J=7 Hz), 4.22 (2H, d, J=5 Hz), 3.89 (2H, s), 3.61 (2H, d, J=12 Hz), 3.40 (3H, s), 2.82 (2H, d, J=7 Hz), 2.66 (2H, t, J=12 Hz), 2.53 (3H, s), 2.05-1.98 (1H, m), 1.75 (2H, d, J=12 Hz), 1.54-1.44 (2H, m), 1.32 (3H, t, J=7 Hz).

(3) Ethyl [({2-[(1-{4-[4-(acetoxymethyl)benzyl]phenyl}piperidin-4-yl)methyl]-5-hydroxy-6-methylpyrimidin-4-yl}carbonyl)amino]acetate

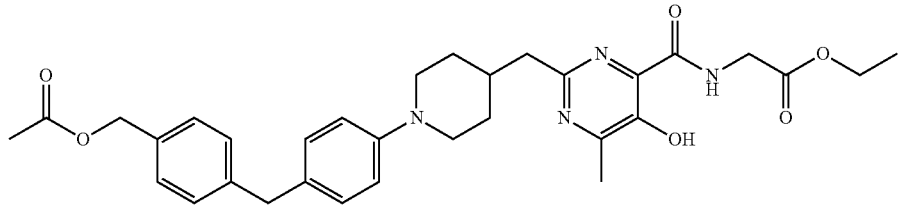

[Chemical 48]

Ethyl {[(5-hydroxy-2-{[1-(4-{4-[(methoxymethoxy)methyl]benzyl}phenyl)piperidin-4-yl]methyl}-6-methylpyrimidin-4-yl)carbonyl]amino}acetate (1.1 g, 1.9 mmol) was dissolved in ethyl acetate (14 mL), and a solution of hydrogen chloride in dioxane (4 M, 7 mL, 28 mmol) was added at room temperature, followed by stirring at the same temperature for 12 hours. A saturated aqueous sodium hydrogencarbonate solution was added to the reaction solution, followed by extraction with ethyl acetate, and subsequently the organic layer was dried over anhydrous sodium sulfate. After the solvent was distilled off under reduced pressure, the resulting residue was purified by chromatography on a silica gel column (Moritex Corporation, elution solvent: hexane/ethyl acetate), and a fraction corresponding to the Rf value=0.60 (hexane/ethyl acetate=1/1) by thin layer chromatography was concentrated under reduced pressure to afford the title compound (0.74 g, 1.3 mmol) as a yellow oil (yield 69%).

$^1$H-NMR (500 MHz, CDCl$_3$) δ: 11.35 (1H, s), 8.48 (1H, t, J=5 Hz), 7.28-7.23 (2H, m), 7.17 (2H, d, J=7 Hz), 7.04 (2H, d, J=7 Hz), 6.86 (2H, d, J=7 Hz), 5.06 (2H, s), 4.28 (2H, q, J=7 Hz), 4.22 (2H, d, J=5 Hz), 3.89 (2H, s), 3.61 (2H, d, J=12 Hz), 2.82 (2H, d, J=7 Hz), 2.66 (2H, t, J=12 Hz), 2.53 (3H, s), 2.08 (3H, s), 2.05-1.97 (1H, m), 1.77-1.70 (2H, m), 1.54-1.46 (2H, m), 1.32 (3H, t, J=7 Hz).

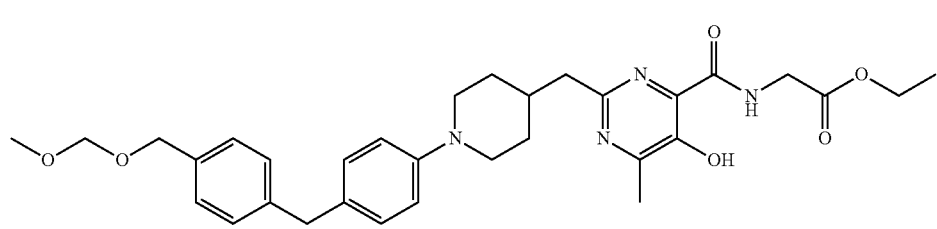

[Chemical 47]

(4) [({5-Hydroxy-2-[(1-{4-[4-(hydroxymethyl)benzyl]phenyl}piperidin-4-yl)methyl]-6-methylpyrimidin-4-yl}carbonyl)amino]acetic acid In accordance with Example 1-(13), but using ethyl [({2-[(1-{4-[4-(acetoxymethyl)benzyl]phenyl}piperidin-4-yl)methyl]-5-hydroxy-6-methylpyrimidin-4-yl}carbonyl)amino]acetate instead of ethyl({[5-hydroxy-2-{(1-[4'-(hydroxymethyl)biphenyl-4-yl]piperidin-4-yl}methyl)-6-methylpyrimidin-4-yl]carbonyl}amino)acetate, the title compound (yield 61%) was afforded as a yellow solid.

MS m/z: 505 (M+H)$^+$;

$^1$H-NMR (500 MHz, DMSO-d$_6$) δ: 11.90 (1H, s), 9.38 (1H, t, J=6 Hz), 7.20 (2H, d, J=7 Hz), 7.13 (2H, d, J=7 Hz), 7.02 (2H, d, J=8 Hz), 6.82 (2H, d, J=8 Hz), 5.08 (1H, t, J=6 Hz), 4.42 (2H, d, J=6 Hz), 4.00 (2H, d, J=6 Hz), 3.79 (2H, s), 3.58 (2H, d, J=12 Hz), 2.76 (2H, d, J=7 Hz), 2.58 (2H, t, J=12 Hz), 2.43 (3H, s), 2.03 (1H, brs), 1.65 (2H, d, J=12 Hz), 1.38-1.29 (2H, m).

Example 11

[({5-Hydroxy-2-[(1-{4-[3-(hydroxymethyl)benzyl]phenyl}piperidin-4-yl)methyl]-6-methylpyrimidin-4-yl}carbonyl)amino]acetic acid

[Chemical 49]

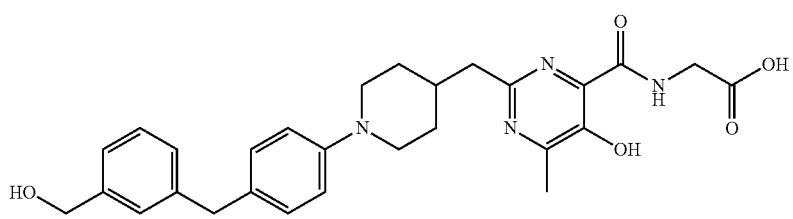

(1) [3-(4-Bromobenzyl)phenyl]methanol

[Chemical 50]

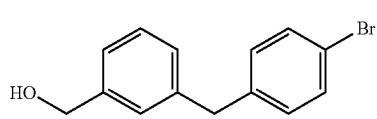

4-Bromobenzyl bromide (6.1 g, 22 mmol) and [3-(hydroxymethyl)phenyl]boronic acid (3.0 g, 20 mmol) were dissolved in a mixed solvent of toluene (40 mL), ethanol (30 mL) and water (20 mL), and tetrakis(triphenylphosphine)palladium (1.1 g, 1.0 mmol) and sodium carbonate (4.2 g, 40 mmol) were added under a nitrogen atmosphere, followed by heating to reflux for 6 hours. Water was added to the reaction solution, followed by extraction with ethyl acetate, and subsequently the organic layer was dried over anhydrous sodium sulfate. After the solvent was distilled off under reduced pressure, the resulting residue was purified by chromatography on a silica gel column (Moritex Corporation, elution solvent: hexane/ethyl acetate), and a fraction corresponding to the Rf value=0.75 (hexane/ethyl acetate=1/1) by thin layer chromatography was concentrated under reduced pressure to afford the title compound (4.7 g, 17 mmol) as a yellow oil (yield 85%).

$^1$H-NMR (500 MHz, CDCl$_3$) δ: 7.40 (2H, d, J=8 Hz), 7.29 (1H, t, J=8 Hz), 7.22 (1H, d, J=8 Hz), 7.17 (1H, s), 7.10 (1H, d, J=8 Hz), 7.06 (2H, d, J=8 Hz), 4.66 (2H, s), 3.93 (2H, s), 1.65 (1H, brs).

(2) 1-Bromo-4-{3-[(methoxymethoxy)methyl]benzyl}benzene

[Chemical 51]

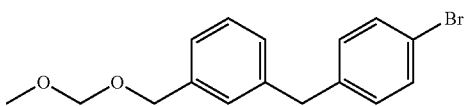

In accordance with Example 10-(1), but using [3-(4-bromobenzyl)phenyl]methanol instead of [4-(4-bromobenzyl)phenyl]methanol, the title compound (yield 65%) was afforded as a colorless oil.

$^1$H-NMR (500 MHz, CDCl$_3$) δ: 7.40 (2H, d, J=7 Hz), 7.28 (1H, t, J=7 Hz), 7.21 (1H, d, J=7 Hz), 7.16 (1H, s), 7.08 (1H, d, J=7 Hz), 7.06 (2H, d, J=7 Hz), 4.70 (2H, s), 4.56 (2H, s), 3.93 (2H, s), 3.40 (3H, s).

(3) [({5-Hydroxy-2-[(1-{4-[3-(hydroxymethyl)benzyl]phenyl}piperidin-4-yl)methyl]-6-methylpyrimidin-4-yl}carbonyl)amino]acetic acid In accordance with Examples 1-(9), 1-(11), 1-(12), 1-(10) and 1-(13), but using 1-bromo-4-{3-[(methoxymethoxy)methyl]benzyl}benzene instead of [(4'-bromobiphenyl-4-yl)methoxy](tert-butyl)dimethylsilane, the title compound (yield 23%) was afforded as a yellow solid.

MS m/z: 505 (M+H)$^+$;

$^1$H-NMR (500 MHz, DMSO-d$_6$) δ: 12.89 (1H, brs), 11.91 (1H, s), 9.41 (1H, t, J=6 Hz), 7.21 (1H, t, J=7 Hz), 7.14 (1H, s), 7.10 (1H, d, J=7 Hz), 7.06 (1H, d, J=7 Hz), 7.05-7.00 (2H, m), 6.87-6.79 (2H, m), 5.14 (1H, brs), 4.44 (2H, s), 4.00 (2H, d, J=6 Hz), 3.80 (2H, brs), 3.58 (2H, d, J=12 Hz), 2.76 (2H, d, J=7 Hz), 2.64-2.54 (2H, m), 2.43 (3H, s), 2.04 (1H, brs), 1.70-1.61 (2H, m), 1.40-1.29 (2H, m).

Example 12

[({5-Hydroxy-2-[(1-{4-[5-(1-hydroxyethyl)pyridin-2-yl]phenyl}piperidin-4-yl)methyl]-6-methylpyrimidin-4-yl}carbonyl)amino]acetic acid

[Chemical 52]

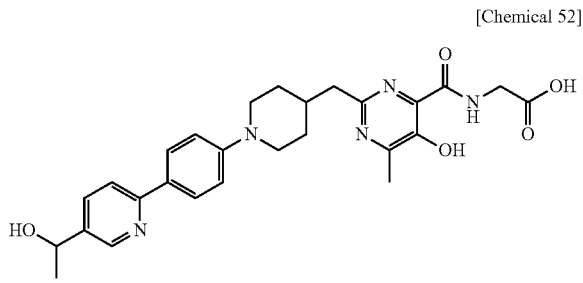 [SMILES: Cc1nc(CC2CCN(c3ccc(-c4ccc(C(C)O)cn4)cc3)CC2)nc(C(=O)NCC(=O)O)c1O]

(1) 2-(4-Bromophenyl)-5-[1-(methoxymethoxy)ethyl]pyridine

[Chemical 53]

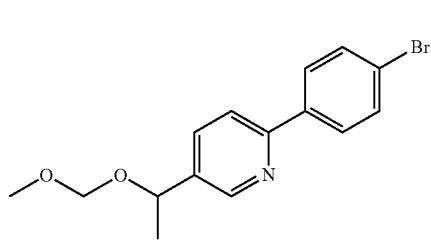

6-(4-Bromophenyl)nicotinaldehyde (3.2 g, 12 mmol) was dissolved in tetrahydrofuran (50 mL), and a solution of methyllithium in diethyl ether (1.0 M, 15 mL, 15 mmol) was added dropwise at −78° C. under a nitrogen atmosphere, followed by stirring at the same temperature for 1 hour. A saturated aqueous ammonium chloride solution was added to the reaction solution, followed by extraction with ethyl acetate, and subsequently the organic layer was concentrated under reduced pressure. The resulting residue was purified by chromatography on a silica gel column (Moritex Corporation, elution solvent: hexane/ethyl acetate), and a fraction corresponding to the Rf value=0.30 (hexane/ethyl acetate=2/1) by thin layer chromatography was concentrated under reduced pressure to afford 1-[6-(4-bromophenyl)pyridin-3-yl]ethanol (2.0 g, 7.2 mmol) as a white solid (yield 59%).

In accordance with Example 10-(1), but using 1-[6-(4-bromophenyl)pyridin-3-yl]ethanol (2.0 g, 7.2 mmol) instead of [4-(4-bromobenzyl)phenyl]methanol, the title compound (1.8 g, 5.6 mmol) was afforded as a pale yellow solid (yield 78%).

$^1$H-NMR (500 MHz, CDCl$_3$) δ: 8.64 (1H, s), 7.87 (2H, d, J=9 Hz), 7.76 (1H, d, J=8 Hz), 7.70 (1H, d, J=8 Hz), 7.60 (2H, d, J=9 Hz), 4.84 (1H, q, J=6 Hz), 4.64 (1H, d, J=7 Hz), 4.58 (1H, d, J=7 Hz), 3.38 (3H, s), 1.54 (3H, d, J=6 Hz).

(2) Benzyl({[5-(benzyloxy)-2-{1-(4-{5-[1-(methoxymethoxy)ethyl]pyridin-2-yl}phenyl)piperidin-4-yl]methyl}-6-methylpyrimidin-4-yl]carbonyl}amino)acetate

[Chemical 54]

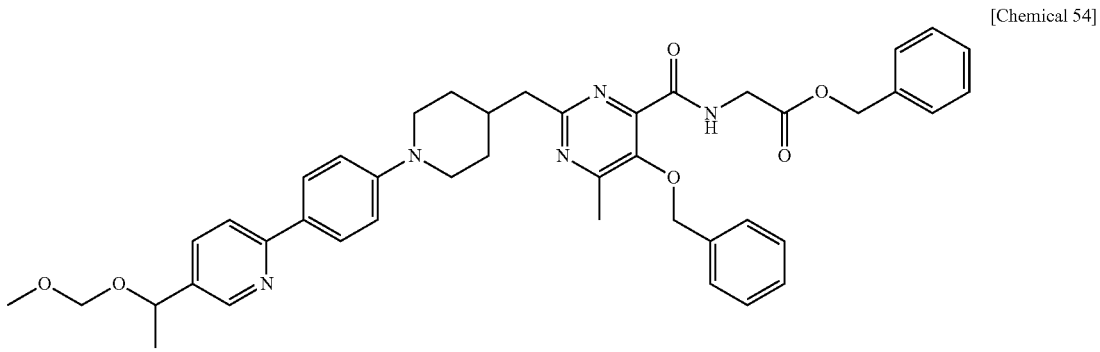 [SMILES: COCOC(C)c1ccc(-c2ccc(N3CCC(Cc4nc(C)c(OCc5ccccc5)c(C(=O)NCC(=O)OCc5ccccc5)n4)CC3)cc2)nc1]

In accordance with Example 1-(9), but using 2-(4-bromophenyl)-5-[1-(methoxymethoxy)ethyl]pyridine instead of [(4'-bromobiphenyl-4-yl)methoxy](tert-butyl)dimethylsilane, tert-butyl 5-(benzyloxy)-2-{[1-(4-{5-[1-(methoxymethoxy)ethyl]pyridin-2-yl}phenyl)piperidin-4-yl]methyl}-6-methylpyrimidine-4-carboxylate was afforded as a yellow oil (yield 45%).

In accordance with Example 1-(11), but using glycine benzyl ester p-toluenesulfonate instead of glycine ethyl ester hydrochloride, and tert-butyl 5-(benzyloxy)-2-{[1-(4-{5-[1-(methoxymethoxy)ethyl]pyridin-2-yl}phenyl)piperidin-4-yl]methyl}-6-methylpyrimidine-4-carboxylate instead of tert-butyl 5-(benzyloxy)-2-({1-[4'-(hydroxymethyl)biphenyl-4-yl]piperidin-4-yl}methyl)-6-methylpyrimidine-4-carboxylate, the title compound (quantitative yield) was afforded as a yellow oil.

$^1$H-NMR (500 MHz, CDCl$_3$) δ: 8.58 (1H, s), 8.39 (1H, t, J=5 Hz), 7.91 (2H, d, J=9 Hz), 7.69-7.64 (2H, m), 7.48 (2H, d, J=7 Hz), 7.40-7.22 (8H, m), 7.00 (2H, d, J=9 Hz), 5.24 (2H, s), 5.11 (2H, s), 4.81 (1H, q, J=7 Hz), 4.62 (1H, d, J=7 Hz), 4.58 (1H, d, J=7 Hz), 4.30 (2H, d, J=5 Hz), 3.80 (2H, d, J=12 Hz), 3.38 (3H, s), 2.88 (2H, d, J=7 Hz), 2.80 (2H, t, J=12 Hz), 2.47 (3H, s), 2.18-2.08 (1H, m), 1.78 (2H, d, J=12 Hz), 1.55-1.48 (2H, m), 1.52 (3H, d, J=7 Hz).-

(3) Benzyl [({5-(benzyloxy)-2-[(1-{4-[5-(1-hydroxyethyl)pyridin-2-yl]phenyl}piperidin-4-yl)methyl]-6-methylpyrimidin-4-yl}carbonyl)amino]acetate

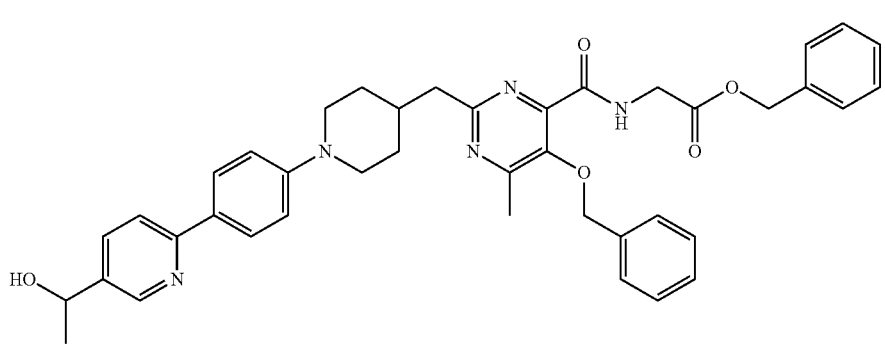

[Chemical 55]

Benzyl({[5-(benzyloxy)-2-{[1-(4-{5-[1-(methoxymethoxy)ethyl]pyridin-2-yl}phenyl)piperidin-4-yl]methyl}-6-methylpyrimidin-4-yl]carbonyl}amino)acetate (0.80 g, 1.1 mmol) was dissolved in ethyl acetate (6 mL), and a solution of hydrogen chloride in dioxane (4 M, 1.5 mL, 6.0 mmol) was added, followed by stirring at room temperature for 1.5 hours. After hexane was added to the reaction solution, the deposited solid was collected by filtration using hexane. To this, was added a saturated aqueous sodium hydrogencarbonate solution, followed by extraction with ethyl acetate, and subsequently the organic layer was concentrated under reduced pressure. The resulting residue was purified by chromatography on a silica gel column (Moritex Corporation, elution solvent: hexane/ethyl acetate), and a fraction corresponding to the Rf value=0.30 (hexane/ethyl acetate=1/1) by thin layer chromatography was concentrated under reduced pressure to afford the title compound (0.32 g, 0.49 mmol) as a yellow solid (yield 44%).

MS m/z: 686 (M+H)$^+$.

(4) [({5-Hydroxy-2-[(1-{4-[5-(1-hydroxyethyl)pyridin-2-yl]phenyl}piperidin-4-yl)methyl]-6-methylpyrimidin-4-yl}carbonyl)amino]acetic acid Benzyl [({5-(benzyloxy)-2-[(1-{4-[5-(1-hydroxyethyl)pyridin-2-yl]phenyl}piperidin-4-yl)methyl]-6-methylpyrimidin-4-yl}carbonyl)amino]acetate (0.10 g, 0.16 mmol) was dissolved in ethyl acetate (30 mL), and 10% palladium-activated carbon (0.25 g) was added, followed by stirring at room temperature for 9 hours under a hydrogen atmosphere. After the reaction solution was filtered with celite, the filtrate was concentrated under reduced pressure. The resulting residue was purified by chromatography on a silica gel column (Moritex Corporation, elution solvent: ethyl acetate/methanol), and a fraction corresponding to the Rf value=0.10 (ethyl acetate/methanol=4/1) by thin layer chromatography was concentrated under reduced pressure to afford the title compound (0.045 g, 0.089 mmol) as a yellow solid (yield 56%).

MS m/z: 506 (M+H)$^+$;

$^1$H-NMR (500 MHz, DMSO-$d_6$) δ: 9.42 (1H, t, J=5 Hz), 9.06 (1H, s), 8.23 (1H, d, J=8 Hz), 8.04 (2H, d, J=8 Hz), 7.98 (1H, d, J=8 Hz), 7.04 (2H, d, J=8 Hz), 4.35 (1H, q, J=7 Hz), 4.00 (2H, d, J=5 Hz), 3.88 (2H, d, J=13 Hz), 2.83-2.77 (4H, m), 2.44 (3H, s), 2.20-2.17 (1H, m), 1.68 (2H, d, J=13 Hz), 1.38 (3H, d, J=7 Hz), 1.36-1.33 (2H, m).

Example 13

{[(5-Hydroxy-2-{[1-(4-{5-[1-(methoxymethoxy)ethyl]pyridin-2-yl}phenyl)piperidin-4-yl]methyl}-6-methylpyrimidin-4-yl)carbonyl]amino}acetic acid

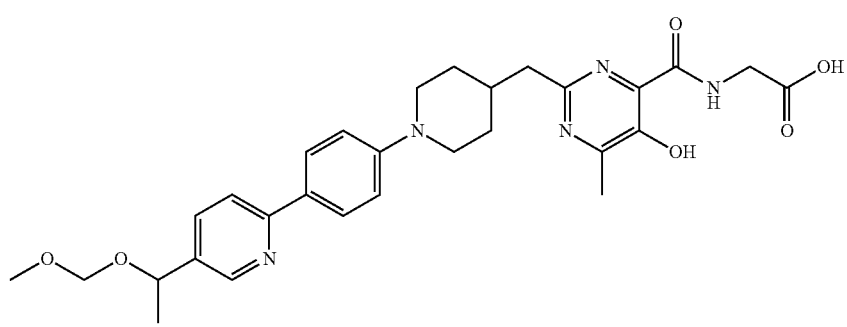

[Chemical 56]

In accordance with Example 12-(4), but using benzyl({[5-(benzyloxy)-2-{[1-(4-{5-[1-(methoxymethoxy)ethyl]pyridin-2-yl}phenyl)piperidin-4-yl]methyl}-6-methylpyrimidin-4-yl]carbonyl}amino)acetate obtained in Example 12-(2) instead of benzyl [({5-(benzyloxy)-2-[(1-{4-[5-(1-hydroxyethyl)pyridin-2-yl]phenyl}piperidin-4-yl)methyl]-6-methylpyrimidin-4-yl}carbonyl)amino]acetate, the title compound was afforded as a pale brown solid (yield 39%).

MS m/z: 550 (M+H)$^+$;

$^1$H-NMR (500 MHz, DMSO-d$_6$) δ: 9.23 (1H, brs), 8.52 (1H, d, J=2 Hz), 7.93 (2H, d, J=8 Hz), 7.82 (1H, d, J=8 Hz), 7.74 (1H, dd, J=8 Hz, 2 Hz), 7.00 (2H, d, J=8 Hz), 4.76 (1H, q, J=7 Hz), 4.61 (1H, d, J=7 Hz), 4.50 (1H, d, J=7 Hz), 3.84-3.76 (4H, m), 3.25 (3H, s), 2.78-2.72 (4H, m), 2.43 (3H, s), 2.13-2.05 (1H, m), 1.69 (2H, d, J=12 Hz), 1.44 (3H, d, J=7 Hz), 1.40-1.30 (2H, m).

Example 14

[({2-[(1-{4-[5-(1-Acetoxyethyl)pyridin-2-yl]phenyl}piperidin-4-yl)methyl]-5-hydroxy-6-methylpyrimidin-4-yl}carbonyl)amino]acetic acid sequently a saturated aqueous sodium hydrogencarbonate solution was added, followed by extraction with ethyl acetate. After the organic layer was concentrated under reduced pressure, the resulting residue was purified by chromatography on a silica gel column (Moritex Corporation, elution solvent: hexane/ethyl acetate), and a fraction corresponding to the Rf value=0.40 (hexane/ethyl acetate=1/1) by thin layer chromatography was concentrated under reduced pressure to afford the title compound (0.12 g, 0.17 mmol) as a yellow oil (yield 48%).

$^1$H-NMR (500 MHz, CDCl$_3$) δ: 8.62 (1H, s), 8.38 (1H, t, J=5 Hz), 7.90 (2H, d, J=9 Hz), 7.68-7.63 (2H, m), 7.48 (2H, d, J=7 Hz), 7.40-7.21 (8H, m), 7.00 (2H, d, J=9 Hz), 5.92 (1H, q, J=6 Hz), 5.24 (2H, s), 5.11 (2H, s), 4.30 (2H, d, J=5 Hz),

[Chemical 57]

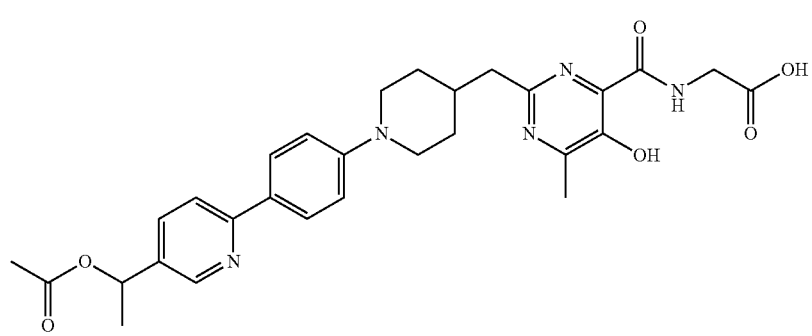

(1) Benzyl [({2-[(1-{4-[5-(1-acetoxyethyl)pyridin-2-yl]phenyl}piperidin-4-yl)methyl]-5-(benzyloxy)-6-methylpyrimidin-4-yl}carbonyl)amino]acetate 3.80 (2H, d, J=13 Hz), 2.88 (2H, d, J=7 Hz), 2.81 (2H, t, J=13 Hz), 2.47 (3H, s), 2.16-2.05 (1H, m), 2.09 (3H, s), 1.78 (2H, d, J=13 Hz), 1.58 (3H, d, J=6 Hz), 1.57-1.48 (2H, m).

[Chemical 58]

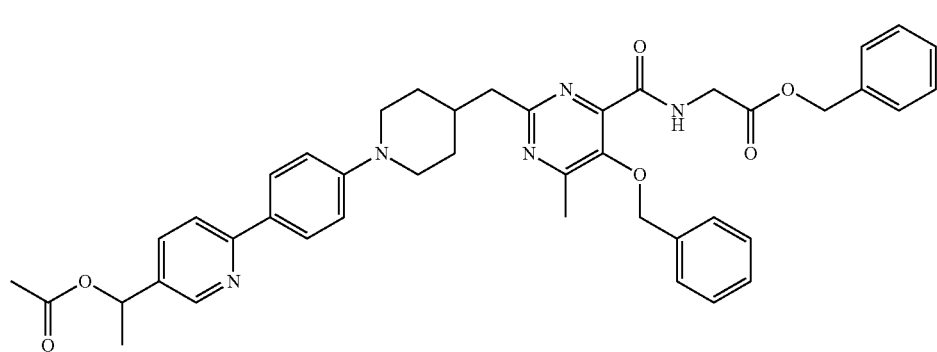

Benzyl [({5-(benzyloxy)-2-[(1-{4-[5-(1-hydroxyethyl)pyridin-2-yl]phenyl}piperidin-4-yl)methyl]-6-methylpyrimidin-4-yl}carbonyl)amino]acetate (0.24 g, 0.35 mmol) obtained in Example 12-(3) was dissolved in dichloromethane (30 mL), and acetic anhydride (0.050 mL, 0.52 mmol) and triethylamine (1.8 mL) were added, followed by stirring at room temperature for 12 hours. Acetic anhydride (1.8 mL) and pyridine (0.90 mL) were added to the reaction solution, followed by stirring for further 12 hours, and sub- (2) [({2-[(1-{4-[5-(1-Acetoxyethyl)pyridin-2-yl]phenyl}piperidin-4-yl)methyl]-5-hydroxy-6-methylpyrimidin-4-yl}carbonyl)amino]acetic acid In accordance with Example 12-(4), but using benzyl [({2-[(1-{4-[5-(1-acetoxyethyl)pyridin-2-yl]phenyl}piperidin-4-yl)methyl]-5-(benzyloxy)-6-methylpyrimidin-4-yl}carbonyl)amino]acetate instead of benzyl [({5-(benzyloxy)-2-[(1-{4-[5-(1-hydroxyethyl)pyridin-2-yl]

phenyl}piperidin-4-yl)methyl]-6-methylpyrimidin-4-yl}carbonyl)amino]acetate, the title compound (yield 98%) was afforded as a pale yellow solid.

MS m/z: 548 (M+H)$^+$;

$^1$H-NMR (500 MHz, DMSO-d$_6$) δ: 9.40 (1H, t, J=6 Hz), 8.57 (1H, d, J=2 Hz), 7.93 (2H, d, J=9 Hz), 7.82 (1H, d, J=8 Hz), 7.78 (1H, dd, J=8 Hz, 2 Hz), 7.00 (2H, d, J=9 Hz), 5.83 (1H, q, J=6 Hz), 3.98 (2H, d, J=6 Hz), 3.81 (2H, d, J=12 Hz), 2.79-2.73 (4H, m), 2.44 (3H, s), 2.16-2.08 (1H, m), 2.05 (3H, s), 1.68 (2H, d, J=12 Hz), 1.52 (3H, d, J=6 Hz), 1.40-1.30 (2H, m).

Example 15

[({5-Hydroxy-2-[(1-{4-[5-(hydroxymethyl)pyridin-2-yl]phenyl}piperidin-4-yl)methyl]-6-methylpyrimidin-4-yl}carbonyl)amino]acetic acid

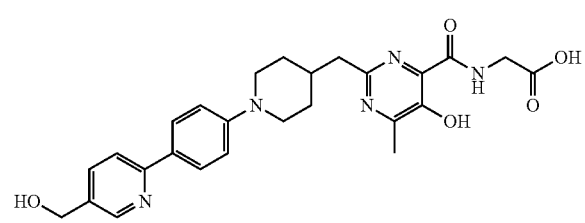

[Chemical 59]

(1) 2-(4-Bromophenyl)-5-[(methoxymethoxy)methyl]pyridine

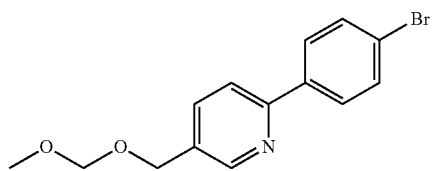

[Chemical 60]

In accordance with Example 11-(1), but using (6-bromopyridin-3-yl)methanol instead of 4-bromobenzyl bromide, and 4-bromophenylboronic acid instead of [3-(hydroxymethyl)phenyl]boronic acid, [6-(4-bromophenyl)pyridin-3-yl]methanol was afforded as a white solid (yield 51%).

In accordance with Example 10-(1), but using [6-(4-bromophenyl)pyridin-3-yl]methanol instead of [4-(4-bromobenzyl)phenyl]methanol, the title compound (quantitative yield) was afforded as a white solid.

$^1$H-NMR (500 MHz, CDCl$_3$) δ: 8.66 (1H, s), 7.88 (2H, d, J=8 Hz), 7.77 (1H, d, J=8 Hz), 7.70 (1H, d, J=8 Hz), 7.60 (2H, d, J=8 Hz), 4.74 (2H, s), 4.65 (2H, s), 3.43 (3H, s).

(2) Ethyl {[(5-hydroxy-2-{[1-(4-{5-[(methoxymethoxy)methyl]pyridin-2-yl}phenyl)piperidin-4-yl]methyl}-6-methylpyrimidin-4-yl)carbonyl]amino}acetate

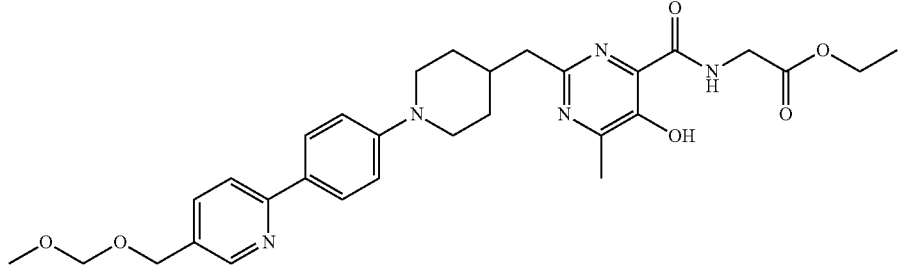

[Chemical 61]

In accordance with Examples 1-(9), 1-(11) and 1-(12), but using 2-(4-bromophenyl)-5-[(methoxymethoxy)methyl]pyridine instead of [(4'-bromobiphenyl-4-yl)methoxy](tert-butyl)dimethylsilane, the title compound (yield 22%) was afforded as a white solid.

MS m/z: 564 (W+H);

$^1$H-NMR (500 MHz, CDCl$_3$) δ: 11.37 (1H, s), 8.60 (1H, s), 8.50 (1H, t, J=5 Hz), 7.90 (2H, d, J=8 Hz), 7.70 (1H, d, J=8 Hz), 7.65 (1H, d, J=8 Hz), 7.00 (2H, d, J=8 Hz), 4.73 (2H, s), 4.62 (2H, s), 4.28 (2H, q, J=7 Hz), 4.22 (2H, d, J=5 Hz), 3.79 (2H, d, J=12 Hz), 3.42 (3H, s), 2.84-2.77 (4H, m), 2.54 (3H, s), 2.13-2.07 (1H, m), 1.78 (2H, d, J=12 Hz), 1.54-1.46 (2H, m), 1.33 (3H, t, J=7 Hz).

(3) [({5-Hydroxy-2-[(1-{4-[5-(hydroxymethyl)pyridin-2-yl]phenyl}piperidin-4-yl)methyl]-6-methylpyrimidin-4-yl}carbonyl)amino]acetic acid In accordance with Examples 12-(3) and 1-(13), but using ethyl {[(5-hydroxy-2-{[1-(4-{5-[(methoxymethoxy)methyl]pyridin-2-yl}phenyl)piperidin-4-yl]methyl}-6-methylpyrimidin-4-yl)carbonyl]amino}acetate instead of benzyl({[5-(benzyloxy)-2-{[1-(4-{5-[1-(methoxymethoxy)ethyl]pyridin-2-yl}phenyl)piperidin-4-yl]methyl}-6-methylpyrimidin-4-yl]carbonyl}amino)acetate, the title compound (yield 87%) was afforded as a yellow solid.

MS m/z: 492 (M+H)$^+$;

$^1$H-NMR (500 MHz, DMSO-d$_6$) δ: 9.39 (1H, t, J=5 Hz), 8.50 (1H, s), 7.92 (2H, d, J=8 Hz), 7.80 (1H, d, J=8 Hz), 7.71 (1H, d, J=8 Hz), 7.00 (2H, d, J=8 Hz), 5.28 (1H, t, J=5 Hz), 4.52 (2H, d, J=5 Hz), 3.98 (2H, d, J=5 Hz), 3.80 (2H, d, J=13 Hz), 2.79-2.72 (4H, m), 2.44 (3H, s), 2.17-2.07 (1H, m), 1.68 (2H, d, J=13 Hz), 1.40-1.30 (2H, m).

Example 16

[({2-[(1-{4-[5-(Ethoxycarbonyl)pyridin-2-yl]phenyl}piperidin-4-yl)methyl]-5-hydroxy-6-methylpyrimidin-4-yl}carbonyl)amino]acetic acid

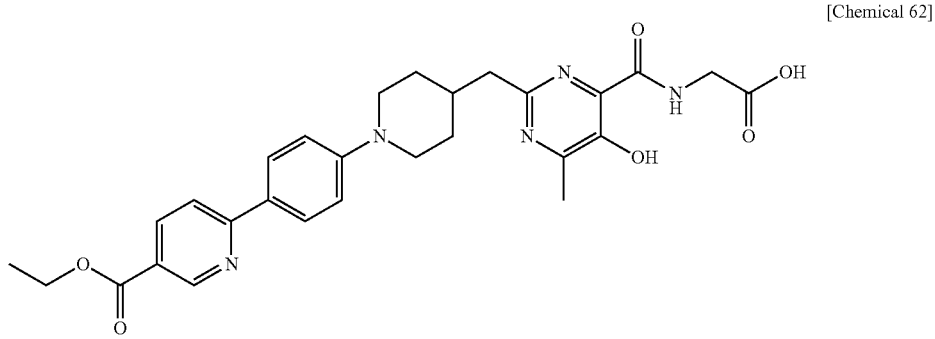 [SMILES: CCOC(=O)c1ccc(-c2ccc(N3CCC(Cc4nc(C)c(O)c(C(=O)NCC(=O)O)n4)CC3)cc2)nc1]

[Chemical 62]

(1) Ethyl 6-(4-bromophenyl)nicotinate

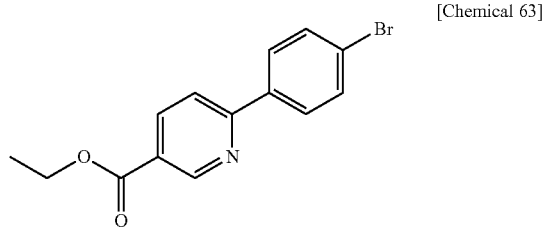 [SMILES: CCOC(=O)c1ccc(-c2ccc(Br)cc2)nc1]

[Chemical 63]

In accordance with Example 11-(1), but using ethyl 6-bromonicotinate instead of 4-bromobenzylbromide, and 4-bromophenylboronic acid instead of [3-(hydroxymethyl)phenyl]boronic acid, the title compound (yield 98%) was afforded as a white solid.

$^1$H-NMR (500 MHz, CDCl$_3$) δ: 9.28 (1H, s), 8.36 (1H, d, J=8 Hz), 7.96 (2H, d, J=8 Hz), 7.80 (1H, d, J=8 Hz), 7.64 (2H, d, J=8 Hz), 4.44 (2H, q, J=7 Hz), 1.43 (3H, t, J=7 Hz).

(2) tert-Butyl 5-(benzyloxy)-2-[(1-{4-[5-(ethoxycarbonyl)pyridin-2-yl]phenyl}piperidin-4-yl)methyl]-6-methylpyrimidine-4-carboxylate

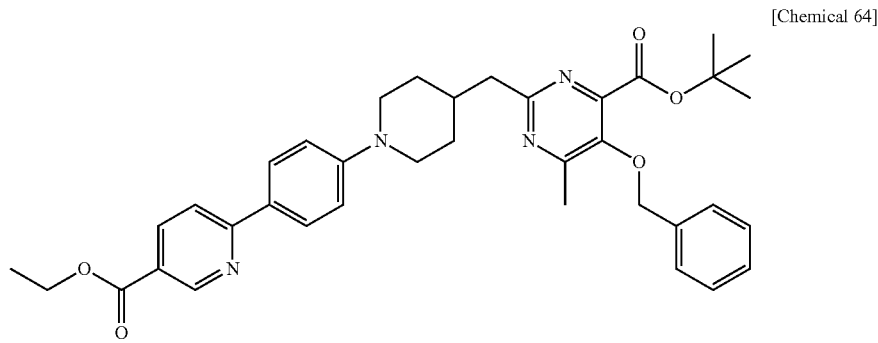 [SMILES: CCOC(=O)c1ccc(-c2ccc(N3CCC(Cc4nc(C)c(OCc5ccccc5)c(C(=O)OC(C)(C)C)n4)CC3)cc2)nc1]

[Chemical 64]

In accordance with Example 1-(9), but using ethyl 6-(4-bromophenyl)nicotinate instead of [(4'-bromobiphenyl-4-yl)methoxy](tert-butyl)dimethylsilane, the title compound (yield 23%) was afforded as a yellow oil.

$^1$H-NMR (500 MHz, CDCl$_3$) δ: 9.21 (1H, s), 8.26 (1H, d, J=8 Hz), 7.99 (2H, d, J=8 Hz), 7.72 (1H, d, J=8 Hz), 7.43-7.38 (5H, m), 7.00 (2H, d, J=8 Hz), 5.01 (2H, s), 4.42 (2H, q, J=7 Hz), 3.83 (2H, d, J=12 Hz), 2.91-2.81 (4H, m), 2.46 (3H, s), 2.20-2.12 (1H, m), 1.80 (2H, d, J=12 Hz), 1.59 (9H, s), 1.57-1.48 (2H, m), 1.42 (3H, t, J=7 Hz).

(3) Ethyl 6-{4-[4-({4-[(2-tert-butoxy-2-oxoethyl)carbamoyl]-5-hydroxy-6-methylpyrimidin-2-yl}methyl)piperidin-1-yl]phenyl}nicotinate

[Chemical 65]

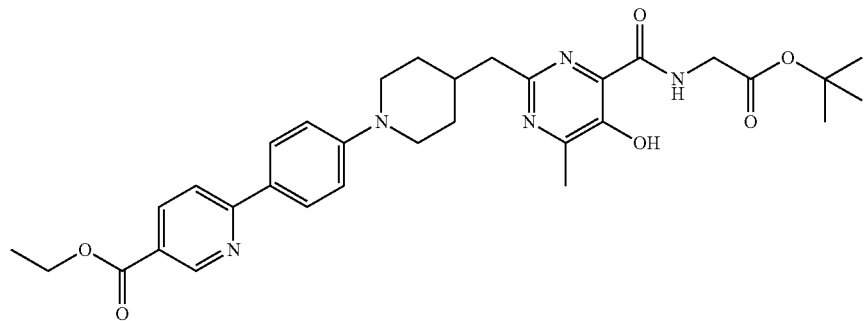

tert-Butyl 5-(benzyloxy)-2-[(1-{4-[5-(ethoxycarbonyl)pyridin-2-yl]phenyl}piperidin-4-yl)methyl]-6-methylpyrimidine-4-carboxylate (0.25 g, 0.40 mmol) was dissolved in dichloromethane (5 mL), and trifluoroacetic acid (10 mL) was added, followed by stirring at room temperature for 12 hours. The reaction solution was concentrated under reduced pressure, and a saturated aqueous sodium hydrogencarbonate solution was added, followed by extraction with ethyl acetate. After the organic layer was dried over anhydrous sodium sulfate, the solvent was distilled off under reduced pressure to afford 2-[(1-{4-[5-(ethoxycarbonyl)pyridin-2-yl]phenyl}piperidin-4-yl)methyl]-5-hydroxy-6-methylpyrimidine-4-carboxylic acid.

This was dissolved in a mixed solvent of tetrahydrofuran (20 mL) and methanol (20 mL), and glycine tert-butyl ester hydrochloride (0.13 g, 0.80 mmol), 4-(4,6-dimethoxy-1,3,5-triazin-2-yl)-4-methylmorpholinium chloride (0.22 g, 0.80 mmol) and N-methylmorpholine (0.40 mL, 4.0 mmol) were added, followed by stirring at room temperature for 12 hours. The reaction solution was concentrated under reduced pressure, and ethyl acetate was added, and subsequently the organic layer was washed with water. After the solvent was distilled off under reduced pressure, the resulting residue was purified by chromatography on a silica gel column (Moritex Corporation, elution solvent: hexane/ethyl acetate), and a fraction corresponding to the Rf value=0.70 (hexane/ethyl acetate=1/1) by thin layer chromatography was concentrated under reduced pressure to afford the title compound (0.043 g, 0.073 mmol) as a yellow solid (yield 18%).

$^1$H-NMR (500 MHz, CDCl$_3$) δ: 11.45 (1H, s), 9.21 (1H, s), 8.46 (1H, t, J=5 Hz), 8.29-8.23 (1H, m), 7.99 (2H, d, J=7 Hz), 7.74-7.68 (1H, m), 6.99 (2H, d, J=7 Hz), 4.42 (2H, q, J=7 Hz), 4.12 (2H, d, J=5 Hz), 3.84 (2H, d, J=13 Hz), 2.89-2.79 (4H, m), 2.54 (3H, s), 2.15-2.08 (1H, m), 1.86-1.45 (4H, m), 1.52 (9H, s), 1.42 (3H, t, J=7 Hz).

(4) [({2-[(1-{4-[5-(Ethoxycarbonyl)pyridin-2-yl]phenyl}piperidin-4-yl)methyl]-5-hydroxy-6-methylpyrimidin-4-yl}carbonyl)amino]acetic acid Ethyl 6-{4-[4-({4-[(2-tert-butoxy-2-oxoethyl)carbamoyl]-5-hydroxy-6-methylpyrimidin-2-yl}methyl)piperidin-1-yl]phenyl}nicotinate (0.043 g, 0.073 mmol) was dissolved in dichloromethane (5 mL), and trifluoroacetic acid (5 mL) was added at room temperature, followed by stirring for 12 hours. Hydrochloric acid (1 M) was added to the reaction solution, followed by extraction with ethyl acetate, and subsequently the organic layer was concentrated under reduced pressure. After the resulting residue was purified by chromatography on a silica gel column (Moritex Corporation, elution solvent: ethyl acetate/methanol), a fraction corresponding to the Rf value=0.10 (ethyl acetate/methanol=4/1) by thin layer chromatography was concentrated under reduced pressure. The resulting residue was dissolved in ethyl acetate, followed by addition of diisopropyl ether, and subsequently the deposited solid was collected by filtration using diisopropyl ether to afford the title compound (0.020 g, 0.037 mmol) as a pale yellow solid (yield 51%).

MS m/z: 534 (M+H)$^+$;

$^1$H-NMR (500 MHz, DMSO-d$_6$) δ: 9.36 (1H, brs), 9.06 (1H, d, J=2 Hz), 8.23 (1H, dd, J=8 Hz, 2 Hz), 8.04 (2H, d, J=9 Hz), 7.99 (1H, d, J=8 Hz), 7.04 (2H, d, J=9 Hz), 4.35 (2H, q, J=7 Hz), 3.93 (2H, brs), 3.88 (2H, d, J=12 Hz), 2.83-2.77 (4H, m), 2.45 (3H, s), 2.19-2.11 (1H, m), 1.70 (2H, d, J=12 Hz), 1.39-1.30 (2H, m), 1.35 (3H, t, J=7 Hz).

Example 17

[({2-[(1-{4-[2-(Ethoxycarbonyl)benzyl]phenyl}piperidin-4-yl)methyl]-5-hydroxy-6-methylpyrimidin-4-yl}carbonyl)amino]acetic acid

[Chemical 66]

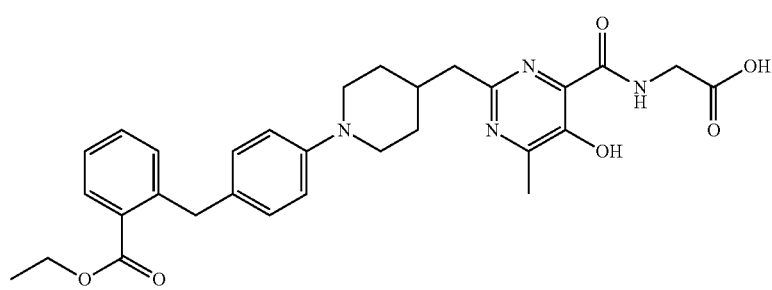

(1) Ethyl 2-(4-bromobenzyl)benzoate

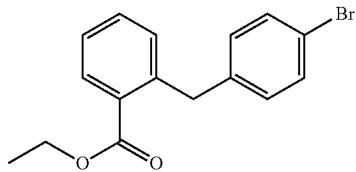

In accordance with Example 11-(1), but using [2-(ethoxycarbonyl)phenyl]boronic acid instead of [3-(hydroxymethyl)phenyl]boronic acid, the title compound (yield 78%) was afforded as a colorless oil.

$^1$H-NMR (500 MHz, CDCl$_3$) δ: 7.92 (1H, d, J=8 Hz), 7.44 (1H, t, J=8 Hz), 7.37 (2H, d, J=8 Hz), 7.31 (1H, t, J=8 Hz), 7.20 (1H, d, J=8 Hz), 7.02 (2H, d, J=8 Hz), 4.33 (2H, s), 4.28 (2H, q, J=7 Hz), 1.31 (3H, t, J=7 Hz).

(2) tert-Butyl({[5-(benzyloxy)-6-methyl-2-(piperidin-4-ylmethyl)pyrimidin-4-yl]carbonyl}amino)acetate hydrochloride

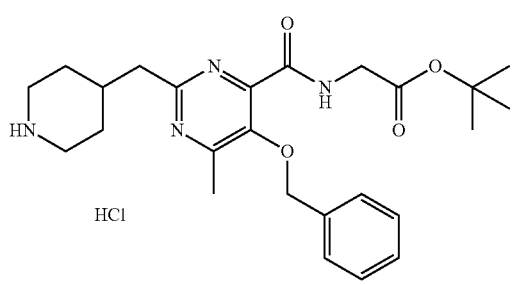

In accordance with Examples 1-(11) and 1-(7), but using tert-butyl 5-(benzyloxy)-2-{[1-(tert-butoxycarbonyl)piperidin-4-yl]methyl}-6-methylpyrimidine-4-carboxylate obtained in Example 1-(6) instead of tert-butyl 5-(benzyloxy)-2-{1-[4'-(hydroxymethyl)biphenyl-4-yl]piperidin-4-yl}methyl)-6-methylpyrimidine-4-carboxylate, and glycine tert-butyl ester hydrochloride instead of glycine ethyl ester hydrochloride, the title compound (yield 72%) was afforded as a white solid.

$^1$H-NMR (500 MHz, CD$_3$OD) δ: 7.46-7.45 (2H, m), 7.36-7.35 (3H, m), 5.11 (2H, s), 4.05 (2H, s), 3.38 (2H, d, J=13 Hz), 2.99 (2H, t, J=13 Hz), 2.90 (2H, d, J=7 Hz), 2.45 (3H, s), 2.36-2.27 (1H, m), 1.92 (2H, d, J=13 Hz), 1.56-1.49 (2H, m), 1.49 (9H, s).

(3) Ethyl 2-{4-[4-({5-(benzyloxy)-4-[(2-tert-butoxy-2-oxoethyl)carbamoyl]-6-methylpyrimidin-2-yl}methyl)piperidin-1-yl]benzyl}benzoate

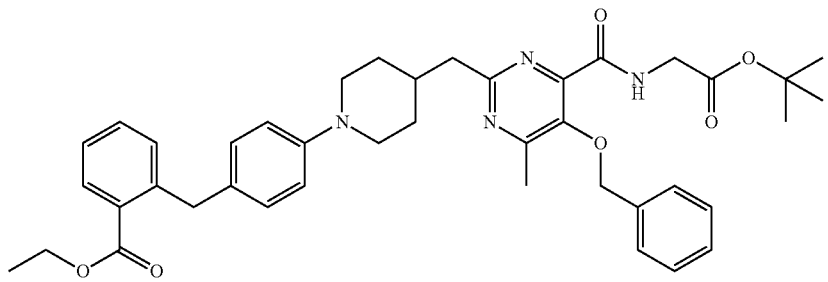

In accordance with Example 1-(9), but using tert-butyl ({[5-(benzyloxy)-6-methyl-2-(piperidin-4-ylmethyl)pyrimidin-4-yl]carbonyl}amino)acetate hydrochloride instead of tert-butyl 5-(benzyloxy)-6-methyl-2-(piperidin-4-ylmethyl)pyrimidine-4-carboxylate hydrochloride, and ethyl 2-(4-bromobenzyl)benzoate instead of [(4'-bromobiphenyl-4-yl)methoxy](tert-butyl)dimethylsilane, the title compound (yield 72%) was afforded as a white solid.

MS m/z: 693 (M+H)$^+$.

(4) [({2-[(1-{4-[2-(Ethoxycarbonyl)benzyl]phenyl}piperidin-4-yl)methyl]-5-hydroxy-6-methylpyrimidin-4-yl}carbonyl)amino]acetic acid In accordance with Example 16-(4), but using ethyl 2-{4-[4-({5-(benzyloxy)-4-[(2-tert-butoxy-2-oxoethyl)carbamoyl]-6-methylpyrimidin-2-yl}methyl)piperidin-1-yl]benzyl}benzoate instead of ethyl 6-{4-[4-({4-[(2-tert-butoxy-2-oxoethyl)carbamoyl]-5-hydroxy-6-methylpyrimidin-2-yl}methyl)piperidin-1-yl]phenyl}nicotinate, the title compound (yield 12%) was afforded as a yellow solid.

MS m/z: 547 (M+H)$^+$;

$^1$H-NMR (500 MHz, CD$_3$OD) δ: 7.82 (1H, d, J=8 Hz), 7.46 (1H, t, J=8 Hz), 7.30 (1H, t, J=8 Hz), 7.27 (1H, d, J=8 Hz), 7.07 (4H, brs), 4.30 (2H, s), 4.24 (2H, q, J=7 Hz), 4.05 (2H, s), 3.58 (2H, d, J=12 Hz), 2.90 (2H, t, J=12 Hz), 2.84 (2H, d, J=7 Hz), 2.49 (3H, s), 2.21-2.12 (1H, m), 1.82 (2H, d, J=12 Hz), 1.62-1.53 (2H, m), 1.27 (3H, t, J=7 Hz).

Example 18

{[(5-Hydroxy-2-{[1-(4-{[6-(2-hydroxyethoxy)pyridin-3-yl]methyl}phenyl)piperidin-4-yl]methyl}-6-methylpyrimidin-4-yl)carbonyl]amino}acetic acid

[Chemical 70]

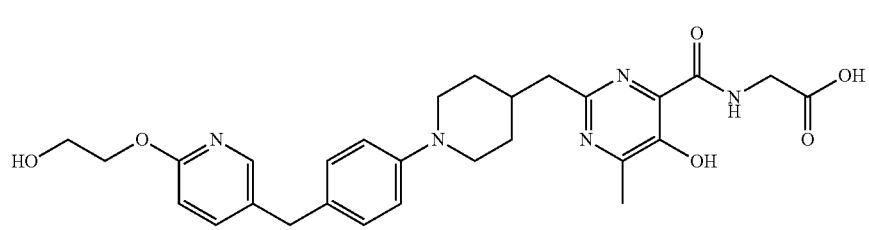

(1) N,6-Dimethoxy-N-methylnicotinamide

[Chemical 71]

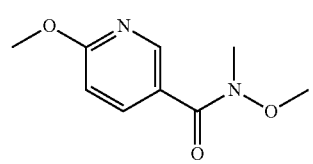

In accordance with Example 5-(1), but using 6-methoxynicotinic acid instead of (4'-bromobiphenyl-4-yl)acetic acid, the title compound (yield 92%) was afforded as a colorless oil.

$^1$H-NMR (500 MHz, CDCl$_3$) δ: 8.65 (1H, s), 8.00 (1H, d, J=9 Hz), 6.76 (1H, d, J=9 Hz), 3.99 (3H, s), 3.58 (3H, s), 3.38 (3H, s).

(2) (4-Bromophenyl)(6-methoxypyridin-3-yl)methanone

[Chemical 72]

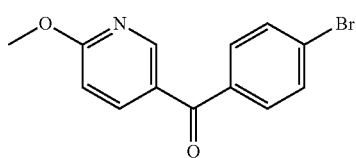

1,4-Dibromobenzene (6.5 g, 27 mmol) was dissolved in tetrahydrofuran (120 mL), and a solution of n-butyllithium in hexane (2.6 M, 10 mL, 27 mmol) was added at −78° C., followed by stirring at the same temperature for 30 minutes. A solution of N,6-dimethoxy-N-methylnicotinamide (2.7 g, 14 mmol) in tetrahydrofuran (20 mL) was added to the reaction solution, followed by stirring at −78° C. for further 30 minutes. Water was added to the reaction solution, followed by extraction with ethyl acetate, and subsequently the organic layer was concentrated under reduced pressure. The resulting residue was purified by chromatography on a silica gel column (Moritex Corporation, elution solvent: hexane/ethyl acetate), and a fraction corresponding to the Rf value=0.50 (hexane/ethyl acetate=10/1) by thin layer chromatography was concentrated under reduced pressure to afford the title compound (2.8 g, 9.4 mmol) as a white solid (yield 69%).

$^1$H-NMR (500 MHz, CDCl$_3$) δ: 8.59 (1H, s), 8.07 (1H, d, J=8 Hz), 7.66 (4H, s), 6.85 (1H, d, J=8 Hz), 4.03 (3H, s).

(3) 2-{[5-(4-Bromobenzyl)pyridin-2-yl]oxy}ethanol

[Chemical 73]

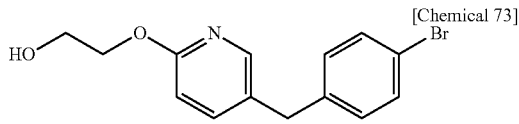 [SMILES: OCCOc1ccc(Cc2ccc(Br)cc2)cn1]

(4-Bromophenyl)(6-methoxypyridin-3-yl)methanone (0.88 g, 3.0 mmol), hydrazine monohydrate (1.5 mL, 30 mmol) and potassium hydroxide (0.60 g, 12 mmol) were dissolved in ethylene glycol (10 mL), followed by stirring at 140° C. for 20 minutes. After the reaction solution was cooled to room temperature, water was added, followed by extraction with diethyl ether. After the organic layer was concentrated under reduced pressure, the resulting residue was purified by chromatography on a silica gel column (Moritex Corporation, elution solvent: hexane/ethyl acetate), and a fraction corresponding to the Rf value=0.30 (hexane/ethyl acetate=1/1) by thin layer chromatography was concentrated under reduced pressure to afford the title compound (0.38 g, 1.2 mmol) as a colorless oil (yield 41%).

$^1$H-NMR (500 MHz, CDCl$_3$) δ: 7.95 (1H, s), 7.41 (2H, d, J=8 Hz), 7.36 (1H, d, J=9 Hz), 7.03 (2H, d, J=8 Hz), 6.72 (1H, d, J=9 Hz), 4.48-4.35 (2H, m), 3.97-3.90 (2H, m), 3.85 (2H, s), 3.84-3.75 (1H, m).

(4) 5-(4-Bromobenzyl)-2-(2-{[tert-butyl(dimethyl)silyl]oxy}ethoxy)pyridine

[Chemical 74]

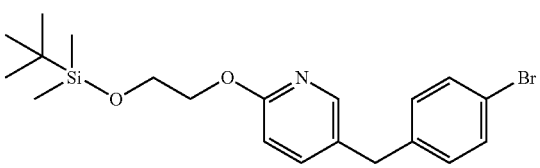

In accordance with Example 1-(8), but using 2-{[5-(4-bromobenzyl)pyridin-2-yl]oxy}ethanol instead of (4'-bromobiphenyl-4-yl)methanol, the title compound (yield 77%) was afforded as a colorless oil.

$^1$H-NMR (500 MHz, CDCl$_3$) δ: 7.96 (1H, s), 7.40 (2H, d, J=8 Hz), 7.31 (1H, d, J=8 Hz), 7.02 (2H, d, J=8 Hz), 6.68 (1H, d, J=8 Hz), 4.37-4.32 (2H, m), 3.98-3.92 (2H, m), 3.83 (2H, s), 0.89 (9H, s), 0.07 (6H, s).

(5) Ethyl({[5-(benzyloxy)-2-{[1-(4-{[6-(2-{[tert-butyl(dimethyl)silyl]oxy}ethoxy)pyridin-3-yl]methyl}phenyl)piperidin-4-yl]methyl}-6-methylpyrimidin-4-yl]carbonyl}amino)acetate concentrated under reduced pressure to afford the title compound (0.31 g, 0.47 mmol) as a yellow oil (yield 66%).

$^1$H-NMR (500 MHz, CDCl$_3$) δ: 8.35 (1H, t, J=5 Hz), 7.95 (1H, s), 7.48 (1H, d, J=6 Hz), 7.43-7.32 (5H, m), 7.03 (2H, d, J=9 Hz), 6.87 (2H, d, J=9 Hz), 6.71 (1H, d, J=6 Hz), 5.12 (2H, s), 4.46-4.40 (2H, m), 4.27 (2H, q, J=7 Hz), 4.25 (2H, d, J=5 Hz), 4.04-3.96 (1H, m), 3.97-3.90 (2H, m), 3.81 (2H, s), 3.63 (2H, d, J=12 Hz), 2.89 (2H, d, J=7 Hz), 2.69 (2H, t, J=12 Hz), 2.46 (3H, s), 2.11-2.04 (1H, m), 1.76 (2H, d, J=12 Hz), 1.53 (2H, dq, J=12 Hz, 3 Hz), 1.32 (3H, t, J=7 Hz).

[Chemical 75]

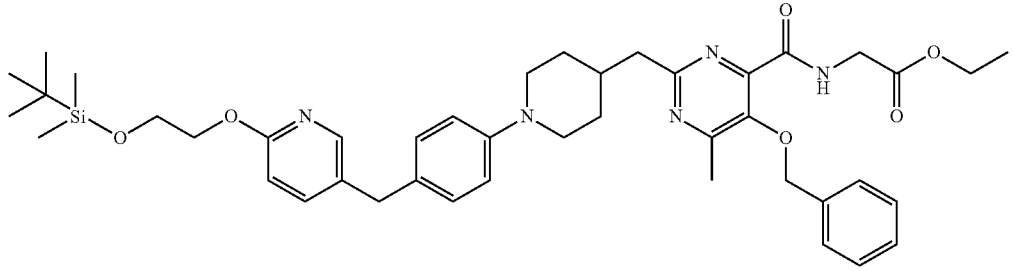

In accordance with Examples 1-(9) and 1-(11), but using 5-(4-bromobenzyl)-2-(2-{[tert-butyl(dimethyl)silyl]oxy}ethoxy)pyridine instead of [(4'-bromobiphenyl-4-yl)methoxy](tert-butyl)dimethylsilane, the title compound was afforded as a crude product.

MS m/z: 768 (M+H)$^+$.

(6) Ethyl({[5-(benzyloxy)-2-{[1-(4-{[6-(2-hydroxyethoxy)pyridin-3-yl]methyl}phenyl)piperidin-4-yl]methyl}-6-methylpyrimidin-4-yl]carbonyl}amino)acetate (7) {[(5-Hydroxy-2-{[1-(4-{[6-(2-hydroxyethoxy)pyridin-3-yl]methyl}phenyl)piperidin-4-yl]methyl}-6-methylpyrimidin-4-yl)carbonyl]amino}acetic acid In accordance with Examples 1-(12) and 1-(13), but using ethyl({[5-(benzyloxy)-2-{[1-(4-{[6-(2-hydroxyethoxy)pyridin-3-yl]methyl}phenyl)piperidin-4-yl]methyl}-6-methylpyrimidin-4-yl]carbonyl}amino)acetate instead of ethyl ({[5-(benzyloxy)-2-{(1-[4'-(hydroxymethyl)biphenyl-4-yl]

[Chemical 76]

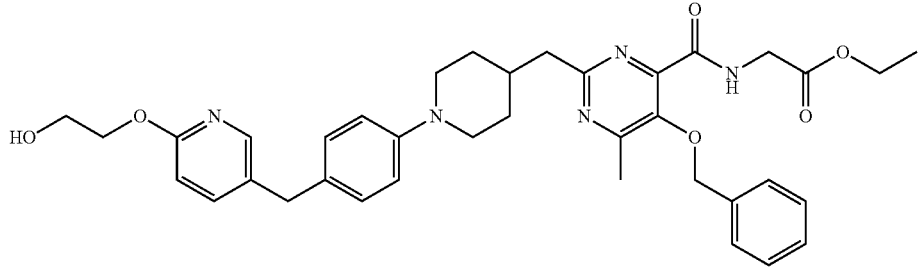

A crude product of ethyl({[5-(benzyloxy)-2-{[1-(4-{[6-(2-{[tert-butyl(dimethyl)silyl]oxy}ethoxy)pyridin-3-yl]methyl}phenyl)piperidin-4-yl]methyl}-6-methylpyrimidin-4-yl]carbonyl}amino)acetate was dissolved in tetrahydrofuran (20 mL), and a solution of tetrabutylammonium fluoride in tetrahydrofuran (1.0 M, 1.4 mL, 4.8 mmol) was added at 0° C., followed by stirring at the same temperature for 1 hour. Water was added to the reaction solution, followed by extraction with ethyl acetate, and subsequently the organic layer was concentrated under reduced pressure. The resulting residue was purified by chromatography on a silica gel column (Moritex Corporation, elution solvent: hexane/ethyl acetate), and a fraction corresponding to the Rf value=0.50 (ethyl acetate) by thin layer chromatography was piperidin-4-yl}methyl)-6-methylpyrimidin-4-yl] carbonyl}amino)acetate, the title compound (yield 50%) was afforded as a white solid.

MS m/z: 536 (M+H)$^+$;

$^1$H-NMR (500 MHz, DMSO-d$_6$) δ: 12.87 (1H, brs), 11.90 (1H, s), 9.39 (1H, t, J=5 Hz), 8.00 (1H, s), 7.48 (1H, d, J=8 Hz), 7.03 (2H, d, J=8 Hz), 6.83 (2H, d, J=8 Hz), 6.71 (1H, d, J=8 Hz), 4.80 (1H, brs), 4.25-4.16 (2H, m), 4.00 (2H, d, J=5 Hz), 3.74 (2H, s), 3.72-3.63 (2H, m), 3.58 (2H, d, J=12 Hz), 2.76 (2H, d, J=7 Hz), 2.59 (2H, t, J=12 Hz), 2.43 (3H, s), 2.09-2.00 (1H, m), 1.64 (2H, d, J=12 Hz), 1.33 (2H, dq, J=12 Hz, 3 Hz).

Example 19

[({5-Hydroxy-2-[(1-{5-[4-(hydroxymethyl)phenyl]pyridin-2-yl}piperidin-4-yl)methyl]-6-methylpyrimidin-4-yl}carbonyl)amino]acetic acid

[Chemical 77]

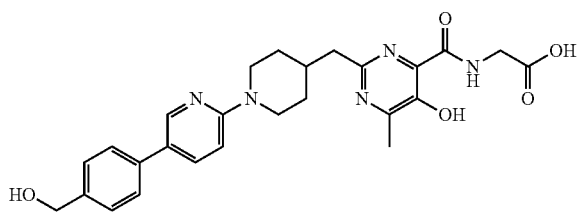

(1) tert-Butyl 5-(benzyloxy)-2-{[1-(5-bromopyridin-2-yl)piperidin-4-yl]methyl}-6-methylpyrimidine-4-carboxylate

[Chemical 78]

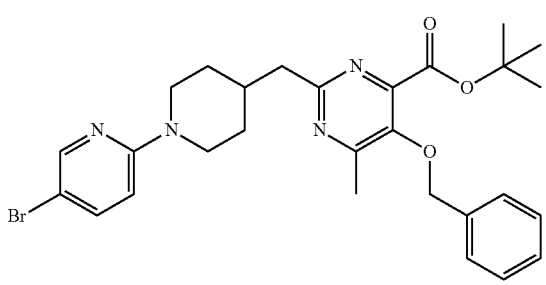

tert-Butyl 5-(benzyloxy)-6-methyl-2-(piperidin-4-ylmethyl)pyrimidine-4-carboxylate hydrochloride (6.5 g, 15 mmol), 2,5-dibromopyridine (5.3 g, 7.5 mmol) and potassium carbonate (6.2 g, 45 mmol) were suspended in N,N-dimethylformamide (150 mL), followed by stirring at 100° C. for 22 hours. The reaction solution was concentrated under reduced pressure, followed by addition of ethyl acetate, and subsequently the organic layer was washed with water. After the solvent was distilled off under reduced pressure, the resulting residue was purified by chromatography on a silica gel column (Moritex Corporation, elution solvent: hexane/ethyl acetate), and a fraction corresponding to the Rf value=0.40 (hexane/ethyl acetate=4/1) by thin layer chromatography was concentrated under reduced pressure to afford the title compound (2.3 g, 4.1 mmol) as a colorless oil (yield 27%).

$^1$H-NMR (500 MHz, CDCl$_3$) δ: 8.16 (1H, s), 7.49 (1H, d, J=9 Hz), 7.45-7.33 (5H, m), 6.55 (1H, d, J=9 Hz), 5.01 (2H, s), 4.21 (2H, d, J=12 Hz), 2.87 (2H, t, J=7 Hz), 2.83 (2H, t, J=12 Hz), 2.45 (3H, s), 2.24-2.14 (1H, m), 1.75 (2H, d, J=12 Hz), 1.59 (9H, s), 1.37 (2H, dq, J=12 Hz, 3 Hz).

(2) tert-Butyl 5-(benzyloxy)-2-[(1-{5-[4-({[tert-butyl(dimethyl)silyl]oxy}methyl)phenyl]pyridin-2-yl}piperidin-4-yl)methyl]-6-methylpyrimidine-4-carboxylate

[Chemical 79]

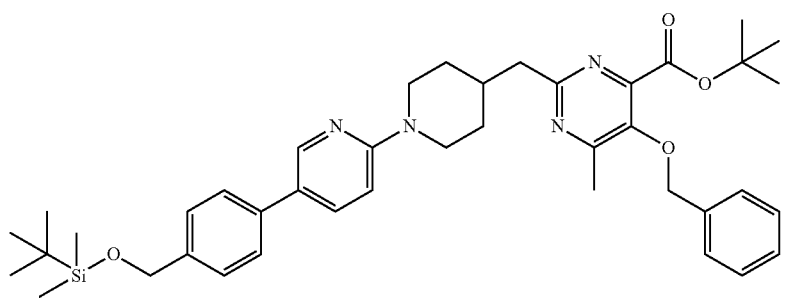

tert-Butyl 5-(benzyloxy)-2-{[1-(5-bromopyridin-2-yl)piperidin-4-yl]methyl}-6-methylpyrimidine-4-carboxylate (1.1 g, 2.0 mmol) was dissolved in 1,4-dioxane (20 mL), and bis(pinacolato)diboron (0.60 g, 2.4 mmol), a [1,1'-bis(diphenylphosphino)ferrocene]palladium dichloride dichloromethane complex (0.16 g, 0.20 mmol) and potassium acetate (0.59 g, 6.0 mmol) were added, followed by heating to reflux for 21 hours. The reaction solution was cooled to room temperature, and subsequently the insolubles were filtered with celite, and the filtrate was concentrated under reduced pressure to afford tert-butyl 5-(benzyloxy)-6-methyl-2-({1-[4-(4,4,5,5-tetramethyl-1,3,2-dioxaborolane-2-yl)pyridin-2-yl}piperidin-4-yl)methyl]pyrimidine-4-carboxylate.

This was dissolved in a mixed solvent of toluene (16 mL), ethanol (10 mL) and water (10 mL), and tert-butyl[(4-iodobenzyl)oxy]dimethylsilane (0.84 g, 2.4 mmol), tetrakis(triphenylphosphine)palladium (0.46 g, 0.40 mmol) and sodium carbonate (1.1 g, 10 mmol) were added, followed by heating to reflux for 1 hour. After the reaction solution was cooled to room temperature, water was added, followed by extraction with ethyl acetate. After the organic layer was concentrated under reduced pressure, the resulting residue was purified by chromatography on a silica gel column (Moritex Corporation, elution solvent: hexane/ethyl acetate), and a fraction corresponding to the Rf value=0.40 (hexane/ethyl acetate=4/1) by thin layer chromatography was concentrated under reduced pressure to afford the title compound (0.82 g, 1.2 mmol) as a pale yellow oil (yield 59%).

$^1$H-NMR (500 MHz, CDCl$_3$) δ: 8.43 (1H, s), 7.69 (1H, d, J=9 Hz), 7.49 (2H, d, J=8 Hz), 7.43-7.35 (5H, m), 7.41 (2H, d, J=8 Hz), 6.73 (1H, d, J=9 Hz), 5.01 (2H, s), 4.77 (2H, s), 4.32 (2H, d, J=12 Hz), 2.87 (2H, t, J=7 Hz), 2.83 (2H, t, J=12

Hz), 2.46 (3H, s), 2.26-2.16 (1H, m), 1.78 (2H, d, J=12 Hz), 1.60 (9H, s), 1.43 (2H, dq, J=12 Hz, 3 Hz), 0.96 (9H, s), 0.12 (6H, s).

(3) [({5-Hydroxy-2-[(1-{5-[4-(hydroxymethyl)phenyl]pyridin-2-yl}piperidin-4-yl)methyl]-6-methylpyrimidin-4-yl}carbonyl)amino]acetic acid In accordance with Examples 1-(10) to 1-(13), but using tert-butyl 5-(benzyloxy)-2-[(1-{5-[4-({[tert-butyl(dimethyl)silyl]oxy}methyl)phenyl]pyridin-2-yl}piperidin-4-yl)methyl]-6-methylpyrimidine-4-carboxylate instead of tert-butyl 5-(benzyloxy)-2-{(1-[4'-({[tert-butyl(dimethyl)silyl]oxy}methyl)biphenyl-4-yl]piperidin-4-yl}methyl)-6-methylpyrimidine-4-carboxylate, the title compound (yield 50%) was afforded as a white solid.

MS m/z: 492 (M+H)$^+$;

$^1$H-NMR (500 MHz, DMSO-d$_6$) δ: 8.99 (1H, brs), 8.42 (1H, s), 7.80 (1H, d, J=9 Hz), 7.56 (2H, d, J=8 Hz), 7.35 (2H, d, J=8 Hz), 6.90 (1H, d, J=9 Hz), 5.20 (1H, brs), 4.51 (2H, s), 4.32 (2H, d, J=13 Hz), 3.51 (2H, brs), 2.83 (2H, t, J=13 Hz), 2.74 (2H, d, J=7 Hz), 2.42 (3H, s), 2.20-2.08 (1H, m), 1.68 (2H, d, J=13 Hz), 1.26 (2H, dq, J=13 Hz, 3 Hz).

Example 20

[({5-Hydroxy-2-[(1-{5-[4-(2-hydroxypropyl)phenyl]pyridin-2-yl}piperidin-4-yl)methyl]-6-methylpyrimidin-4-yl}carbonyl)amino]acetic acid

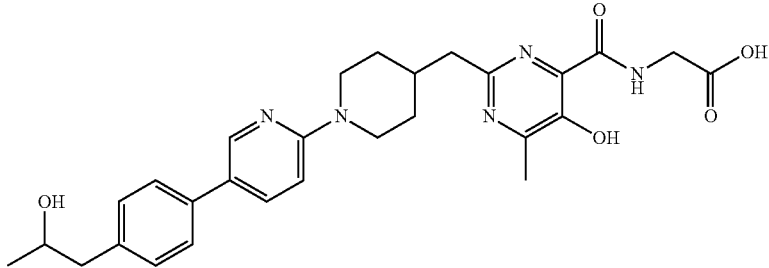

[Chemical 80]

(1) 1-Bromo-4-[2-(methoxymethoxy)propyl]benzene

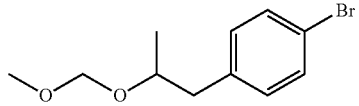

[Chemical 81]

In accordance with Example 6-(3), but using 1-(4-bromophenyl)propan-2-ol instead of 2-(4'-bromobiphenyl-4-yl)-2-methylpropan-1-ol, the title compound (yield 89%) was afforded as a colorless oil.

$^1$H-NMR (500 MHz, CDCl$_3$) δ: 7.40 (2H, d, J=8 Hz), 7.09 (2H, d, J=8 Hz), 4.64 (1H, d, J=7 Hz), 4.50 (1H, d, J=7 Hz), 3.96-3.83 (1H, m), 3.18 (3H, s), 2.84-2.73 (1H, m), 2.72-2.61 (1H, m), 1.17 (3H, d, J=6 Hz).

(2) [({5-hydroxy-2-[(1-{5-[4-(2-hydroxypropyl)phenyl]pyridin-2-yl}piperidin-4-yl)methyl]-6-methylpyrimidin-4-yl}carbonyl)amino]acetic acid In accordance with Examples 19-(2) and 1-(10) to 1-(13), but using 1-bromo-4-[2-(methoxymethoxy)propyl]benzene instead of tert-butyl[(4-iodobenzyl)oxy]dimethylsilane, the title compound (yield 11%) was afforded as a white solid.

MS m/z: 520 (M+H)$^+$;

$^1$H-NMR (500 MHz, DMSO-d$_6$) δ: 9.32 (1H, t, J=5 Hz), 8.40 (1H, s), 7.79 (1H, d, J=9 Hz), 7.50 (2H, d, J=8 Hz), 7.23 (2H, d, J=8 Hz), 6.89 (1H, d, J=9 Hz), 4.60 (1H, brs), 4.32 (2H, d, J=12 Hz), 3.90 (2H, d, J=5 Hz), 3.86-3.80 (1H, m), 2.83 (2H, t, J=7 Hz), 2.76 (2H, d, J=7 Hz), 2.71-2.63 (2H, m), 2.44 (3H, s), 2.09-2.00 (1H, m), 1.66 (2H, d, J=12 Hz), 1.25 (2H, dq, J=12 Hz, 3 Hz), 1.04 (3H, d, J=6 Hz).

Example 21

[({5-Hydroxy-2-[(1-{5-[4-(2-hydroxy-1,1-dimethyl-ethyl)phenyl]pyridin-2-yl}piperidin-4-yl)methyl]-6-methylpyrimidin-4-yl}carbonyl)amino]acetic acid

[Chemical 82]

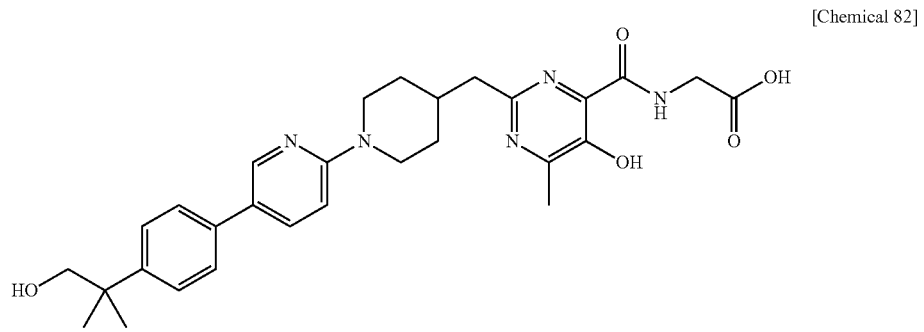 [SMILES: Cc1nc(CC2CCN(c3ccc(-c4ccc(C(C)(C)CO)cc4)cn3)CC2)nc(C(=O)NCC(=O)O)c1O]

In accordance with Examples 20-(1) and 20-(2), but using 2-(4-bromophenyl)-2-methylpropan-1-ol instead of 1-(4-bromophenyl)propan-2-ol, the title compound (yield 11%) was afforded as a white solid.

MS m/z: 534 (M+H)+;

$^1$H-NMR (500 MHz, DMSO-$d_6$) δ: 9.42 (1H, t, J=5 Hz), 8.40 (1H, d, J=3 Hz), 7.79 (1H, dd, J=9 Hz, 3 Hz), 7.51 (2H, d, J=8 Hz), 7.40 (2H, d, J=8 Hz), 6.89 (1H, d, J=9 Hz), 4.67 (1H, brs), 4.32 (2H, d, J=13 Hz), 4.00 (2H, d, J=5 Hz), 3.42 (2H, s), 2.83 (2H, d, J=7 Hz), 2.76 (2H, t, J=12 Hz), 2.44 (3H, s), 2.25-2.10 (1H, m), 1.68 (2H, d, J=12 Hz), 1.36 (2H, dq, J=12 Hz, 3 Hz), 1.23 (6H, s).

Example 22

({[2-{(1-[2-Chloro-4'-(hydroxymethyl)biphenyl-4-yl]piperidin-4-yl}methyl)-5-hydroxy-6-methylpyrimidin-4-yl]carbonyl}amino)acetic acid

[Chemical 83]

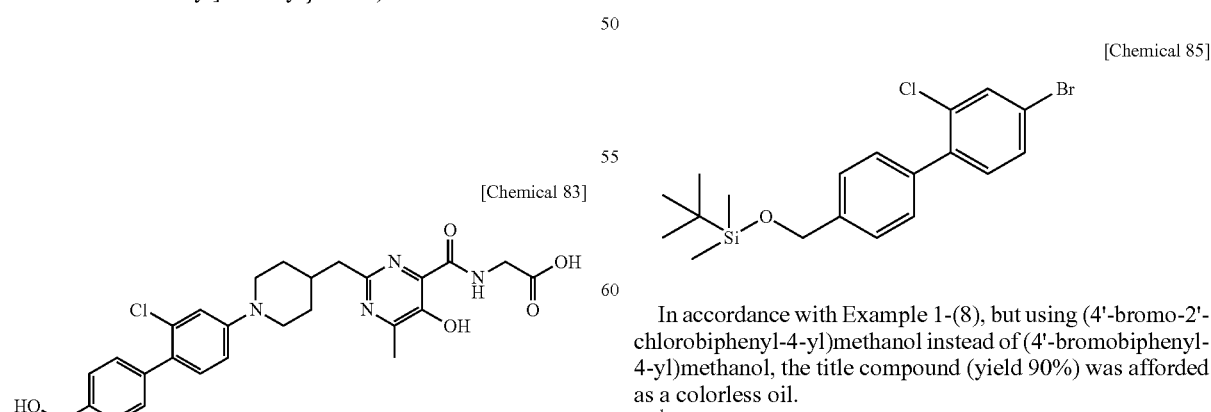

(1) (4'-Bromo-2'-chlorobiphenyl-4-yl)methanol

[Chemical 84]

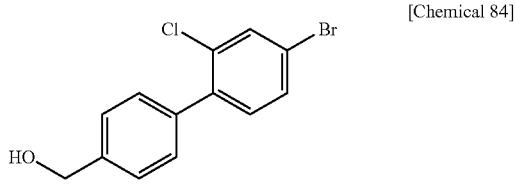 [SMILES: Cc1cc(Br)ccc1-c1ccc(CO)cc1]

In accordance with Example 4-(2), but using [4-(hydroxymethyl)phenyl]boronic acid instead of 4-bromophenylboronic acid, and 4-bromo-2-chloro-1-iodobenzene instead of tert-butyl[2-(4-iodophenyl)ethoxy]dimethylsilane, the title compound (yield 12%) was afforded as a yellow solid.

$^1$H-NMR (500 MHz, CDCl$_3$) δ: 7.65 (1H, d, J=2 Hz), 7.48-7.40 (5H, m), 7.21 (1H, d, J=8 Hz), 4.77 (2H, d, J=6 Hz), 1.71 (1H, t, J=6 Hz).

(2) [(4'-Bromo-2'-chlorobiphenyl-4-yl)methoxy](tert-butyl)dimethylsilane

[Chemical 85]

In accordance with Example 1-(8), but using (4'-bromo-2'-chlorobiphenyl-4-yl)methanol instead of (4'-bromobiphenyl-4-yl)methanol, the title compound (yield 90%) was afforded as a colorless oil.

$^1$H-NMR (500 MHz, CDCl$_3$) δ: 7.64 (1H, d, J=2 Hz), 7.45 (1H, dd, J=8 Hz, 2 Hz), 7.41-7.36 (4H, m), 7.21 (1H, d, J=8 Hz), 4.80 (2H, s), 0.96 (9H, s), 0.13 (6H, s).

(3) Ethyl({[5-(benzyloxy)-2-{(1-[2-chloro-4'-(hydroxymethyl)biphenyl-4-yl]piperidin-4-yl}methyl)-6-methylpyrimidin-4-yl]carbonyl}amino)acetate tography was concentrated under reduced pressure to afford the title compound (0.74 g, 1.3 mmol) as a yellow oil (yield 90%).

[Chemical 86]

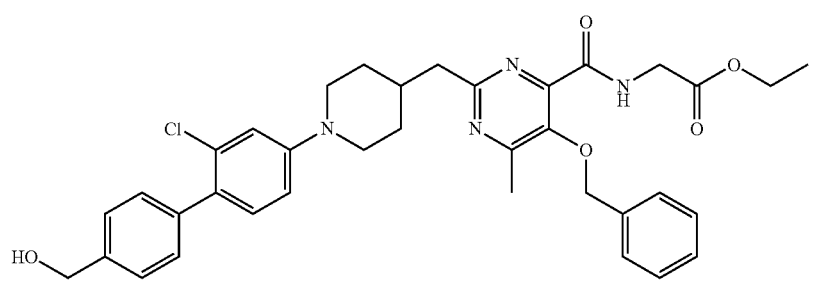

In accordance with Examples 1-(9) to 1-(11), but using [(4'-bromo-2'-chlorobiphenyl-4-yl)methoxy](tert-butyl)dimethylsilane instead of [(4'-bromobiphenyl-4-yl)methoxy](tert-butyl)dimethylsilane, the title compound (yield 62%) was afforded as a yellow amorphous solid.

$^1$H-NMR (500 MHz, CDCl$_3$) δ: 8.37 (1H, t, J=5 Hz), 7.53-7.17 (10H, m), 7.00 (1H, s), 6.88 (1H, d, J=8 Hz), 5.13 (2H, s), 4.75 (2H, d, J=6 Hz), 4.28 (2H, q, J=7 Hz), 4.26 (2H, d, J=5 Hz), 3.73 (2H, d, J=12 Hz), 2.90 (2H, d, J=7 Hz), 2.80 (2H, t, J=12 Hz), 2.47 (3H, s), 2.19-2.08 (1H, m), 1.79 (2H, d, J=12 Hz), 1.62-1.45 (2H, m), 1.32 (3H, t, J=7 Hz).

(4) Ethyl [({2-[(1-{2-chloro-4'-[(2,2,2-trifluoroacetoxy)methyl]biphenyl-4-yl}piperidin-4-yl)methyl]-5-hydroxy-6-methylpyrimidin-4-yl}carbonyl)amino]acetate

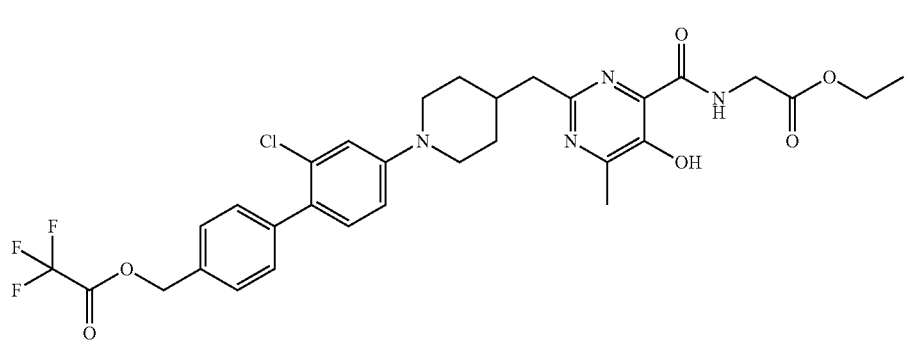

[Chemical 87]

Ethyl({[5-(benzyloxy)-2-({1-[2-chloro-4'-(hydroxymethyl)biphenyl-4-yl]piperidin-4-yl}methyl)-6-methylpyrimidin-4-yl]carbonyl}amino)acetate (0.96 g, 1.5 mmol) was dissolved in dichloromethane (20 mL), and trifluoroacetic acid (20 mL) was added under a nitrogen atmosphere, followed by stirring at room temperature for 7 hours. An aqueous sodium hydrogencarbonate solution was added to the reaction solution for neutralization, followed by extraction with dichloromethane, and subsequently the organic layer was concentrated under reduced pressure. The resulting residue was purified by chromatography on a silica gel column (Moritex Corporation, elution solvent: dichloromethane/ethyl acetate), and a fraction corresponding to the Rf value=0.80 (dichloromethane/ethyl acetate=4/1) by thin layer chroma- $^1$H-NMR (500 MHz, CDCl$_3$) δ: 11.39 (1H, s), 8.50 (1H, t, J=5 Hz), 7.48 (2H, d, J=8 Hz), 7.43 (2H, d, J=8 Hz), 7.20 (1H, d, J=9 Hz), 6.99 (1H, s), 6.87 (1H, d, J=9 Hz), 5.40 (2H, s), 4.29 (2H, q, J=7 Hz), 4.23 (2H, d, J=5 Hz), 3.73 (2H, d, J=12 Hz), 2.84 (2H, d, J=7 Hz), 2.79 (2H, t, J=12 Hz), 2.55 (3H, s), 2.14-2.04 (1H, m), 1.78 (2H, d, J=12 Hz), 1.49 (2H, q, J=12 Hz), 1.33 (3H, t, J=7 Hz).

(5) ({[2-({1-[2-Chloro-4'-(hydroxymethyl)biphenyl-4-yl]piperidin-4-yl}methyl)-5-hydroxy-6-methylpyrimidin-4-yl]carbonyl}amino)acetic acid In accordance with Example 1-(13), but using ethyl [({2-[(1-{2-chloro-4'-[(2,2,2-trifluoroacetoxy)methyl]biphenyl-4-yl}piperidin-4-yl)methyl]-5-hydroxy-6-methylpyrimidin-4-yl}carbonyl)amino]acetate instead of ethyl ({[5-hydroxy-2-({1-[4'-(hydroxymethyl)biphenyl-4-yl]piperidin-4-yl}methyl)-6-methylpyrimidin-4-yl]carbonyl}amino)acetate, the title compound (yield 55%) was afforded as a white solid.

MS m/z: 525 (M+H)$^+$;

$^1$H-NMR (500 MHz, DMSO-d$_6$) δ: 9.34 (1H, t, J=5 Hz), 7.37-7.32 (4H, m), 7.20 (1H, d, J=9 Hz), 7.01 (1H, s), 6.97 (1H, d, J=9 Hz), 5.22 (1H, brs), 4.53 (2H, s), 3.92 (2H, d, J=5 Hz), 3.76 (2H, d, J=12 Hz), 2.78 (2H, d, J=7 Hz), 2.74 (2H, t, J=12 Hz), 2.44 (3H, s), 2.15-2.05 (1H, m), 1.68 (2H, d, J=12 Hz), 1.34 (2H, q, J=12 Hz).

Example 23

({[5-Hydroxy-2-{(1-[4'-(hydroxymethyl)-2-methyl-biphenyl-4-yl]piperidin-4-yl}methyl)-6-methylpyrimidin-4-yl]carbonyl}amino)acetic acid

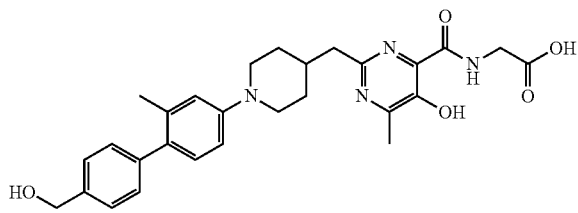

(1) (4'-Bromo-2'-methylbiphenyl-4-yl)methanol

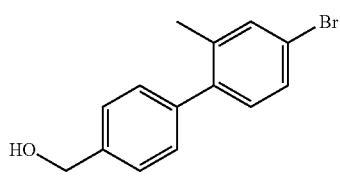

In accordance with Example 4-(2), but using [4-(hydroxymethyl)phenyl]boronic acid instead of (4-bromophenyl)boronic acid, and 4-bromo-1-iodo-2-methylbenzene instead of tert-butyl[2-(4-iodophenyl)ethoxy]dimethylsilane, the title compound (yield 7.1%) was afforded as a yellow oil.

$^1$H-NMR (500 MHz, CDCl$_3$) δ: 7.45-7.41 (3H, m), 7.37 (1H, d, J=8 Hz), 7.29 (2H, d, J=8 Hz), 7.09 (1H, d, J=8 Hz), 4.77 (2H, d, J=6 Hz), 2.24 (3H, s), 1.70 (1H, t, J=6 Hz).

(2) [(4'-Bromo-2'-methylbiphenyl-4-yl)methoxy](tert-butyl)dimethylsilane

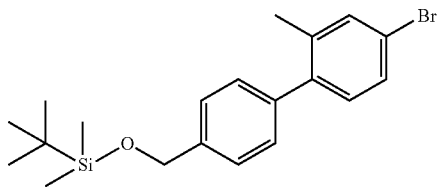

In accordance with Example 1-(8), but using (4'-bromo-2'-methylbiphenyl-4-yl)methanol instead of (4'-bromobiphenyl-4-yl)methanol, the title compound (yield 89%) was afforded as a colorless oil.

$^1$H-NMR (500 MHz, CDCl$_3$) δ: 7.42 (1H, s), 7.39-7.34 (3H, m), 7.25 (2H, d, J=8 Hz), 7.09 (1H, d, J=8 Hz), 4.79 (2H, s), 2.24 (3H, s), 0.97 (9H, s), 0.13 (6H, s).

(3) ({[5-Hydroxy-2-{(1-[4'-(hydroxymethyl)-2-methylbiphenyl-4-yl]piperidin-4-yl}methyl)-6-methylpyrimidin-4-yl]carbonyl}amino)acetic acid In accordance with Examples 1-(9) to 1-(13), but using [(4'-bromo-2'-methylbiphenyl-4-yl)methoxy](tert-butyl)dimethylsilane instead of [(4'-bromobiphenyl-4-yl)methoxy](tert-butyl)dimethylsilane, the title compound (yield 27%) was afforded as a pale yellowish white solid.

MS m/z: 505 (M+H)$^+$;

$^1$H-NMR (500 MHz, DMSO-d$_6$) δ: 9.15 (1H, brs), 7.33 (2H, d, J=8 Hz), 7.24 (2H, d, J=8 Hz), 7.02 (1H, d, J=8 Hz), 6.84 (1H, s), 6.80 (1H, d, J=8 Hz), 4.52 (2H, s), 3.75-3.66 (4H, m), 2.77 (2H, d, J=7 Hz), 2.66 (2H, t, J=12 Hz), 2.43 (3H, s), 2.20 (3H, s), 2.10-1.99 (1H, m), 1.69 (2H, d, J=12 Hz), 1.36 (2H, q, J=12 Hz).

Example 24

({[2-{(1-[3'-Chloro-4'-(hydroxymethyl)biphenyl-4-yl]piperidin-4-yl}methyl)-5-hydroxy-6-methylpyrimidin-4-yl]carbonyl}amino)acetic acid

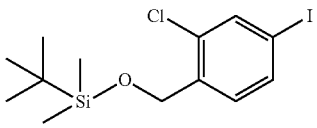

(1) tert-Butyl[(2-chloro-4-iodobenzyl)oxy]dimethylsilane

2-Chloro-4-iodobenzoic acid (5.0 g, 18 mmol) was dissolved in tetrahydrofuran (7 mL), and a solution of a borane-tetrahydrofuran complex in tetrahydrofuran (1 M, 21 mL, 23 mmol) was added at 0° C., followed by stirring at room temperature for 3 days. Water and a saturated aqueous sodium hydrogencarbonate solution were added to the reaction solution, followed by extraction with ethyl acetate. The organic layer was washed with a saturated aqueous sodium chloride solution, and dried over anhydrous sodium sulfate, and subsequently the solvent was distilled off under reduced pressure to afford (2-chloro-4-iodophenyl)methanol (4.8 g, 18 mmol) as a white solid (quantitative yield).

In accordance with Example 1-(8), but using (2-chloro-4-iodophenyl)methanol instead of (4'-bromobiphenyl-4-yl)methanol, the title compound (yield 95%) was afforded as a colorless oil.

¹H-NMR (500 MHz, CDCl₃) δ: 7.65 (1H, s), 7.61 (1H, d, J=9 Hz), 7.29 (1H, d, J=9 Hz), 4.72 (2H, s), 0.95 (9H, s), 0.12 (6H, s).

(2) [(4'-Bromo-3-chlorobiphenyl-4-yl)methoxy](tert-butyl)dimethylsilane

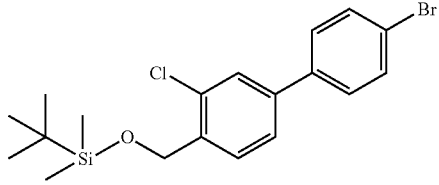

[Chemical 93]

In accordance with Example 11-(1), but using tert-butyl [(2-chloro-4-iodobenzyl)oxy]dimethylsilane instead of 4-bromobenzyl bromide, and (4-bromophenyl)boronic acid instead of [3-(hydroxymethyl)phenyl]boronic acid, the title compound (yield 96%) was afforded as a colorless oil.

¹H-NMR (500 MHz, CDCl₃) δ: 7.63 (1H, d, J=8 Hz), 7.57 (2H, d, J=8 Hz), 7.52-7.41 (4H, m), 4.82 (2H, s), 0.98 (9H, s), 0.15 (6H, s).

(3) ({[2-{(1-[3'-Chloro-4'-(hydroxymethyl)biphenyl-4-yl]piperidin-4-yl}methyl)-5-hydroxy-6-methylpyrimidin-4-yl]carbonyl}amino)acetic acid In accordance with Examples 1-(9) to 1-(13), but using [(4'-bromo-3-chlorobiphenyl-4-yl)methoxy](tert-butyl)dimethylsilane instead of [(4'-bromobiphenyl-4-yl)methoxy](tert-butyl)dimethylsilane, the title compound (yield 31%) was afforded as a pale yellowish white solid.

MS m/z: 525 (M+H)⁺;

¹H-NMR (500 MHz, DMSO-d₆) δ: 12.90 (1H, brs), 11.92 (1H, s), 9.42 (1H, t, J=6 Hz), 7.61-7.51 (5H, m), 7.02-6.96 (2H, m), 5.38 (1H, brs), 4.57 (2H, d, J=5 Hz), 4.00 (2H, d, J=6 Hz), 3.75 (2H, d, J=12 Hz), 2.80-2.66 (4H, m), 2.44 (3H, s), 2.16-2.04 (1H, m), 1.67 (2H, d, J=12 Hz), 1.35 (2H, q, J=12 Hz).

Example 25

({[5-Hydroxy-2-{(1-[4'-(hydroxymethyl)-2'-methylbiphenyl-4-yl]piperidin-4-yl}methyl)-6-methylpyrimidin-4-yl]carbonyl}amino)acetic acid

[Chemical 94]

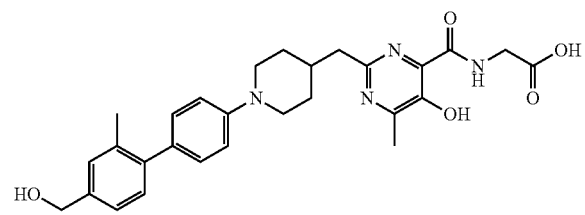

(1) Methyl 4'-bromo-2-methylbiphenyl-4-carboxylate

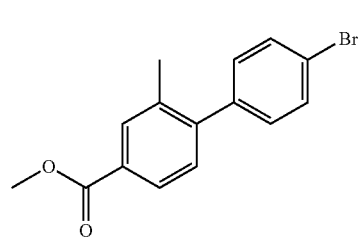

[Chemical 95]

In accordance with Example 19-(2), but using methyl 4-bromo-3-methylbenzoate instead of tert-Butyl 5-(benzyloxy)-2-{[1-(5-bromopyridin-2-yl)piperidin-4-yl]methyl}-6-methylpyrimidine-4-carboxylate, and 1-bromo-4-iodobenzene instead of tert-butyl[(4-iodobenzyl)oxy]dimethylsilane, the title compound (yield 23%) was afforded as a white solid.

¹H-NMR (500 MHz, CDCl₃) δ: 7.96 (1H, s), 7.90 (1H, d, J=9 Hz), 7.57 (2H, d, J=9 Hz), 7.27 (1H, d, J=9 Hz), 7.20 (2H, d, J=9 Hz), 3.94 (3H, s), 2.30 (3H, s).

(2) [(4'-Bromo-2-methylbiphenyl-4-yl)methoxy](tert-butyl)dimethylsilane

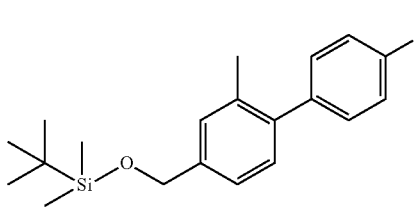

[Chemical 96]

In accordance with Example 6-(2), but using methyl 4'-bromo-2-methylbiphenyl-4-carboxylate instead of ethyl 2-(4'-bromobiphenyl-4-yl)-2-methylpropionate, (4'-bromo-2-methylbiphenyl-4-yl)methanol (yield 97%) was afforded as a colorless oil.

In accordance with Example 1-(8), but using (4'-bromo-2-methylbiphenyl-4-yl)methanol instead of (4'-bromobiphenyl-4-yl)methanol, the title compound (yield 71%) was afforded as a colorless oil.

¹H-NMR (500 MHz, CDCl₃) δ: 7.53 (2H, d, J=8 Hz), 7.24-7.14 (5H, m), 4.75 (2H, s), 2.25 (3H, s), 0.96 (9H, s), 0.13 (6H, s).

(3) ({[5-Hydroxy-2-{(1-[4'-(hydroxymethyl)-2'-methylbiphenyl-4-yl]piperidin-4-yl}methyl)-6-methylpyrimidin-4-yl]carbonyl}amino)acetic acid In accordance with Examples 1-(9) to 1-(13), but using [(4'-bromo-2-methylbiphenyl-4-yl)methoxy](tert-butyl)dimethylsilane instead of [(4'-bromobiphenyl-4-yl)methoxy](tert-butyl)dimethylsilane, the title compound (yield 17%) was afforded as a pale yellowish white solid.

MS m/z: 505 (M+H)⁺;

¹H-NMR (500 MHz, DMSO-d₆) δ: 11.94 (1H, brs), 9.41 (1H, brs), 7.20-7.08 (5H, m), 6.99-6.94 (2H, m), 4.47 (2H, s), 3.99 (2H, d, J=6 Hz), 3.71 (2H, d, J=12 Hz), 2.79 (2H, d, J=7

Hz), 2.68 (2H, t, J=12 Hz), 2.45 (3H, s), 2.23 (3H, s), 2.13-2.02 (1H, m), 1.69 (2H, d, J=12 Hz), 1.37 (2H, q, J=12 Hz).

Example 26

({[5-Hydroxy-2-({1-[4'-(hydroxymethyl)-2,3'-dimethylbiphenyl-4-yl]piperidin-4-yl}methyl)-6-methylpyrimidin-4-yl]carbonyl}amino)acetic acid

[Chemical 97]

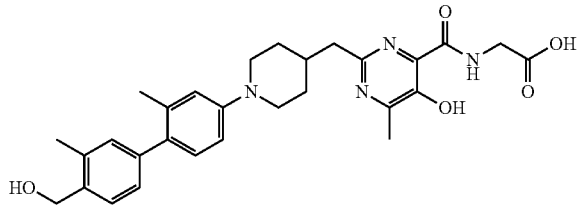

(1) [(4'-Bromo-2',3-dimethylbiphenyl-4-yl)methoxy](tert-butyl)dimethylsilane

[Chemical 98]

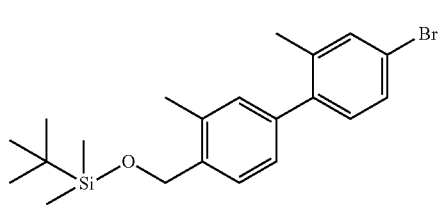

In accordance with Example 19-(2), but using [(4-bromo-2-methylbenzyl)oxy](tert-butyl)dimethylsilane instead of tert-butyl 5-(benzyloxy)-2-{[1-(5-bromopyridin-2-yl)piperidin-4-yl]methyl}-6-methylpyrimidine-4-carboxylate, and 4-bromo-1-iodo-2-methylbenzene instead of tert-butyl[(4-iodobenzyl)oxy]dimethylsilane, the title compound (yield 34%) was afforded as a yellow oil.

$^1$H-NMR (500 MHz, CDCl$_3$) δ: 7.46 (1H, d, J=8 Hz), 7.41 (1H, s), 7.35 (1H, d, J=8 Hz), 7.11 (1H, d, J=8 Hz), 7.08 (1H, d, J=8 Hz), 7.04 (1H, s), 4.75 (2H, s), 2.30 (3H, s), 2.24 (3H, s), 0.97 (9H, s), 0.13 (6H, s).

(2) ({[5-Hydroxy-2-({1-[4'-(hydroxymethyl)-2,3'-dimethylbiphenyl-4-yl]piperidin-4-yl}methyl)-6-methylpyrimidin-4-yl]carbonyl}amino)acetic acid In accordance with Examples 1-(9) to 1-(13), but using [(4'-bromo-2',3-dimethylbiphenyl-4-yl)methoxy](tert-butyl)dimethylsilane instead of [(4'-bromobiphenyl-4-yl)methoxy](tert-butyl)dimethylsilane, the title compound (yield 45%) was afforded as a pale yellowish white solid.

MS m/z: 519 (M+H)$^+$;
$^1$H-NMR (500 MHz, DMSO-d$_6$) δ: 9.36 (1H, t, J=5 Hz), 7.35 (1H, d, J=8 Hz), 7.08 (1H, d, J=8 Hz), 7.05 (1H, s), 7.01 (1H, d, J=8 Hz), 6.83 (1H, s), 6.79 (1H, d, J=8 Hz), 4.51 (2H, s), 3.96 (2H, d, J=5 Hz), 3.70 (2H, d, J=12 Hz), 2.78 (2H, d, J=7 Hz), 2.66 (2H, t, J=12 Hz), 2.44 (3H, s), 2.27 (3H, s), 2.19 (3H, s), 2.13-2.02 (1H, m), 1.68 (2H, d, J=12 Hz), 1.37 (2H, q, J=12 Hz).

Example 27

({[5-Hydroxy-2-{(1-[4'-(2-hydroxybutyl)biphenyl-4-yl]piperidin-4-yl}methyl)-6-methylpyrimidin-4-yl]carbonyl}amino)acetic acid

[Chemical 99]

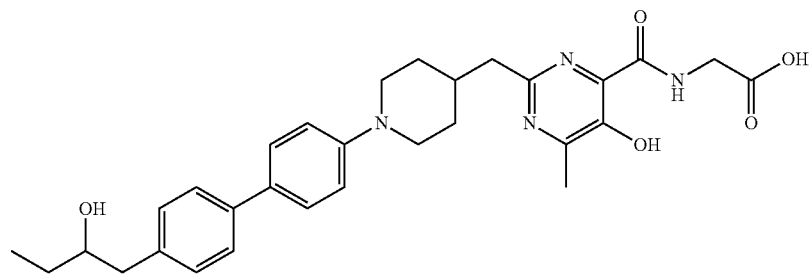

In accordance with Examples 5-(2) to 5-(5), but using a mixed solution of ethyllithium in benzene and cyclohexane (benzene/cyclohexane=9/1) instead of a solution of methyllithium in diethyl ether, the title compound (yield 3.6%) was afforded as a pale yellow solid.

MS m/z: 533 (M+H)$^+$;
$^1$H-NMR (500 MHz, DMSO-d$_6$) δ: 12.89 (1H, brs), 11.91 (1H, s), 9.29 (1H, t, J=5 Hz), 7.48 (2H, d, J=9 Hz), 7.47 (2H, d, J=9 Hz), 7.22 (2H, d, J=8 Hz), 6.98 (2H, d, J=8 Hz), 4.48 (1H, d, J=5 Hz), 4.00 (2H, d, J=5 Hz), 3.86-3.80 (1H, m), 3.73 (2H, d, J=12 Hz), 2.78 (2H, d, J=7 Hz), 2.74-2.67 (2H, m), 2.63 (2H, d, J=6 Hz), 2.44 (3H, s), 2.15-2.03 (1H, m), 1.68 (2H, d, J=12 Hz), 1.36 (2H, dq, J=12 Hz, 3 Hz), 1.35-1.22 (2H, m), 0.88 (3H, t, J=7 Hz).

Example 28

[({5-Hydroxy-2-[(1-{4-[4-(2-hydroxypropyl)benzyl]phenyl}piperidin-4-yl)methyl]-6-methylpyrimidin-4-yl}carbonyl)amino]acetic acid

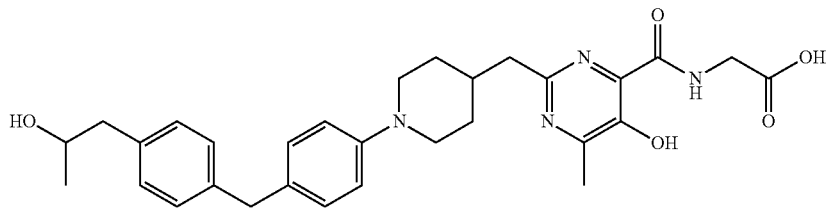

[Chemical 100]

In accordance with Example 19-(2), but using 1-bromo-4-[2-(methoxymethoxy)propyl]benzene instead of tert-butyl 5-(benzyloxy)-2-{[1-(5-bromopyridin-2-yl)piperidin-4-yl]methyl}-6-methylpyrimidine-4-carboxylate, and 1-bromo-4-(bromomethyl)benzene instead of tert-butyl[(4-iodobenzyl)oxy]dimethylsilane, a crude product of 1-bromo-4-{4-[2-(methoxymethoxy)propyl]benzyl}benzene was afforded as a yellow oil.

In accordance with Examples 1-(9) to 1-(13), but using a crude product of 1-bromo-4-{4-[2-(methoxymethoxy)propyl]benzyl}benzene instead of [(4'-bromobiphenyl-4-yl)methoxy](tert-butyl)dimethylsilane, the title compound (yield 15%) was afforded as a white solid.

MS m/z: 533 (M+H)$^+$;

$^1$H-NMR (500 MHz, DMSO-d$_6$) δ: 12.87 (1H, brs), 11.91 (1H, s), 9.42 (1H, t, J=5 Hz), 7.08 (4H, s), 7.03 (2H, d, J=7 Hz), 6.83 (2H, d, J=7 Hz), 4.53 (1H, brs), 4.00 (2H, d, J=5 Hz), 3.76 (2H, s), 3.79-3.72 (1H, m), 3.58 (2H, d, J=12 Hz), 2.76 (2H, t, J=7 Hz), 2.66-2.45 (4H, m), 2.44 (3H, s), 2.09-2.00 (1H, m), 1.66 (2H, d, J=12 Hz), 1.35 (2H, dq, J=12 Hz, 3 Hz), 1.00 (3H, d, J=6 Hz).

Example 29

[({5-Hydroxy-2-[(1-{4-[4-(2-hydroxy-1,1-dimethylethyl)benzyl]phenyl}piperidin-4-yl)methyl]-6-methylpyrimidin-4-yl}carbonyl)amino]acetic acid

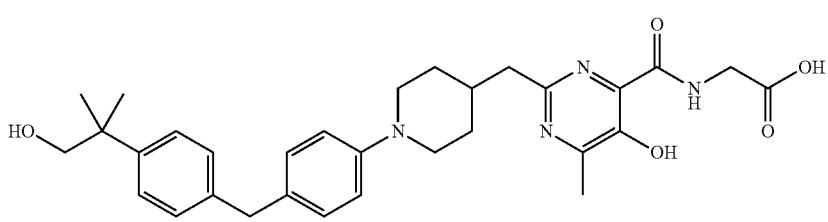

[Chemical 101]

In accordance with Example 28, but using 1-bromo-4-[2-(methoxymethoxy)-1,1-dimethylethyl]benzene instead of 1-bromo-4-[2-(methoxymethoxy)propyl]benzene, the title compound (yield 12%) was afforded as a white solid.

MS m/z: 547 (M+H)$^+$;

$^1$H-NMR (500 MHz, DMSO-d$_6$) δ: 11.92 (1H, s), 9.43 (1H, t, J=5 Hz), 7.23 (2H, d, J=5 Hz), 7.11 (2H, d, J=5 Hz), 7.04 (2H, brs), 6.84 (2H, brs), 4.65 (1H, brs), 4.00 (2H, d, J=5 Hz), 3.76 (2H, s), 3.58 (2H, d, J=12 Hz), 3.42 (2H, s), 2.78 (2H, d, J=7 Hz), 2.70 (2H, t, J=12 Hz), 2.44 (3H, s), 2.11-2.00 (1H, m), 1.66 (2H, d, J=12 Hz), 1.36 (2H, dq, J=12 Hz, 3 Hz), 1.17 (6H, s).

Example 30

({[2-{(1-[4'-(1,1-Difluoro-2-hydroxyethyl)biphenyl-4-yl]piperidin-4-yl}methyl)-5-hydroxy-6-methylpyrimidin-4-yl]carbonyl}amino)acetic acid

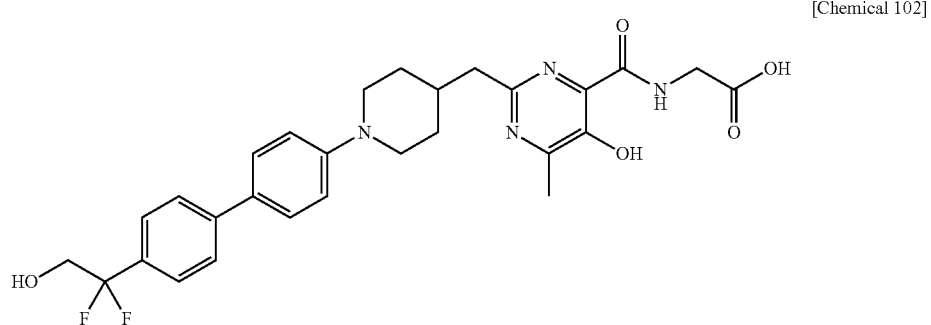 [SMILES: Cc1nc(CC2CCN(c3ccc(-c4ccc(C(F)(F)CO)cc4)cc3)CC2)nc(C(=O)NCC(=O)O)c1O]

[Chemical 102]

(1) Ethyl (4'-bromobiphenyl-4-yl)(difluoro)acetate

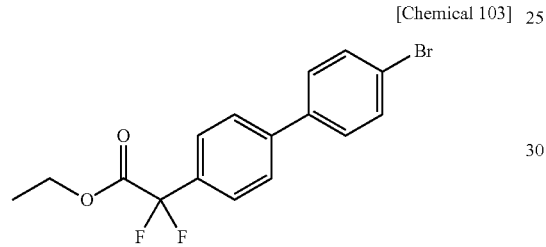

[Chemical 103]

In accordance with Example 11-(1), but using ethyl 4-iodophenylacetate instead of 4-bromobenzyl bromide, and (4-bromophenyl)boronic acid instead of [3-(hydroxymethyl)phenyl]boronic acid, ethyl (4'-bromobiphenyl-4-yl)acetate (yield 71%) was afforded as a white solid.

Ethyl (4'-bromobiphenyl-4-yl)acetate (3.1 g, 9.8 mmol) was dissolved in tetrahydrofuran (50 mL), followed by addition of a solution of lithium hexamethyldisilazide in tetrahydrofuran (1 M, 12 mL, 12 mmol) at −78° C. under a nitrogen atmosphere, and stirring for 20 minutes, and subsequently N-fluorobenzenesulfonimide (3.7 g, 12 mmol) was added at the same temperature, followed by stirring for 20 minutes. To the reaction solution, at −78° C., a solution of lithium hexamethyldisilazide in tetrahydrofuran (1 M, 12 mL, 12 mmol) was added, followed by stirring for 20 minutes, and subsequently at the same temperature N-fluorobenzenesulfonimide (3.7 g, 12 mmol) was added, followed by stirring for a further 1 hour. A saturated aqueous ammonium chloride solution was added to the reaction solution, followed by extraction with ethyl acetate, and subsequently the extract was concentrated under reduced pressure. The resulting residue was purified by chromatography on a silica gel column (Moritex Corporation, elution solvent: hexane/ethyl acetate), and a fraction corresponding to the Rf value=0.70 (hexane/ethyl acetate=4/1) by thin layer chromatography was concentrated under reduced pressure to afford the title compound (2.8 g, 7.8 mmol) as a pale yellow oil (yield 79%).

$^1$H-NMR (500 MHz, CDCl$_3$) δ: 7.68 (2H, d, J=8 Hz), 7.63 (2H, d, J=8 Hz), 7.61 (2H, d, J=8 Hz), 7.46 (2H, d, J=8 Hz), 4.33 (2H, q, J=7 Hz), 1.33 (3H, t, J=7 Hz).

(2) 2-(4'-Bromobiphenyl-4-yl)-2,2-difluoroethanol

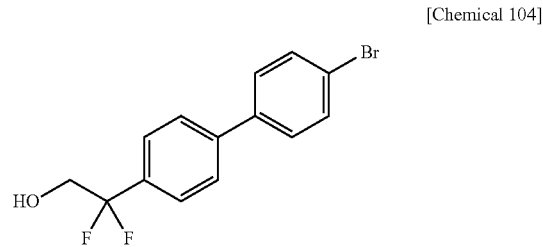 [SMILES: OCC(F)(F)c1ccc(-c2ccc(Br)cc2)cc1]

[Chemical 104]

Ethyl (4'-bromobiphenyl-4-yl)(difluoro)acetate (2.8 g, 7.8 mmol) was dissolved in methanol (20 mL), and sodium borohydride (0.59 g, 16 mmol) was added at 0° C., followed by stirring at room temperature for 30 minutes. The reaction solution was concentrated under reduced pressure, and hydrochloric acid (1 M) was added to the residue, which was subsequently extracted with ethyl acetate, and the organic layer was dried over anhydrous sodium sulfate. After the solvent was distilled off under reduced pressure, the resulting residue was purified by chromatography on a silica gel column (Moritex Corporation, elution solvent: hexane/ethyl acetate), and a fraction corresponding to the Rf value=0.50 (hexane/ethyl acetate=1/1) by thin layer chromatography was concentrated under reduced pressure to afford the title compound (2.4 g, 7.7 mmol) as a white solid (yield 99%).

$^1$H-NMR (500 MHz, CDCl$_3$) δ: 7.64-7.58 (6H, m), 7.49-7.44 (2H, m), 4.02 (2H, dt, J=13 Hz, 6 Hz).

(3) [2-(4'-Bromobiphenyl-4-yl)-2,2-difluoroethoxy](tert-butyl)dimethylsilane

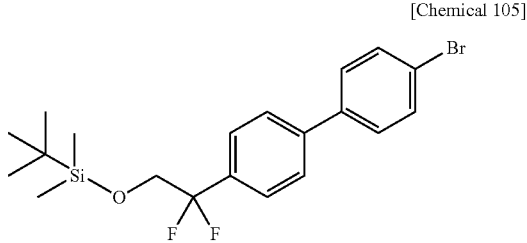 [SMILES: CC(C)(C)[Si](C)(C)OCC(F)(F)c1ccc(-c2ccc(Br)cc2)cc1]

[Chemical 105]

In accordance with Example 1-(8), but using 2-(4'-bromo-biphenyl-4-yl)-2,2-difluoroethanol instead of (4'-bromobiphenyl-4-yl)methanol, the title compound (yield 97%) was afforded as a colorless oil.

$^1$H-NMR (500 MHz, CDCl$_3$) δ: 7.61-7.56 (6H, m), 7.47 (2H, d, J=7 Hz), 3.99 (2H, t, J=12 Hz), 0.85 (9H, s), 0.02 (6H, s).

(4) Ethyl({[5-(benzyloxy)-2-{(1-[4'-(1,1-difluoro-2-hydroxyethyl)biphenyl-4-yl]piperidin-4-yl}methyl)-6-methylpyrimidin-4-yl]carbonyl}amino)acetate

[Chemical 106]

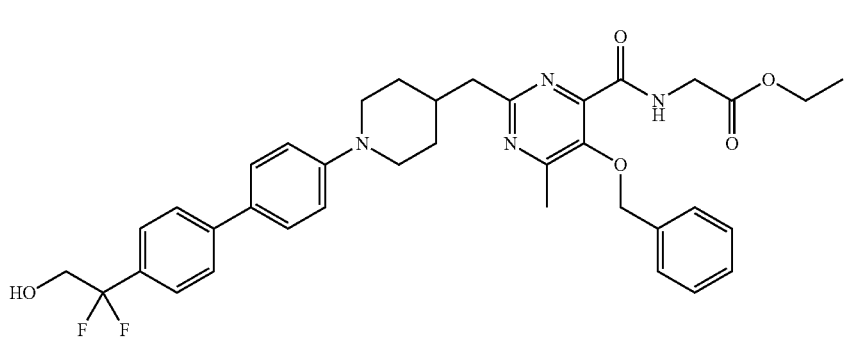

In accordance with Examples 1-(9) to 1-(11), but using [2-(4'-bromobiphenyl-4-yl)-2,2-difluoroethoxy](tert-butyl)dimethylsilane instead of [(4'-bromobiphenyl-4-yl)methoxy](tert-butyl)dimethylsilane, the title compound (yield 59%) was afforded as a white solid.

MS m/z: 659 (M+H)$^+$;

$^1$H-NMR (500 MHz, CDCl$_3$) δ: 8.37 (1H, d, J=5 Hz), 7.62 (2H, d, J=8 Hz), 7.55-7.48 (6H, m), 7.41-7.35 (3H, m), 7.01 (2H, d, J=8 Hz), 5.12 (2H, s), 4.27 (2H, q, J=6 Hz), 4.24 (2H, d, J=5 Hz), 4.00 (2H, t, J=13 Hz), 3.76 (2H, d, J=12 Hz), 2.90 (2H, d, J=7 Hz), 2.80 (2H, t, J=12 Hz), 2.47 (3H, s), 2.19-2.08 (1H, m), 1.78 (2H, d, J=12 Hz), 1.60-1.48 (2H, m), 1.32 (3H, t, J=6 Hz).

(5) ({[2-({1-[4'-(1,1-Difluoro-2-hydroxyethyl)biphenyl-4-yl]piperidin-4-yl}methyl)-5-hydroxy-6-methylpyrimidin-4-yl]carbonyl}amino)acetic acid In accordance with Examples 1-(12) and 1-(13), but using ethyl({[5-(benzyloxy)-2-({1-[4'-(1,1-difluoro-2-hydroxyethyl)biphenyl-4-yl]piperidin-4-yl}methyl)-6-methylpyrimidin-4-yl]carbonyl}amino)acetate instead of ethyl ({[5-(benzyloxy)-2-({1-[4'-(hydroxymethyl)biphenyl-4-yl]piperidin-4-yl}methyl)-6-methylpyrimidin-4-yl]carbonyl}amino)acetate, the title compound (yield 84%) was afforded as a pale yellow solid.

MS m/z: 541 (M+H)$^+$;

$^1$H-NMR (500 MHz, DMSO-d$_6$) δ: 11.92 (1H, s), 9.43 (1H, t, J=6 Hz), 7.70 (2H, d, J=8 Hz), 7.56 (2H, d, J=8 Hz), 7.54 (2H, d, J=8 Hz), 7.09-6.97 (2H, m), 5.67 (1H, brs), 4.02 (2H, d, J=6 Hz), 3.87 (2H, t, J=14 Hz), 3.76 (2H, d, J=12 Hz), 2.78 (2H, d, J=7 Hz), 2.78-2.67 (2H, m), 2.45 (3H, s), 2.18-2.06 (1H, m), 1.69 (2H, d, J=12 Hz), 1.43-1.31 (2H, m).

Example 31

({[2-({1-[4'-(1,1-Difluoro-2-hydroxypropyl)biphenyl-4-yl]piperidin-4-yl}methyl)-5-hydroxy-6-methylpyrimidin-4-yl]carbonyl}amino)acetic acid

[Chemical 107]

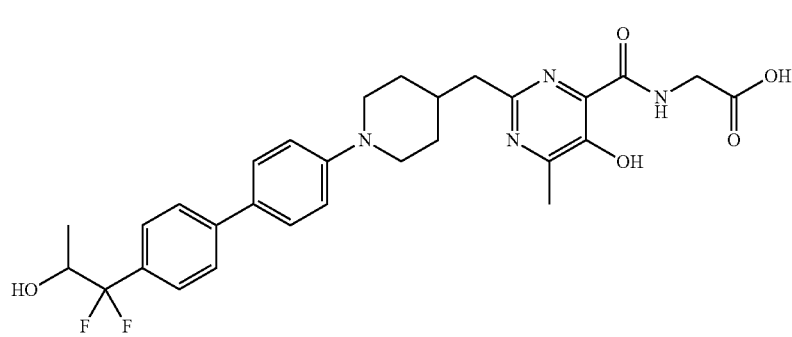

(1) 1-(4'-Bromobiphenyl-4-yl)-1,1-difluoropropan-2-ol

[Chemical 108]

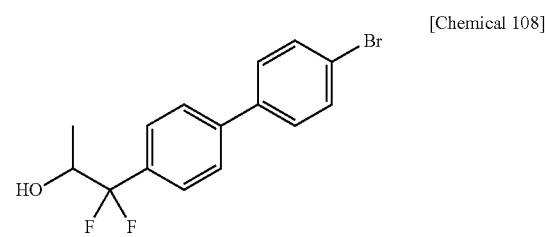 [SMILES: CC(O)C(F)(F)c1ccc(-c2ccc(Br)cc2)cc1]

Ethyl (4'-bromobiphenyl-4-yl)(difluoro)acetate (1.8 g, 5.1 mmol) obtained in Example 30-(1) was dissolved in tetrahydrofuran (20 mL), and a solution of methyllithium in diethyl ether (1.1 M, 14 mL, 15 mmol) was added under a nitrogen atmosphere at −78° C., followed by stirring at the same temperature for 30 minutes. A saturated aqueous ammonium chloride solution was added to the reaction solution, followed by extraction with ethyl acetate, and subsequently the extract was concentrated under reduced pressure to afford 1-(4'-bromobiphenyl-4-yl)-1,1-difluoroacetone as a pale yellow oil.

This was dissolved in tetrahydrofuran (30 mL), and sodium borohydride (0.59 g, 16 mmol) was added, followed by stirring at room temperature for 30 minutes. Hydrochloric acid (1 M) was added to the reaction solution, followed by extraction with ethyl acetate, and subsequently the extract was washed with a saturated aqueous sodium chloride solution, and the organic layer was dried over anhydrous sodium sulfate. After the solvent was distilled off under reduced pressure, the resulting residue was purified by chromatography on a silica gel column (Moritex Corporation, elution solvent: hexane/ethyl acetate), and a fraction corresponding to the Rf value=0.30 (hexane/ethyl acetate=4/1) by thin layer chromatography was concentrated under reduced pressure to afford the title compound (0.89 g, 2.7 mmol) as a yellow oil (yield 53%).

$^1$H-NMR (500 MHz, CDCl$_3$) δ: 7.63-7.57 (6H, m), 7.46 (2H, d, J=9 Hz), 4.25-4.16 (1H, m), 1.27 (3H, d, J=7 Hz).

(2) ({[2-{(1-[4'-(1,1-Difluoro-2-hydroxypropyl)biphenyl-4-yl]piperidin-4-yl}methyl)-5-hydroxy-6-methylpyrimidin-4-yl]carbonyl}amino)acetic acid In accordance with Examples 1-(9) and 1-(11) to 1-(13), but using 1-(4'-bromobiphenyl-4-yl)-1,1-difluoropropan-2-ol instead of [(4'-bromobiphenyl-4-yl)methoxy](tert-butyl)dimethylsilane, the title compound (yield 19%) was afforded as a pale yellow solid.

MS m/z: 555 (M+H)$^+$;

$^1$H-NMR (500 MHz, DMSO-d$_6$) δ: 11.93 (1H, s), 9.44 (1H, t, J=6 Hz), 7.71 (2H, d, J=8 Hz), 7.70-7.52 (4H, m), 7.51 (2H, d, J=8 Hz), 4.13-4.04 (1H, m), 4.01 (2H, d, J=6 Hz), 3.79-3.70 (2H, m), 2.84-2.72 (2H, m), 2.80 (2H, d, J=7 Hz), 2.45 (3H, s), 2.21-2.10 (1H, m), 1.78-1.69 (2H, m), 1.52-1.33 (2H, m), 1.10 (3H, d, J=6 Hz).

Example 32

({[2-{(1-[4'-(1,1-Difluoro-2-hydroxy-2-methylpropyl)biphenyl-4-yl]piperidin-4-yl}methyl)-5-hydroxy-6-methylpyrimidin-4-yl]carbonyl}amino)acetic acid (1) 1-(4'-Bromobiphenyl-4-yl)-1,1-difluoro-2-methylpropan-2-ol

[Chemical 110]

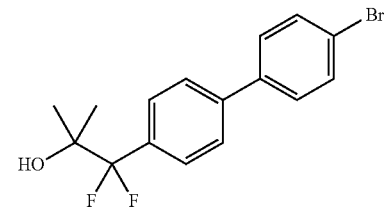

Ethyl (4'-bromobiphenyl-4-yl)(difluoro)acetate (0.10 g, 0.28 mmol) obtained in Example 30-(1) was dissolved in tetrahydrofuran (20 mL), and a solution of methylmagnesium iodide in diethyl ether (3.0 M, 1.0 mL, 3.0 mmol) was added under a nitrogen atmosphere at room temperature, followed by stirring at the same temperature for 5 hours. Hydrochloric acid (1 M) was added to the reaction solution, followed by extraction with ethyl acetate, and subsequently the extract was dried over anhydrous sodium sulfate. After the solvent was distilled off under reduced pressure, the resulting residue was purified by chromatography on a silica gel column (Moritex Corporation, elution solvent: hexane/ethyl acetate), and a fraction corresponding to the Rf value=0.35 (hexane/ethyl acetate=4/1) by thin layer chromatography was concentrated under reduced pressure to afford the title compound (0.063 g, 0.18 mmol) as a yellow oil (yield 62%).

$^1$H-NMR (500 MHz, CDCl$_3$) δ: 7.63-7.56 (6H, m), 7.46 (2H, d, J=8 Hz), 1.35 (6H, s).

(2) ({[2-{(1-[4'-(1,1-Difluoro-2-hydroxy-2-methylpropyl)biphenyl-4-yl]piperidin-4-yl}methyl)-5-hydroxy-6-methylpyrimidin-4-yl]carbonyl}amino)acetic acid In accordance with Examples 1-(9) and 1-(11) to 1-(13), but using 1-(4'-bromobiphenyl-4-yl)-1,1-difluoro-2-methylpropan-2-ol instead of [(4'-bromobiphenyl-4-yl)methoxy](tert-butyl)dimethylsilane, the title compound (yield 11%) was afforded as a pale yellow solid.

MS m/z: 569 (M+H)$^+$;

$^1$H-NMR (500 MHz, DMSO-d$_6$) δ: 11.92 (1H, s), 9.43 (1H, t, J=6 Hz), 7.67 (2H, d, J=8 Hz), 7.59-7.55 (2H, m), 7.49 (2H, d, J=8 Hz), 7.08-7.00 (2H, m), 4.00 (2H, d, J=6 Hz), 3.76 (2H, d, J=12 Hz), 2.78 (2H, d, J=7 Hz), 2.78-2.70 (2H, m),

[Chemical 109]

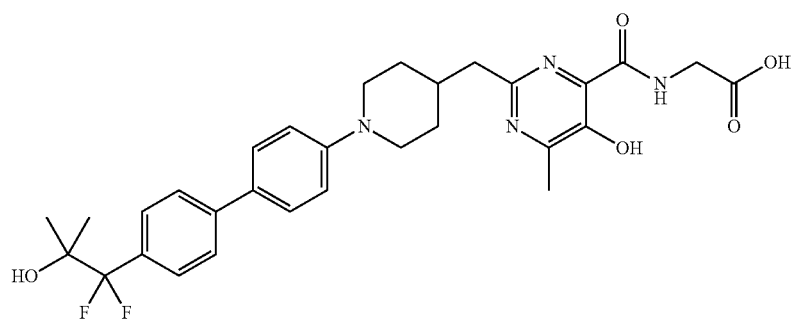

2.45 (3H, s), 2.16-2.06 (1H, m), 1.70 (2H, d, J=12 Hz), 1.44-1.32 (2H, m), 1.19 (6H, s).

Example 33

{[(5-[(2,2-Dimethylpropanoyl)oxy]-2-{[1-(4'-{[(2,2-dimethylpropanoyl)oxy]methyl}biphenyl-4-yl)piperidin-4-yl]methyl}-6-methylpyrimidin-4-yl)carbonyl]amino}acetic acid purified by chromatography on a silica gel column (Moritex Corporation, elution solvent: dichloromethane/methanol), and a fraction corresponding to the Rf value=0.55 (dichloromethane/methanol=10/1) by thin layer chromatography was concentrated under reduced pressure to afford the title compound (0.14 g, 0.24 mmol) as a pale yellow solid (yield 39%).

$^1$H-NMR (400 MHz, CDCl$_3$) δ: 11.34 (1H, s), 8.50 (1H, t, J=6 Hz), 7.56 (2H, d, J=9 Hz), 7.50 (2H, d, J=9 Hz), 7.40 (2H, d, J=9 Hz), 7.42-7.34 (5H, m), 7.00 (2H, d, J=9 Hz), 5.25 (2H,

[Chemical 111]

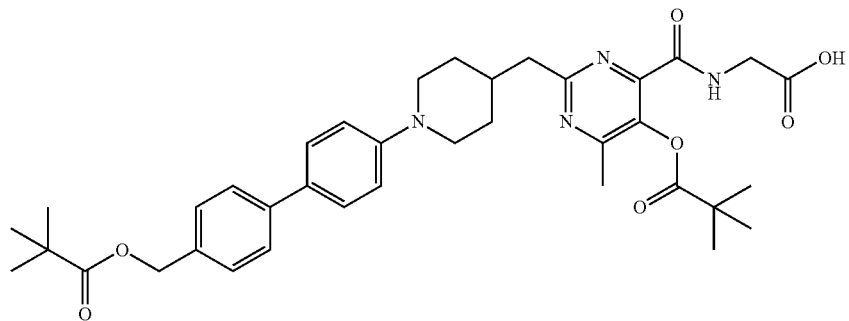

(1) Benzyl({[5-hydroxy-2-{(1-[4'-(hydroxymethyl)biphenyl-4-yl]piperidin-4-yl}methyl)-6-methylpyrimidin-4-yl]carbonyl}amino)acetate s), 4.72 (2H, s), 4.28 (2H, d, J=6 Hz), 3.73 (2H, d, J=12 Hz), 2.83 (2H, d, J=7 Hz), 2.76 (2H, t, J=12 Hz), 2.54 (3H, s), 2.12-1.99 (1H, m), 1.77 (2H, d, J=12 Hz), 1.71-1.43 (2H, m).

[Chemical 112]

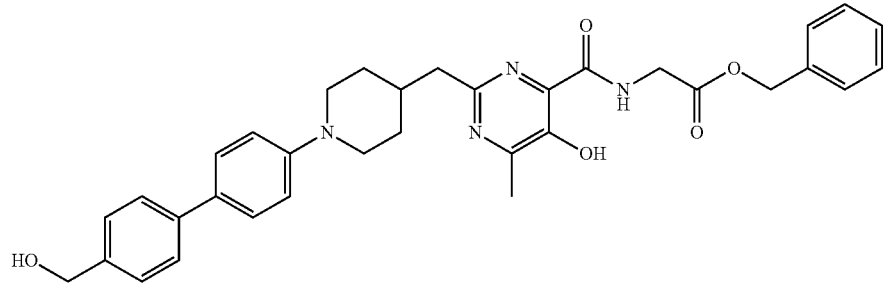

({[5-Hydroxy-2-{(1-[4'-(hydroxymethyl)biphenyl-4-yl]piperidin-4-yl}methyl)-6-methylpyrimidin-4-yl]carbonyl}amino)acetic acid (0.30 g, 0.61 mmol) obtained in Example 1-(13) was dissolved in dichloromethane (10 mL), and benzyl bromide (0.21 g, 1.2 mmol) and triethylamine (0.26 mL, 1.8 mmol) were added, followed by stirring at room temperature for 2 days. After the reaction solution was concentrated under reduced pressure, the resulting residue was (2) 4-{[2-(Benzyloxy)-2-oxoethyl]carbamoyl}-2-{[1-(4'-{[(2,2-dimethylpropanoyl)oxy]methyl}biphenyl-4-yl)piperidin-4-yl]methyl}-6-methylpyrimidin-5-yl pivalate

[Chemical 113]

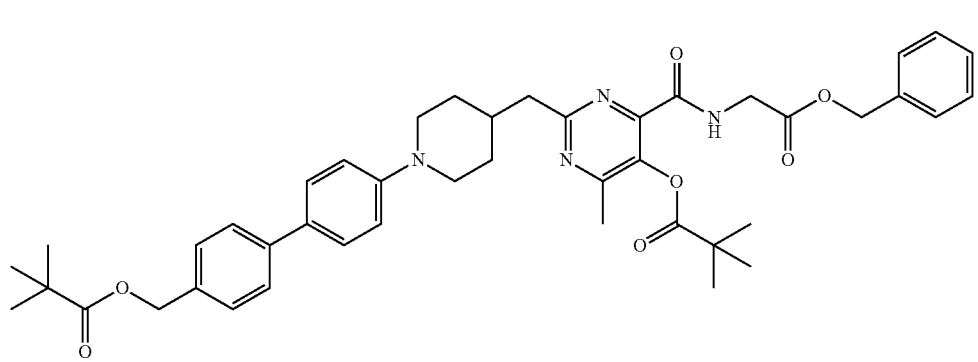

Benzyl({[5-hydroxy-2-{(1-[4'-(hydroxymethyl)biphenyl-4-yl]piperidin-4-yl}methyl)-6-methylpyrimidin-4-yl]carbonyl}amino)acetate (0.025 g, 0.043 mmol) and pivaloyl chloride (0.016 g, 0.13 mmol) were dissolved in dichloromethane (3 mL), and pyridine (0.010 mL, 0.12 mmol) and 4-dimethylaminopyridine (0.016 g, 0.13 mmol) were added, followed by stirring at room temperature for 2 days. After the reaction solution was concentrated under reduced pressure, the resulting residue was purified by chromatography on a silica gel column (Moritex Corporation, elution solvent: dichloromethane/methanol), and a fraction corresponding to the Rf value=0.35 (hexane/ethyl acetate=2/1) by thin layer chromatography was concentrated under reduced pressure to afford the title compound (0.017 g, 0.022 mmol) as a pale yellow solid (yield 52%).

$^1$H-NMR (400 MHz, CDCl$_3$) δ: 8.44 (1H, t, J=5 Hz), 7.55 (2H, d, J=9 Hz), 7.50 (2H, d, J=9 Hz), 7.40-7.32 (7H, m), 7.00 (2H, d, J=9 Hz), 5.22 (2H, s), 5.13 (2H, s), 4.24 (2H, d, J=5 Hz), 3.74 (2H, d, J=12 Hz), 2.92 (2H, d, J=7 Hz), 2.77 (2H, t, J=12 Hz), 2.47 (3H, s), 2.18-2.04 (1H, m), 1.80 (2H, d, J=12 Hz), 1.61-1.47 (2H, m), 1.43 (9H, s), 1.24 (9H, s).

(3) {[(5-[(2,2-Dimethylpropanoyl)oxy]-2-{[1-(4'-{[(2,2-dimethylpropanoyl)oxy]methyl}biphenyl-4-yl)piperidin-4-yl]methyl}-6-methylpyrimidin-4-yl)carbonyl]amino}acetic acid In accordance with Example 12-(4), but using 4-{[2-(benzyloxy)-2-oxoethyl]carbamoyl}-2-{[1-(4'-{[(2,2-dimethylpropanoyl)oxy]methyl}biphenyl-4-yl)piperidin-4-yl]methyl}-6-methylpyrimidin-5-yl pivalate instead of benzyl [({5-(benzyloxy)-2-[(1-{4-[5-(1-hydroxyethyl)pyridin-2-yl]phenyl}piperidin-4-yl)methyl]-6-methylpyrimidin-4-yl}carbonyl)amino]acetate, the title compound (yield 43%) was afforded as a pale yellow solid.

MS m/z: 659 (M+H)$^+$;

$^1$H-NMR (400 MHz, CDCl$_3$) δ: 8.71 (1H, brs), 7.47 (2H, d, J=8 Hz), 7.38 (2H, d, J=8 Hz), 7.32 (2H, d, J=8 Hz), 6.84 (2H, d, J=8 Hz), 5.10 (2H, s), 3.80 (2H, brs), 3.56 (2H, d, J=12 Hz), 2.79 (2H, d, J=7 Hz), 2.57 (2H, t, J=12 Hz), 2.32 (3H, s), 2.05-1.91 (1H, m), 1.64 (2H, d, J=12 Hz), 1.45-1.31 (2H, m), 1.28 (9H, s), 1.22 (9H, s).

Example 34

{[(2-{[1-(4'-{[(2,2-Dimethylpropanoyl)oxy]methyl}biphenyl-4-yl)piperidin-4-yl]methyl}-5-hydroxy-6-methylpyrimidin-4-yl)carbonyl]amino}acetic acid

[Chemical 114]

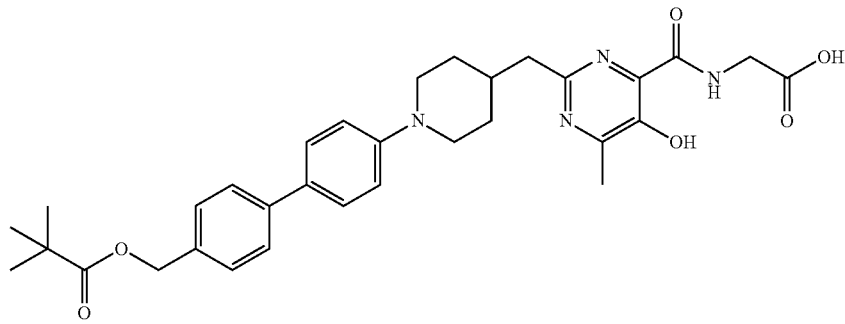

(1) Benzyl({[5-(benzyloxy)-2-({1-[4'-(hydroxymethyl)biphenyl-4-yl]piperidin-4-yl}methyl)-6-methylpyrimidin-4-yl]carbonyl}amino)acetate

[Chemical 115]

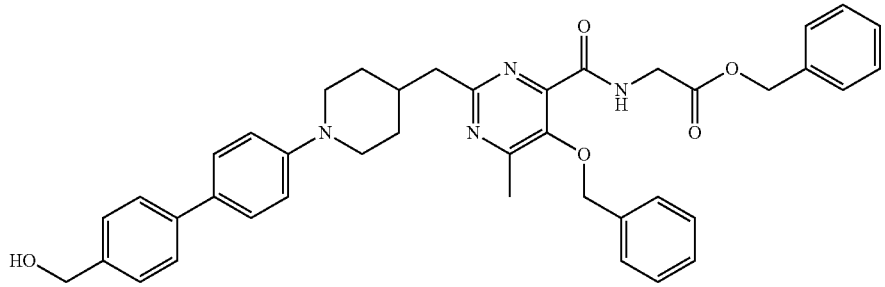

In accordance with Example 1-(11), but using glycine benzyl ester instead of glycine ethyl ester hydrochloride, the title compound (yield 42%) was afforded as a white solid.

¹H-NMR (500 MHz, CDCl₃) δ: 8.37 (1H, t, J=5 Hz), 7.56 (2H, d, J=8 Hz), 7.50 (2H, d, J=9 Hz), 7.48 (2H, d, J=8 Hz), 7.42-7.31 (10H, m), 7.00 (2H, d, J=9 Hz), 5.24 (2H, s), 5.11 (2H, s), 4.72 (2H, d, J=5 Hz), 4.30 (2H, d, J=5 Hz), 3.74 (2H, d, J=12 Hz), 2.89 (2H, d, J=7 Hz), 2.78 (2H, t, J=12 Hz), 2.46 (3H, s), 2.16-2.06 (1H, m), 1.78 (2H, d, J=12 Hz), 1.65 (1H, t, J=5 Hz), 1.60-1.48 (2H, m).

(2) [4'-(4-{[5-(Benzyloxy)-4-{[2-(benzyloxy)-2-oxoethyl]carbamoyl}-6-methylpyrimidin-2-yl]methyl}piperidin-1-yl)biphenyl-4-yl]methyl pivalate

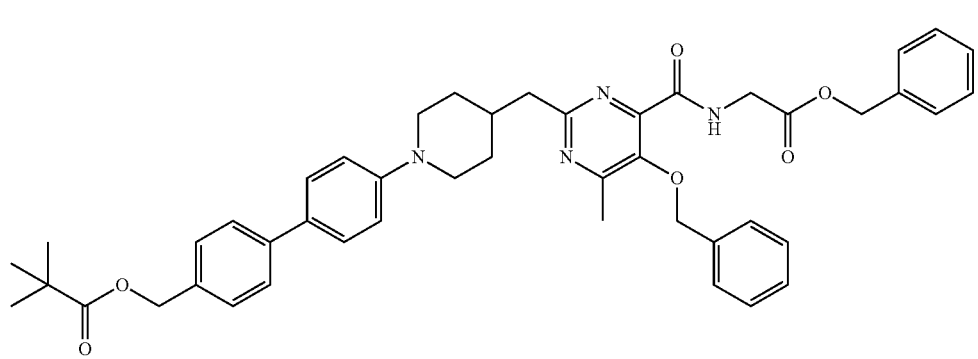

[Chemical 116]

In accordance with Example 33-(2), but using benzyl({[5-(benzyloxy)-2-{(1-[4'-(hydroxymethyl)biphenyl-4-yl]piperidin-4-yl}methyl)-6-methylpyrimidin-4-yl]carbonyl}amino)acetate instead of benzyl({[5-hydroxy-2-{(1-[4'-(hydroxymethyl)biphenyl-4-yl]piperidin-4-yl}methyl)-6-methylpyrimidin-4-yl]carbonyl}amino)acetate, the title compound (yield 79%) was afforded as a pale yellow oil.

¹H-NMR (400 MHz, CDCl₃) δ: 8.37 (1H, t, J=5 Hz), 7.55 (2H, d, J=8 Hz), 7.50 (2H, d, J=9 Hz), 7.48 (2H, d, J=8 Hz), 7.42-7.33 (10H, m), 7.00 (2H, d, J=9 Hz), 5.24 (2H, s), 5.13 (2H, s), 5.11 (2H, s), 4.30 (2H, d, J=5 Hz), 3.75 (2H, d, J=12 Hz), 2.89 (2H, d, J=7 Hz), 2.78 (2H, t, J=12 Hz), 2.47 (3H, s), 2.18-2.06 (1H, m), 1.79 (2H, d, J=12 Hz), 1.60-1.47 (2H, m), 1.24 (9H, s).

(3) {[(2-{[1-(4'-{[(2,2-Dimethylpropanoyl)oxy]methyl}biphenyl-4-yl)piperidin-4-yl]methyl}-5-hydroxy-6-methylpyrimidin-4-yl)carbonyl]amino}acetic acid In accordance with Example 12-(4), but using [4'-(4-{[5-(benzyloxy)-4-{[2-(benzyloxy)-2-oxoethyl]carbamoyl}-6-methylpyrimidin-2-yl]methyl}piperidin-1-yl)biphenyl-4-yl]methyl pivalate instead of benzyl [({5-(benzyloxy)-2-[(1-{4-[5-(1-hydroxyethyl)pyridin-2-yl]phenyl}piperidin-4-yl)methyl]-6-methylpyrimidin-4-yl}carbonyl)amino]acetate, the title compound (yield 28%) was afforded as a yellow solid.

MS m/z: 575 (M+H)⁺;

¹H-NMR (400 MHz, CDCl₃) δ: 11.53 (1H, brs), 8.58 (1H, brs), 7.51 (4H, d, J=8 Hz), 7.36 (2H, d, J=8 Hz), 7.16 (2H, d, J=8 Hz), 5.12 (2H, s), 3.69 (2H, d, J=12 Hz), 3.52 (2H, brs), 2.93-2.74 (4H, m), 2.50 (3H, s), 2.13-1.98 (1H, m), 1.87-1.59 (4H, m), 1.24 (9H, s).

Example 35

({[5-Hydroxy-2-{(1-[4'-(methoxymethyl)biphenyl-4-yl]piperidin-4-yl}methyl)-6-methylpyrimidin-4-yl]carbonyl}amino)acetic acid

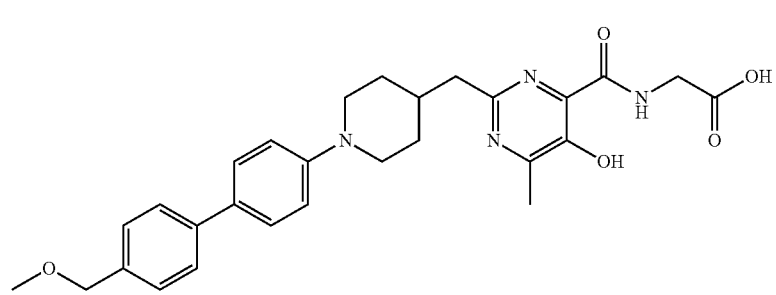

[Chemical 117]

(1) (4'-Bromobiphenyl-4-yl)methyl methyl ether

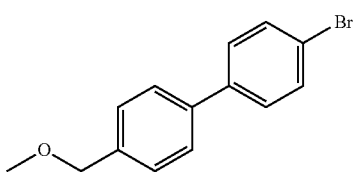

[Chemical 118]

(4'-Bromobiphenyl-4-yl)methanol (1.2 g, 4.6 mmol) was dissolved in tetrahydrofuran (20 mL), and methyl iodide (0.97 g, 6.8 mmol), and then sodium hydride (63%, 0.26 g, 6.8 mmol) were added under a nitrogen atmosphere at 4° C., followed by stirring at room temperature for 30 minutes. A saturated aqueous ammonium chloride solution was added to the reaction solution, followed by extraction with ethyl acetate. After the solvent was distilled off under reduced pressure, the resulting residue was purified by chromatography on a silica gel column (Moritex Corporation, elution solvent: hexane/dichloromethane), and a fraction corresponding to the Rf value=0.50 (hexane/dichloromethane=1/1) by thin layer chromatography was concentrated under reduced pressure to afford the title compound (1.2 g, 4.3 mmol) as a white solid (yield 95%).

$^1$H-NMR (500 MHz, CDCl$_3$) δ: 7.58-7.53 (4H, m), 7.48-7.44 (2H, m), 7.43-7.40 (2H, m), 4.50 (2H, s), 3.42 (3H, s).

(2) ({[5-Hydroxy-2-{(1-[4'-(methoxymethyl)biphenyl-4-yl]piperidin-4-yl}methyl)-6-methylpyrimidin-4-yl]carbonyl}amino)acetic acid In accordance with Examples 1-(9), 1-(11), 22-(4) and 1-(13), but using (4'-bromobiphenyl-4-yl)methyl methyl ether instead of [(4'-bromobiphenyl-4-yl)methoxy](tert-butyl)dimethylsilane, the title compound (yield 26%) was afforded as a pale yellowish white solid.

MS m/z: 505 (M+H)$^+$;

$^1$H-NMR (500 MHz, DMSO-d$_6$) δ: 12.90 (1H, brs), 11.92 (1H, s), 9.40 (1H, t, J=6 Hz), 7.57 (2H, d, J=8 Hz), 7.51 (2H, d, J=8 Hz), 7.34 (2H, d, J=8 Hz), 7.00 (2H, d, J=8 Hz), 4.41 (2H, s), 4.00 (2H, d, J=6 Hz), 3.75 (2H, d, J=12 Hz), 3.29 (3H, s), 2.78 (2H, d, J=7 Hz), 2.71 (2H, t, J=12 Hz), 2.44 (3H, s), 2.15-2.05 (1H, m), 1.68 (2H, d, J=12 Hz), 1.37 (2H, dq, J=12 Hz, 3 Hz).

Example 36

({[2-{(1-[2'-Fluoro-4'-(hydroxymethyl)biphenyl-4-yl]piperidin-4-yl}methyl)-5-hydroxy-6-methylpyrimidin-4-yl]carbonyl}amino)acetic acid

[Chemical 119]

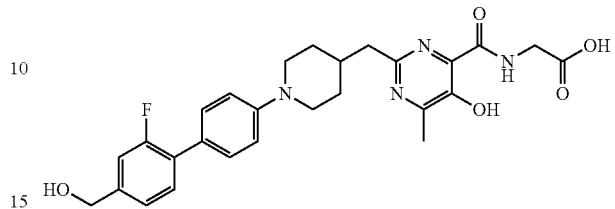

(1) tert-Butyl 5-(benzyloxy)-2-{[1-(4-bromophenyl)piperidin-4-yl]methyl}-6-methylpyrimidine-4-carboxylate

[Chemical 120]

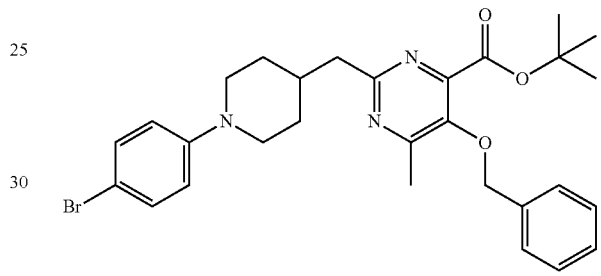

In accordance with Example 1-(9), but using 1,4-dibromobenzene instead of [(4'-bromobiphenyl-4-yl)methoxy](tert-butyl)dimethylsilane, the title compound (yield 18%) was afforded as an orange oil.

$^1$H-NMR (500 MHz, CDCl$_3$) δ: 7.46-7.35 (5H, m), 7.31 (2H, d, J=8 Hz), 6.80 (2H, d, J=8 Hz), 5.01 (2H, s), 3.62 (2H, d, J=12 Hz), 2.89 (2H, d, J=7 Hz), 2.69 (2H, t, J=12 Hz), 2.46 (3H, s), 2.15-2.03 (1H, m), 1.77 (2H, d, J=12 Hz), 1.59 (9H, s), 1.51 (2H, q, J=12 Hz).

(2) tert-Butyl 5-(benzyloxy)-2-{(1-[4'-({[tert-butyl(dimethyl)silyl]oxy}methyl)-2'-fluorobiphenyl-4-yl]piperidin-4-yl}methyl)-6-methylpyrimidine-4-carboxylate

[Chemical 121]

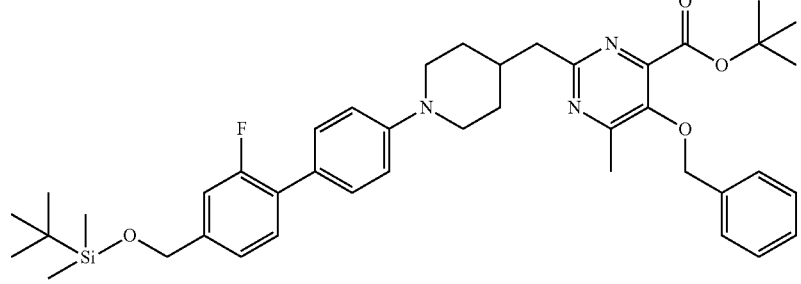

In accordance with Example 19-(2), but using tert-butyl 5-(benzyloxy)-2-{[1-(4-bromophenyl)piperidin-4-yl]methyl}-6-methylpyrimidine-4-carboxylate instead of tert-butyl 5-(benzyloxy)-2-{[1-(5-bromopyridin-2-yl)piperidin-4-yl]methyl}-6-methylpyrimidine-4-carboxylate, and [(4-bromo-3-fluorobenzyl)oxy](tert-butyl)dimethylsilane instead of tert-butyl[(4-iodobenzyl)oxy]dimethylsilane, the title compound (yield 16%) was afforded as a pale yellow oil.

$^1$H-NMR (500 MHz, CDCl$_3$) δ: 7.48-7.35 (8H, m), 7.14-7.08 (2H, m), 6.99 (2H, d, J=8 Hz), 5.01 (2H, s), 4.75 (2H, s), 3.74 (2H, d, J=12 Hz), 2.91 (2H, d, J=7 Hz), 2.76 (2H, t, J=12 Hz), 2.47 (3H, s), 2.17-2.06 (1H, m), 1.79 (2H, d, J=12 Hz), 1.58 (9H, s), 1.54 (2H, q, J=12 Hz), 0.96 (9H, s), 0.12 (6H, s).

(3) ({[2-{(1-[2'-Fluoro-4'-(hydroxymethyl)biphenyl-4-yl]piperidin-4-yl}methyl)-5-hydroxy-6-methylpyrimidin-4-yl]carbonyl}amino)acetic acid In accordance with Examples 1-(10), 1-(11), 22-(4) and 1-(13), but using tert-butyl 5-(benzyloxy)-2-{(1-[4'-({[tert-butyl(dimethyl)silyl]oxy}methyl)-2'-fluorobiphenyl-4-yl]piperidin-4-yl}methyl)-6-methylpyrimidine-4-carboxylate instead of tert-butyl 5-(benzyloxy)-2-{(1-[4'-({[tert-butyl(dimethyl)silyl]oxy}methyl)biphenyl-4-yl]piperidin-4-yl}methyl)-6-methylpyrimidine-4-carboxylate, the title compound (yield 37%) was afforded as a white solid.

MS m/z: 509 (M+H)$^+$;

$^1$H-NMR (500 MHz, DMSO-d$_6$) δ: 12.91 (1H, brs), 11.92 (1H, s), 9.43 (1H, t, J=5 Hz), 7.42 (1H, t, J=9 Hz), 7.39 (2H, d, J=8 Hz), 7.20-7.15 (2H, m), 7.01 (2H, d, J=8 Hz), 5.33 (1H, brs), 4.52 (2H, s), 4.00 (2H, d, J=5 Hz), 3.75 (2H, d, J=12 Hz), 2.78 (2H, d, J=7 Hz), 2.71-2.63 (2H, m), 2.45 (3H, s), 2.16-2.06 (1H, m), 1.69 (2H, d, J=12 Hz), 1.36 (2H, dq, J=12 Hz, 3 Hz).

Example 37

({[2-({1-[3'-Fluoro-4'-(hydroxymethyl)biphenyl-4-yl]piperidin-4-yl}methyl)-5-hydroxy-6-methylpyrimidin-4-yl]carbonyl}amino)acetic acid

[Chemical 122]

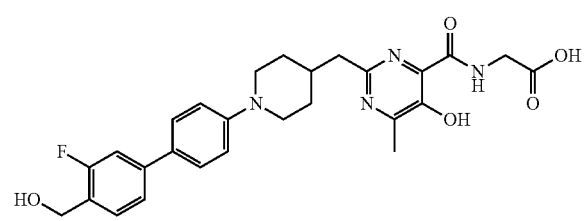

In accordance with Examples 36-(2), 1-(10), 1-(11), 22-(4) and 1-(13), but using [(4-bromo-2-fluorobenzyl)oxy](tert-butyl)dimethylsilane instead of [(4-bromo-3-fluorobenzyl)oxy](tert-butyl)dimethylsilane, the title compound (yield 12%) was afforded as a pale red solid.

MS m/z: 509 (M+H)$^+$;

$^1$H-NMR (500 MHz, DMSO-d$_6$) δ: 12.91 (1H, brs), 11.92 (1H, s), 9.43 (1H, t, J=5 Hz), 7.55 (2H, d, J=8 Hz), 7.50-7.41 (2H, m), 7.38 (1H, d, J=12 Hz), 6.99 (2H, d, J=8 Hz), 5.26 (1H, brs), 4.54 (2H, d, J=4 Hz), 4.00 (2H, d, J=5 Hz), 3.76 (2H, d, J=12 Hz), 2.78 (2H, d, J=7 Hz), 2.77-2.67 (2H, m), 2.45 (3H, s), 2.18-2.06 (1H, m), 1.69 (2H, d, J=12 Hz), 1.36 (2H, dq, J=12 Hz, 3 Hz).

Example 38

({[2-({1-[2-Fluoro-4'-(hydroxymethyl)biphenyl-4-yl]piperidin-4-yl}methyl)-5-hydroxy-6-methylpyrimidin-4-yl]carbonyl}amino)acetic acid

[Chemical 123]

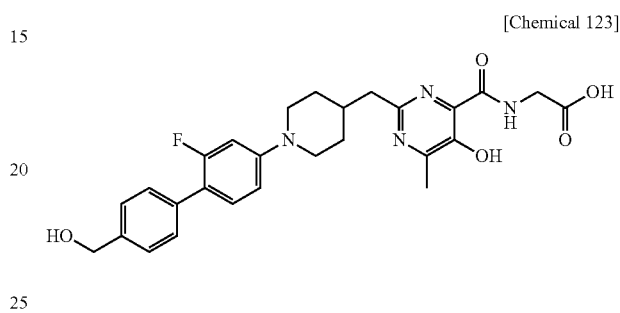

(1) [(4'-Bromo-2'-fluorobiphenyl-4-yl)methoxy](tert-butyl)dimethylsilane

[Chemical 124]

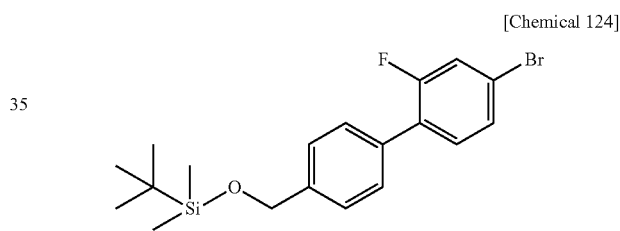

In accordance with Example 4-(2), but using tert-butyl[(4-iodobenzyl)oxy]dimethylsilane instead of tert-butyl[2-(4-iodophenyl)ethoxy]dimethylsilane, and (4-bromo-2-fluorophenyl)boronic acid instead of (4-bromophenyl)boronic acid, the title compound (yield 57%) was afforded as a yellow oil.

$^1$H-NMR (500 MHz, CDCl$_3$) δ: 7.48 (2H, d, J=7 Hz), 7.40 (2H, d, J=7 Hz), 7.38-7.27 (3H, m), 4.79 (2H, s), 0.97 (9H, s), 0.12 (6H, s).

(2) ({[2-{(1-[2-Fluoro-4'-(hydroxymethyl)biphenyl-4-yl]piperidin-4-yl}methyl)-5-hydroxy-6-methylpyrimidin-4-yl]carbonyl}amino)acetic acid In accordance with Examples 1-(9) to 1-(11), 22-(4) and 1-(13), but using [(4'-bromo-2'-fluorobiphenyl-4-yl)methoxy](tert-butyl)dimethylsilane instead of [(4'-bromobiphenyl-4-yl)methoxy](tert-butyl)dimethylsilane, the title compound (yield 19%) was afforded as a white solid.

MS m/z: 509 (M+H)$^+$;

$^1$H-NMR (500 MHz, DMSO-d$_6$) δ: 12.91 (1H, brs), 11.92 (1H, s), 9.43 (1H, t, J=5 Hz), 7.43 (2H, d, J=8 Hz), 7.35 (2H, d, J=8 Hz), 7.33 (1H, d, J=8 Hz), 6.86-6.77 (2H, m), 5.21 (1H, brs), 4.51 (2H, s), 4.00 (2H, d, J=5 Hz), 3.78 (2H, d, J=12 Hz), 2.77 (2H, d, J=7 Hz), 2.77-2.70 (2H, m), 2.44 (3H, s), 2.17-2.06 (1H, m), 1.66 (2H, d, J=12 Hz), 1.34 (2H, dq, J=12 Hz, 3 Hz).

Example 39

({[2-{(1-[3-Fluoro-4'-(hydroxymethyl)biphenyl-4-yl]piperidin-4-yl}methyl)-5-hydroxy-6-methylpyrimidin-4-yl]carbonyl}amino)acetic acid

[Chemical 125]

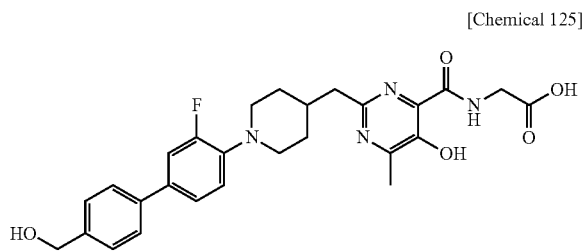 [SMILES: Cc1nc(CC2CCN(c3ccc(-c4ccc(CO)cc4)cc3F)CC2)nc(C(=O)NCC(=O)O)c1O]

(1) [(4'-Bromo-3'-fluorobiphenyl-4-yl)methoxy](tert-butyl)dimethylsilane

[Chemical 126]

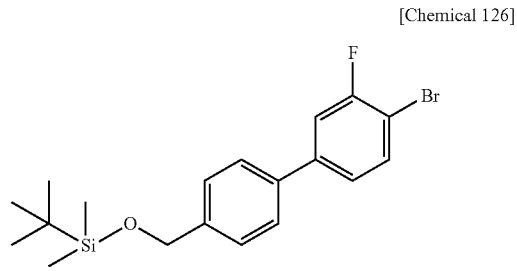 [SMILES: CC(C)(C)[Si](C)(C)OCc1ccc(-c2ccc(Br)c(F)c2)cc1]

In accordance with Example 4-(2), but using tert-butyl[(4-iodobenzyl)oxy]dimethylsilane instead of tert-butyl[2-(4-iodophenyl)ethoxy]dimethylsilane, and (4-bromo-3-fluorophenyl)boronic acid instead of (4-bromophenyl)boronic acid, the title compound (yield 73%) was afforded as a white solid.

$^1$H-NMR (500 MHz, CDCl$_3$) δ: 7.59 (1H, t, J=6 Hz), 7.52 (2H, d, J=7 Hz), 7.40 (2H, d, J=7 Hz), 7.35 (1H, d, J=11 Hz), 7.25 (1H, d, J=6 Hz), 4.79 (2H, s), 0.97 (9H, s), 0.12 (6H, s).

(2) ({[2-{(1-[3-Fluoro-4'-(hydroxymethyl)biphenyl-4-yl]piperidin-4-yl}methyl)-5-hydroxy-6-methylpyrimidin-4-yl]carbonyl}amino)acetic acid In accordance with Examples 1-(9) to 1-(11), 22-(4) and 1-(13), but using [(4'-bromo-3'-fluorobiphenyl-4-yl)methoxy](tert-butyl)dimethylsilane instead of [(4'-bromobiphenyl-4-yl)methoxy](tert-butyl)dimethylsilane, the title compound (yield 5.2%) was afforded as a white solid.

MS m/z: 509 (M+H)$^+$;

$^1$H-NMR (500 MHz, DMSO-d$_6$) δ: 12.91 (1H, brs), 11.93 (1H, s), 9.42 (1H, t, J=5 Hz), 7.60 (2H, d, J=8 Hz), 7.47-7.39 (2H, m), 7.36 (2H, d, J=8 Hz), 7.09 (1H, t, J=9 Hz), 5.22 (1H, t, J=5 Hz), 4.51 (2H, d, J=5 Hz), 4.00 (2H, d, J=5 Hz), 3.36 (2H, d, J=12 Hz), 2.81 (2H, d, J=7 Hz), 2.73-2.63 (2H, m), 2.45 (3H, s), 2.13-2.03 (1H, m), 1.71 (2H, d, J=12 Hz), 1.44 (2H, dq, J=12 Hz, 3 Hz).

Example 40

({[5-Hydroxy-2-({1-[4'-(hydroxymethyl)-3'-methyl-biphenyl-4-yl]piperidin-4-yl}methyl)-6-methylpyrimidin-4-yl]carbonyl}amino)acetic acid

[Chemical 127]

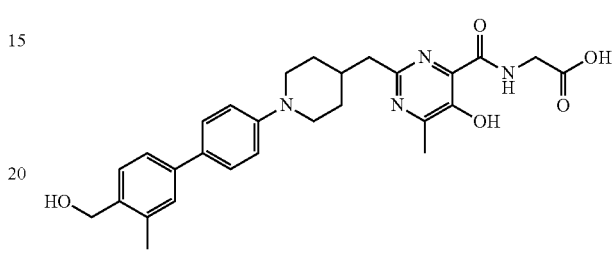

In accordance with Examples 36-(2), 1-(10), 1-(11), 22-(4) and 1-(13), but using [(4-bromo-2-methylbenzyl)oxy](tert-butyl)dimethylsilane instead of [(4-bromo-3-fluorobenzyl)oxy](tert-butyl)dimethylsilane, the title compound (yield 15%) was afforded as a white solid.

MS m/z: 505 (M+H)$^+$;

$^1$H-NMR (400 MHz, DMSO-d$_6$) δ: 12.88 (1H, brs), 11.91 (1H, s), 9.38 (1H, t, J=6 Hz), 7.49 (2H, d, J=9 Hz), 7.37 (1H, d, J=9 Hz), 7.36 (1H, s), 7.35 (1H, d, J=9 Hz), 6.98 (2H, d, J=9 Hz), 5.02 (1H, brs), 4.49 (2H, d, J=3 Hz), 4.00 (2H, d, J=6 Hz), 3.73 (2H, d, J=12 Hz), 2.78 (2H, d, J=7 Hz), 2.70 (2H, dt, J=12 Hz, 3 Hz), 2.44 (3H, s), 2.29 (3H, s), 2.17-2.01 (1H, m), 1.69 (2H, d, J=12 Hz), 1.37 (2H, dq, J=12 Hz, 3 Hz).

Example 41

({[2-({1-[3',5'-Difluoro-4'-(hydroxymethyl)biphenyl-4-yl]piperidin-4-yl}methyl)-5-hydroxy-6-methylpyrimidin-4-yl]carbonyl}amino)acetic acid

[Chemical 128]

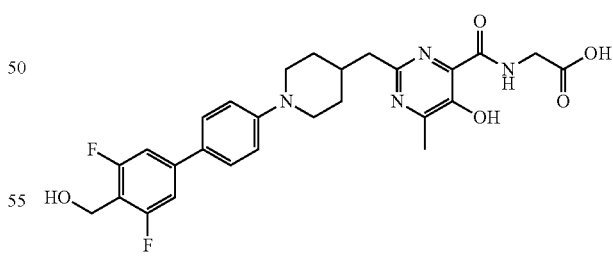

In accordance with Examples 36-(2), 1-(10), 1-(11), 22-(4) and 1-(13), but using [(4-bromo-2,6-difluorobenzyl)oxy](tert-butyl)dimethylsilane instead of [(4-bromo-3-fluorobenzyl)oxy](tert-butyl)dimethylsilane, the title compound (yield 9%) was afforded as a white solid.

MS m/z: 527 (M+H)$^+$;

$^1$H-NMR (400 MHz, DMSO-d$_6$) δ: 12.86 (1H, brs), 11.90 (1H, s), 9.39 (1H, t, J=6 Hz), 7.60 (2H, d, J=9 Hz), 7.33 (2H, d, J=9 Hz), 6.99 (2H, d, J=9 Hz), 5.19 (1H, brs), 4.49 (2H, s), 4.01 (2H, d, J=6 Hz), 3.79 (2H, d, J=12 Hz), 2.78 (2H, d, J=7 Hz), 2.75 (2H, t, J=12 Hz), 2.44 (3H, s), 2.19-2.04 (1H, m), 1.68 (2H, d, J=12 Hz), 1.35 (2H, dq, J=12 Hz, 3 Hz).

Example 42

({[2-{(1-[3',5'-Dichloro-4'-(hydroxymethyl)biphenyl-4-yl]piperidin-4-yl}methyl)-5-hydroxy-6-methylpyrimidin-4-yl]carbonyl}amino)acetic acid

[Chemical 129]

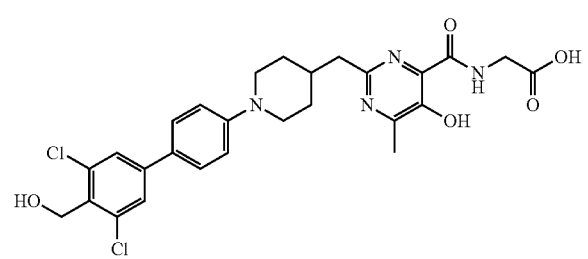

In accordance with Examples 36-(2), 1-(10), 1-(11), 22-(4) and 1-(13), but using [(4-bromo-2,6-dichlorobenzyl)oxy](tert-butyl)dimethylsilane instead of [(4-bromo-3-fluorobenzyl)oxy](tert-butyl)dimethylsilane, the title compound (yield 15%) was afforded as a white solid.

MS m/z: 559 (M+H)$^+$;

$^1$H-NMR (400 MHz, DMSO-d$_6$) δ: 12.88 (1H, brs), 11.91 (1H, s), 9.40 (1H, t, J=6 Hz), 7.67 (2H, s), 7.60 (2H, d, J=9 Hz), 6.99 (2H, d, J=9 Hz), 5.18 (1H, t, J=4 Hz), 4.68 (2H, d, J=4 Hz), 4.01 (2H, d, J=6 Hz), 3.79 (2H, d, J=12 Hz), 2.78 (2H, d, J=7 Hz), 2.73 (2H, t, J=12 Hz), 2.44 (3H, s), 2.19-2.05 (1H, m), 1.68 (2H, d, J=12 Hz), 1.34 (2H, dq, J=12 Hz, 3 Hz).

Example 43

({[2-{(1-[3',5'-Dimethyl-4'-(hydroxymethyl)biphenyl-4-yl]piperidin-4-yl}methyl)-5-hydroxy-6-methylpyrimidin-4-yl]carbonyl}amino)acetic acid

[Chemical 130]

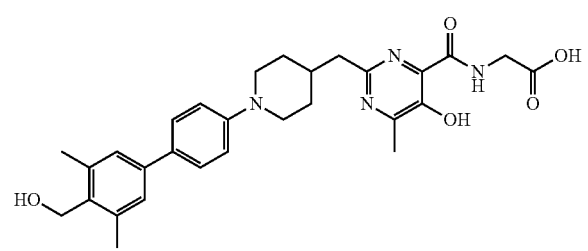

In accordance with Examples 36-(2), 1-(10), 1-(11), 22-(4) and 1-(13), but using [(4-bromo-2,6-dimethylbenzyl)oxy](tert-butyl)dimethylsilane instead of [(4-bromo-3-fluorobenzyl)oxy](tert-butyl)dimethylsilane, the title compound (yield 4%) was afforded as a white solid.

MS m/z: 519 (M+H)$^+$;

$^1$H-NMR (400 MHz, DMSO-d$_6$) δ: 12.87 (1H, brs), 11.90 (1H, s), 9.39 (1H, t, J=6 Hz), 7.48 (2H, d, J=9 Hz), 7.21 (2H, s), 6.97 (2H, d, J=9 Hz), 4.65 (1H, t, J=5 Hz), 4.49 (2H, d, J=5 Hz), 4.01 (2H, d, J=6 Hz), 3.72 (2H, d, J=12 Hz), 2.78 (2H, d, J=7 Hz), 2.70 (2H, dt, J=12 Hz, 3 Hz), 2.44 (3H, s), 2.39 (6H, s), 2.16-2.02 (1H, m), 1.68 (2H, d, J=12 Hz), 1.37 (2H, dq, J=12 Hz, 3 Hz).

Example 44

({[5-Hydroxy-2-{(1-[4'-(hydroxymethyl)biphenyl-4-yl]piperidin-4-yl}methyl)-6-methylpyrimidin-4-yl]carbonyl}amino)acetic acid-d2

[Chemical 131]

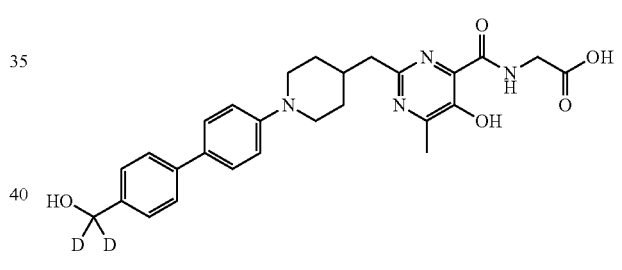

(1) Ethyl({[5-(benzyloxy)-2-{[1-(4'-formylbiphenyl-4-yl)piperidin-4-yl]methyl}-6-methylpyrimidin-4-yl]carbonyl}amino)acetate

[Chemical 132]

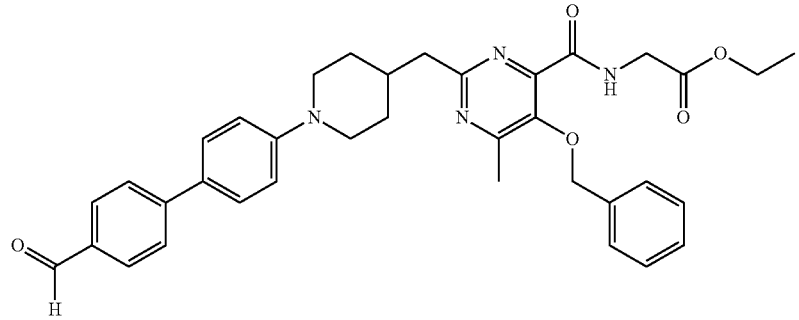

Oxalyl chloride (0.31 g, 2.5 mmol) was dissolved in dichloromethane (5 mL), and a solution of dimethyl sulfoxide (0.18 g, 2.3 mmol) in dichloromethane (4 mL) was added dropwise at −78° C., followed by stirring at the same temperature for 15 minutes. To the reaction solution was added dropwise a solution of ethyl({[5-(benzyloxy)-2-{(1-[4'-(hydroxymethyl)biphenyl-4-yl]piperidin-4-yl}methyl)-6-methylpyrimidin-4-yl]carbonyl}amino)acetate (1.0 g, 1.6 mmol) obtained in Example 1-(11) in dichloromethane (26 mL), followed by stirring at the same temperature for 25 minutes, and subsequently triethylamine (1.1 mL, 8.2 mmol) was added dropwise, and the temperature was raised to room temperature over 1.5 hours. Water was added to the reaction solution, followed by extraction with dichloromethane, and subsequently the extract was washed with a saturated aqueous sodium chloride solution, and dried over anhydrous sodium sulfate. After the solvent was distilled off under reduced pressure, the resulting residue was purified by chromatography on a silica gel column (Biotage Ltd., elution solvent: dichloromethane/ethyl acetate) to afford the title compound (0.85 g, 1.4 mmol) as a yellow solid (yield 85%).

$^1$H-NMR (400 MHz, CDCl$_3$) δ: 10.01 (1H, s), 8.34 (1H, t, J=5 Hz), 7.90 (2H, d, J=8 Hz), 7.72 (2H, d, J=8 Hz), 7.57 (2H, d, J=9 Hz), 7.51-7.46 (2H, m), 7.42-7.33 (3H, m), 7.01 (2H, d, J=9 Hz), 5.12 (2H, s), 4.27 (2H, q, J=7 Hz), 4.24 (2H, d, J=5 Hz), 3.79 (2H, d, J=12 Hz), 2.90 (2H, d, J=7 Hz), 2.83 (2H, dt, J=12 Hz, 3 Hz), 2.47 (3H, s), 2.23-2.07 (1H, m), 1.80 (2H, d, J=12 Hz), 1.53 (2H, dq, J=12 Hz, 3 Hz), 1.32 (3H, t, J=7 Hz).

(2) Ethyl({[5-(benzyloxy)-2-{(1-[4'-(hydroxymethyl)biphenyl-4-yl]piperidin-4-yl}methyl)-6-methylpyrimidin-4-yl]carbonyl}amino)acetate-d1

[Chemical 133]

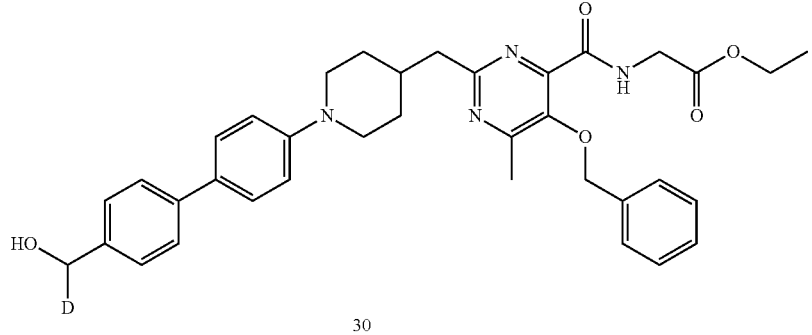

Ethyl({[5-(benzyloxy)-2-{[1-(4'-formylbiphenyl-4-yl)piperidin-4-yl]methyl}-6-methylpyrimidin-4-yl]carbonyl}amino)acetate (0.85 g, 1.4 mmol) was dissolved in a mixed solvent of deuterated methanol (7.5 mL) and dichloromethane (7.5 mL), and deuterated sodium borohydride (0.059 g, 1.4 mmol) was added at 0° C., followed by stirring at the same temperature for 45 minutes. Deuterated water was added to the reaction solution, the solvent was distilled off under reduced pressure, and subsequently the resulting residue was purified by chromatography on a silica gel column (Biotage Ltd., elution solvent: dichloromethane/ethyl acetate) to afford the title compound (0.74 g, 1.2 mmol) as a white solid (yield 87%).

$^1$H-NMR (400 MHz, CDCl$_3$) δ: 8.35 (1H, t, J=5 Hz), 7.55 (2H, d, J=8 Hz), 7.52-7.46 (2H, m), 7.50 (2H, d, J=9 Hz), 7.40 (2H, d, J=8 Hz), 7.38-7.35 (3H, m), 7.00 (2H, d, J=9 Hz), 5.12 (2H, s), 4.69 (1H, s), 4.26 (2H, q, J=7 Hz), 4.24 (2H, d, J=5 Hz), 3.74 (2H, d, J=12 Hz), 2.90 (2H, d, J=7 Hz), 2.78 (2H, dt, J=12 Hz, 3 Hz), 2.46 (3H, s), 2.19-2.05 (1H, m), 1.79 (2H, d, J=12 Hz), 1.71 (1H, brs), 1.54 (2H, dq, J=12 Hz, 3 Hz), 1.32 (3H, t, J=7 Hz).

(3) Ethyl({[5-(benzyloxy)-2-{[1-(4'-formylbiphenyl-4-yl)piperidin-4-yl]methyl}-6-methylpyrimidin-4-yl]carbonyl}amino)acetate-d1

[Chemical 134]

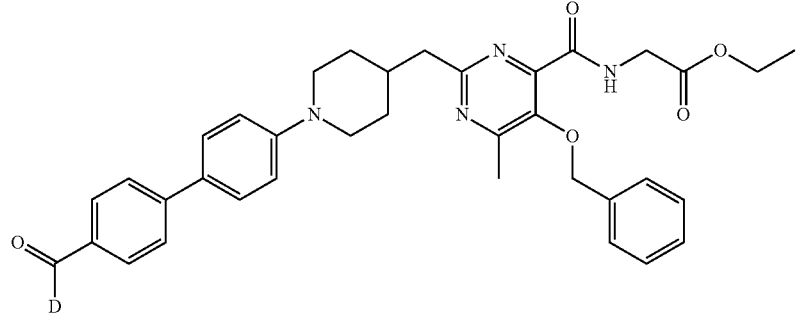

In accordance with Example 44-(1), but using ethyl({[5-(benzyloxy)-2-({1-[4'-(hydroxymethyl)biphenyl-4-yl]piperidin-4-yl}methyl)-6-methylpyrimidin-4-yl]carbonyl}amino)acetate-d1 instead of ethyl({[5-(benzyloxy)-2-({1-[4'-(hydroxymethyl)biphenyl-4-yl]piperidin-4-yl}methyl)-6-methylpyrimidin-4-yl]carbonyl}amino)acetate, the title compound and ethyl({[5-(benzyloxy)-2-{1-(4'-formylbiphenyl-4-yl)piperidin-4-yl]methyl}-6-methylpyrimidin-4-yl]carbonyl}amino)acetate were afforded as a 5:1 mixture (yield 87%).

$^1$H-NMR (400 MHz, CDCl$_3$) δ: 10.01 (0.2H, s), 8.34 (1H, t, J=5 Hz), 7.90 (2H, d, J=8 Hz), 7.72 (2H, d, J=8 Hz), 7.57 (2H, d, J=9 Hz), 7.51-7.46 (2H, m), 7.42-7.32 (3H, m), 7.01 (2H, d, J=9 Hz), 5.12 (2H, s), 4.27 (2H, q, J=7 Hz), 4.24 (2H, d, J=5 Hz), 3.80 (2H, d, J=12 Hz), 2.90 (2H, d, J=7 Hz), 2.83 (2H, dt, J=12 Hz, 3 Hz), 2.47 (3H, s), 2.22-2.08 (1H, m), 1.79 (2H, d, J=12 Hz), 1.53 (2H, dq, J=12 Hz, 3 Hz), 1.32 (3H, t, J=7 Hz).

(4) Ethyl({[5-(benzyloxy)-2-({1-[4'-(hydroxymethyl)biphenyl-4-yl]piperidin-4-yl}methyl)-6-methylpyrimidin-4-yl]carbonyl}amino)acetate-d2

Hz), 2.47 (3H, s), 2.20-2.05 (1H, m), 1.79 (2H, d, J=12 Hz), 1.64-1.49 (3H, m), 1.32 (3H, t, J=7 Hz).

(5) ({[5-Hydroxy-2-({1-[4'-(hydroxymethyl)biphenyl-4-yl]piperidin-4-yl}methyl)-6-methylpyrimidin-4-yl]carbonyl}amino)acetic acid-d2

In accordance with Examples 22-(4) and 1-(13), but using ethyl({[5-(benzyloxy)-2-({1-[4'-(hydroxymethyl)biphenyl-4-yl]piperidin-4-yl}methyl)-6-methylpyrimidin-4-yl]carbonyl}amino)acetate-d2 instead of ethyl({[5-(benzyloxy)-2-({1-[2-chloro-4'-(hydroxymethyl)biphenyl-4-yl]piperidin-4-yl}methyl)-6-methylpyrimidin-4-yl]carbonyl}amino)acetate, and deuterated trifluoroacetic acid, methanol, aqueous sodium hydroxide solution and hydrochloric acid, the title compound (yield 80%) was afforded as a yellowish white solid.

MS m/z: 493 (M+H)$^+$;

$^1$H-NMR (400 MHz, DMSO-d$_6$) δ: 12.88 (1H, brs), 11.91 (1H, s), 9.38 (1H, t, J=5 Hz), 7.54 (2H, d, J=9 Hz), 7.50 (2H, d, J=9 Hz), 7.34 (2H, d, J=9 Hz), 6.99 (2H, d, J=9 Hz), 5.10 (1H, s), 4.00 (2H, d, J=5 Hz), 3.73 (2H, d, J=12 Hz), 2.78 (2H,

[Chemical 135]

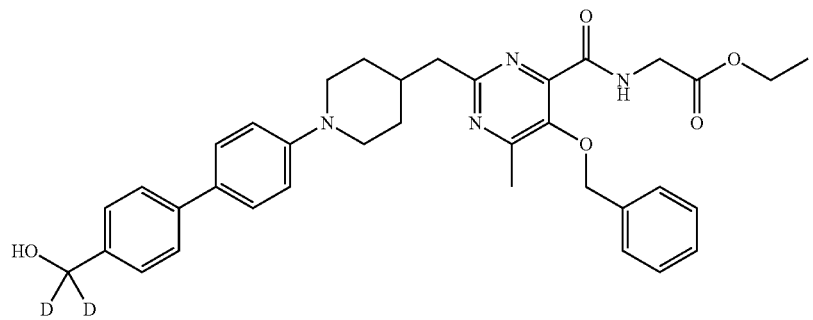

The operations of Examples 44-(2) and 44-(3) were repeated twice with respect to ethyl({[5-(benzyloxy)-2-{1-(4'-formylbiphenyl-4-yl)piperidin-4-yl]methyl}-6-methylpyrimidin-4-yl]carbonyl}amino)acetate-d1, and subsequently the operation of Example 44-(2) was carried out to afford the title compound (yield 51%) as a white solid.

$^1$H-NMR (400 MHz, CDCl$_3$) δ: 8.35 (1H, t, J=5 Hz), 7.56 (2H, d, J=8 Hz), 7.52-7.46 (2H, m), 7.50 (2H, d, J=9 Hz), 7.40 (2H, d, J=8 Hz), 7.42-7.33 (3H, m), 7.00 (2H, d, J=9 Hz), 5.12 (2H, s), 4.27 (2H, q, J=7 Hz), 4.24 (2H, d, J=5 Hz), 3.74 (2H, d, J=12 Hz), 2.90 (2H, d, J=7 Hz), 2.78 (2H, dt, J=12 Hz, 2 d, J=7 Hz), 2.71 (2H, dt, J=12 Hz, 3 Hz), 2.44 (3H, s), 2.19-2.02 (1H, m), 1.69 (2H, d, J=12 Hz), 1.37 (2H, dq, J=12 Hz, 3 Hz).

Example 45

[({5-Hydroxy-2-[(1-{4'-[(2S)-2-hydroxypropyl]biphenyl-4-yl}piperidin-4-yl)methyl]-6-methylpyrimidin-4-yl}carbonyl)amino]acetic acid

[Chemical 136]

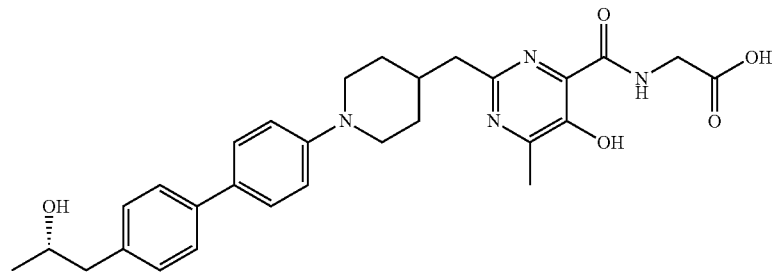

(1) (2S)-1-(4'-Bromobiphenyl-4-yl)propan-2-ol

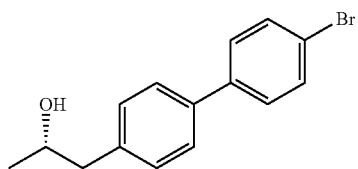

[Chemical 137]

A solution of n-butylmagnesium chloride in tetrahydrofuran (2 M, 0.40 mL, 0.80 mmol) was diluted with tetrahydrofuran (1 mL), and a solution of n-butyllithium in hexane (2.8 M, 0.57 mL, 1.6 mmol) was added under a nitrogen atmosphere at 0° C., followed by stirring at the same temperature for 10 minutes to prepare a solution of tri-n-butylmagnesium lithium in tetrahydrofuran.

4,4'-Dibromobiphenyl (0.62 g, 2.0 mmol) was dissolved in tetrahydrofuran (5 mL), and a solution of tri-n-butylmagnesium lithium in tetrahydrofuran was added under a nitrogen atmosphere at 0° C., which was stirred at the same temperature for 1 hour, followed by addition of (2S)-2-methyloxirane (0.15 mL, 2.2 mmol). The temperature of the reaction solution was raised to room temperature, followed by stirring for 30 minutes, and subsequently a saturated aqueous ammonium chloride solution was added, followed by extraction with ethyl acetate. After the solvent was distilled off under reduced pressure, the resulting residue was purified by chromatography on a silica gel column (Moritex Corporation, elution solvent: hexane/ethyl acetate), and a fraction corresponding to the Rf value=0.40 (hexane/ethyl acetate=2/1) by thin layer chromatography was concentrated under reduced pressure to afford the title compound (0.23 g, 0.79 mmol) as a white solid (yield 39%).

$^1$H-NMR was the same as in Example 5-(3).

(2) [(1S)-2-(4'-Bromobiphenyl-4-yl)-1-methylethoxyl](tert-butyl)dimethylsilane

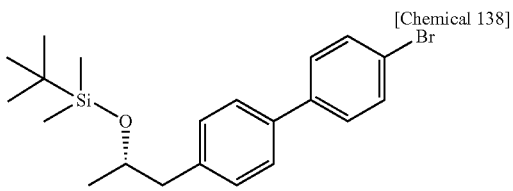 [SMILES: C[C@@H](Cc1ccc(-c2ccc(Br)cc2)cc1)O[Si](C)(C)C(C)(C)C]

[Chemical 138]

(2S)-1-(4'-Bromobiphenyl-4-yl)propan-2-ol (0.23 g, 0.79 mmol) and imidazole (0.11 g, 1.6 mmol) were dissolved in N,N-dimethylformamide (5 mL), and tert-butyldimethylchlorosilane (0.24 g, 1.6 mmol) was added under a nitrogen atmosphere, followed by stirring at room temperature for 1 hour. Diethyl ether was added to the reaction solution, followed by sequential washing with water and hydrochloric acid (1 M). After the solvent was distilled off under reduced pressure, the resulting residue was purified by chromatography on a silica gel column (Moritex Corporation, elution solvent: hexane/ethyl acetate), and a fraction corresponding to the Rf value=0.80 (hexane/ethyl acetate=10/1) by thin layer chromatography was concentrated under reduced pressure to afford the title compound (0.25 g, 0.62 mmol) as a white solid (yield 78%).

$^1$H-NMR was the same as in Example 5-(4).

(3) [({5-Hydroxy-2-[(1-{4'-[(2S)-2-hydroxypropyl]biphenyl-4-yl}piperidin-4-yl)methyl]-6-methylpyrimidin-4-yl}carbonyl)amino]acetic acid In accordance with Examples 1-(9) to 1-(13), but using [(1S)-2-(4'-bromobiphenyl-4-yl)-1-methylethoxyl](tert-butyl)dimethylsilane instead of [(4'-bromobiphenyl-4-yl)methoxy](tert-butyl)dimethylsilane, the title compound (yield 37%) was afforded as a white solid.

$[\alpha]_D^{20}$ +8.9° (c=1.00, DMF)

MS and $^1$H-NMR were the same as in Example 5-(5).

Example 46

[({5-Hydroxy-2-[(1-{4'-[(2R)-2-hydroxypropyl]biphenyl-4-yl}piperidin-4-yl)methyl]-6-methylpyrimidin-4-yl}carbonyl)amino]acetic acid

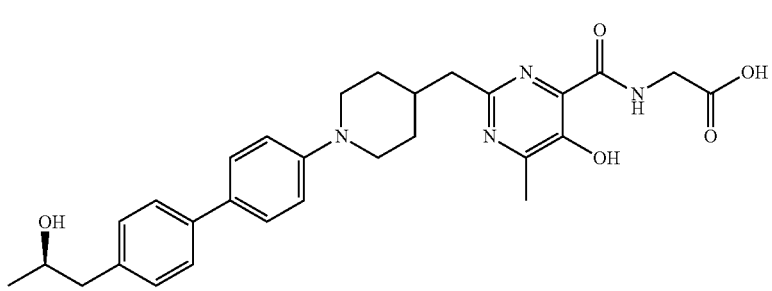

[Chemical 139]

In accordance with Examples 45-(1) to 45-(3), but using (2R)-2-methyloxirane instead of (2S)-2-methyloxirane, the title compound (yield 18%) was afforded as a white solid.

$[\alpha]_D^{20}$ -8.9° (c=1.00, DMF).

MS and $^1$H-NMR were the same as in Example 5-(5).

Example 47

[({5-Hydroxy-2-[(1-{4'-[(2S)-2-hydroxybutyl]biphenyl-4-yl}piperidin-4-yl)methyl]-6-methylpyrimidin-4-yl}carbonyl)amino]acetic acid

[Chemical 140]

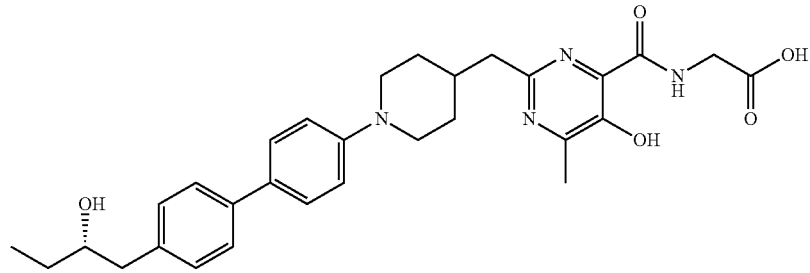

In accordance with Examples 45-(1) to 45-(3), but using (2S)-2-ethyloxirane instead of (2S)-2-methyloxirane, the title compound (yield 8.2%) was afforded as a white solid.
$[\alpha]_D^{19}$ +14.3° (c=1.00, DMF).
MS and $^1$H-NMR were the same as in Example 27.

Example 48

[({5-Hydroxy-2-[(1-{4'-[(2R)-2-hydroxybutyl]biphenyl-4-yl}piperidin-4-yl)methyl]-6-methylpyrimidin-4-yl}carbonyl)amino]acetic acid

[Chemical 141]

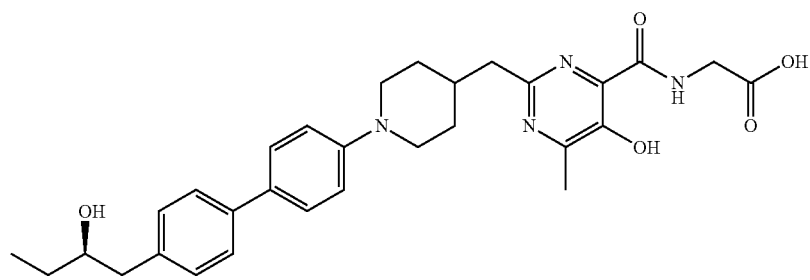

In accordance with Examples 45-(1) to 45-(3), but using (2R)-2-ethyloxirane instead of (2S)-2-methyloxirane, the title compound (yield 8.2%) was afforded as a white solid.
$[\alpha]_D^{20}$ −14.3° (c=1.00, DMF).
MS and $^1$H-NMR were the same as in Example 27.

Example 49

[({5-Hydroxy-2-[(1-{4'-[(2R)-2-hydroxy-3-methoxypropyl]biphenyl-4-yl}piperidin-4-yl)methyl]-6-methylpyrimidin-4-yl}carbonyl)amino]acetic acid

[Chemical 142]

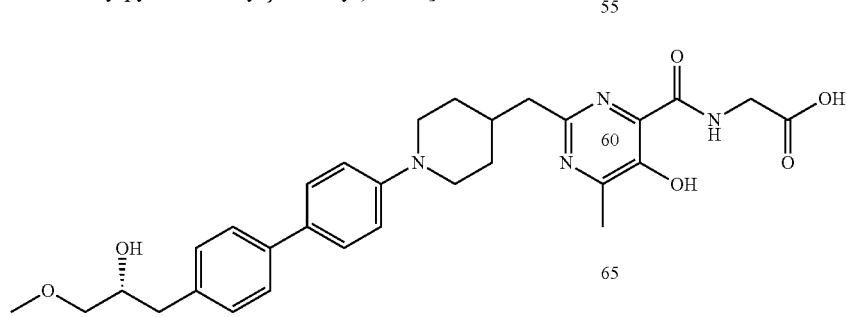

In accordance with Examples 45-(1) to 45-(3), but using (2R)-2-(methoxymethyl)oxirane instead of (2S)-2-methyloxirane, the title compound (yield 6.6%) was afforded as a white solid.

$[\alpha]_D^{20}$ +6.5° (c=1.00, DMF).

MS m/z: 549 (M+H)$^+$;

$^1$H-NMR (500 MHz, DMSO-d$_6$) δ: 12.87 (1H, brs), 11.91 (1H, s), 9.40 (1H, t, J=5 Hz), 7.48 (2H, d, J=9 Hz), 7.47 (2H, d, J=9 Hz), 7.23 (2H, d, J=8 Hz), 6.99 (2H, d, J=8 Hz), 4.75 (1H, brs), 4.00 (2H, d, J=5 Hz), 3.83-3.73 (1H, m), 3.73 (2H, d, J=12 Hz), 3.26 (3H, s), 3.23 (2H, d, J=5 Hz), 2.78 (2H, d, J=7 Hz), 2.74-2.67 (2H, m), 2.63 (2H, d, J=6 Hz), 2.44 (3H, s), 2.15-2.03 (1H, m), 1.68 (2H, d, J=12 Hz), 1.36 (2H, dq, J=12 Hz, 3 Hz).

Example 50

[({5-Hydroxy-2-[(1-{4'-[(2S)-2-hydroxy-3-methoxypropyl]biphenyl-4-yl}piperidin-4-yl)methyl]-6-methylpyrimidin-4-yl}carbonyl)amino]acetic acid

[Chemical 143]

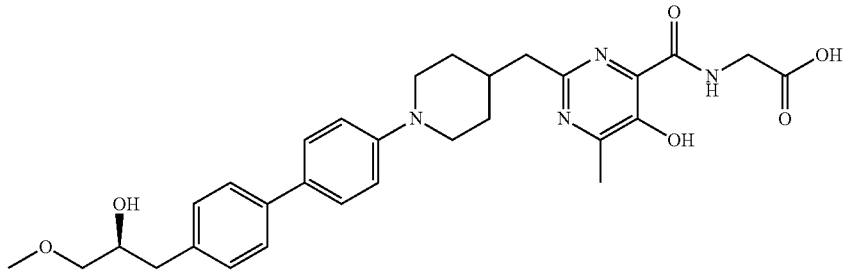

In accordance with Examples 45-(1) to 45-(3), but using (2S)-2-(methoxymethyl)oxirane instead of (2S)-2-methyloxirane, the title compound (yield 9.4%) was afforded as a white solid.

$[\alpha]_D^{21}$ –6.7° (c=1.00, DMF).

MS and $^1$H-NMR were the same as in Example 49.

Example 51

({[5-Hydroxy-2-{(1-[4'-(3-hydroxypropyl)biphenyl-4-yl]piperidin-4-yl}methyl)-6-methylpyrimidin-4-yl]carbonyl}amino)acetic acid

[Chemical 144]

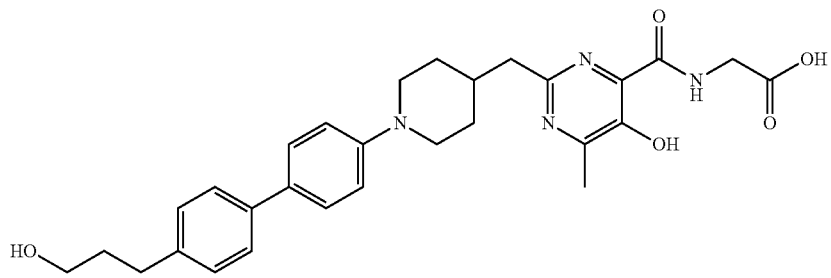

In accordance with Examples 36-(2) and 1-(10) to 1-(13), but using [3-(4-bromophenyl)propoxy](tert-butyl)dimethylsilane instead of [(4-bromo-3-fluorobenzyl)oxy](tert-butyl)dimethylsilane, the title compound (yield 9%) was afforded as a pale yellowish white solid.

MS m/z: 519 (W+H);

$^1$H-NMR (500 MHz, DMSO-d$_6$) δ: 12.88 (1H, brs), 11.91 (1H, s), 9.40 (1H, t, J=6 Hz), 7.49 (2H, d, J=8 Hz), 7.48 (2H, d, J=8 Hz), 7.22 (2H, d, J=8 Hz), 6.98 (2H, d, J=8 Hz), 4.47 (1H, t, J=6 Hz), 4.01 (2H, d, J=6 Hz), 3.73 (2H, d, J=12 Hz), 3.43 (2H, q, J=6 Hz), 2.78 (2H, d, J=7 Hz), 2.70 (2H, t, J=12 Hz), 2.61 (2H, t, J=7 Hz), 2.44 (3H, s), 2.14-2.04 (1H, m), 1.76-1.65 (4H, m), 1.37 (2H, dq, J=12 Hz, 3 Hz).

Example 52

({[5-Hydroxy-2-{(1-[4'-(hydroxymethyl)-3'-isopropylbiphenyl-4-yl]piperidin-4-yl}methyl)-6-methylpyrimidin-4-yl]carbonyl}amino)acetic acid

[Chemical 145]

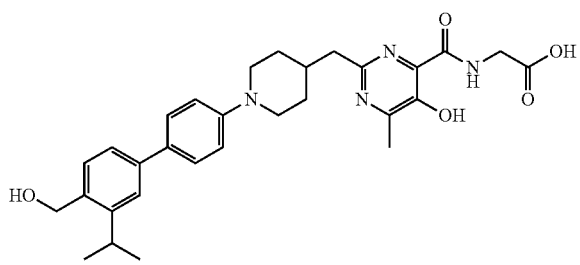

(1) 2-[5-Bromo-2-({[tert-butyl(dimethyl)silyl]oxy}methyl)phenyl]propan-2-ol

[Chemical 146]

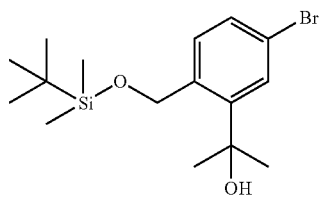

2-[5-Bromo-2-(hydroxymethyl)phenyl]propan-2-ol (1.1 g, 4.4 mmol) and imidazole (0.78 g, 12 mmol) were dissolved in N,N-dimethylformamide (5 mL), and tert-butyldimethylchlorosilane (0.86 g, 5.7 mmol) was added, followed by stirring at room temperature overnight. Water was added to the reaction solution, followed by extraction with hexane, and subsequently the extract was washed sequentially with water and a saturated aqueous sodium chloride solution, and dried over anhydrous sodium sulfate. After the organic layer was concentrated under reduced pressure, the resulting residue was purified by chromatography on a silica gel column (Biotage Ltd., elution solvent: hexane/ethyl acetate) to afford the title compound (1.1 g, 3.1 mmol) as a colorless oil (yield 70%).

$^1$H-NMR (400 MHz, CDCl$_3$) δ: 7.43 (1H, d, J=2 Hz), 7.31 (1H, dd, J=8, 2 Hz), 7.16 (1H, d, J=8 Hz), 4.93 (2H, s), 4.34 (1H, s), 1.61 (6H, s), 0.91 (9H, s), 0.11 (6H, s).

(2) [(4-Bromo-2-isopropenylbenzyl)oxy](tert-butyl)dimethylsilane

[Chemical 147]

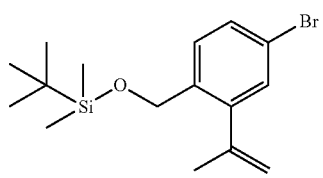

2-[5-Bromo-2-({[tert-butyl(dimethyl)silyl]oxy}methyl)phenyl]propan-2-ol (0.79 g, 2.2 mmol) was dissolved in dichloromethane (7 mL), and triethylamine (0.61 mL, 4.4 mmol) and methanesulfonyl chloride (0.34 mL, 4.4 mmol) were sequentially added dropwise at 0° C., followed by stirring at room temperature for 3 hours. Water, hexane and ethyl acetate were added to the reaction solution, followed by extraction with hexane. The extract was washed sequentially with hydrochloric acid (1 M), a saturated aqueous sodium hydrogencarbonate solution and a saturated aqueous sodium chloride solution, and subsequently dried over anhydrous sodium sulfate.

After the organic layer was concentrated under reduced pressure, the resulting residue was dissolved in dichloromethane (12 mL), and 1,8-diazabicyclo[5.4.0]undec-7-ene (DBU) (3.3 mL, 22 mmol) was added, followed by stirring at room temperature overnight. The reaction solution was concentrated under reduced pressure, and water and hexane were added, followed by extraction with hexane. The extract was washed sequentially with hydrochloric acid (1 M), a saturated aqueous sodium hydrogencarbonate solution and a saturated aqueous sodium chloride solution, and subsequently dried over anhydrous sodium sulfate. After the solvent was distilled off under reduced pressure, the resulting residue was purified by chromatography on a silica gel column (Biotage Ltd., elution solvent: hexane) to afford the title compound (0.56 g, 1.6 mmol) as a colorless oil (yield 74%).

$^1$H-NMR (400 MHz, CDCl$_3$) δ: 7.39 (1H, d, J=9 Hz), 7.38 (1H, d, J=9 Hz), 7.25 (1H, brs), 5.21 (1H, s), 4.84 (1H, s), 4.65 (2H, s), 2.01 (3H, s), 0.92 (9H, s), 0.08 (6H, s).

(3) tert-Butyl 5-(benzyloxy)-2-{(1-[4'-(hydroxymethyl)-3'-isopropenylbiphenyl-4-yl]piperidin-4-yl}methyl)-6-methylpyrimidine-4-carboxylate

[Chemical 148]

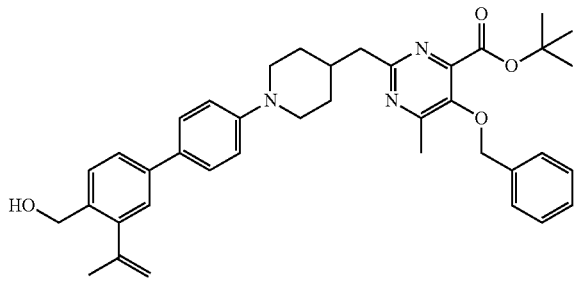

In accordance with Examples 36-(2) and 18-(6), but using [(4-bromo-2-isopropenylbenzyl)oxy](tert-butyl)dimethylsilane instead of [(4-bromo-3-fluorobenzyl)oxy](tert-butyl)dimethylsilane, the title compound (yield 72%) was afforded as a yellow oil.

$^1$H-NMR (400 MHz, CDCl$_3$) δ: 7.52-7.33 (8H, m), 7.49 (2H, d, J=9 Hz), 6.99 (2H, d, J=9 Hz), 5.28-5.23 (1H, m), 5.01 (2H, s), 4.97-4.93 (1H, m), 4.71 (2H, s), 3.73 (2H, d, J=12 Hz), 2.91 (2H, d, J=7 Hz), 2.75 (2H, dt, J=12 Hz, 3 Hz), 2.46 (3H, s), 2.17-2.06 (4H, m), 1.80 (2H, d, J=12 Hz), 1.74 (1H, brs), 1.59 (9H, s), 1.53 (2H, dq, J=12 Hz, 3 Hz).-

(4) Ethyl({[5-(benzyloxy)-2-{(1-[4'-(hydroxymethyl)-3'-isopropenylbiphenyl-4-yl]piperidin-4-yl}methyl)-6-methylpyrimidin-4-yl]carbonyl}amino)acetate

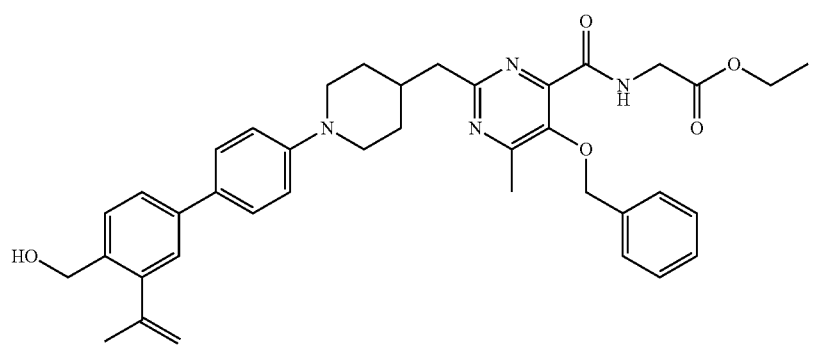

[Chemical 149]

In accordance with Example 1-(11), but using tert-butyl 5-(benzyloxy)-2-{(1-[4'-(hydroxymethyl)-3'-isopropenylbiphenyl-4-yl]piperidin-4-yl}methyl)-6-methylpyrimidine-4-carboxylate instead of tert-butyl 5-(benzyloxy)-2-{(1-[4'-(hydroxymethyl)biphenyl-4-yl]piperidin-4-yl}methyl)-6-methylpyrimidine-4-carboxylate, the title compound (yield 83%) was afforded as a yellow oil.

$^1$H-NMR (400 MHz, CDCl$_3$) δ: 8.36 (1H, t, J=5 Hz), 7.53-7.45 (6H, m), 7.41-7.30 (4H, m), 6.99 (2H, d, J=9 Hz), 5.28-5.23 (1H, m), 5.12 (2H, s), 4.97-4.94 (1H, m), 4.72 (2H, d, J=4 Hz), 4.27 (2H, q, J=7 Hz), 4.25 (2H, d, J=5 Hz), 3.74 (2H, d, J=12 Hz), 2.90 (2H, d, J=7 Hz), 2.78 (2H, dt, J=12 Hz, 3 Hz), 2.47 (3H, s), 2.17-2.07 (4H, m), 1.79 (2H, d, J=12 Hz), 1.74 (1H, brs), 1.54 (2H, dq, J=12 Hz, 3 Hz), 1.32 (3H, t, J=7 Hz).

(5) Ethyl({[5-hydroxy-2-{(1-[4'-(hydroxymethyl)-3'-isopropylbiphenyl-4-yl]piperidin-4-yl}methyl)-6-methylpyrimidin-4-yl]carbonyl}amino)acetate

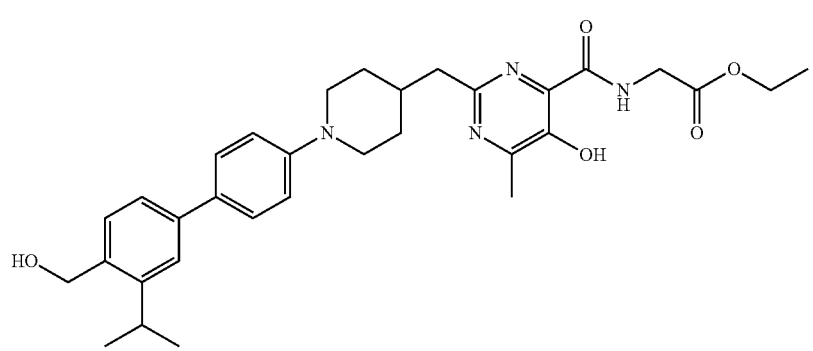

[Chemical 150]

Ethyl({[5-(benzyloxy)-2-{(1-[4'-(hydroxymethyl)-3'-isopropenylbiphenyl-4-yl]piperidin-4-yl}methyl)-6-methylpyrimidin-4-yl]carbonyl}amino)acetate (0.094 g, 0.14 mmol) was dissolved in methanol (3 mL), and a palladium-activated carbon ethylenediamine complex (0.090 g) was added, followed by stirring at room temperature for 2 hours under a hydrogen atmosphere. The reaction solution was filtered with celite, the filtrate was concentrated under reduced pressure, and subsequently the resulting residue was purified by chromatography on a silica gel column (Biotage Ltd., elution solvent: dichloromethane/ethyl acetate) to afford the title compound (0.049 g, 0.088 mmol) as a yellowish white amorphous solid (yield 60%).

$^1$H-NMR (400 MHz, CDCl$_3$) δ: 11.37 (1H, brs), 8.51 (1H, t, J=5 Hz), 7.50 (1H, s), 7.49 (2H, d, J=9 Hz), 7.36 (2H, s), 7.00 (2H, d, J=9 Hz), 4.76 (2H, s), 4.28 (2H, q, J=7 Hz), 4.22 (2H, d, J=5 Hz), 3.73 (2H, d, J=12 Hz), 3.38-3.25 (1H, m), 2.83 (2H, d, J=7 Hz), 2.76 (2H, dt, J=12 Hz, 3 Hz), 2.54 (3H, s), 2.14-1.99 (1H, m), 1.78 (2H, d, J=12 Hz), 1.74 (1H, brs), 1.52 (2H, dq, J=12 Hz, 3 Hz), 1.33 (3H, t, J=7 Hz), 1.30 (6H, d, J=7 Hz).

(6) ({[5-Hydroxy-2-{(1-[4'-(hydroxymethyl)-3'-isopropylbiphenyl-4-yl]piperidin-4-yl}methyl)-6-methylpyrimidin-4-yl]carbonyl}amino)acetic acid In accordance with Example 1-(13), but using ethyl({[5-hydroxy-2-{(1-[4'-(hydroxymethyl)-3'-isopropylbiphenyl-4-yl]piperidin-4-yl}methyl)-6-methylpyrimidin-4-yl]carbonyl}amino)acetate instead of ethyl({[5-hydroxy-2-({1-[4'-(hydroxymethyl)biphenyl-4-yl]piperidin-4-yl}methyl)-6-methylpyrimidin-4-yl]carbonyl}amino)acetate, the title compound (yield 85%) was afforded as a white solid.

MS m/z: 533 (M+H)$^+$;

$^1$H-NMR (400 MHz, DMSO-d$_6$) δ: 12.88 (1H, s), 11.92 (1H, s), 9.41 (1H, t, J=6 Hz), 7.51 (2H, brs), 7.45 (1H, s), 7.36 (2H, brs), 7.02 (2H, brs), 4.56 (2H, s), 4.01 (2H, d, J=6 Hz), 3.72 (2H, d, J=12 Hz), 3.28-3.15 (1H, m), 2.87-2.62 (2H, m), 2.80 (2H, d, J=7 Hz), 2.45 (3H, s), 2.12 (1H, brs), 1.80-1.61 (2H, m), 1.53-1.31 (2H, m), 1.23 (6H, d, J=7 Hz).

Example 53

[({2-[(1-{5-[3-Fluoro-4-(hydroxymethyl)phenyl]pyridin-2-yl}piperidin-4-yl)methyl]-5-hydroxy-6-methylpyrimidin-4-yl}carbonyl)amino]acetic acid

[Chemical 151]

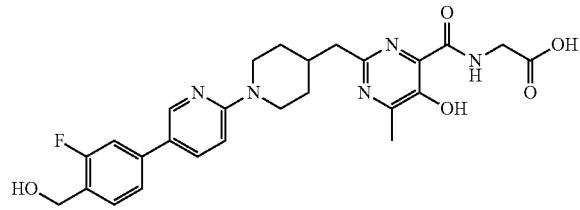

In accordance with Example 1-(11), but using tert-butyl 5-(benzyloxy)-2-{[1-(5-bromopyridin-2-yl)piperidin-4-yl]methyl}-6-methylpyrimidine-4-carboxylate (1.8 g, 3.2 mmol) obtained in Example 19-(1) instead of tert-butyl 5-(benzyloxy)-2-{(1-[4'-(hydroxymethyl)biphenyl-4-yl]piperidin-4-yl}methyl)-6-methylpyrimidine-4-carboxylate, ethyl({[5-(benzyloxy)-2-{[1-(5-bromopyridin-2-yl)piperidin-4-yl]methyl}-6-methylpyrimidin-4-yl]carbonyl}amino)acetate (1.7 g, 2.9 mmol) was afforded as a pale yellow oil (yield 92%).

In accordance with Examples 19-(2), 1-(10), 22-(4) and 1-(13), but using ethyl({[5-(benzyloxy)-2-{[1-(5-bromopyridin-2-yl)piperidin-4-yl]methyl}-6-methylpyrimidin-4-yl]carbonyl}amino)acetate instead of tert-butyl 5-(benzyloxy)-2-{[1-(5-bromopyridin-2-yl)piperidin-4-yl]methyl}-6-methylpyrimidine-4-carboxylate, and [(4-bromo-2-fluorobenzyl)oxy](tert-butyl)dimethylsilane instead of tert-butyl[(4-iodobenzyl)oxy]dimethylsilane, the title compound (yield 21%) was afforded as a white solid.

MS m/z: 510 (M+H)$^+$;
$^1$H-NMR (500 MHz, DMSO-d$_6$) δ: 12.87 (1H, brs), 11.92 (1H, s), 9.38 (1H, t, J=5 Hz), 8.46 (1H, d, J=3 Hz), 7.85 (1H, dd, J=9 Hz, 3 Hz), 7.50-7.40 (3H, m), 6.99 (1H, d, J=9 Hz), 5.25 (1H, t, J=6 Hz), 4.54 (2H, d, J=6 Hz), 4.33 (2H, d, J=13 Hz), 3.99 (2H, d, J=5 Hz), 2.85 (2H, t, J=13 Hz), 2.76 (2H, d, J=7 Hz), 2.44 (3H, s), 2.25-2.14 (1H, m), 1.66 (2H, d, J=13 Hz), 1.24 (2H, dq, J=13 Hz, 3 Hz).

Example 54

[({2-[(1-{5-[3-Chloro-4-(hydroxymethyl)phenyl]pyridin-2-yl}piperidin-4-yl)methyl]-5-hydroxy-6-methylpyrimidin-4-yl}carbonyl)amino]acetic acid

[Chemical 152]

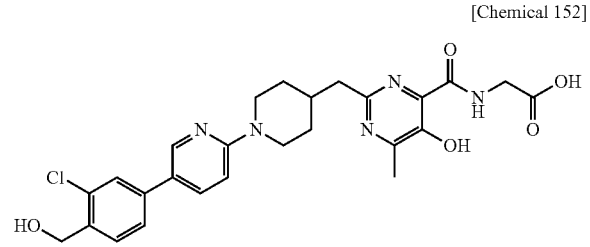 [SMILES: Cc1cc(-c2ccc(N3CCC(Cc4nc(C)c(O)c(C(=O)NCC(=O)O)n4)CC3)nc2)ccc1CO]

In accordance with Example 53, but using [(4-bromo-2-chlorobenzyl)oxy](tert-butyl)dimethylsilane instead of [(4-bromo-2-fluorobenzyl)oxy](tert-butyl)dimethylsilane, the title compound (yield 22%) was afforded as a white solid.

MS m/z: 526 (M+H)$^+$;
$^1$H-NMR (500 MHz, DMSO-d$_6$) δ: 12.89 (1H, brs), 11.92 (1H, s), 9.39 (1H, t, J=5 Hz), 8.46 (1H, d, J=3 Hz), 7.86 (1H, dd, J=9 Hz, 3 Hz), 7.66 (1H, s), 7.63-7.54 (2H, m), 6.90 (1H, d, J=9 Hz), 5.40 (1H, t, J=5 Hz), 4.57 (2H, d, J=5 Hz), 4.35 (2H, d, J=13 Hz), 4.00 (2H, d, J=5 Hz), 2.85 (2H, t, J=13 Hz), 2.77 (2H, d, J=7 Hz), 2.45 (3H, s), 2.25-2.16 (1H, m), 1.67 (2H, d, J=13 Hz), 1.25 (2H, dq, J=13 Hz, 3 Hz).

Example 55

[({5-Hydroxy-2-[(1-{5-[4-(hydroxymethyl)-3-methylphenyl]pyridin-2-yl}piperidin-4-yl)methyl]-6-methylpyrimidin-4-yl}carbonyl)amino]acetic acid

[Chemical 153]

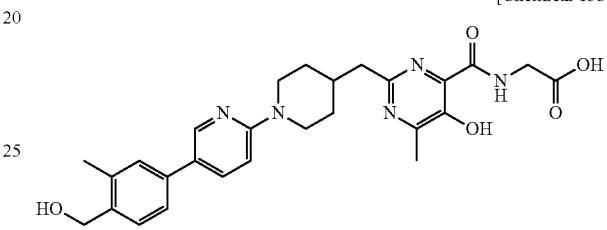

In accordance with Example 53, but using [(4-bromo-2-methylbenzyl)oxy](tert-butyl)dimethylsilane instead of [(4-bromo-2-fluorobenzyl)oxy](tert-butyl)dimethylsilane, the title compound (yield 18%) was afforded as a white solid.

MS m/z: 506 (M+H)$^+$;
$^1$H-NMR (500 MHz, DMSO-d$_6$) δ: 12.89 (1H, brs), 11.91 (1H, s), 9.39 (1H, t, J=5 Hz), 8.41 (1H, d, J=2 Hz), 7.80 (1H, dd, J=9 Hz, 2 Hz), 7.41-7.35 (3H, m), 6.88 (1H, d, J=9 Hz), 5.05 (1H, t, J=5 Hz), 4.49 (2H, d, J=5 Hz), 4.32 (2H, d, J=13 Hz), 4.00 (2H, d, J=5 Hz), 2.83 (2H, t, J=13 Hz), 2.76 (2H, d, J=7 Hz), 2.44 (3H, s), 2.29 (3H, s), 2.24-2.14 (1H, m), 1.66 (2H, d, J=13 Hz), 1.24 (2H, dq, J=13 Hz, 3 Hz).

Formulation Examples

Formulation Example 1

Injection 1.5% by weight of a compound of the Examples is stirred in 10% by volume of propylene glycol, then adjusted to a fixed volume with water for injection, and subsequently sterilized to obtain an injection.

Formulation Example 2

Hard Capsule 100 mg of a powdery compound of the Examples, 128.7 mg lactose, 70 mg cellulose and 1.3 mg magnesium stearate are mixed, passed through 60 mesh sieve, and subsequently the resulting powders are put into 250 mg of No. 3 gelatin capsule to obtain capsules.

Formulation Example 3

Tablet 100 mg of a powdery compound of the Examples, 124 mg lactose, 25 mg cellulose and 1 mg magnesium stearate are mixed, and tableted with a tablet-making machine to obtain tablets each having 200 mg. This tablet can be coated as necessary.

Test Example

The pharmacological activity of the compounds of the present invention were confirmed by the testing indicated below.

In vitro erythropoietin (EPO) induction activity of test compounds was evaluated using human liver cancer-derived cell line Hep3B (ATCC, Manassas, Va.). Hep3B cells were cultured overnight at 37° C. in Dulbecco's modified Eagle's medium (DMEM) in the presence of 10% fetal bovine serum (FBS) (24-well plate, $1.0 \times 10^5$ cells/well). After replacing with fresh DMEM (+10% FBS) containing a test compound dissolved in 0.5% dimethyl sulfoxide (DMSO) (prepared to a concentration of 12.5 μM) or a solvent control (0.5% DMSO), the cells were cultured for 24 hours at 37° C. After recovering the culture supernatant, EPO concentration in the culture supernatant was quantified using a human EPO ELISA kit (StemCell Technologies).

The EPO concentration in the case of using a compound of each example as a test compound was expressed as a multiple of the EPO concentration in the control. The results are shown in Table 1. The EPO concentration in the case of using a compound of each example was remarkably increased compared with the EPO concentration of the solvent control. Namely, the compounds of the present invention demonstrated superior EPO production-enhancing activity, and are useful as a medicament (in particular, a medicament for prophylaxis or treatment of anemia).

TABLE 1

| Number of Compound of Example | EPO Concentration (multiple) |
|---|---|
| Control (0.5% DMSO) | 1 |
| 1 | 55 |
| 3 | 24 |
| 4 | 73 |
| 5 | 48 |
| 6 | 36 |
| 7 | 50 |
| 8 | 94 |
| 9 | 36 |
| 16 | 47 |
| 20 | 11 |
| 24 | 30 |
| 25 | 22 |
| 26 | 13 |
| 27 | 30 |
| 30 | 23 |
| 35 | 53 |
| 36 | 25 |
| 37 | 31 |
| 38 | 24 |
| 39 | 18 |
| 40 | 25 |
| 41 | 20 |
| 42 | 28 |
| 44 | 26 |
| 45 | 41 |
| 46 | 45 |
| 47 | 34 |
| 48 | 42 |
| 49 | 18 |
| 50 | 23 |

INDUSTRIAL APPLICABILITY

The compound of the present invention, pharmacologically acceptable ester thereof or pharmacologically acceptable salt thereof has a superior EPO production-enhancing activity, and is useful for diseases or the like caused by decreased EPO. Specifically, the compound of the present invention, pharmacologically acceptable ester thereof or pharmacologically acceptable salt thereof is useful as a medicament for the prophylaxis and/or treatment of anemia, preferably nephrogenic anemia, anemia of prematurity, anemia incidental to chronic diseases, anemia incidental to cancer chemotherapy, cancerous anemia, inflammation-associated anemia, or anemia incidental to congestive heart failure, more preferably anemia incidental to chronic kidney disease, and can also be used as a medicament for the prophylaxis and/or treatment of ischemic cerebrovascular disease.

The invention claimed is:
1. A compound represented by formula (1):

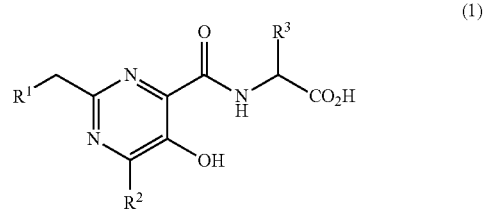

wherein,
$R^1$ represents a group represented by formula (1A):

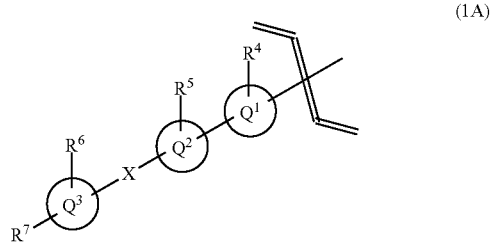

wherein,
$R^4$ and $R^5$ each independently represents a hydrogen atom, a halogen atom or a $C_1$-$C_6$ alkyl group,
$R^6$ represents a hydrogen atom, a halogen atom, a $C_1$-$C_6$ alkyl group, a carbamoyl group, a $C_1$-$C_6$ alkylcarbamoyl group, or a ($C_1$-$C_6$ alkyl)($C_1$-$C_6$ alkyl)carbamoyl group,
$R^7$ represents a hydroxy $C_1$-$C_6$ alkyl group which may have 1 or 2 substituents independently selected from substituent group α, a hydroxyhalo $C_1$-$C_6$ alkyl group which may have 1 or 2 substituents independently selected from substituent group α, a $C_1$-$C_6$ alkoxy $C_1$-$C_6$ alkyl group which may have 1 or 2 substituents independently selected from substituent group α, a ($C_1$-$C_6$ alkoxy) carbonyl group which may have 1 or 2 substituents independently selected from substituent group α, a $C_1$-$C_6$ alkoxy $C_1$-$C_6$ alkoxy $C_1$-$C_6$ alkyl group which may have 1 or 2 substituents independently selected from substituent group α, a hydroxy $C_1$-$C_6$ alkoxy group which may have 1 or 2 substituents independently selected from substituent group α, a $C_1$-$C_6$ alkylcarbamoyl group which may have 1 or 2 substituents independently selected from substituent group α, a ($C_1$-$C_6$ alkyl)($C_1$-$C_6$ alkyl)carbamoyl group which may have 1 or 2 substituents independently selected from substituent group α, a $C_1$-$C_6$ alkoxycarbamoyl group which may have 1 or 2 substituents independently selected from substituent group α, a $C_1$-$C_6$ alkylcarbamoyl $C_1$-$C_6$ alkyl group which may have 1 or 2 substituents independently selected from substituent group α, a ($C_1$-$C_6$ alkyl)($C_1$-$C_6$ alkyl)carbamoyl $C_1$-$C_6$ alkyl group which may have 1 or 2 substituents independently selected from substituent group α, a $C_2$-$C_7$ alkanoylamino group which may have 1 or 2 substituents independently selected from substituent group α, a $C_2$-$C_7$ alkanoylamino $C_1$-$C_6$ alkyl group which may have 1 or 2 substituents independently selected from substituent group α, or a $C_2$-$C_7$ alkanoyloxy $C_1$-$C_6$ alkyl group which may have 1 or 2 substituents independently selected from substituent group α, substituent group α represents a group consisting of an oxo group, a hydroxy group, an amino group, a carboxy group, a carbamoyl group, a $C_1$-$C_6$ alkoxy group, a halo $C_1$-$C_6$ alkoxy group, a $C_2$-$C_7$ alkanoylamino group, a hydroxyimino group, and a $C_1$-$C_6$ alkoxyimino group, ring $Q^1$ represents a monocyclic heterocyclic group, wherein the heterocyclic group comprises a 5- to 7-membered aromatic heterocycle and non-aromatic heterocycle, and contains 1 or 2 atoms selected from the group consisting of a nitrogen atom, a sulfur atom and an oxygen atom, ring $Q^2$ represents a monocyclic hydrocarbon ring group, wherein the hydrocarbon ring group comprises a 5- to 7-membered aromatic hydrocarbon ring and a non-aromatic hydrocarbon ring, or a monocyclic heterocyclic group, wherein the heterocyclic group comprises a 5- to 7-membered aromatic heterocycle and non-aromatic heterocycle, and contains 1 or 2 atoms selected from the group consisting of a nitrogen atom, a sulfur atom and an oxygen atom, ring $Q^3$ represents a monocyclic hydrocarbon ring group, wherein the hydrocarbon ring group comprises a 5- to 7-membered aromatic hydrocarbon ring and a non-aromatic hydrocarbon ring, or a monocyclic heterocyclic group, wherein the heterocyclic group comprises a 5- to 7-membered aromatic heterocycle and non-aromatic heterocycle, and contains 1 or 2 atoms selected from the group consisting of a nitrogen atom, a sulfur atom and an oxygen atom, and X represents a single bond, methylene, or ethylene, $R^2$ represents a $C_1$-$C_3$ alkyl group or a methylsulfanyl group, and $R^3$ represents a hydrogen atom or a methyl group, a pharmacologically acceptable ester thereof, or a pharmacologically acceptable salt thereof.

2. The compound, pharmacologically acceptable ester thereof, or pharmacologically acceptable salt thereof according to claim 1, wherein $R^2$ is a methyl group or a methylsulfanyl group.

3. The compound, pharmacologically acceptable ester thereof, or pharmacologically acceptable salt thereof according to claim 1, wherein $R^2$ is a methyl group.

4. The compound, pharmacologically acceptable ester thereof, or pharmacologically acceptable salt thereof according to claim 1, wherein $R^3$ is a hydrogen atom.

5. The compound, pharmacologically acceptable ester thereof, or pharmacologically acceptable salt thereof according to claim 1, wherein $R^4$ is a hydrogen atom.

6. The compound, pharmacologically acceptable ester thereof, or pharmacologically acceptable salt thereof according to claim 1, wherein $R^5$ is a hydrogen atom, a halogen atom or a methyl group.

7. The compound, pharmacologically acceptable ester thereof, or pharmacologically acceptable salt thereof according to claim 1, wherein $R^5$ is a hydrogen atom.

8. The compound, pharmacologically acceptable ester thereof, or pharmacologically acceptable salt thereof according to claim 1, wherein $R^6$ is a hydrogen atom, a halogen atom, or a methyl group.

9. The compound, pharmacologically acceptable ester thereof, or pharmacologically acceptable salt thereof according to claim 1, wherein $R^6$ is a hydrogen atom.

10. The compound, pharmacologically acceptable ester thereof, or pharmacologically acceptable salt thereof according to claim 1, wherein $R^7$ is a hydroxy $C_1$-$C_6$ alkyl group, a hydroxyhalo $C_1$-$C_6$ alkyl group, a $C_1$-$C_6$ alkoxy $C_1$-$C_6$ alkyl group, a hydroxy $C_1$-$C_6$ alkoxy $C_1$-$C_6$ alkyl group, a ($C_1$-$C_6$ alkoxy)carbonyl group, a $C_1$-$C_6$ alkoxy $C_1$-$C_6$ alkoxy $C_1$-$C_6$ alkyl group, a hydroxy $C_1$-$C_6$ alkoxy group, a $C_1$-$C_6$ alkylcarbamoyl group, a ($C_1$-$C_6$ alkyl)($C_1$-$C_6$ alkyl)carbamoyl group, a hydroxy $C_1$-$C_6$ alkylcarbamoyl group, a $C_1$-$C_6$ alkoxycarbamoyl group, a $C_1$-$C_6$ alkylcarbamoyl $C_1$-$C_6$ alkyl group, a ($C_1$-$C_6$ alkyl)($C_1$-$C_6$ alkyl)carbamoyl $C_1$-$C_6$ alkyl group, or a hydroxy $C_1$-$C_6$ alkylcarbamoyl $C_1$-$C_6$ alkyl group.

11. The compound, pharmacologically acceptable ester thereof, or pharmacologically acceptable salt thereof according to claim 1, wherein $R^7$ is a hydroxymethyl group, a 1-hydroxyethyl group, a 2-hydroxyethyl group, a 1,1-difluoro-2-hydroxyethyl group, a 2-hydroxypropyl group, a 3-hydroxypropyl group, a 1,1-difluoro-2-hydroxypropyl group, a 2-hydroxybutyl group, a 2-hydroxy-1,1-dimethylethyl group, a 1,1-difluoro-2-hydroxy-2-methylpropyl group, a methoxymethyl group, a 2-hydroxy-3-methoxypropyl group, a methoxycarbonyl group, an ethoxycarbonyl group, a methoxymethoxymethyl group, a 1-methoxymethoxyethyl group, a 2-hydroxyethoxy group, a methylcarbamoyl group, a dimethylcarbamoyl group, a methylcarbamoylmethyl group, a dimethylcarbamoylmethyl group, a hydroxyethylcarbamoyl group, or a hydroxyethylcarbamoylmethyl group.

12. The compound, pharmacologically acceptable ester thereof, or pharmacologically acceptable salt thereof according to claim 1, wherein $R^7$ is a hydroxymethyl group, a 1-hydroxyethyl group, a 2-hydroxyethyl group, a 2-hydroxypropyl group, a 3-hydroxypropyl group, a 2-hydroxybutyl group, a 2-hydroxy-1,1-dimethylethyl group, a methoxymethyl group, a 2-hydroxy-3-methoxypropyl group, an ethoxycarbonyl group, a 1-methoxymethoxyethyl group, a 2-hydroxyethoxy group, a methylcarbamoyl group, a dimethylcarbamoyl group, or a dimethylcarbamoylmethyl group.

13. The compound, pharmacologically acceptable ester thereof, or pharmacologically acceptable salt thereof according to claim 1, wherein the ring $Q^1$ is a monocyclic heterocyclic group, wherein the heterocyclic group comprises a 6-membered aromatic heterocycle and non-aromatic heterocycle, and contains 1 or 2 nitrogen atoms.

14. The compound, pharmacologically acceptable ester thereof, or pharmacologically acceptable salt thereof according to claim 1, wherein the ring $Q^1$ is a piperidyl group.

15. The compound, pharmacologically acceptable ester thereof, or pharmacologically acceptable salt thereof according to claim 1, wherein the ring $Q^2$ is a monocyclic hydrocarbon ring group (wherein the hydrocarbon ring group comprises a 6-membered aromatic hydrocarbon ring and a non-aromatic hydrocarbon ring), or a monocyclic heterocyclic group, wherein the heterocyclic group comprises a 6-membered aromatic heterocycle and non-aromatic heterocycle, and contains 1 or 2 nitrogen atoms.

16. The compound, pharmacologically acceptable ester thereof, or pharmacologically acceptable salt thereof according to claim 1, wherein the ring $Q^2$ is a phenyl group or a pyridyl group.

17. The compound, pharmacologically acceptable ester thereof, or pharmacologically acceptable salt thereof according to claim 1, wherein the ring $Q^3$ is a monocyclic hydrocarbon ring group, wherein the hydrocarbon ring group comprises a 6-membered aromatic hydrocarbon ring and a non-aromatic hydrocarbon ring, or a monocyclic heterocyclic group, wherein the heterocyclic group comprises a 6-membered aromatic heterocycle and non-aromatic heterocycle, and contains 1 or 2 nitrogen atoms.

18. The compound, pharmacologically acceptable ester thereof, or pharmacologically acceptable salt thereof according to claim 1, wherein the ring $Q^3$ is a phenyl group or a pyridyl group.

19. The compound, pharmacologically acceptable ester thereof, or pharmacologically acceptable salt thereof according to claim 1, wherein X is a single bond or methylene.

20. The compound, pharmacologically acceptable ester thereof, or pharmacologically acceptable salt thereof according to claim 1, wherein:

$R^1$ is a group represented by formula (1B)

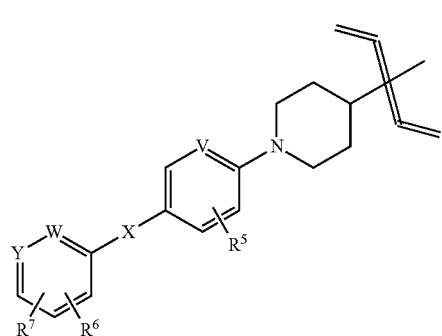

(1B)

wherein,
$R^5$ represents a hydrogen atom, a halogen atom or a $C_1$-$C_6$ alkyl group,
$R^6$ represents a hydrogen atom, a halogen atom, a $C_1$-$C_6$ alkyl group, a carbamoyl group, a $C_1$-$C_6$ alkylcarbamoyl group, or a ($C_1$-$C_6$ alkyl)($C_1$-$C_6$ alkyl)carbamoyl group,
$R^7$ represents a hydroxymethyl group, a 1-hydroxyethyl group, a 2-hydroxyethyl group, a 1,1-difluoro-2-hydroxyethyl group, a 2-hydroxypropyl group, a 3-hydroxypropyl group, a 1,1-difluoro-2-hydroxypropyl group, a 2-hydroxybutyl group, a 2-hydroxy-1,1-dimethylethyl group, a 1,1-difluoro-2-hydroxy-2-methylpropyl group, a methoxymethyl group, a 2-hydroxy-3-methoxypropyl group, a methoxycarbonyl group, an ethoxycarbonyl group, a methoxymethoxymethyl group, a 1-methoxymethoxyethyl group, a 2-hydroxyethoxy group, a methylcarbamoyl group, a dimethylcarbamoyl group, a methylcarbamoylmethyl group, a dimethylcarbamoylmethyl group, a hydroxyethylcarbamoyl group, or a hydroxyethylcarbamoylmethyl group,
V, W and Y, each independently, represent a carbon atom having 1 hydrogen atom or a nitrogen atom, and
X represents a single bond or methylene.

21. The compound, pharmacologically acceptable ester thereof, or pharmacologically acceptable salt thereof according to claim 1, wherein:

$R^1$ represents a group represented by formula (1B-1), (1B-2), (1B-3), (1B-4), (1B-5), (1B-6), (1B-7), or (1B-8)

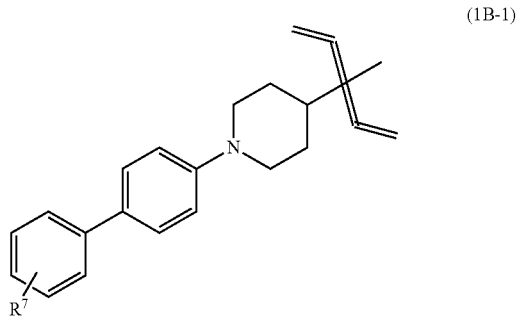

(1B-1)

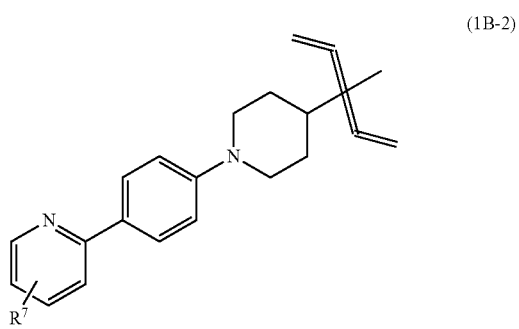

(1B-2)

(1B-3)

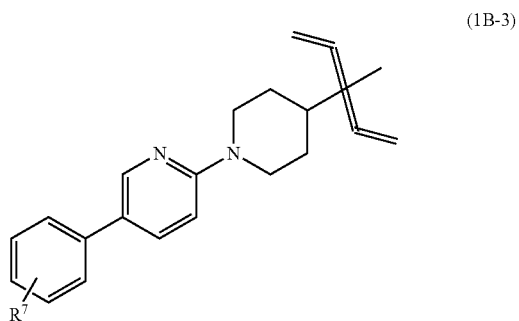

(1B-4)

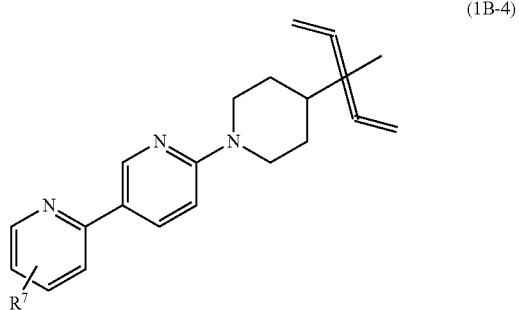

(1B-5)

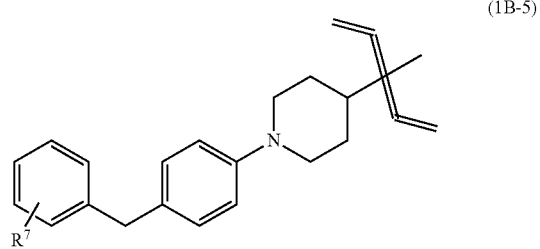

-continued

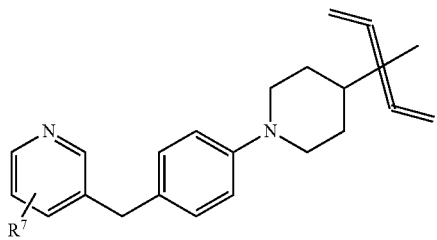
(1B-6)

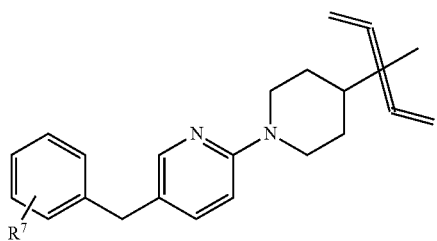
(1B-7)

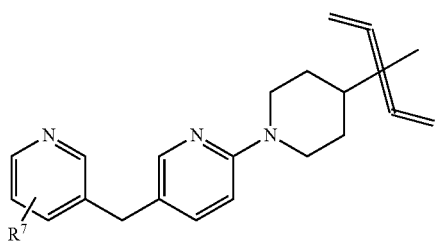
(1B-8)

wherein,

R⁷ represents a hydroxymethyl group, a 1-hydroxyethyl group, a 2-hydroxyethyl group, a 1,1-difluoro-2-hydroxyethyl group, a 2-hydroxypropyl group, a 3-hydroxypropyl group, a 1,1-difluoro-2-hydroxypropyl group, a 2-hydroxybutyl group, a 2-hydroxy-1,1-dimethylethyl group, a 1,1-difluoro-2-hydroxy-2-methylpropyl group, a methoxymethyl group, a 2-hydroxy-3-methoxypropyl group, a methoxycarbonyl group, an ethoxycarbonyl group, a methoxymethoxymethyl group, a 1-methoxymethoxyethyl group, a 2-hydroxyethoxy group, a methylcarbamoyl group, a dimethylcarbamoyl group, a methylcarbamoylmethyl group, a dimethylcarbamoylmethyl group, a hydroxyethylcarbamoyl group, or a hydroxyethylcarbamoylmethyl group.

22. The compound, pharmacologically acceptable ester thereof, or pharmacologically acceptable salt thereof according to claim 1, wherein:

R¹ represents a group represented by formula (1B-1), (1B-2), (1B-3), (1B-5), or (1B-6)

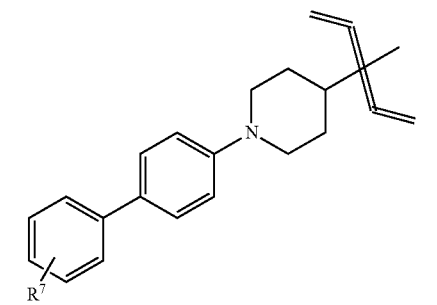
(1B-1)

-continued

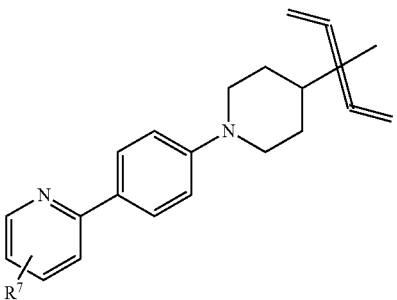
(1B-2)

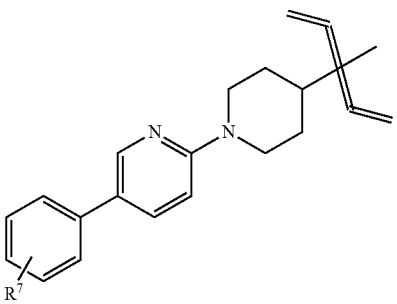
(1B-3)

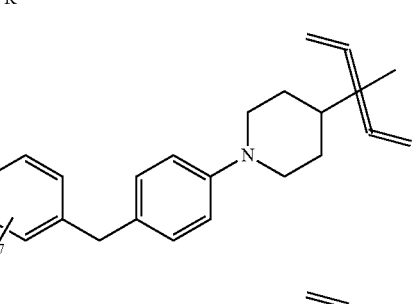
(1B-5)

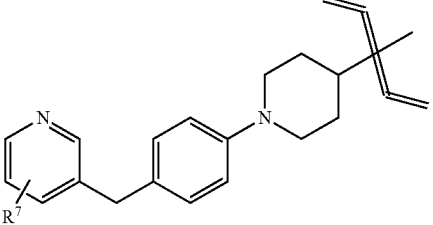
(1B-6)

wherein,

R⁷ represents a hydroxymethyl group, a 1-hydroxyethyl group, a 2-hydroxyethyl group, a 1,1-difluoro-2-hydroxyethyl group, a 2-hydroxypropyl group, a 3-hydroxypropyl group, a 1,1-difluoro-2-hydroxypropyl group, a 2-hydroxybutyl group, a 2-hydroxy-1,1-dimethylethyl group, a 1,1-difluoro-2-hydroxy-2-methylpropyl group, a methoxymethyl group, a 2-hydroxy-3-methoxypropyl group, a methoxycarbonyl group, an ethoxycarbonyl group, a methoxymethoxymethyl group, a 1-methoxymethoxyethyl group, a 2-hydroxyethoxy group, a methylcarbamoyl group, a dimethylcarbamoyl group, a methylcarbamoylmethyl group, a dimethylcarbamoylmethyl group, a hydroxyethylcarbamoyl group, or a hydroxyethylcarbamoylmethyl group.

23. The compound, pharmacologically acceptable ester thereof, or pharmacologically acceptable salt thereof according to claim 20, wherein R⁷ represents a hydroxymethyl group, a 1-hydroxyethyl group, a 2-hydroxyethyl group, a 2-hydroxypropyl group, a 3-hydroxypropyl group, a 2-hydroxybutyl group, a 2-hydroxy-1,1-dimethylethyl group, a methoxymethyl group, a 2-hydroxy-3-methoxypropyl group, an ethoxycarbonyl group, a 1-methoxymethoxyethyl group, a 2-hydroxyethoxy group, a methylcarbamoyl group, a dimethylcarbamoyl group, or a dimethylcarbamoylmethyl group.

24. The compound, pharmacologically acceptable ester thereof, or pharmacologically acceptable salt thereof according to claim 20, wherein, in the case where $R^7$ represents a group having a hydroxy group (a hydroxy $C_1$-$C_6$ alkyl group, a hydroxyhalo $C_1$-$C_6$ alkyl group, a hydroxy $C_1$-$C_6$ alkoxy group, a hydroxy $C_1$-$C_6$ alkylcarbamoyl group, or a hydroxy $C_1$-$C_6$ alkylcarbamoyl $C_1$-$C_6$ alkyl group), the hydroxy group forms an ester bond with a $C_1$-$C_6$ alkanoyl group.

25. The compound or pharmacologically acceptable salt thereof according to claim 1, selected from the following:

({[5-hydroxy-2-({1-[4'-(hydroxymethyl)biphenyl-4-yl]piperidin-4-yl}methyl)-6-methylpyrimidin-4-yl]carbonyl}amino)acetic acid, ({[2-({1-[4'-(acetoxymethyl)biphenyl-4-yl]piperidin-4-yl}methyl)-5-hydroxy-6-methylpyrimidin-4-yl]carbonyl}amino)acetic acid, ({[5-hydroxy-2-({1-[4'-(1-hydroxyethyl)biphenyl-4-yl]piperidin-4-yl}methyl)-6-methylpyrimidin-4-yl]carbonyl}amino)acetic acid, ({[5-hydroxy-2-({1-[4'-(2-hydroxyethyl)biphenyl-4-yl]piperidin-4-yl}methyl)-6-methylpyrimidin-4-yl]carbonyl}amino)acetic acid, ({[5-hydroxy-2-({1-[4'-(2-hydroxypropyl)biphenyl-4-yl]piperidin-4-yl}methyl)-6-methylpyrimidin-4-yl]carbonyl}amino)acetic acid, ({[5-hydroxy-2-({1-[4'-(2-hydroxy-1,1-dimethylethyl)biphenyl-4-yl]piperidin-4-yl}methyl)-6-methylpyrimidin-4-yl]carbonyl}amino)acetic acid, ({[2-({1-[4'-(dimethylcarbamoyl)biphenyl-4-yl]piperidin-4-yl}methyl)-5-hydroxy-6-methylpyrimidin-4-yl]carbonyl}amino)acetic acid, ({[5-hydroxy-6-methyl-2-({1-[4'-(methylcarbamoyl)biphenyl-4-yl]piperidin-4-yl}methyl)pyrimidin-4-yl]carbonyl}amino)acetic acid,

[({2-[(1-{4'-[2-(dimethylamino)-2-oxoethyl]biphenyl-4-yl}piperidin-4-yl)methyl]-5-hydroxy-6-methylpyrimidin-4-yl}carbonyl)amino]acetic acid,

[({5-hydroxy-2-[(1-{4-[4-(hydroxymethyl)benzyl]phenyl}piperidin-4-yl)methyl]-6-methylpyrimidin-4-yl}carbonyl)amino]acetic acid,

[({5-hydroxy-2-[(1-{4-[3-(hydroxymethyl)benzyl]phenyl}piperidin-4-yl)methyl]-6-methylpyrimidin-4-yl}carbonyl)amino]acetic acid,

[({5-hydroxy-2-[(1-{4-[5-(1-hydroxyethyl)pyridin-2-yl]phenyl}piperidin-4-yl)methyl]-6-methylpyrimidin-4-yl}carbonyl)amino]acetic acid, {[(5-hydroxy-2-{[1-(4-{5-[1-(methoxymethoxy)ethyl]pyridin-2-yl}phenyl)piperidin-4-yl]methyl}-6-methylpyrimidin-4-yl)carbonyl]amino}acetic acid,

[({2-[(1-{4-[5-(1-acetoxyethyl)pyridin-2-yl]phenyl}piperidin-4-yl)methyl]-5-hydroxy-6-methylpyrimidin-4-yl}carbonyl)amino]acetic acid,

[({5-hydroxy-2-[(1-{4-[5-(hydroxymethyl)pyridin-2-yl]phenyl}piperidin-4-yl)methyl]-6-methylpyrimidin-4-yl}carbonyl)amino]acetic acid,

[({2-[(1-{4-[5-(ethoxycarbonyl)pyridin-2-yl]phenyl}piperidin-4-yl)methyl]-5-hydroxy-6-methylpyrimidin-4-yl}carbonyl)amino]acetic acid,

[({2-[(1-{4-[2-(ethoxycarbonyl)benzyl]phenyl}piperidin-4-yl)methyl]-5-hydroxy-6-methylpyrimidin-4-yl}carbonyl)amino]acetic acid, {[(5-hydroxy-2-{[1-(4-{[6-(2-hydroxyethoxy)pyridin-3-yl]methyl}phenyl)piperidin-4-yl]methyl}-6-methylpyrimidin-4-yl)carbonyl]amino}acetic acid,

[({5-hydroxy-2-[(1-{5-[4-(hydroxymethyl)phenyl]pyridin-2-yl}piperidin-4-yl)methyl]-6-methylpyrimidin-4-yl}carbonyl)amino]acetic acid,

[({5-hydroxy-2-[(1-{5-[4-(2-hydroxypropyl)phenyl]pyridin-2-yl}piperidin-4-yl)methyl]-6-methylpyrimidin-4-yl}carbonyl)amino]acetic acid,

[({5-hydroxy-2-[(1-{5-[4-(2-hydroxy-1,1-dimethylethyl)phenyl]pyridin-2-yl}piperidin-4-yl)methyl]-6-methylpyrimidin-4-yl}carbonyl)amino]acetic acid, ({[2-({1-[2-chloro-4'-(hydroxymethyl)biphenyl-4-yl]piperidin-4-yl}methyl)-5-hydroxy-6-methylpyrimidin-4-yl]carbonyl}amino)acetic acid, ({[5-hydroxy-2-({1-[4'-(hydroxymethyl)-2-methylbiphenyl-4-yl]piperidin-4-yl}methyl)-6-methylpyrimidin-4-yl]carbonyl}amino)acetic acid, ({[2-({1-[3'-chloro-4'-(hydroxymethyl)biphenyl-4-yl]piperidin-4-yl}methyl)-5-hydroxy-6-methylpyrimidin-4-yl]carbonyl}amino)acetic acid, ({[5-hydroxy-2-({1-[4'-(hydroxymethyl)-2'-methylbiphenyl-4-yl]piperidin-4-yl}methyl)-6-methylpyrimidin-4-yl]carbonyl}amino)acetic acid, ({[5-hydroxy-2-({1-[4'-(hydroxymethyl)-2,3'-dimethylbiphenyl-4-yl]piperidin-4-yl}methyl)-6-methylpyrimidin-4-yl]carbonyl}amino)acetic acid, ({[5-hydroxy-2-({1-[4'-(2-hydroxybutyl)biphenyl-4-yl]piperidin-4-yl}methyl)-6-methylpyrimidin-4-yl]carbonyl}amino)acetic acid,

[({5-hydroxy-2-[(1-{4-[4-(2-hydroxypropyl)benzyl]phenyl}piperidin-4-yl)methyl]-6-methylpyrimidin-4-yl}carbonyl)amino]acetic acid,

[({5-hydroxy-2-[(1-{4-[4-(2-hydroxy-1,1-dimethylethyl)benzyl]phenyl}piperidin-4-yl)methyl]-6-methylpyrimidin-4-yl}carbonyl)amino]acetic acid, ({[2-({1-[4'-(1,1-difluoro-2-hydroxyethyl)biphenyl-4-yl]piperidin-4-yl}methyl)-5-hydroxy-6-methylpyrimidin-4-yl]carbonyl}amino)acetic acid, ({[2-({1-[4'-(1,1-difluoro-2-hydroxypropyl)biphenyl-4-yl]piperidin-4-yl}methyl)-5-hydroxy-6-methylpyrimidin-4-yl]carbonyl}amino)acetic acid, ({[2-({1-[4'-(1,1-difluoro-2-hydroxy-2-methylpropyl)biphenyl-4-yl]piperidin-4-yl}methyl)-5-hydroxy-6-methylpyrimidin-4-yl]carbonyl}amino)acetic acid, {[(5-[(2,2-dimethylpropanoyl)oxy]-2-{[1-(4'-{[(2,2-dimethylpropanoyl)oxy]methyl}biphenyl-4-yl)piperidin-4-yl]methyl}-6-methylpyrimidin-4-yl)carbonyl]amino}acetic acid, {[(2-{[1-(4'-{[(2,2-dimethylpropanoyl)oxy]methyl}biphenyl-4-yl)piperidin-4-yl]methyl}-5-hydroxy-6-methylpyrimidin-4-yl)carbonyl]amino}acetic acid, ({[5-hydroxy-2-({1-[4'-(methoxymethyl)biphenyl-4-yl]piperidin-4-yl}methyl)-6-methylpyrimidin-4-yl]carbonyl}amino)acetic acid, ({[2-({1-[2'-fluoro-4'-(hydroxymethyl)biphenyl-4-yl]piperidin-4-yl}methyl)-5-hydroxy-6-methylpyrimidin-4-yl]carbonyl}amino)acetic acid, ({[2-({1-[3'-fluoro-4'-(hydroxymethyl)biphenyl-4-yl]piperidin-4-yl}methyl)-5-hydroxy-6-methylpyrimidin-4-yl]carbonyl}amino)acetic acid, ({[2-({1-[2-fluoro-4'-(hydroxymethyl)biphenyl-4-yl]piperidin-4-yl}methyl)-5-hydroxy-6-methylpyrimidin-4-yl]carbonyl}amino)acetic acid, ({[2-({1-[3-fluoro-4'-(hydroxymethyl)biphenyl-4-yl]piperidin-4-yl}methyl)-5-hydroxy-6-methylpyrimidin-4-yl]carbonyl}amino)acetic acid, ({[5-hydroxy-2-({1-[4'-(hydroxymethyl)-3'-methylbiphenyl-4-yl]piperidin-4-yl}methyl)-6-methylpyrimidin-4-yl]carbonyl}amino)acetic acid, ({[2-({1-[3',5'-difluoro-4'-(hydroxymethyl)biphenyl-4-yl]piperidin-4-yl}methyl)-5-hydroxy-6-methylpyrimidin-4-yl]carbonyl}amino)acetic acid, ({[2-({1-[3',5'-dichloro-4'-(hydroxymethyl)biphenyl-4-yl]piperidin-4-yl}methyl)-5-hydroxy-6-methylpyrimidin-4-yl]carbonyl}amino)acetic acid, ({[2-({1-[3',5'-dimethyl-4'-(hydroxymethyl)biphenyl-4-yl]piperidin-4-yl}methyl)-5-hydroxy-6-methylpyrimidin-4-yl]carbonyl}amino)acetic acid,

[({5-hydroxy-2-[(1-{4'-[2-hydroxy-3-methoxypropyl]biphenyl-4-yl}piperidin-4-yl)methyl]-6-methylpyrimidin-4-yl}carbonyl)amino]acetic acid, ({[5-hydroxy-2-({1-[4'-(3-hydroxypropyl)biphenyl-4-yl]piperidin-4-yl}methyl)-6-methylpyrimidin-4-yl]carbonyl}amino)acetic acid, ({[5-hydroxy-2-({1-[4'-(hydroxymethyl)-3'-isopropylbiphenyl-4-yl]piperidin-4-yl}methyl)-6-methylpyrimidin-4-yl]carbonyl}amino)acetic acid,

[({2-[(1-{5-[3-fluoro-4-(hydroxymethyl)phenyl]pyridin-2-yl}piperidin-4-yl)methyl]-5-hydroxy-6-methylpyrimidin-4-yl}carbonyl)amino]acetic acid,

[({2-[(1-{5-[3-chloro-4-(hydroxymethyl)phenyl]pyridin-2-yl}piperidin-4-yl)methyl]-5-hydroxy-6-methylpyrimidin-4-yl}carbonyl)amino]acetic acid, or

[({5-hydroxy-2-[(1-{5-[4-(hydroxymethyl)-3-methylphenyl]pyridin-2-yl}piperidin-4-yl)methyl]-6-methylpyrimidin-4-yl}carbonyl)amino]acetic acid.

26. A pharmaceutical composition containing as an active ingredient a compound, pharmacologically acceptable ester thereof, or pharmacologically acceptable salt thereof according to claim 1.

27. The pharmaceutical composition according to claim 26, for the prophylaxis and/or treatment of anemia.

28. The pharmaceutical composition according to claim 27, wherein the anemia is nephrogenic anemia, anemia of prematurity, anemia incidental to chronic diseases, anemia incidental to cancer chemotherapy, cancerous anemia, inflammation-associated anemia, or anemia incidental to congestive heart failure.

29. The pharmaceutical composition according to claim 27, wherein the anemia is anemia incidental to chronic kidney disease.

30. The pharmaceutical composition according to claim 26, for producing erythropoietin.

31. A method for producing erythropoietin, comprising: administering a pharmacologically effective amount of a compound, pharmacologically acceptable ester thereof, or pharmacologically acceptable salt thereof according to claim 1 to a mammal or bird.

32. A method for the treatment of anemia caused by decreased erythropoietin, comprising: administering a pharmacologically effective amount of a compound, pharmacologically acceptable ester thereof, or pharmacologically acceptable salt thereof according to claim 1 to a mammal.

33. The method according to claim 32, wherein the anemia is nephrogenic anemia, anemia of prematurity, anemia incidental to chronic diseases, anemia incidental to cancer chemotherapy, cancerous anemia, inflammation-associated anemia, or anemia incidental to congestive heart failure.

34. The method according to claim 32, wherein the anemia is anemia incidental to chronic kidney disease.

35. A method according to claim 32, wherein the mammal is a human.

36. The compound or pharmacologically acceptable salt thereof according to claim 1, wherein the compound represented by formula (1) is ({[5-hydroxy-2-({1-[4'-(2-hydroxypropyl)biphenyl-4-yl]piperidin-4-yl}methyl)-6-methylpyrimidin-4-yl]carbonyl}amino)acetic acid.

37. The compound or pharmacologically acceptable salt thereof according to claim 1, wherein the compound represented by formula (1) is ({[5-hydroxy-2-({1-[4'-((2S)-2-hydroxypropyl)biphenyl-4-yl]piperidin-4-yl}methyl)-6-methylpyrimidin-4-yl]carbonyl}amino)acetic acid.

38. The compound or pharmacologically acceptable salt thereof according to claim 1, wherein the compound represented by formula (1) is ({[5-hydroxy-2-({1-[4'-((2R)-2-hydroxypropyl)biphenyl-4-yl]piperidin-4-yl}methyl)-6-methylpyrimidin-4-yl]carbonyl}amino)acetic acid.

39. The compound or pharmacologically acceptable salt thereof according to claim 1, wherein the compound represented by formula (1) is ({[5-hydroxy-2-({1-[4'-(hydroxymethyl)biphenyl-4-yl]piperidin-4-yl}methyl)-6-methylpyrimidin-4-yl]carbonyl}amino)acetic acid.

40. A pharmaceutical composition containing as an active ingredient a compound, pharmacologically acceptable ester thereof, or pharmacologically acceptable salt thereof according to claim 36.

41. A pharmaceutical composition containing as an active ingredient a compound, pharmacologically acceptable ester thereof, or pharmacologically acceptable salt thereof according to claim 37.

42. A pharmaceutical composition containing as an active ingredient a compound, pharmacologically acceptable ester thereof, or pharmacologically acceptable salt thereof according to claim 38.

43. A pharmaceutical composition containing as an active ingredient a compound, pharmacologically acceptable ester thereof, or pharmacologically acceptable salt thereof according to claim 39.

44. A method for the treatment of anemia caused by decreased erythropoietin, comprising: administering a pharmacologically effective amount of a compound or pharmacologically acceptable salt thereof according to claim 36 to a human.

45. The method according to claim 44, wherein the anemia is nephrogenic anemia, anemia of prematurity, anemia incidental to chronic diseases, anemia incidental to cancer chemotherapy, cancerous anemia, inflammation-associated anemia, or anemia incidental to congestive heart failure.

46. The method according to claim 44, wherein the anemia is anemia incidental to chronic kidney disease.

47. A method for the treatment of anemia caused by decreased erythropoietin, comprising: administering a pharmacologically effective amount of a compound or pharmacologically acceptable salt thereof according to claim 37 to a human.

48. The method according to claim 47, wherein the anemia is nephrogenic anemia, anemia of prematurity, anemia incidental to chronic diseases, anemia incidental to cancer chemotherapy, cancerous anemia, inflammation-associated anemia, or anemia incidental to congestive heart failure.

49. The method according to claim 47, wherein the anemia is anemia incidental to chronic kidney disease.

50. A method for the treatment of anemia caused by decreased erythropoietin, comprising: administering a pharmacologically effective amount of a compound or pharmacologically acceptable salt thereof according to claim 38 to a human.

51. The method according to claim 50, wherein the anemia is nephrogenic anemia, anemia of prematurity, anemia incidental to chronic diseases, anemia incidental to cancer chemotherapy, cancerous anemia, inflammation-associated anemia, or anemia incidental to congestive heart failure.

52. The method according to claim 50, wherein the anemia is anemia incidental to chronic kidney disease.

53. A method for the treatment of anemia caused by decreased erythropoietin, comprising: administering a pharmacologically effective amount of a compound or pharmacologically acceptable salt thereof according to claim 39 to a human.

54. The method according to claim 53, wherein the anemia is nephrogenic anemia, anemia of prematurity, anemia incidental to chronic diseases, anemia incidental to cancer chemotherapy, cancerous anemia, inflammation-associated anemia, or anemia incidental to congestive heart failure.

55. The method according to claim 53, wherein the anemia is anemia incidental to chronic kidney disease.

* * * * *